United States Patent
Ferretti et al.

(10) Patent No.: US 10,005,760 B2
(45) Date of Patent: Jun. 26, 2018

(54) FORMS AND COMPOSITIONS OF AN ERK INHIBITOR

(71) Applicant: Celgene CAR LLC, Pembroke (BM)

(72) Inventors: Antonio Christian Ferretti, Summit, NJ (US); Lianfeng Huang, Basking Ridge, NJ (US); Ying Li, Millburn, NJ (US); John Traverse, Lebanon, NJ (US); Jean Xu, Warren, NJ (US); Kelvin Hin-Yeong Yong, Westfield, NJ (US); Daozhong Zou, Raritan, NJ (US)

(73) Assignee: Celgene CAR LLC, Pembroke (BM)

( * ) Notice: Subject to any disclaimer, the term of this patent is extended or adjusted under 35 U.S.C. 154(b) by 0 days. days.

(21) Appl. No.: 15/502,639

(22) PCT Filed: Aug. 12, 2015

(86) PCT No.: PCT/US2015/044783
§ 371 (c)(1),
(2) Date: Feb. 8, 2017

(87) PCT Pub. No.: WO2016/025561
PCT Pub. Date: Feb. 18, 2016

(65) Prior Publication Data
US 2017/0226083 A1   Aug. 10, 2017

Related U.S. Application Data

(60) Provisional application No. 62/037,066, filed on Aug. 13, 2014.

(51) Int. Cl.
| C07D 401/12 | (2006.01) |
| C07D 403/12 | (2006.01) |
| A61K 31/506 | (2006.01) |
| A61P 35/00 | (2006.01) |

(52) U.S. Cl.
CPC .......... *C07D 401/12* (2013.01); *A61K 31/506* (2013.01); *C07D 403/12* (2013.01); *C07B 2200/13* (2013.01)

(58) Field of Classification Search
CPC .. C07D 239/48; C07D 401/12; C07D 403/12; A61K 31/506
USPC ............ 544/310; 514/275, 86; 435/184, 375
See application file for complete search history.

(56) References Cited

U.S. PATENT DOCUMENTS

| | | | |
|---|---|---|---|
| 3,609,152 A | 9/1971 | Hess et al. | |
| 4,337,341 A | 6/1982 | Zimmerman | |
| 4,879,303 A | 11/1989 | Davison et al. | |
| 5,786,476 A | 7/1998 | Fuso | |
| 5,958,935 A | 9/1999 | Davis et al. | |
| 6,093,716 A | 7/2000 | Davis et al. | |
| 6,114,333 A | 9/2000 | Davis et al. | |
| 6,127,376 A | 10/2000 | Davey et al. | |
| 6,160,010 A | 12/2000 | Uckun et al. | |
| 6,262,088 B1 | 7/2001 | Phillips | |
| 6,469,168 B1 | 10/2002 | Simonek et al. | |
| 6,579,983 B1 | 6/2003 | Batchelor et al. | |
| 6,593,326 B1 | 7/2003 | Bradbury et al. | |
| 6,838,464 B2 | 1/2005 | Pease et al. | |
| 6,878,717 B2 | 4/2005 | De Corte et al. | |
| 6,908,906 B2 | 6/2005 | Takita et al. | |
| 6,939,874 B2 | 9/2005 | Harmange et al. | |
| 7,037,917 B2 | 5/2006 | De Corte et al. | |
| 7,060,827 B2 | 6/2006 | Singh et al. | |
| 7,122,542 B2 | 10/2006 | Singh et al. | |
| 7,125,879 B2 | 10/2006 | Guillemont et al. | |
| 7,176,212 B2 | 2/2007 | Breault et al. | |
| 7,202,033 B2 | 4/2007 | Prescott et al. | |
| 7,241,769 B2 | 7/2007 | Stadtmueller et al. | |
| 7,276,510 B2 | 10/2007 | Kukla et al. | |
| 7,282,504 B2 | 10/2007 | Armistead et al. | |
| 7,288,547 B2 | 10/2007 | Lucking et al. | |
| 7,329,671 B2 | 2/2008 | Singh et al. | |
| 7,329,672 B2 | 2/2008 | Singh et al. | |
| 7,332,484 B2 | 2/2008 | Singh et al. | |
| 7,432,377 B2 | 10/2008 | Chew et al. | |
| 7,435,814 B2 | 10/2008 | Singh et al. | |
| 7,449,458 B2 | 11/2008 | Bhamidipati et al. | |
| 7,452,879 B2 | 11/2008 | Singh et al. | |
| 7,485,724 B2 | 2/2009 | Singh et al. | |
| 7,491,732 B2 | 2/2009 | Li et al. | |
| 7,498,435 B2 | 3/2009 | Singh et al. | |
| 7,500,137 B2 | 3/2009 | Park | |
| 7,504,396 B2 | 3/2009 | Nunes et al. | |
| 7,514,444 B2 | 4/2009 | Honigberg et al. | |
| 7,514,445 B2 | 4/2009 | Freyne et al. | |
| 7,514,446 B2 | 4/2009 | Davis-Ward et al. | |
| 7,517,886 B2 | 4/2009 | Singh et al. | |
| 7,528,143 B2 | 5/2009 | Noronha et al. | |

(Continued)

FOREIGN PATENT DOCUMENTS

| AU | 2009251863 A1 | 12/2009 |
| CA | 2375182 A1 | 12/2000 |

(Continued)

OTHER PUBLICATIONS

Deschenes-Simard et al. Cancer Res. 2014, 74(2); 412-9.*
Little et al. Oncogene (2013) 32, 1207-1215.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
U.S. Appl. No. 13/518,833, filed Jun. 22, 2012, Gray et al.
U.S. Appl. No. 13/882,958, filed Jul. 8, 2013, Pandey et al.
U.S. Appl. No. 15/422,617, filed Feb. 2, 2017, Haq et al.
Adult Non-Hodgkin Lymphoma Treatment (PDQ®), Nat. Can. Inst., retreived Jul. 28, 2014 from web: http://www.cancer.gov/cancertopics/pdg/treatment/adult-non-hodqkins/HealthProfessional/page1.
Advani, R.H. et al., Bruton Tyrosine Kinase Inhibitor Ibrutinib (PCI-32765) Has Significant Activity in Patients With Relapsed/Refractory B-Cell Malignancies, J. Clin. Oncol., pp. 1-9 (2012).

(Continued)

*Primary Examiner* — Venkataraman Balasubramanian
(74) *Attorney, Agent, or Firm* — Choate, Hall & Stewart LLP; Kristen C. Buteau

(57) ABSTRACT

The present invention provides compounds, compositions thereof, and methods of using the same for the inhibition of one or both of ERK1 and ERK2.

21 Claims, 100 Drawing Sheets

(56) References Cited

U.S. PATENT DOCUMENTS

| | | |
|---|---|---|
| 7,531,548 B2 | 5/2009 | Guillemont et al. |
| 7,540,908 B2 | 6/2009 | Sao et al. |
| 7,540,909 B2 | 6/2009 | Sao et al. |
| 7,550,460 B2 | 6/2009 | Singh et al. |
| 7,553,357 B2 | 6/2009 | Sao et al. |
| 7,557,207 B2 | 7/2009 | Cooper et al. |
| 7,557,210 B2 | 7/2009 | Singh et al. |
| 7,582,648 B2 | 9/2009 | Singh et al. |
| 7,589,200 B2 | 9/2009 | Singh et al. |
| 7,642,351 B2 | 1/2010 | Singh et al. |
| 7,655,797 B2 | 2/2010 | Singh et al. |
| 7,659,280 B2 | 2/2010 | Clough et al. |
| 7,713,987 B2 | 5/2010 | Bhamidipati et al. |
| 7,718,662 B1 | 5/2010 | Chen et al. |
| 7,741,330 B1 | 6/2010 | Chen et al. |
| 7,803,939 B2 | 9/2010 | Singh et al. |
| 7,812,029 B1 | 10/2010 | Singh et al. |
| 7,820,819 B2 | 10/2010 | Singh et al. |
| 7,825,116 B2 | 11/2010 | Singh et al. |
| 7,834,024 B2 | 11/2010 | Li et al. |
| 7,858,633 B2 | 12/2010 | Li et al. |
| 7,863,286 B2 | 1/2011 | Argade et al. |
| 7,879,984 B2 | 2/2011 | Martin et al. |
| 7,884,111 B2 | 2/2011 | Argade et al. |
| 7,893,074 B2 | 2/2011 | Garcia-Echeverria et al. |
| 7,906,644 B2 | 3/2011 | Singh et al. |
| 7,915,273 B2 | 3/2011 | Argade et al. |
| 7,947,698 B2 | 5/2011 | Atuegbu et al. |
| 7,989,465 B2 | 8/2011 | Singh et al. |
| 8,003,789 B2 | 8/2011 | De Corte et al. |
| 8,088,781 B2 | 1/2012 | Honigberg et al. |
| 8,133,900 B2 | 3/2012 | Hood et al. |
| 8,148,525 B2 | 4/2012 | Singh et al. |
| 8,153,640 B2 | 4/2012 | Guillemont et al. |
| 8,158,621 B2 | 4/2012 | Singh et al. |
| 8,163,902 B2 | 4/2012 | Bhamidipati et al. |
| 8,188,276 B2 | 5/2012 | Singh et al. |
| 8,193,197 B2 | 6/2012 | Li et al. |
| 8,206,711 B2 | 6/2012 | White et al. |
| 8,263,590 B2 | 9/2012 | Garcia-Echeverria et al. |
| 8,299,087 B2 | 10/2012 | Li et al. |
| 8,304,422 B2 | 11/2012 | Atuegbu et al. |
| 8,334,296 B2 | 12/2012 | Singh et al. |
| 8,338,439 B2 | 12/2012 | Singh et al. |
| 8,399,433 B2 | 3/2013 | Appari et al. |
| 8,399,450 B2 | 3/2013 | Michellys et al. |
| 8,399,472 B2 | 3/2013 | Li et al. |
| 8,410,266 B2 | 4/2013 | Singh et al. |
| 8,415,365 B2 | 4/2013 | Li et al. |
| 8,450,335 B2 | 5/2013 | Singh et al. |
| 8,501,751 B2 | 8/2013 | Honigberg et al. |
| 8,530,466 B2 | 9/2013 | Masuda et al. |
| 8,530,655 B2 | 9/2013 | De Corte et al. |
| 8,557,806 B2 | 10/2013 | Singh et al. |
| 8,563,568 B2 | 10/2013 | Witowski et al. |
| 8,609,679 B2 | 12/2013 | Singh et al. |
| 8,697,694 B2 | 4/2014 | Arasappan et al. |
| 8,710,222 B2 | 4/2014 | Singh et al. |
| 8,735,404 B2 | 5/2014 | Honigberg et al. |
| 8,748,438 B2 | 6/2014 | Honigberg et al. |
| 8,748,597 B2 | 6/2014 | Singh et al. |
| 8,796,255 B2 | 8/2014 | Lee et al. |
| 8,822,685 B2 | 9/2014 | Singh et al. |
| 8,835,430 B2 | 9/2014 | Singh et al. |
| 8,853,397 B2 | 10/2014 | Singh et al. |
| 8,883,435 B2 | 11/2014 | Honigberg et al. |
| 8,883,803 B2 | 11/2014 | Honigberg et al. |
| 8,975,249 B2 | 3/2015 | Lee et al. |
| 9,012,462 B2 | 4/2015 | Wang et al. |
| 9,145,387 B2 * | 9/2015 | Haq .................. C07D 401/12 |
| 9,212,181 B2 | 12/2015 | Singh et al. |
| 9,296,737 B2 | 3/2016 | Singh et al. |
| 9,409,921 B2 | 8/2016 | Singh et al. |
| 9,504,686 B2 | 11/2016 | Haq et al. |
| 9,561,228 B2 | 2/2017 | Haq et al. |
| 9,796,700 B2 | 10/2017 | Haq et al. |
| 2002/0147339 A1 | 10/2002 | Batchelor et al. |
| 2004/0002395 A1 | 1/2004 | Poynor |
| 2004/0019067 A1 | 1/2004 | Armistead et al. |
| 2004/0023957 A1 | 2/2004 | Wang et al. |
| 2004/0077661 A1 | 4/2004 | Arbiser |
| 2004/0180914 A1 | 9/2004 | Batchelor et al. |
| 2005/0004125 A1 | 1/2005 | Freyne et al. |
| 2005/0014753 A1 | 1/2005 | Ding et al. |
| 2005/0085637 A1 | 4/2005 | Cheung et al. |
| 2005/0209221 A1 | 9/2005 | Nunes et al. |
| 2005/0272083 A1 | 12/2005 | Seshagiri |
| 2006/0030018 A1 | 2/2006 | Zuccola et al. |
| 2006/0079543 A1 | 4/2006 | Sum et al. |
| 2006/0084644 A1 | 4/2006 | Pal et al. |
| 2006/0084645 A1 | 4/2006 | Pal et al. |
| 2006/0100227 A1 | 5/2006 | Baenteli et al. |
| 2006/0148800 A1 | 7/2006 | Stadtmueller et al. |
| 2006/0160803 A1 | 7/2006 | Adams et al. |
| 2006/0247241 A1 | 11/2006 | Garcia-Echeverria et al. |
| 2006/0247262 A1 | 11/2006 | Baenteli et al. |
| 2006/0270694 A1 | 11/2006 | Wong |
| 2006/0293311 A1 | 12/2006 | Li et al. |
| 2007/0010668 A1 | 1/2007 | Davis-Ward et al. |
| 2007/0032493 A1 | 2/2007 | Foley et al. |
| 2007/0066658 A1 | 3/2007 | Chappell |
| 2007/0141143 A1 | 6/2007 | Smithey et al. |
| 2007/0203161 A1 | 8/2007 | Argade et al. |
| 2007/0203162 A1 | 8/2007 | Li et al. |
| 2007/0208022 A1 | 9/2007 | Guillemont et al. |
| 2007/0208034 A1 | 9/2007 | Stadlwieser |
| 2007/0259904 A1 | 11/2007 | Noronha et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0039622 A1 | 2/2008 | Singh et al. |
| 2008/0058358 A1 | 3/2008 | Luecking et al. |
| 2008/0076921 A1 | 3/2008 | Honigberg et al. |
| 2008/0132504 A1 | 6/2008 | Garcia-Echeverria et al. |
| 2008/0139582 A1 | 6/2008 | Honigberg et al. |
| 2008/0167330 A1 | 7/2008 | Luecking et al. |
| 2008/0176866 A1 | 7/2008 | Jautelat et al. |
| 2008/0182852 A1 | 7/2008 | Johnson et al. |
| 2008/0194603 A1 | 8/2008 | Li et al. |
| 2008/0194605 A1 | 8/2008 | Heinrich et al. |
| 2008/0207613 A1 | 8/2008 | Styles et al. |
| 2008/0207913 A1 | 8/2008 | Breitenkamp et al. |
| 2008/0214501 A1 | 9/2008 | Pan et al. |
| 2008/0221089 A1 | 9/2008 | Argade et al. |
| 2008/0260754 A1 | 10/2008 | Li et al. |
| 2008/0261977 A1 | 10/2008 | Eatherton et al. |
| 2008/0279867 A1 | 11/2008 | Atuegbu et al. |
| 2008/0300268 A1 | 12/2008 | Singh et al. |
| 2008/0312438 A1 | 12/2008 | Singh et al. |
| 2009/0030197 A1 | 1/2009 | Chew et al. |
| 2009/0088371 A1 | 4/2009 | Grossbard |
| 2009/0131436 A1 | 5/2009 | Imbach et al. |
| 2009/0137588 A1 | 5/2009 | Singh et al. |
| 2009/0156622 A1 | 6/2009 | Singh et al. |
| 2009/0171086 A1 | 7/2009 | Singh et al. |
| 2009/0181987 A1 | 7/2009 | Honigberg et al. |
| 2009/0215803 A1 | 8/2009 | Rice et al. |
| 2009/0286778 A1 | 11/2009 | Combs et al. |
| 2009/0298830 A1 | 12/2009 | Mann et al. |
| 2009/0318407 A1 | 12/2009 | Bauer et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0029610 A1 | 2/2010 | Singh et al. |
| 2010/0041677 A1 | 2/2010 | Honigberg et al. |
| 2010/0081679 A1 | 4/2010 | Greul et al. |
| 2010/0088912 A1 | 4/2010 | Higgs et al. |
| 2010/0144706 A1 | 6/2010 | Zahn et al. |
| 2010/0173285 A1 | 7/2010 | Varmus et al. |
| 2010/0197918 A1 | 8/2010 | Singh et al. |
| 2010/0249092 A1 | 9/2010 | Singh et al. |
| 2010/0254905 A1 | 10/2010 | Honigberg et al. |
| 2011/0027856 A1 | 2/2011 | Li et al. |

(56) References Cited

U.S. PATENT DOCUMENTS

| | | |
|---|---|---|
| 2011/0028405 A1 | 2/2011 | Harrison et al. |
| 2011/0039868 A1 | 2/2011 | Honigberg et al. |
| 2011/0071158 A1 | 3/2011 | Sapountzis et al. |
| 2011/0098280 A1 | 4/2011 | Garcia-Echeverria et al. |
| 2011/0098288 A1 | 4/2011 | Major et al. |
| 2011/0105472 A1 | 5/2011 | Greul et al. |
| 2011/0144330 A1 | 6/2011 | Singh et al. |
| 2011/0190261 A1 | 8/2011 | Dong et al. |
| 2011/0207736 A1 | 8/2011 | Gray et al. |
| 2011/0212077 A1 | 9/2011 | Noronha et al. |
| 2011/0224235 A1 | 9/2011 | Honigberg et al. |
| 2011/0245156 A1 | 10/2011 | Sielecki-Dzurdz |
| 2011/0245284 A1 | 10/2011 | Greul et al. |
| 2011/0281322 A1 | 11/2011 | Honigberg et al. |
| 2011/0281850 A1 | 11/2011 | Flynn et al. |
| 2012/0021434 A1 | 1/2012 | Foley et al. |
| 2012/0040968 A1 | 2/2012 | Shimada et al. |
| 2012/0065201 A1 | 3/2012 | Honigberg et al. |
| 2012/0071497 A1 | 3/2012 | Buggy et al. |
| 2012/0077832 A1 | 3/2012 | Witowski et al. |
| 2012/0083006 A1 | 4/2012 | Ramsden et al. |
| 2012/0087915 A1 | 4/2012 | Buggy et al. |
| 2012/0088912 A1 | 4/2012 | Honigberg et al. |
| 2012/0094999 A1 | 4/2012 | Gray et al. |
| 2012/0101113 A1 | 4/2012 | Honigberg et al. |
| 2012/0101114 A1 | 4/2012 | Honigberg et al. |
| 2012/0142667 A1 | 6/2012 | Ramsden et al. |
| 2012/0149687 A1 | 6/2012 | Lee et al. |
| 2012/0149722 A1 | 6/2012 | Lee et al. |
| 2012/0157426 A1 | 6/2012 | Lee et al. |
| 2012/0165328 A1 | 6/2012 | Honigberg et al. |
| 2012/0165332 A1 | 6/2012 | Major et al. |
| 2012/0172385 A1 | 7/2012 | Harrison et al. |
| 2012/0184013 A1 | 7/2012 | Honigberg et al. |
| 2012/0184567 A1 | 7/2012 | Honigberg et al. |
| 2012/0190697 A1 | 7/2012 | Guillemont et al. |
| 2012/0202264 A1 | 8/2012 | Honigberg et al. |
| 2012/0213795 A1 | 8/2012 | Li et al. |
| 2012/0270237 A9 | 10/2012 | Ramsden et al. |
| 2012/0296089 A1 | 11/2012 | Honigberg et al. |
| 2012/0316135 A1 | 12/2012 | Dalgarno et al. |
| 2012/0329130 A1 | 12/2012 | Honigberg et al. |
| 2013/0035334 A1 | 2/2013 | Honigberg et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0109709 A1 | 5/2013 | Witowski et al. |
| 2013/0137708 A1 | 5/2013 | Garske et al. |
| 2013/0142807 A1 | 6/2013 | Li et al. |
| 2013/0150349 A1 | 6/2013 | Singh et al. |
| 2013/0165462 A1 | 6/2013 | Singh et al. |
| 2013/0231306 A1 | 9/2013 | Crew et al. |
| 2013/0267530 A1 | 10/2013 | Lai |
| 2013/0267531 A1 | 10/2013 | Lai et al. |
| 2014/0057929 A1 | 2/2014 | Witowski et al. |
| 2014/0134265 A1 | 5/2014 | Buggy et al. |
| 2014/0140991 A1 | 5/2014 | Daniel et al. |
| 2014/0142123 A1 | 5/2014 | Honigberg et al. |
| 2014/0142128 A1 | 5/2014 | Daniel et al. |
| 2014/0142129 A1 | 5/2014 | Daniel et al. |
| 2014/0163027 A1 | 6/2014 | Verner et al. |
| 2014/0163046 A1 | 6/2014 | Honigberg et al. |
| 2014/0179720 A1 | 6/2014 | Tester et al. |
| 2014/0187564 A1 | 7/2014 | Honigberg et al. |
| 2014/0187565 A1 | 7/2014 | Honigberg et al. |
| 2014/0213574 A1 | 7/2014 | Singh et al. |
| 2014/0228322 A1 | 8/2014 | Haq et al. |
| 2014/0303154 A1 | 10/2014 | Singh et al. |
| 2014/0303191 A1 | 10/2014 | Buggy et al. |
| 2014/0330007 A1 | 11/2014 | Singh et al. |
| 2014/0371241 A1 | 12/2014 | Buggy et al. |
| 2015/0005297 A1 | 1/2015 | Singh et al. |
| 2015/0025055 A1 | 1/2015 | Lee et al. |
| 2015/0038518 A1 | 2/2015 | Balasubramanian |
| 2016/0002176 A1 | 1/2016 | Haq et al. |
| 2016/0082008 A1 | 3/2016 | Haq et al. |
| 2016/0303121 A1 | 10/2016 | Singh et al. |
| 2017/0100397 A1 | 4/2017 | Singh et al. |
| 2017/0137406 A1 | 5/2017 | Haq et al. |
| 2017/0210729 A1 | 7/2017 | Haq et al. |

FOREIGN PATENT DOCUMENTS

| | | |
|---|---|---|
| CA | 2463822 A1 | 5/2003 |
| CA | 2553729 A1 | 8/2005 |
| CA | 2608367 A1 | 12/2006 |
| CA | 2673125 A1 | 4/2008 |
| CA | 2710118 A1 | 7/2009 |
| CA | 2717529 A1 | 9/2009 |
| CA | 2757671 A1 | 10/2010 |
| CA | 2760061 A1 | 11/2010 |
| CA | 2763720 A1 | 12/2010 |
| CN | 102558149 A | 7/2012 |
| CN | 103159742 A | 6/2013 |
| CN | 103664878 A | 3/2014 |
| EP | 1 054 004 A1 | 11/2000 |
| EP | 1187816 A1 | 3/2002 |
| EP | 1448556 A1 | 8/2004 |
| EP | 1597251 A2 | 11/2005 |
| EP | 1904457 A2 | 4/2008 |
| EP | 1990342 A1 | 11/2008 |
| EP | 2089369 A2 | 8/2009 |
| EP | 2234986 A2 | 10/2010 |
| EP | 2276747 A1 | 1/2011 |
| EP | 2414337 A1 | 2/2012 |
| EP | 2428508 A1 | 3/2012 |
| EP | 2443095 A1 | 4/2012 |
| JP | H07-41461 A | 2/1995 |
| WO | WO-96/28427 A1 | 9/1996 |
| WO | WO-97/19065 A1 | 5/1997 |
| WO | WO-99/31073 A1 | 6/1999 |
| WO | WO-00/027825 A1 | 5/2000 |
| WO | WO-00/046203 A2 | 8/2000 |
| WO | WO-00/078731 A1 | 12/2000 |
| WO | WO-01/047897 A1 | 7/2001 |
| WO | WO-01/060816 A1 | 8/2001 |
| WO | WO-01/064654 A1 | 9/2001 |
| WO | WO-01/064655 A1 | 9/2001 |
| WO | WO-01/085699 A2 | 11/2001 |
| WO | WO-02/064586 A2 | 8/2002 |
| WO | WO-02/083653 A1 | 10/2002 |
| WO | WO-03/016306 A1 | 2/2003 |
| WO | WO-03/030909 A1 | 4/2003 |
| WO | WO-03/037891 A1 | 5/2003 |
| WO | WO-03/063794 A2 | 8/2003 |
| WO | WO-03/066601 A1 | 8/2003 |
| WO | WO-2004/014382 A1 | 2/2004 |
| WO | WO-2004/031232 A1 | 4/2004 |
| WO | WO-2004/056786 A2 | 7/2004 |
| WO | WO-2004/069812 A1 | 8/2004 |
| WO | WO-2004/074244 A2 | 9/2004 |
| WO | WO-2004/080980 A1 | 9/2004 |
| WO | WO-2004/096224 A2 | 11/2004 |
| WO | WO-2005/013996 A2 | 2/2005 |
| WO | WO-2005/016893 A2 | 2/2005 |
| WO | WO-2005/016894 A1 | 2/2005 |
| WO | WO-2005/026130 A1 | 3/2005 |
| WO | WO-2005/026158 A1 | 3/2005 |
| WO | WO-2005/063722 A1 | 7/2005 |
| WO | WO-2005/070890 A2 | 8/2005 |
| WO | WO-2005/118544 A2 | 12/2005 |
| WO | WO-2006/021544 A1 | 3/2006 |
| WO | WO-2006/038001 A1 | 4/2006 |
| WO | WO-2006/045066 A2 | 4/2006 |
| WO | WO-2006/053109 A1 | 5/2006 |
| WO | WO-2006/055561 A2 | 5/2006 |
| WO | WO-2006/068770 A1 | 6/2006 |
| WO | WO-2006/074057 A2 | 7/2006 |
| WO | WO-2006/078846 A1 | 7/2006 |
| WO | WO-2006/101977 A2 | 9/2006 |
| WO | WO-2006/108487 A1 | 10/2006 |
| WO | WO-2006/124874 A2 | 11/2006 |
| WO | WO-2006/128129 A2 | 11/2006 |
| WO | WO-2006/129100 A1 | 12/2006 |

(56) References Cited

FOREIGN PATENT DOCUMENTS

| | | |
|---|---|---|
| WO | WO-2006/133426 A2 | 12/2006 |
| WO | WO-2007/027238 A2 | 3/2007 |
| WO | WO-2007/048064 A2 | 4/2007 |
| WO | WO-2007/053452 A1 | 5/2007 |
| WO | WO-2007/056151 A2 | 5/2007 |
| WO | WO-2007/085833 A2 | 8/2007 |
| WO | WO-2007/089768 A2 | 8/2007 |
| WO | WO-2007/098507 A2 | 8/2007 |
| WO | WO-2007/113254 A1 | 10/2007 |
| WO | WO-2007/113256 A1 | 10/2007 |
| WO | WO-2007/120339 A1 | 10/2007 |
| WO | WO-2007/120980 A2 | 10/2007 |
| WO | WO-2007/125351 A1 | 11/2007 |
| WO | WO-2008/005538 A2 | 1/2008 |
| WO | WO-2008/009458 A1 | 1/2008 |
| WO | WO-2008/025556 A1 | 3/2008 |
| WO | WO-2008/049123 A2 | 4/2008 |
| WO | WO-2008/064274 A1 | 5/2008 |
| WO | WO-2008/073687 A2 | 6/2008 |
| WO | WO-2008/074515 A1 | 6/2008 |
| WO | WO-2008/079719 A1 | 7/2008 |
| WO | WO-2008/079907 A1 | 7/2008 |
| WO | WO-2008/080964 A1 | 7/2008 |
| WO | WO-2008/080965 A2 | 7/2008 |
| WO | WO-2008/088303 A1 | 7/2008 |
| WO | WO-2008/092199 A1 | 8/2008 |
| WO | WO-2008/093687 A1 | 8/2008 |
| WO | WO-2008/107096 A1 | 9/2008 |
| WO | WO-2008/115738 A1 | 9/2008 |
| WO | WO-2008/115742 A1 | 9/2008 |
| WO | WO-2008/118822 A1 | 10/2008 |
| WO | WO-2008/118823 A2 | 10/2008 |
| WO | WO-2008/147831 A1 | 12/2008 |
| WO | WO-2009/012421 A1 | 1/2009 |
| WO | WO-2009/017838 A2 | 2/2009 |
| WO | WO-2009/029682 A1 | 3/2009 |
| WO | WO-2009/032668 A2 | 3/2009 |
| WO | WO-2009/032694 A1 | 3/2009 |
| WO | WO-2009/032703 A1 | 3/2009 |
| WO | WO-2009/080638 A2 | 7/2009 |
| WO | WO-2009/105675 A1 | 8/2009 |
| WO | WO-2009/112490 A1 | 9/2009 |
| WO | WO-2009/115267 A2 | 9/2009 |
| WO | WO-2009/127642 A2 | 10/2009 |
| WO | WO-2009/132202 A1 | 10/2009 |
| WO | WO-2009/136995 A2 | 11/2009 |
| WO | WO-2009/143389 A1 | 11/2009 |
| WO | WO-2009/158571 A1 | 12/2009 |
| WO | WO-2010/025833 A1 | 3/2010 |
| WO | WO-2010/077740 A2 | 7/2010 |
| WO | WO-2010/081679 A2 | 7/2010 |
| WO | WO-2010/112210 A1 | 10/2010 |
| WO | WO-2010/128659 A1 | 11/2010 |
| WO | WO-2010/129053 A1 | 11/2010 |
| WO | WO-2010/141406 A2 | 12/2010 |
| WO | WO-2010/146132 A1 | 12/2010 |
| WO | WO-2011/079231 A1 | 6/2011 |
| WO | WO-2011/090760 A1 | 7/2011 |
| WO | WO-2011/140338 A1 | 11/2011 |
| WO | WO-2011/153514 A2 | 12/2011 |
| WO | WO-2011/153553 A2 | 12/2011 |
| WO | WO-2012/021444 A1 | 2/2012 |
| WO | WO-2012/061299 A1 | 5/2012 |
| WO | WO-2012/061303 A1 | 5/2012 |
| WO | WO-2012/061415 A1 | 5/2012 |
| WO | WO-2012/064706 A1 | 5/2012 |
| WO | WO-2012/078492 A1 | 6/2012 |
| WO | WO-2012/100459 A1 | 8/2012 |
| WO | WO-2012/135801 A1 | 10/2012 |
| WO | WO-2012/151561 A1 | 11/2012 |
| WO | WO-2012/158843 A2 | 11/2012 |
| WO | WO-2012/170976 A2 | 12/2012 |
| WO | WO-2013/063401 A1 | 5/2013 |
| WO | WO-2013/138495 A1 | 9/2013 |
| WO | WO-2013/138502 A1 | 9/2013 |
| WO | WO-2013/173518 A1 | 11/2013 |
| WO | WO-2014/025128 A1 | 2/2014 |
| WO | WO-2014/039452 A1 | 3/2014 |
| WO | WO-2014/074580 A1 | 5/2014 |
| WO | WO-2014/081709 A2 | 5/2014 |
| WO | WO-2014/081712 A2 | 5/2014 |
| WO | WO-2014/081714 A2 | 5/2014 |
| WO | WO-2014/100748 A1 | 6/2014 |
| WO | WO-2014/124230 A2 | 8/2014 |
| WOWO-PCT/US15/44783 | | 8/2015 |
| WOWO-PCT/US15/44793 | | 8/2015 |
| WOWO-PCT/US15/44890 | | 8/2015 |
| WOWO-PCT/US15/44917 | | 8/2015 |
| WOWO-PCT/US15/44918 | | 8/2015 |
| WOWO-PCT/US15/44919 | | 8/2015 |
| WOWO-PCT/US15/44928 | | 8/2015 |
| WOWO-PCT/US15/44929 | | 8/2015 |
| WOWO-PCT/US15/44930 | | 8/2015 |
| WOWO-PCT/US15/44931 | | 8/2015 |
| WOWO-PCT/US15/44932 | | 8/2015 |
| WOWO-PCT/US15/44936 | | 8/2015 |

OTHER PUBLICATIONS

Aliagas-Martin, I. et al., A class of 2,4-bisanilinopyrimidine Aurora A inhibitors with unusually high selectivity against Aurora B, J. Med. Chem. 52:3300-3307 (2009).

Andrulis, I. et al., Neu/ErbB-2 amplification identifies a poor-prognosis group of women with node-negative breast cancer, J Clin Oncol 16:1340-9 (1998).

Aronov, A.M. et al., Flipped out: structure-guided design of selective pyrazolylpyrrole ERK inhibitors, J. Med. Chem., 50(6)1280-7 (2007).

Aronov, A.M. et al., Structure-guided design of potent and selective pyrimidylpyrrole inhibitors of extracellular signal-regulated kinase (ERK) using conformational control, J. Med. Chem., 52(20):6362-8 (2009).

Balmana et al., BRCA in breast cancer: ESMO Clinical Recommendations, Annals of Oncology, 20(Supplement 4): iv19-iv20 (2009).

Bamborough, P. et al., N-4-Pyrimidinyl-1H-indazol-4-amine inhibitors of Lck: Indazoles as phenol isosteres with improved pharmacokinetics, Bioorg. & Med. Chem. Lett. 17:4363-4368 (2007).

Brown, J.R. et al., Phase Ib trial of AVL-292, a covalent inhibitor of Bruton's tyrosine kinase (Btk), in chronic lymphocytic leukemia (CLL) and B-non-Hodgkin lymphoma (B-NHL), J. Clin. Oncol., 30, (2012).

Brunton, L.L. et al., eds., Chemotherapy of Neoplastic Diseases, in Goodman & Gilman's: The Pharmacological Basis of Therapeutics, 11th edition, pp. 853-908 (2008).

Buggy, J.J. et al., Bruton tyrosine kinase (BTK) and its role in B-cell malignancy, Int. Rev. Immunol., 31(2): 119-32 (2012).

Calvo, E. et al., Administration of CI-1033, an Irreversible Pan-erbB Tyrosine Kinase Inhibitor, Is Feasible on a 7-Day Off Schedule: A Phase I Pharmacokinetic and Food Effect Study, Clinical Cancer Research, 10: 7112-7120 (2004).

Carter, T. et al, Inhibition of drug-resistant mutants of ABL, KIT, and EGF receptor kinases, Proc. Natl. Acad. Sci. USA 102(31):11011-11016 (2005).

Chabner, B.A. et al., Chemotherapy of Neoplastic Diseases, Neoplastic Agents, Goodman & Gilman's: The Pharmacological Basis of Therapeutics, 11th edition, Brunton, L.L. et al., eds., pp. 1315-1403 (2006).

Clovis Oncology, Press Release, "Clovis Oncology's CO-1686 Demonstrates Compelling Clinical Activity and Progression-free Survival (PFS) in Updated Phase 1/2 Study Results in Patients with EGFR-Mutant Non-small Cell Lung Cancer (NSCLC)", May 31, 2014.

Cohen, M. et al., Structural bioinformatics-based design of selective, irreversible inhibitors, Science 308:1318-1321 (2005).

Curto, M. et al., Contact-dependent inhibition of EGFR signaling by Nf2/Merlin, J Cell Biol 177:893-903 (2007).

(56) References Cited

OTHER PUBLICATIONS

Dickson, M.A., and Schwartz, G.K., Development of cell-cycle inhibitors for cancer therapy, Current Oncology, 16(2): 36-43 (2009).
Ding, K. et al., Design, Synthesis and Biological Evaluation of Novel Conformationally Constrained Inhibitors Targeting Epidermal Growth Factor Receptor T790M mutant, J. Med. Chem., Just Accepted Manuscript, 1-36 (2012).
Evans, E. et al.,. Clinical Development of AVL-292; A Potent, Selective Covalent Btk Inhibitor for the Treatment of B Cell Malignancies, Blood (ASH Annual Meeting Abstracts), 118: 3485 (2011).
Eve, H.E. et al.,. Single-agent lenalidomide in relapsed/refractory mantle cell lymphoma: results from a UK phase II study suggest activity and possible gender differences, Br. J. Haematol., 159(2): 154-63 (2012).
Fabian, M. et al., A small molecule-kinase interaction map for clinical kinase inhibitors, Nature Biotechnology, 23(3): 329 (2005).
Fallon, K. et al., Constitutive activation of the neuregulin-1/erbB signaling pathway promotes the proliferation of a human peripheral neuroepithelioma cell line, J Neuro Oncol 66:273-84 (2004).
Frank, D., STAT signaling in the pathogenesis and treatment of cancer, Mol. Med. 5 :432-456 (1999).
Friday, B.B., and Adjei, A.A., Advances in targeting the Ras/Raf/MEK/Erk mitogen-activated protein kinase cascade with MEK inhibitors for cancer therapy, Clinical Cancer Research, 14(2): 342-346 (2008).
Friedberg, J.W. et al., Inhibition of Syk with fostamatinib disodium has significant clinical activity in non-Hodgkin lymphoma and chronic lymphocytic leukemia, Blood, 115(13): 2578-85 (2010).
Fry, D. et al., Specific, irreversible inactivation of the epidermal growth factor receptor and erbB2, by a new class of tyrosine kinase inhibitor, Proc. Natl. Acad. Sci. USA 95:12022-12027 (1998).
Galustian, C. et al., Thalidomide-derived immunomodulatory drugs as therapeutic agents, Expert. Opin. Biol. Ther., 4(12): 1963-70 (2004).
Ghoneim, K., Synthesis and evaluation of some 2-, 4-, di- substituted -6-methylpyrimidine derivatives for antimicrobial activity, J. Indian Chem. Soc. 63(10):914-917 (1986).
Ghosh, D., 2-4-bis (arylamino) -5- methylpyrimidines as antimicrobial agents, J. Med. Chem. 10(5):974 (1967).
Ghosh, D., 2-4-bis (arylamino) -6- methylpyrimidines as antimicrobial agents, J. Indian Chem. Soc. 58(5):512-573 (1981).
Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (2008).
Gunnellini, M. and Falchi, L., Therapeutic Activity of Lenalidomide in Mantle Cell Lymphoma and Indolent Non-Hodgkin's Lymphomas, Adv. Hematol., Article ID 523842, 7 pages (2012).
Hacken, E.T. and Burger, J.A., Microenvironment dependency in Chronic Lymphocytic Leukemia: The basis for new targeted therapies, Pharmacology & Therapeutics, http://dx.doi.org/10.1016/j.pharmthera.2014.07.003, (2014).
Harris N.L. et al., Lymphoma classification: from Real to WHO and beyond. In: DeVita VT, Hellman S, Rosenberg SA, eds. Cancer: Principles and Practice of Oncology Updates. Philadelphia, Pa: Lippincott-Raven, 13(3): 1-14 (1999).
Hernandez-Ilizaliturri, F.J. et al., Higher response to lenalidomide in relapsed/refractory diffuse large B-cell lymphoma in nongerminal center B-cell-like than in germinal center B-cell-like phenotype, Cancer, 117(22): 5058-66 (2011).
Hur, W. et al., Clinical stage EGFR inhibitors irreversibly alkylate Bmx kinase, Bioorg. Med. Chem. Lett. 18:5916-5919 (2008).
International Search Report for PCT/US09/48784, 8 pages (dated Nov. 16, 2009).
International Search Report for PCT/US10/31714, 4 pages (dated Aug. 13, 2010).
International Search Report for PCT/US10/62432, 4 pages (dated May 26, 2011).
International Search Report for PCT/US11/58610, 4 pages (dated Mar. 27, 2012).
International Search Report for PCT/US11/58616, 3 pages (dated Mar. 27, 2012).
International Search Report for PCT/US11/59726, 3 pages (dated Mar. 20, 2012).
International Search Report for PCT/US13/70772, 3 pages (dated Mar. 25, 2014).
International Search Report for PCT/US13/70776, 4 pages (dated Mar. 25, 2014).
International Search Report for PCT/US2014/015256, 6 pages (dated Aug. 5, 2014).
International Search Report for PCT/US2015/044783, 2 pages (dated Oct. 30, 2015).
International Search Report of PCT/US09/48784, 8 pages (dated Nov. 16, 2009).
International Search Report of PCT/US11/46926, 2 pages (dated Dec. 22, 2011).
International Search Report of PCT/US13/30982, 2 pages (dated May 30, 2013).
International Search Report of PCT/US13/30996, 2 pages (dated May 30, 2013).
International Search Report of PCT/US13/70766, 4 pages (dated Mar. 25, 2014).
Irish, J. et al., Altered B-cell receptor signaling kinetics distinguish human follicular lymphoma B cells from tumor-infiltrating nonmalignant B cells, Blood, 108(9): 3135-42 (2006).
Jaffe E.S. and Pittaluga S., Aggressive B-cell lymphomas: a review of new and old entities in the WHO classification, Hematology Am. Soc. Hematol. Educ. Program, 506-14 (2011).
Jemal, A. et al., Cancer statistics, CA Cancer J. Clin., 53(1): 5-26 (2003).
Johnson, J. et al., Relationships between drug activity in NCI preclinical in vitro and in vivo models and early clinical trials, British Journal of Cancer, 84(10): 1424-1431 (2001).
Kataja V. and Castiglione M., Primary breast cancer: ESMO clinical recommendations for diagnosis, treatment and follow-up, Annals of Oncology, 20(Supplement 4): iv10-iv14 (2009).
Kiesewetter, B. et al., A phase II study of lenalidomide in patients with extranodal marginal zone B-cell lymphoma of the mucosa associated lymphoid tissue (MALT-lymphoma), Haematologica, 98(3):353-6 (2013).
Kirken, R., Targeting Jak3 for immune suppression and allograft acceptance, Transplant. Proc. 33 :3268-3270 (2001).
Kumar, A., et al, Structure and Clinical Relevance of the Epidermal Growth Factor Receptor in Human Cancer, Journal of Clinical Oncology 26(10):1742-1751 (2008).
Kuster, B., ed., Chapters 1 and 2, Kinase Inhibitors: Methods and Protocols, Methods in Molecular Biology, vol. 795, Humana Press, 46 pages (2012).
Kwak, E. et al., Irreversible inhibitors of the EGF receptor may circumvent acquired resistance to gefitinib, Proc. Natl. Acad. Sci. USA 102:7665-7670 (2005).
Lajeunesse, D. et al., A systematic screen for dominant second-site modifiers of Merlin/NF2 phenotypes reveals an interaction with blistered/DSRF and scribbler, Genetics 158:667-79 (2001).
Leonard, J. et al., A randomized trial of lenalidomide alone versus lenalidomide plus rituximab in patients with recurrent follicular lymphoma, J. Clin. Oncol., 30 (2012).
Li, D. et al., BIBW2992, an irreversible EGFR/HER2 inhibitor highly effective in preclinical lung cancer models, Oncogene 27:4702-4711 (2008).
Liddle, J. et al., Discovery of GSK143, a highly potent, selective and orally efficacious spleen tyrosine kinase inhibitor, Bioorg. Med. Chem. Lett., 21(20):6188-94 (2011).
Lin, N. and Winer, E., New targets for therapy in breast cancer: Small molecule tyrosine kinase inhibitors, Breast Cancer Res 6:204-210 (2004).
Liu, Q. et al., Developing Irreversible Inhibitors of the Protein Kinase Cysteinome, Chemistry & Biology, 20:146-159 (2013).
Malaviya, R. et al., Targeting Janus Kinase 3 in Mast Cells Prevents Immediate Hypersensitivity Reactions and Anaphylaxis, J. Biol. Chem. 274 :27028-27038 (1999).

(56) References Cited

OTHER PUBLICATIONS

McClatchey, A. and Giovannini, M., Membrane organization and tumorigenesis—the NF2 tumor suppressor, Merlin, Genes Dev 19:2265-77 (2005).

McCubrey, J.A. et al., Targeting survival cascades induced by activation of Ras/Raf/MEK/ERK, PI3K/PTEN/Akt/mTOR and Jak/STAT pathways for effective leukemia therapy, Leukemia, 22(4): 708-722 (2008).

McDaniel J.M. et al., Molecular action of lenalidomide in lymphocytes and hematologic malignancies, Adv. Hematol., Article ID 513702, 9 pages (2012).

Merriam-Webster's Online Directory, "Prevent" download on Apr. 7, 2008 from "http//www.merriam-webster.com/dictionary/prevent", p. 1 of 1.

Minkovsky, N. and Berezov, A., BIBW-2992, a dual receptor tyrosine kinase inhibitor for the treatment of solid tumors, Curr Opin Invest Drugs 9:1336-1346 (2008).

Montagut, C. and Settleman, J., Targeting the RAF-MEK-ERK pathway in cancer therapy, Cancer Letters, 283(2): 125-134 (2009).

Nastoupil, L.J. et al., Diffuse large B-cell lymphoma: current treatment approaches, Oncology, 26(5): 488-95 (2012).

Nelson et al., Screening for breast cancer: an update for the U.S. Preventive Services Task Force, Ann. Intern Med, 151(10): 727-737 (2009).

Ogiso, et al., Crystal Structure of the Complex of Human Epidermal Growth Factor and Receptor Extracellular Domains, Cell, vol. 110, 775-787 (2002).

Pearce, H.L. et al., Failure modes in anticancer drug discovery and development, Cancer Drug Design and Discovery Edited by Stephen Neidle, 18: 424-435 (2008).

Pelton, P. et al., Ruffling membrane, stress fiber, cell spreading and proliferation abnormalities in human Schwann cells, Oncogene 17:2195-2209 (1998).

PubChem CID 44594695. Feb. 1, 2010. [Retrieved from the Internet May 15, 2011: http://pubchem.ncbi.nlm.nih.gov/summary.cgi?cid=44594695&loc=ec_rcs].

Readinger, J. et al., Selective Targeting of ITK Blocks Multiple Steps of HIV Replication, Proc. Natl. Acad. Sci. USA 105: 6684-6689 (2008).

Rinaldi, A. et al., Genomic and expression profiling identifies the B-cell associated tyrosine kinase Syk as a possible therapeutic target in mantle cell lymphoma, Br. J. Haematol., 132(3): 303-16 (2006).

Roberts, P.J., and Der, C.J., Targeting the Raf-MEK-ERK mitogen-activated protein kinase cascade for the treatment of cancer, Oncogene, 26(22): 3291-3310 (2007).

Ruiz-Ballesteros, E. et al., Splenic marginal zone lymphoma: proposal of new diagnostic and prognostic markers identified after tissue and cDNA microarray analysis. Blood, 106(5): 1831-8 (2005).

Sakamoto, T. et al., Blockade of the ERK pathway enhances the therapeutic efficacy of the histone deacetylase inhibitor MS-275 in human tumor xenograft models, Biochem. Biophys. Res. Commun., 433(4):456-62 (2013).

Schlessingerman, Mass of an Adult Male, The Physics Factbook (2003), retreived Jul. 22, 2014 from web: http://hypertexbook.com/facts/2003/AlexSchleesingerman.shtml.

Seidel, H. et al., Pharmaceutical intervention in the JAK/STAT signaling pathway, Oncogene 19: 2645-2656 (2000).

Seipelt, I et al., Dual Inhibition of PI3K and Erk1/2 shows synergy and efficacy in human tumor cells, either by using drug combinations or novel dual PI3K/Erk inhibitors, Aeterna Zentaris GmbH, AACR Poster, Abstract #871 (2012).

Sequist, L., Second—Generation Epidermal Growth Factor Receptor Tyrosine Kinase Inhibitors in Non-Small Cell Lung Cancer, The Oncologist 12(3):325-330 (2007).

Simone, J.V., Oncology: Introduction, Cecil Textbook of Medicine, 20th Edition, 1: 1004-1010 (1995).

Singh, J. et al, Structure-based design of a potent, selective, and irreversible inhibitor of the catalytic domain of the erbB receptor subfamily of protein tyrosine kinases, J. Med. Chem. 40:1130-1135 (1997).

Soria, J-C. et al., "Abstract # 1354: First-In-Human Evaluation of CO-1686, an Irreversible, Highly Selective Tyrosine Kinase Inhibitor of Mutations of EGFR (Activating and T790M)," 15th World Conference on Lung Cancer, Oct. 27, 2013.

Steelman, L.S. et al., Contributions of the Raf/MEK/ERK, PI3K/PTEN/Akt/mTOR and Jak/STAT pathways to leukemia, Leukemia, 22(4): 686-707 (2008).

Steelman, L.S. et al., Roles of the Ras/Raf/MEK/ERK pathway in leukemia therapy, Leukemia, 25(7): 1080-1097 (2011).

Steinhardt, J.J. and Gartenhaus, R.B., Promising Personalized Therapeutic Options for Diffuse Large B-cell Lymphoma Subtypes with Oncogene Addictions, Clin. Cancer Res., 18(17): 4538-48 (2012).

Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).

Sudbeck, E. et al., Structure-based Design of Specific Inhibitors of Janus Kinase 3 as Apoptosis-inducing Antileukemic Agents, Clin. Cancer Res. 5: 1569-1582 (1999).

Tohnya, T.M. et al., A phase I study of oral CC-5013 (lenalidomide, Revlimid), a thalidomide derivative, in patients with refractory metastatic cancer, Clin Prostate Cancer, 2(4): 241-3 (2004).

Trieu, V. et al., A specific inhibitor of janus kinase-3 increases survival in a transgenic mouse model of amyotrophic lateral sclerosis, Biochem. Biophys. Res. Commun. 267 :22-25 (2000).

Walter, A. O. et al., "Discovery of a mutant-selective covalent inhibitor of EGFR that overcomes T790M-mediated resistance in NSCLC," *Cancer Discov.* Dec. 2013; 3(12): 1404-1415.

Walter, A.O. et al., Discovery of a Mutant-Selective Covalent Inhibitor of EGFR that Overcomes T790M Mediated Resistance in NSCLC, Cancer Discovery, 3(12): 1405-1415 (2013).

Westlin, W. et al., Translational medicine enables rapid early clinical development of AVL-292, a highly selective, orally available inhibitor of Bruton's tyrosine kinase, in a phase 1b clinical trial, Cancer Res., 72 (2012).

Wiernik, P.H. et al., Lenalidomide monotherapy in relapsed or refractory aggressive non-Hodgkin's lymphoma, J. Clin. Oncol., 26(30): 4952-7 (2008).

Winer, E.S. et al., A novel Bruton's tyrosine kinase inhibitor for the treatment of lymphoid malignancies, Expert Opin. Investig. Drugs, 21(3): 355-61 (2012).

Witzig, T.E. et al., Lenalidomide oral monotherapy produces durable responses in relapsed or refractory indolent non-Hodgkin's Lymphoma, J. Clin. Oncol., 27(32): 5404-5409 (2009).

Wong, K.-K., Recent developments in anti-cancer agents targeting the Ras/Raf/ MEK/ERK pathway, Recent Patents on Anti-Cancer Drug Discovery, 4(1): 28-35 (2009).

Wong, K. et al, A phase I study with neratinib (HKI-272), an irreversible pan Erb B receptor tyrosine kinase inhibitor, in patients with solid tumors, Clin. Cancer Res. 15(7):2552-2558 (2009).

Written Opinion for PCT/US09/48784, 9 pages (dated Nov. 16, 2009).

Written Opinion for PCT/US10/31714, 7 pages (dated Aug. 13, 2010).

Written Opinion for PCT/US10/62432, 14 pages (dated May 26, 2011).

Written Opinion for PCT/US11/46926, 9 pages (dated Dec. 22, 2011).

Written Opinion for PCT/US11/58610, 8 pages (dated Mar. 27, 2012).

Written Opinion for PCT/US11/58616, 9 pages (dated Mar. 27, 2012).

Written Opinion for PCT/US11/59726, 7 pages (dated Mar. 20, 2012).

Written Opinion for PCT/US13/70772, 10 pages (dated Mar. 25, 2014).

Written Opinion for PCT/US13/70776, 11 pages (dated Mar. 25, 2014).

(56) References Cited

OTHER PUBLICATIONS

Written Opinion for PCT/US2013/070766, 11 pages (dated Mar. 25, 2014).
Written Opinion for PCT/US2014/015256, 6 pages (dated Aug. 5, 2014).
Written Opinion for PCT/US2015/044783, 7 pages (dated Oct. 30, 2015).
Written Opinion of PCT/US13/30982, 12 pages (dated May 30, 2013).
Written Opinion of PCT/US13/30996, 12 pages (dated May 30, 2013).
Yang, Y. et al., Exploiting Synthetic Lethality for the Therapy of ABC Diffuse Large B Cell Lymphoma, Cancer Cell, 21: 723-737 (2012).
Zhang, J. et al., Targeting Cancer with Small Molecule Kinase Inhibitors, Nature Rev. Cancer 9:28-39 (2009).
Zhang, Y. et al., Antitumor Activity of Epidermal Growth Factor Receptor-Related Protein Is Mediated by Inactivation of ErbB Receptors and Nuclear Factor-kB in Pancreatic Cancer, Cancer Res 66:1025-1032 (2006).
Zhou, W. et al. Novel mutant-selective EGFR kinase inhibitors against EGFR T790M, Nature, 462(7276): 1070-1074 (2009).
Zhou, W. et al., Novel mutant-selective EGFR kinase inhibitors against EGFR T790M, Nature, 462(7276): 1070-1074 (2009).
Zhu, D. et al., Immunomodulatory drugs Revlimid (lenalidomide) and CC-4047 induce apoptosis of both hematological and solid tumor cells through NK cell activation. Cancer Immunol. Immunother., 57(12): 1849-59 (2008).
Australian Examination Report for 2011323626, dated Sep. 1, 2014, 3 pages.
Extended European Search Report for EP11816874.9, 5 pages (dated Dec. 12, 2013).
Extended European Search Report for EP11838624.2, 5 pages (dated Jun. 6, 2014).
Extended European Search Report for EP11838628.3, 7 pages (dated Jun. 20, 2014).
Extended European Search Report for EP11839800.7, 8 pages (dated Jun. 24, 2014).
Supplementary European Search Report for EP10844293.0, 8 pages (dated Jun. 27, 2013).

\* cited by examiner

DOSING GROUP
1: FREE BASE
2: HYDROCHLORIDE SALT
3: PHOSPHATE SALT
4: SULFATE SALT
5: BROMIDE SALT

FORMS AND COMPOSITIONS OF AN ERK INHIBITOR

CROSS-REFERENCE TO RELATED APPLICATIONS

The present application is a U.S. national stage entry of International PCT application number PCT/US15/44783, filed Aug. 12, 2015, which claims priority to U.S. provisional application No. 62/037,066, filed Aug. 13, 2014, the entirety of each of which is hereby incorporated herein by reference.

FIELD OF THE INVENTION

The present invention provides various forms and compositions useful as inhibitors of ERK kinases, for example one or both of ERK1 and ERK2 kinases.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

The processes involved in tumor growth, progression, and metastasis are mediated by signaling pathways that are activated in cancer cells. The MAPK or Raf-Mek-ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK occurs via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates one or both of ERK1 and ERK2. When activated, one or both of ERK1 and ERK2 phosphorylates several downstream targets involved in a multitude of cellular events including cytoskeletal changes and transcriptional activation. The ERK/MAPK pathway is one of the most important for cell proliferation, and human tumor data suggest that the ERK/MAPK pathway is frequently activated in many tumors. Ras genes, which are upstream of one or both of ERK1 and ERK2, are mutated in several cancers including colorectal, melanoma, breast, lung, and pancreatic tumors. High Ras activity is accompanied by elevated ERK activity in many human tumors. In addition, activating mutations of BRAF, a serine-threonine kinase of the Raf family, are associated with increased RAF, MEK, and ERK kinase activity. Tumors types with the most frequent mutations in BRAF include melanomas (60%), thyroid cancers (greater than 40%) and colorectal cancers.

Many diseases are associated with abnormal cellular responses, proliferation and evasion of programmed cell-death, triggered by protein kinase-mediated events as described above. Accordingly, there remains a need to find protein kinase inhibitors useful as therapeutic agents.

SUMMARY OF THE INVENTION

It has now been found that novel forms of the present invention, and compositions thereof, are useful as inhibitors of one or more protein kinases and exhibit desirable characteristics for the same. In general, salt forms or freebase forms, and pharmaceutically acceptable compositions thereof, are useful for treating or lessening the severity of a variety of diseases or disorders as described in detail herein.

DETAILED DESCRIPTION OF THE INVENTION

Figure 1:
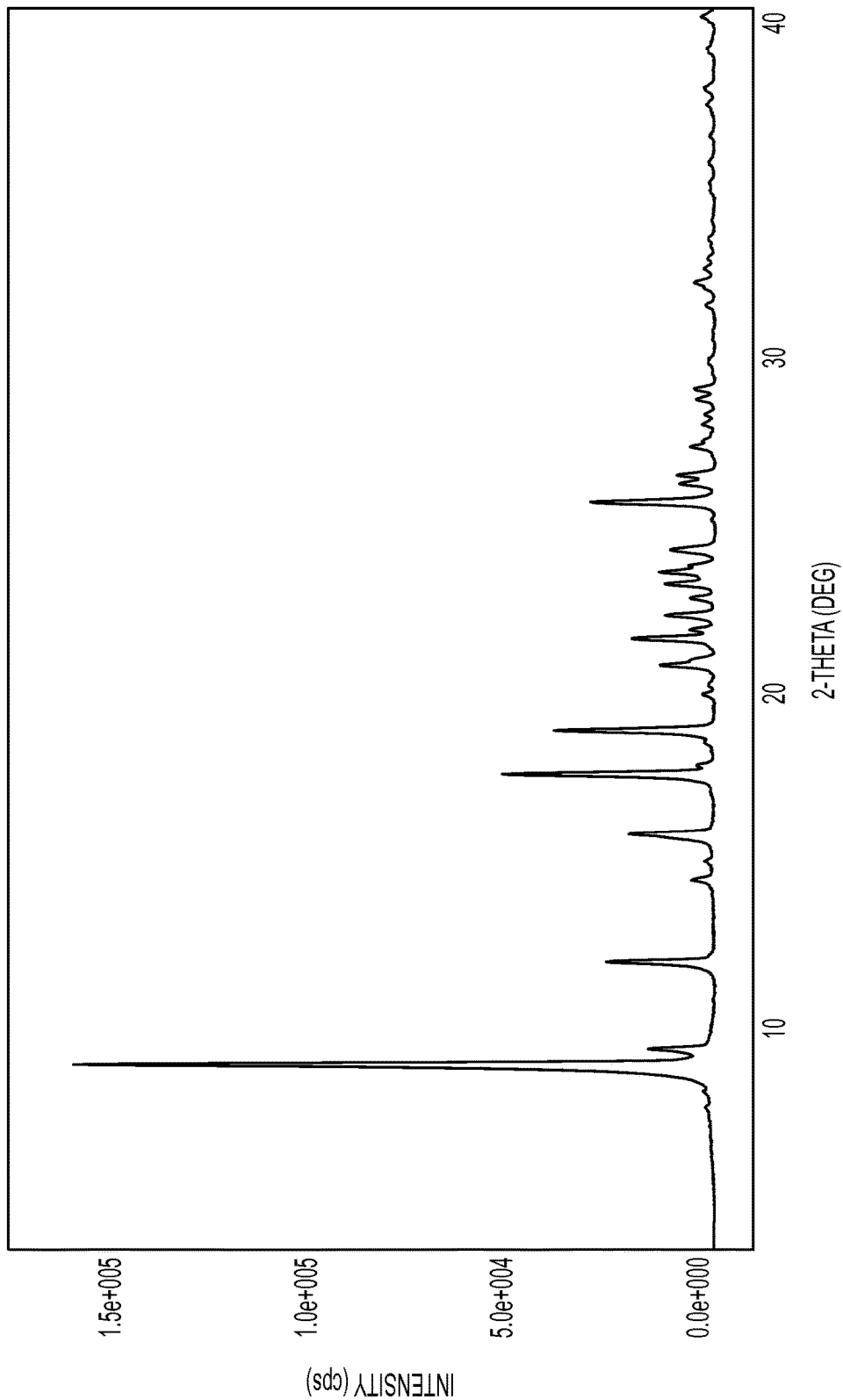
FIG. 1 depicts an XRPD pattern of Form A of compound 1.

General Description of Certain Aspects of the Invention:

PCT patent application serial number PCT/US14/15256, filed Feb. 7, 2014 and published as WO 2014/124230 on Aug. 14, 2014 ("the '230 publication," the entirety of which is hereby incorporated herein by reference), describes certain ERK inhibitor compounds which covalently and irreversibly inhibit activity of one or both of ERK1 and ERK2 kinases. Such compounds include compound 1:

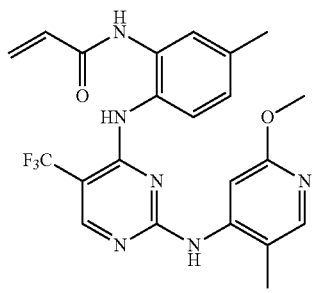

1

Compound 1, N-(2-(2-((2-methoxy-5-methylpyridin-4-yl)amino)-5-(trifluoromethyl)pyrimidin-4-yl)amino)-5-methylphenyl)acrylamide, is designated as compound number 1-90 in the '230 publication and the synthesis of compound 1 is described in detail at Example 94 of the '230 publication, and is reproduced herein for ease of reference.

Compound 1 is active in a variety of assays and therapeutic models demonstrating covalent, irreversible inhibition of one or both of ERK1 and ERK2 kinases (see, e.g., Table A of the '230 publication). Accordingly, compound 1 is useful for treating one or more disorders associated with activity of one or both of ERK1 and ERK2.

It would be desirable to provide a solid form of compound 1 (e.g., as a freebase thereof or salt thereof) that imparts characteristics such as improved aqueous solubility, stability and ease of formulation. Accordingly, the present invention provides both free base forms and salt forms of compound 1.

Free Base Forms of Compound 1

It is contemplated that compound 1 can exist in a variety of physical forms. For example, compound 1 can be in solution, suspension, or in solid form. In certain embodiments, compound 1 is in solid form. When compound 1 is in solid form, said compound may be amorphous, crystalline, or a mixture thereof. Exemplary solid forms are described in more detail below.

In some embodiments, the present invention provides a form of compound 1 substantially free of impurities. As used herein, the term "substantially free of impurities" means that the compound contains no significant amount of extraneous matter. Such extraneous matter may include different forms of compound 1, residual solvents, or any other impurities that may result from the preparation of, and/or isolation of, compound 1. In certain embodiments, at least about 95% by weight of a form of compound 1 is present. In still other embodiments of the invention, at least about 99% by weight of a form of compound 1 is present.

According to one embodiment, a form of compound 1 is present in an amount of at least about 97, 97.5, 98.0, 98.5, 99, 99.5, 99.8 weight percent where the percentages are based on the total weight of the composition. According to another embodiment, a form of compound 1 contains no more than about 3.0 area percent HPLC of total organic impurities and, in certain embodiments, no more than about 1.5 area percent HPLC total organic impurities relative to the total area of the HPLC chromatogram. In other embodiments, a form of compound 1 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for a form of compound 1 is also meant to include all tautomeric forms of compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 1 can exist in a variety of solid forms. Exemplary such forms include polymorphs such as those described herein.

As used herein, the term "polymorph" refers to the different crystal structures into which a compound, or a salt or solvate thereof, can crystallize.

In certain embodiments, compound 1 is a crystalline solid. In other embodiments, compound 1 is a crystalline solid substantially free of amorphous compound 1. As used herein, the term "substantially free of amorphous compound 1" means that the compound contains no significant amount of amorphous compound 1. In certain embodiments, at least about 95% by weight of crystalline compound 1 is present. In still other embodiments of the invention, at least about 99% by weight of crystalline compound 1 is present.

It has been found that compound 1 can exist in at least four distinct polymorphic forms. In certain embodiments, the present invention provides a polymorphic form of compound 1 referred to herein as Form A. In certain embodiments, the present invention provides a polymorphic form of compound 1 referred to herein as Form B. In certain embodiments, the present invention provides a polymorphic form of compound 1 referred to herein as Form C. In certain embodiments, the present invention provides a polymorphic form of compound 1 referred to herein as Form D.

In some embodiments, compound 1 is amorphous. In some embodiments, compound 1 is amorphous, and is substantially free of crystalline compound 1.

Form A of Compound 1

In some embodiments, Form A of compound 1 has at least 1, 2, 3, 4 or 5 spectral peak(s) selected from the peaks listed in Table 1 below.

TABLE 1

XRPD Peak Positions for Form A of Compound 1
Position (°2 θ)

| |
| --- |
| 8.6 |
| 9.0 |
| 11.6 |
| 14.1 |
| 15.3 |
| 15.4 |
| 17.2 |
| 18.5 |
| 20.4 |
| 20.6 |
| 21.2 |
| 21.5 |
| 21.9 |
| 22.9 |
| 23.40 |
| 23.9 |
| 25.3 |
| 25.8 |

TABLE 1-continued

XRPD Peak Positions for Form A of Compound 1
Position (°2 θ)

26.1
27.0

[1] In this and all subsequent tables, the position 2 θ is within ±0.2.

In some embodiments, Form A of compound 1 is characterized in that it has one or more peaks in its X-ray powder diffraction pattern selected from those at about 8.6, 17.2, and 18.5. In some embodiments, Form A of compound 1 is characterized in that it has two or more peaks in its X-ray powder diffraction pattern selected from those at about 8.6, 17.2, and 18.5. In some embodiments, Form A of compound 1 is characterized in that it has all three peaks in its X-ray powder diffraction pattern selected from those at about 8.6, 17.2, and 18.5. As used herein, the term "about", when used in reference to a degree 2-theta value refers to the stated value ±0.2 degree 2-theta.

In certain embodiments, the X-ray powder diffraction pattern is substantially similar to the XRPD provided in FIG. 1.

Methods for preparing Form A of compound 1 are described infra.

Form B of Compound 1

In some embodiments, Form B of compound 1 has at least 1, 2, 3, 4 or 5 spectral peak(s) selected from the peaks listed in Table 2 below.

TABLE 2

XRPD Peak Positions for Form B of Compound 1
Position (°2 θ)

4.6
7.2
8.3
9.3
11.6
13.6
14.4
16.5
17.7
18.7
21.0
21.3
23.2
23.5
24.4
27.5

[1] In this and all subsequent tables, the position 2 θ is within ±0.2.

In some embodiments, Form B of compound 1 is characterized in that it has one or more peaks in its X-ray powder diffraction pattern selected from those at about 7.2, 9.3, and 17.7. In some embodiments, Form B of compound 1 is characterized in that it has two or more peaks in its X-ray powder diffraction pattern selected from those at about 7.2, 9.3, and 17.7. In some embodiments, Form B of compound 1 is characterized in that it has all three peaks in its X-ray powder diffraction pattern selected from those at about 7.2, 9.3 and 17.7.

Figure 4:
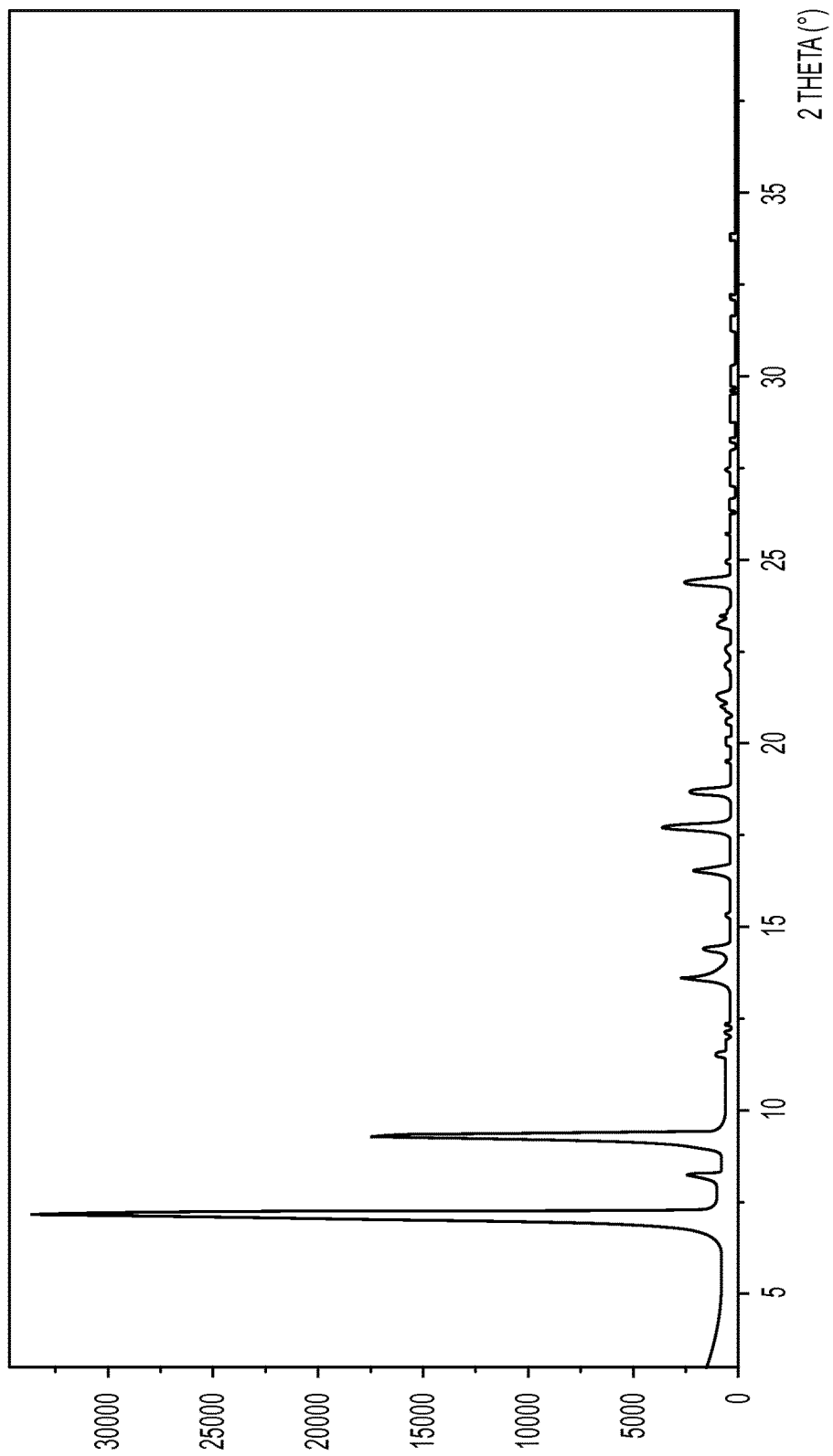
FIG. 4 depicts an XRPD pattern of Form B of compound 1.

In certain embodiments, the X-ray powder diffraction pattern is substantially similar to the XRPD provided in FIG. 4.

Methods for preparing Form B of compound 1 are described infra.

Form C of Compound 1

In some embodiments, Form C of compound 1 has at least 1, 2, 3, 4 or 5 spectral peak(s) selected from the peaks listed in Table 3 below.

TABLE 3

XRPD Peak Positions for Form C of Compound 1
Position (°2 θ)

7.6
8.8
9.6
11.7
12.3
14.5
15.3
15.9
17.5
18.0
20.1
21.0
22.8
23.4
23.8
24.7
25.2
25.5
26.4
27.7

[1] In this and all subsequent tables, the position 2 θ is within ±0.2.

In some embodiments, Form C of compound 1 is characterized in that it has one or more peaks in its X-ray powder diffraction pattern selected from those at about 7.6, 15.3 and 15.9. In some embodiments, Form C of compound 1 is characterized in that it has two or more peaks in its X-ray powder diffraction pattern selected from those at about 7.6, 15.3 and 15.9. In some embodiments, Form C of compound 1 is characterized in that it has all three peaks in its X-ray powder diffraction pattern selected from those at about 7.6, 15.3 and 15.9.

Figure 7:
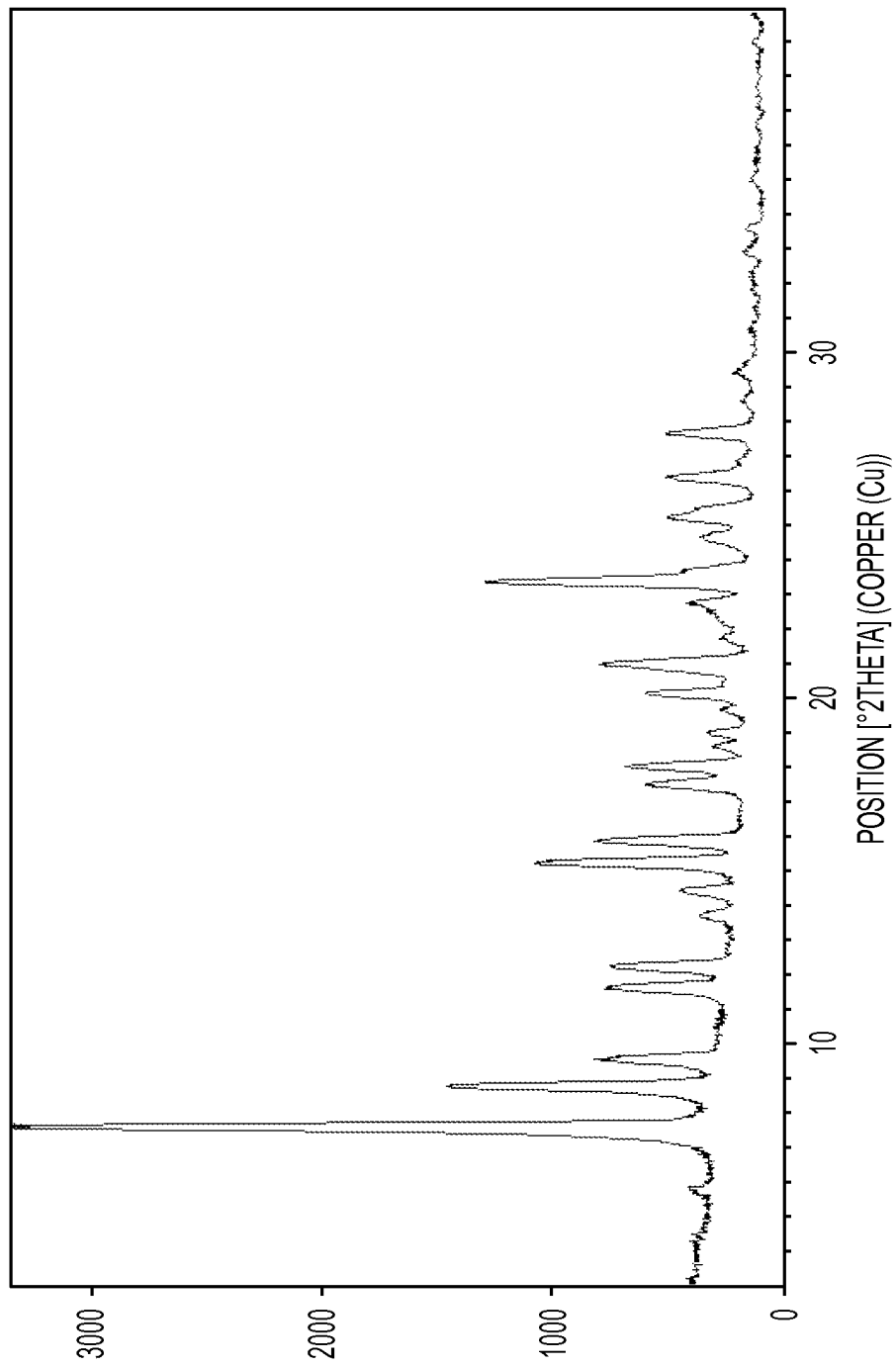
FIG. 7 depicts an XRPD pattern of Form C of compound 1.

In certain embodiments, the X-ray powder diffraction pattern is substantially similar to the XRPD provided in FIG. 7.

Methods for preparing Form C of compound 1 are described infra.

Form D of Compound 1

In some embodiments, Form D of compound 1 has at least 1, 2, 3, 4 or 5 spectral peak(s) selected from the peaks listed in Table 4 below.

TABLE 4

XRPD Peak Positions for Form D of Compound 1
Position (°2 θ)

8.2
8.9
9.5
9.6
10.6
15.0
17.3
17.7
19.1
20.2
21.1
22.0
22.4
23.7
24.7
25.2
25.9
26.5

TABLE 4-continued

XRPD Peak Positions for Form D of Compound 1
Position (°2 θ)

28.6
35.1

[1] In this and all subsequent tables, the position 2 θ is within ±0.2.

In some embodiments, Form D of compound 1 is characterized in that it has one or more peaks in its X-ray powder diffraction pattern selected from those at about 10.6, 15.0, and 17.3. In some embodiments, Form D of compound 1 is characterized in that it has two or more peaks in its X-ray powder diffraction pattern selected from those at about 10.6, 15.0, and 17.3. In some embodiments, Form D of compound 1 is characterized in that it has all three peaks in its X-ray powder diffraction pattern selected from those at about 10.6, 15.0, and 17.3.

Figure 10:
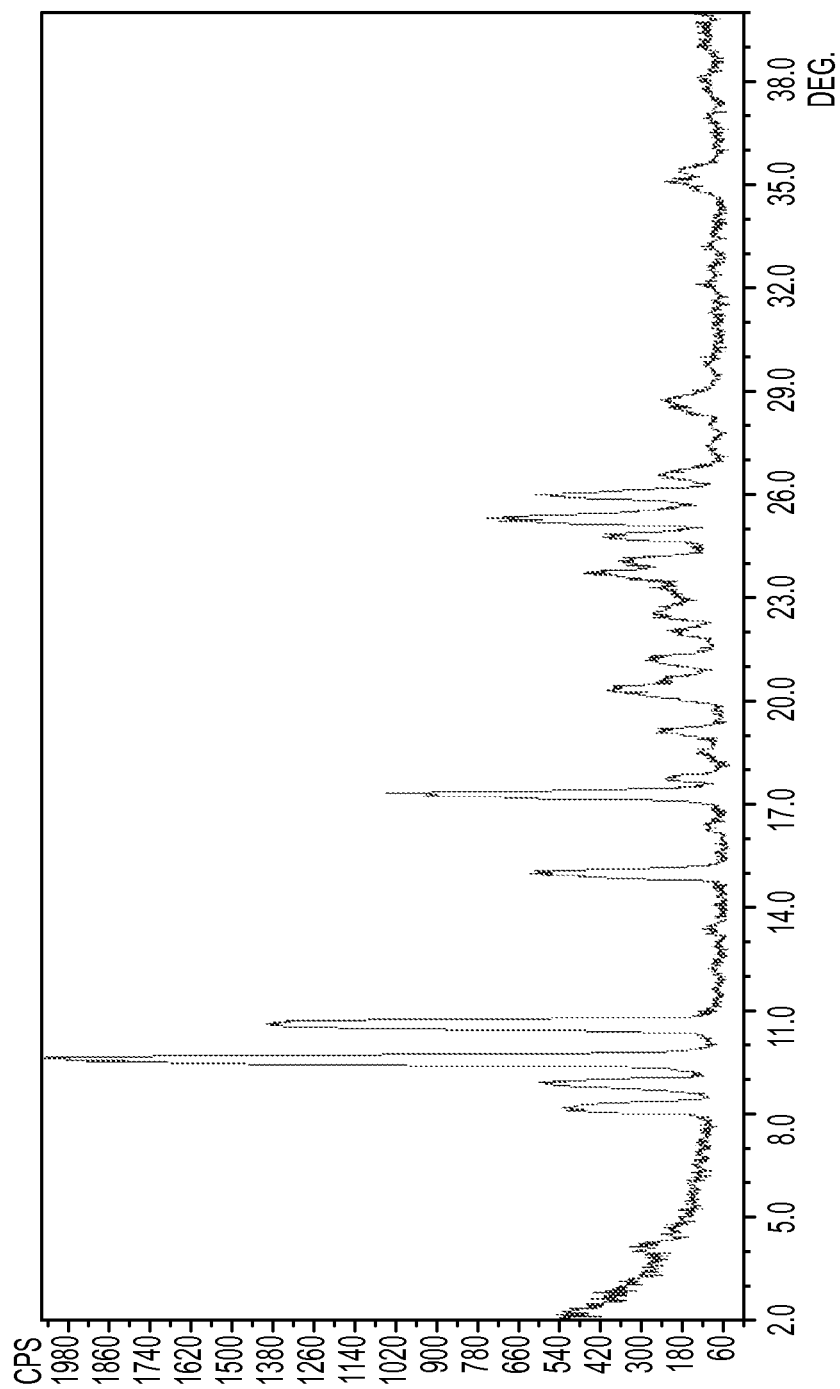
FIG. 10 depicts an XRPD pattern of Form D of compound 1.

In certain embodiments, the X-ray powder diffraction pattern is substantially similar to the XRPD provided in FIG. 10.

Methods for preparing Form D of compound 1 are described infra.

In some embodiments, the present invention provides compound 1:

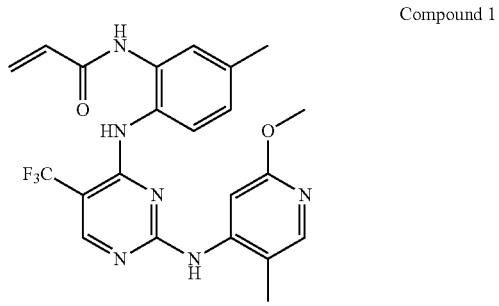 [SMILES: C=CC(=O)Nc1cc(C)ccc1Nc1nc(Nc2cc(OC)ncc2C)ncc1C(F)(F)F]

Compound 1 wherein said compound is crystalline.

In some embodiments, the present invention provides compound 1, wherein said compound is substantially free of amorphous compound 1.

In some embodiments, the present invention provides compound 1, wherein said compound is substantially free of impurities.

In some embodiments, the present invention provides compound 1, wherein said compound has one or more peaks in its XRPD selected from those at about 8.6, about 17.2, and about 18.5 degrees 2-theta. In some such embodiments, the present invention provides compound 1, wherein said compound has at least two peaks in its XRPD selected from those at about 8.6, about 17.2, and about 18.5 degrees 2-theta. In some such embodiments, the present invention provides compound 1, wherein said compound is of Form A.

In some embodiments, the present invention provides compound 1, wherein said compound has an XRPD substantially similar to that depicted in FIG. 1.

In some embodiments, the present invention provides compound 1, wherein said compound has one or more peaks in its XRPD selected from those at about 7.2, about 9.3, and about 17.7 degrees 2-theta. In some such embodiments, the present invention provides compound 1, wherein said compound has at least two peaks in its XRPD selected from those at about 7.2, about 9.3, and about 17.7 degrees 2-theta.

In some such embodiments, the present invention provides compound 1, wherein said compound is of Form B.

In some embodiments, the present invention provides compound 1, wherein said compound has an XRPD substantially similar to that depicted in FIG. 4.

In some embodiments, the present invention provides compound 1, wherein said compound has one or more peaks in its XRPD selected from those at about 7.6, about 15.3, and about 15.9 degrees 2-theta. In some such embodiments, the present invention provides compound 1, wherein said compound has at least two peaks in its XRPD selected from those at about 7.6, about 15.3, and about 15.9 degrees 2-theta. In some such embodiments, the present invention provides compound 1, wherein said compound is of Form C.

In some embodiments, the present invention provides compound 1, wherein said compound has an XRPD substantially similar to that depicted in FIG. 7.

In some embodiments, the present invention provides compound 1, wherein said compound has one or more peaks in its XRPD selected from those at about 10.6, about 15.0, and about 17.3 degrees 2-theta. In some such embodiments, the present invention provides compound 1, wherein said compound has at least two peaks in its XRPD selected from those at about 10.6, about 15.0, and about 17.3 degrees 2-theta. In some such embodiments, the present invention provides compound 1, wherein said compound is of Form D.

In some embodiments, the present invention provides compound 1, wherein said has an XRPD substantially similar to that depicted in FIG. 10.

In some embodiments, the present invention provides a composition comprising compound 1 and a pharmaceutically acceptable carrier or excipient.

In some embodiments, the present invention provides a method of inhibiting one or both of ERK1 and ERK2 in a patient comprising administering to said patient compound 1 or composition thereof.

In some embodiments, the present invention provides a method of treating an ERK1- or ERK2-mediated disorder in a patient, comprising administering to said patient compound 1 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Salt Forms of Compound 1

In some embodiments, an acid and compound 1 are ionically bonded to form one of compounds 2 through 12, described below. It is contemplated that compounds 2 through 12 can exist in a variety of physical forms. For example, compounds 2 through 12 can be in solution, suspension, or in solid form. In certain embodiments, compounds 2 through 12 are in solid form. When compounds 2 through 12 are in solid form, said compounds may be amorphous, crystalline, or a mixture thereof. Exemplary such solid forms of compounds 2 through 12 are described in more detail below.

Compound 2 (Phosphate Salts of Compound 1)

According to one embodiment, the present invention provides a phosphate salt of compound 1, represented by compound 2:

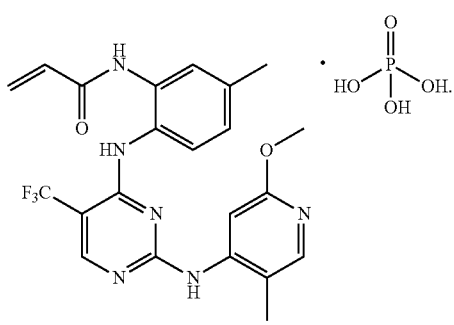

It will be appreciated by one of ordinary skill in the art that the phosphoric acid and compound 1 are ionically bonded to form compound 2. It is contemplated that compound 2 can exist in a variety of physical forms. For example, compound 2 can be in solution, suspension, or in solid form. In certain embodiments, compound 2 is in solid form. When compound 2 is in solid form, said compound may be amorphous, crystalline, or a mixture thereof. Exemplary solid forms are described in more detail below.

In some embodiments, the present invention provides compound 2 substantially free of impurities. As used herein, the term "substantially free of impurities" means that the compound contains no significant amount of extraneous matter. Such extraneous matter may include excess phosphoric acid, excess compound 1, residual solvents, or any other impurities that may result from the preparation of, and/or isolation of, compound 2. In certain embodiments, at least about 95% by weight of compound 2 is present. In still other embodiments of the invention, at least about 99% by weight of compound 2 is present.

According to one embodiment, compound 2 is present in an amount of at least about 97, 97.5, 98.0, 98.5, 99, 99.5, 99.8 weight percent where the percentages are based on the total weight of the composition. According to another embodiment, compound 2 contains no more than about 3.0 area percent HPLC of total organic impurities and, in certain embodiments, no more than about 1.5 area percent HPLC total organic impurities relative to the total area of the HPLC chromatogram. In other embodiments, compound 2 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 2 is also meant to include all tautomeric forms of compound 2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that compound 2 can exist in a variety of solid forms. Exemplary such forms include polymorphs such as those described herein.

In certain embodiments, compound 2 is a crystalline solid. In other embodiments, compound 2 is a crystalline solid substantially free of amorphous compound 2. As used herein, the term "substantially free of amorphous compound 2" means that the compound contains no significant amount of amorphous compound 2. In certain embodiments, at least about 95% by weight of crystalline compound 2 is present. In still other embodiments of the invention, at least about 99% by weight of crystalline compound 2 is present.

It has been found that compound 2 can exist in at least four distinct polymorphic forms. In some embodiments, the present invention provides a polymorphic form of Compound 2 referred to herein as Form A. In certain embodiments, the present invention provides a polymorphic form of compound 2 referred to herein as Form B. In certain embodiments, the present invention provides a polymorphic form of compound 2 referred to herein as Form C. In certain embodiments, the present invention provides a polymorphic form of Compound 2 referred to herein as Form D.

In some embodiments, compound 2 is amorphous. In some embodiments, compound 2 is amorphous, and is substantially free of crystalline compound 2.

Form A of Compound 2

In some embodiments, Form A of compound 2 has at least 1, 2, 3, 4 or 5 spectral peak(s) selected from the peaks listed in Table 5 below.

TABLE 5

| XRPD Peak Positions for Form A of Compound 2 Position (°2 θ) |
|---|
| 5.9 |
| 6.3 |
| 6.8 |
| 9.8 |
| 10.1 |
| 11.1 |
| 13.8 |
| 14.4 |
| 15.4 |
| 16.0 |
| 16.6 |
| 17.3 |
| 17.9 |
| 18.9 |
| 19.2 |
| 19.7 |
| 20.3 |
| 20.8 |
| 21.3 |
| 22.2 |
| 23.0 |
| 23.3 |
| 23.6 |
| 24.0 |
| 24.7 |
| 25.5 |
| 26.0 |
| 26.8 |
| 27.4 |
| 27.9 |
| 28.4 |
| 29.2 |
| 30.5 |
| 31.3 |
| 31.8 |

[1] In this and all subsequent tables, the position 2 θ is within ±0.2.

In some embodiments, Form A of compound 2 is characterized in that it has one or more peaks in its X-ray powder diffraction pattern selected from those at about 6.8, 10.1, and 20.8. In some embodiments, Form A of compound 2 is characterized in that it has two or more peaks in its X-ray powder diffraction pattern selected from those at about 6.8, 10.1, and 20.8. In some embodiments, Form A of compound 2 is characterized in that it has all three peaks in its X-ray powder diffraction pattern selected from those at about 6.8, 10.1, and 20.8.

Figure 13:
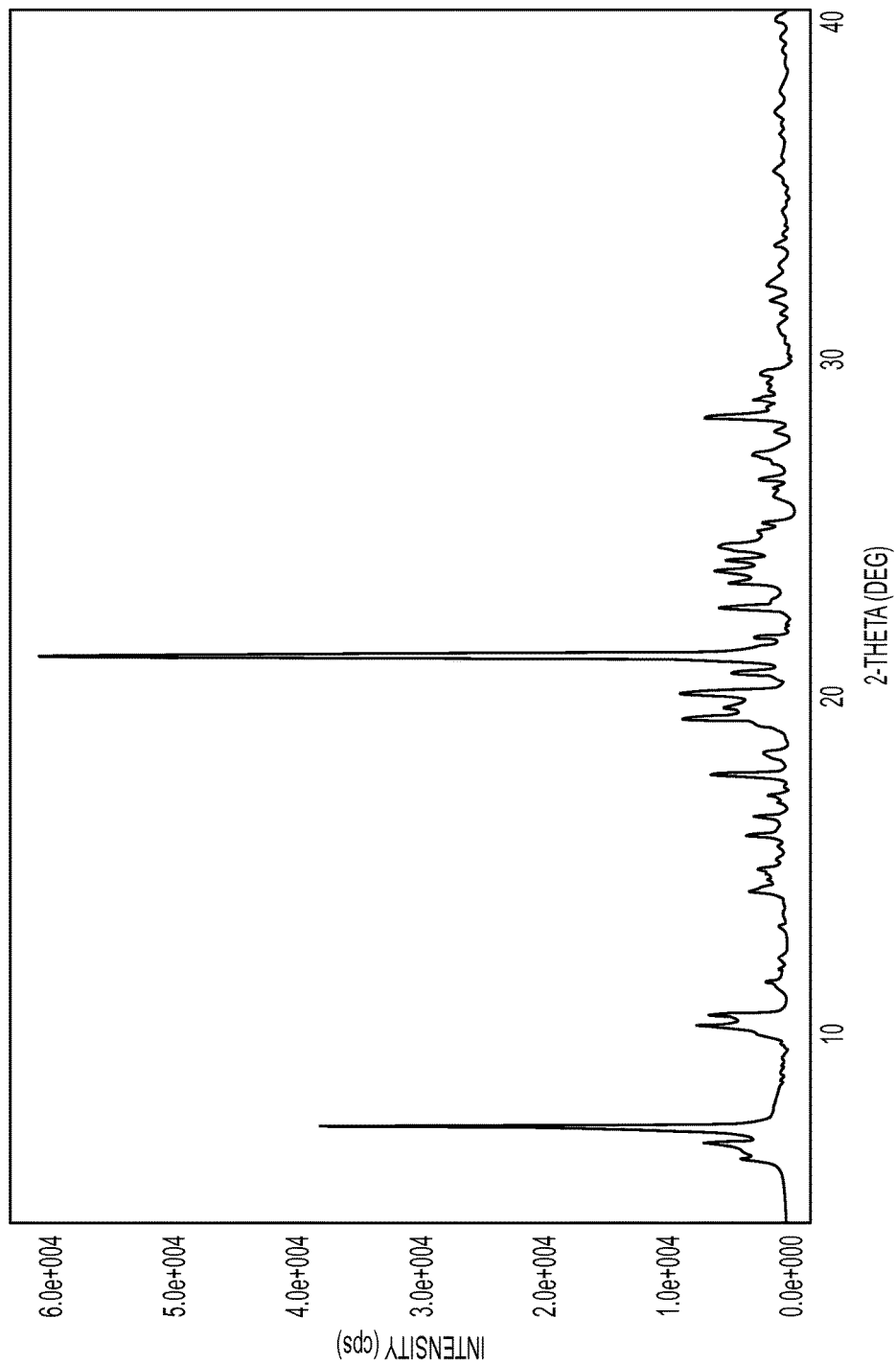
FIG. 13 depicts an XRPD pattern of Form A of compound 2.

In certain embodiments, the X-ray powder diffraction pattern is substantially similar to the XRPD provided in FIG. 13.

Methods for preparing Form A of compound 2 are described infra.

Form B of Compound 2

In some embodiments, Form B of compound 2 has at least 1, 2, 3, 4 or 5 spectral peak(s) selected from the peaks listed in Table 6 below.

TABLE 6

XRPD Peak Positions for Form B of Compound 2
Position (°2 θ)

| |
|---|
| 3.6 |
| 7.3 |
| 8.6 |
| 9.5 |
| 10.7 |
| 12.0 |
| 13.5 |
| 14.6 |
| 15.0 |
| 15.7 |
| 16.6 |
| 18.2 |
| 19.2 |
| 19.9 |
| 20.3 |
| 21.6 |
| 22.0 |
| 22.5 |
| 22.9 |
| 23.4 |
| 24.1 |
| 24.9 |
| 25.3 |
| 25.7 |
| 26.3 |
| 26.9 |
| 27.8 |
| 28.7 |
| 29.5 |
| 30.2 |
| 31.8 |
| 34.2 |
| 36.1 |
| 37.1 |
| 38.8 |
| 39.3 |

[1] In this and all subsequent tables, the position 2 θ is within ±0.2.

In some embodiments, Form B of compound 2 is characterized in that it has one or more peaks in its X-ray powder diffraction pattern selected from those at about 3.6, 7.3, and 15.0. In some embodiments, Form B of compound 2 is characterized in that it has two or more peaks in its X-ray powder diffraction pattern selected from those at about 3.6, 7.3, and 15.0. In some embodiments, Form B of compound 2 is characterized in that it has all three peaks in its X-ray powder diffraction pattern selected from those at about 3.6, 7.3, and 15.0.

Figure 17:
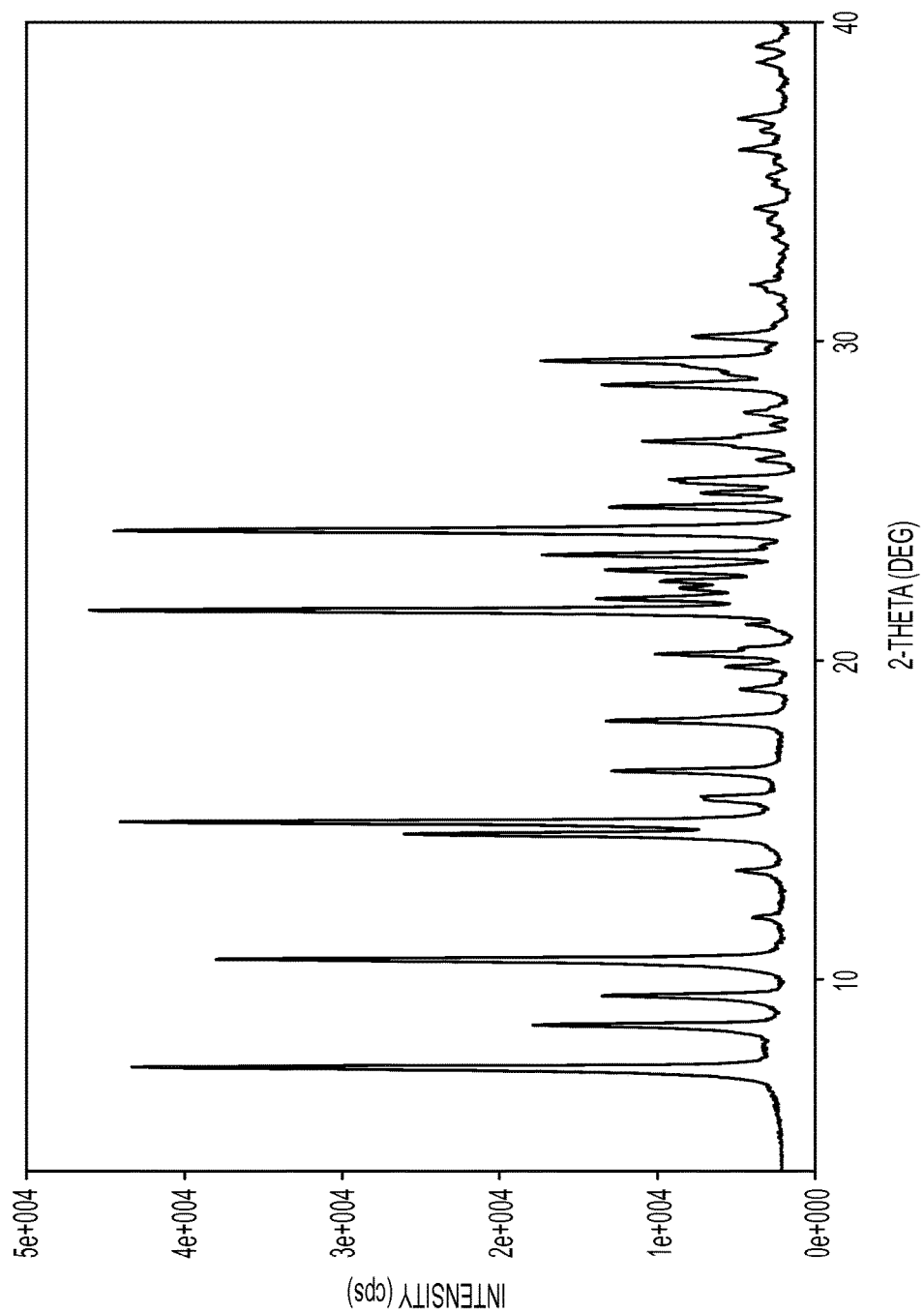
FIG. 17 depicts an XRPD pattern of Form B of compound 2.

In certain embodiments, the X-ray powder diffraction pattern is substantially similar to the XRPD provided in FIG. 17.

Methods for preparing Form B of compound 2 are described infra.

Form C of Compound 2

In some embodiments, Form C of compound 2 has at least 1, 2, 3, 4 or 5 spectral peak(s) selected from the peaks listed in Table 7 below.

TABLE 7

XRPD Peak Positions for Form C of Compound 2
Position (°2 θ)

| |
|---|
| 4.2 |
| 6.8 |
| 8.4 |
| 9.3 |
| 11.6 |
| 12.5 |
| 12.7 |
| 13.7 |
| 15.3 |
| 15.8 |
| 16.5 |
| 18.7 |
| 19.4 |
| 20.5 |
| 22.0 |
| 22.7 |
| 24.5 |
| 25.2 |
| 26.2 |
| 32.0 |

[1] In this and all subsequent tables, the position 2 θ is within ±0.2.

In some embodiments, Form C of compound 2 is characterized in that it has one or more peaks in its X-ray powder diffraction pattern selected from those at about 8.4, 9.3, and 16.5. In some embodiments, Form C of compound 2 is characterized in that it has two or more peaks in its X-ray powder diffraction pattern selected from those at about 8.4, 9.3, and 16.5. In some embodiments, Form C of compound 2 is characterized in that it has all three peaks in its X-ray powder diffraction pattern selected from those at about 8.4, 9.3, and 16.5.

Figure 21:
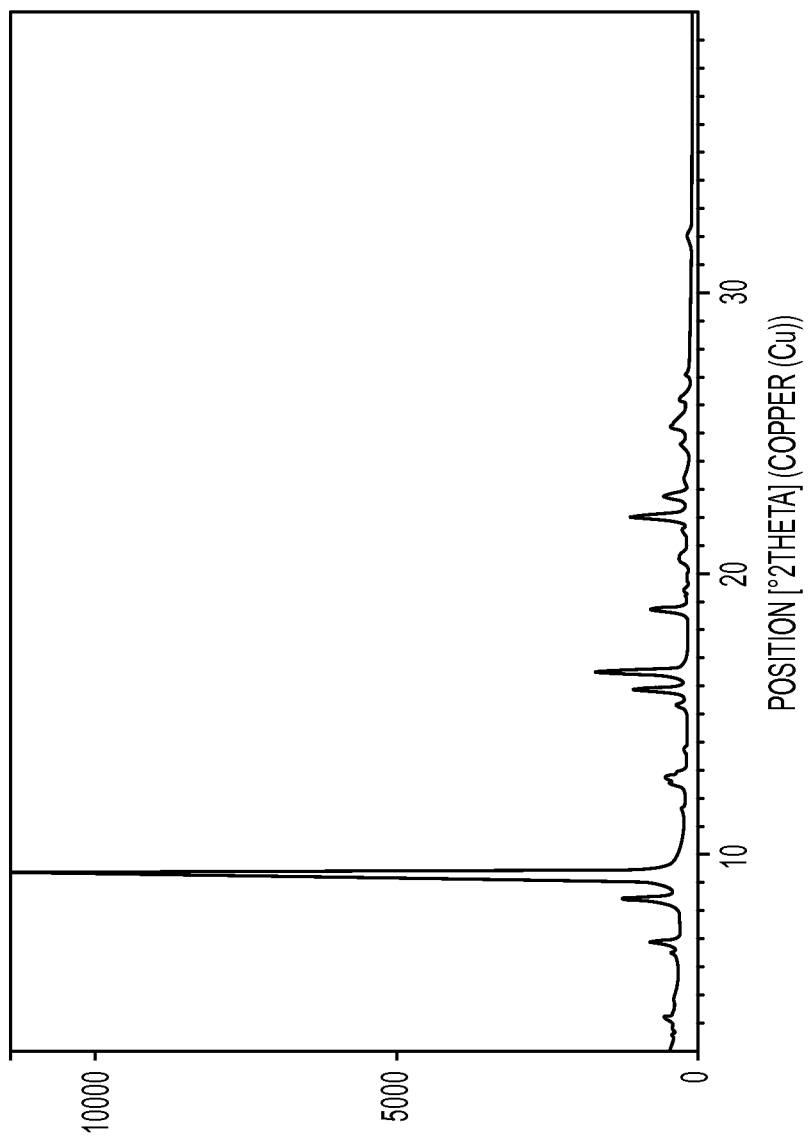
FIG. 21 depicts an XRPD pattern of Form C of compound 2.

In certain embodiments, the X-ray powder diffraction pattern is substantially similar to the XRPD provided in FIG. 21.

Methods for preparing Form C of compound 2 are described infra.

Form D of Compound 2

In some embodiments, Form D of compound 2 has at least 1, 2, 3, 4 or 5 spectral peak(s) selected from the peaks listed in Table 8 below.

TABLE 8

XRPD Peak Positions for Form D of Compound 2
Position (°2 θ)

| |
|---|
| 7.1 |
| 8.1 |
| 9.1 |
| 10.4 |
| 10.6 |
| 11.2 |
| 12.9 |
| 13.9 |
| 15.8 |
| 16.4 |
| 17.2 |
| 17.7 |
| 18.7 |
| 19.0 |
| 20.2 |
| 20.7 |
| 21.0 |
| 22.1 |
| 22.7 |
| 24.5 |
| 25.1 |
| 26.4 |
| 27.4 |
| 27.8 |

TABLE 8-continued

XRPD Peak Positions for Form D of Compound 2
Position (°2 θ)

| Position (°2 θ) |
|---|
| 28.7 |
| 29.1 |
| 31.0 |
| 31.5 |
| 33.8 |
| 36.3 |
| 37.0 |
| 38.0 |

[1] In this and all subsequent tables, the position 2 θ is within ±0.2.

In some embodiments, Form D of compound 2 is characterized in that it has one or more peaks in its X-ray powder diffraction pattern selected from those at about 9.1, 10.4, and 25.1. In some embodiments, Form D of compound 2 is characterized in that it has two or more peaks in its X-ray powder diffraction pattern selected from those at about 9.1, 10.4, and 25.1. In some embodiments, Form D of compound 2 is characterized in that it has all three peaks in its X-ray powder diffraction pattern selected from those at about 9.1, 10.4, and 25.1.

Figure 25:
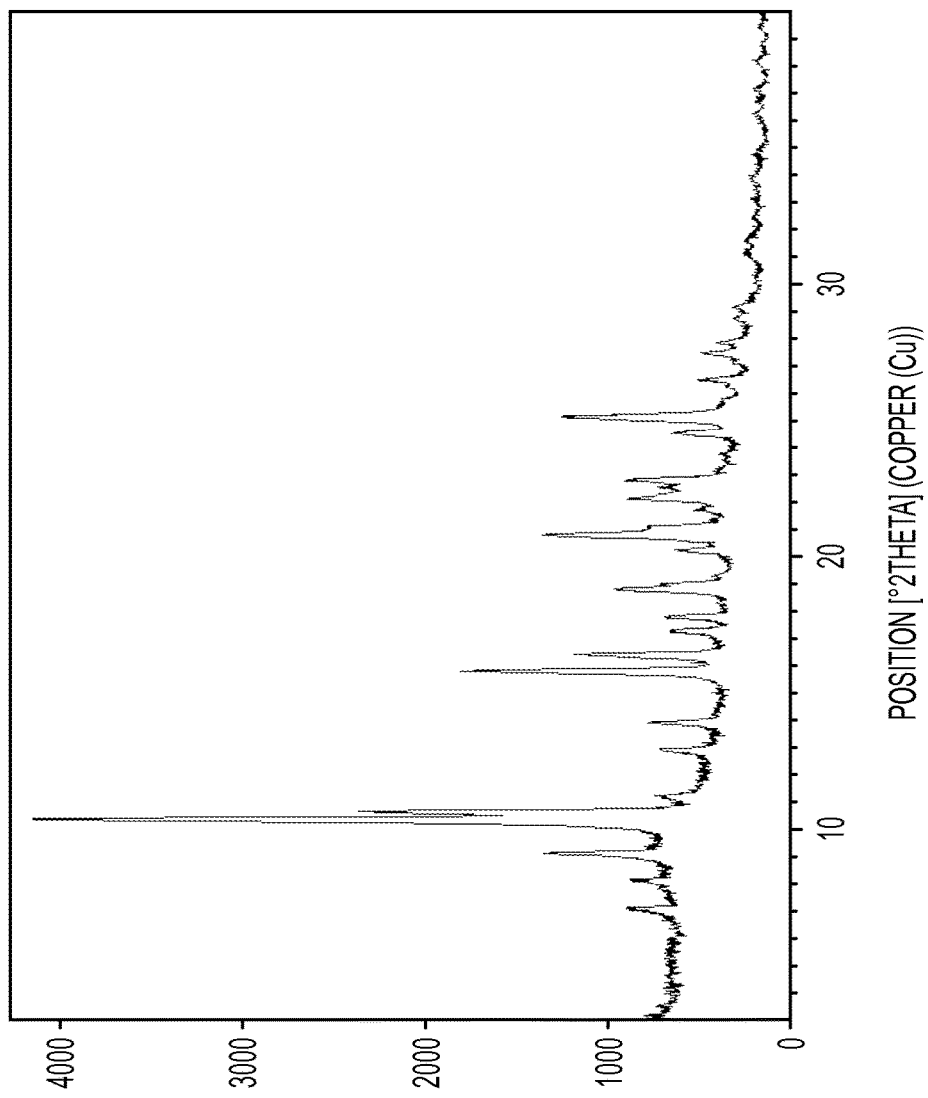
FIG. 25 depicts an XRPD pattern of Form D of compound 2.

In certain embodiments, the X-ray powder diffraction pattern is substantially similar to the XRPD provided in FIG. 25.

Methods for preparing Form D of compound 2 are described infra.

In some embodiments, the present invention provides compound 2:

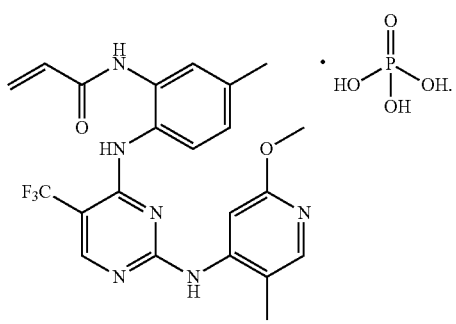

2

In some embodiments, the present invention provides compound 2, wherein said compound is crystalline.

In some embodiments, the present invention provides compound 2, wherein said compound is a crystalline solid substantially free of amorphous compound 2.

In some embodiments, the present invention provides compound 2, wherein said compound is substantially free of impurities.

In some embodiments, the present invention provides compound 2, wherein said compound has one or more peaks in its XRPD selected from those at about 6.8, about 10.1, and about 20.8 degrees 2-theta. In some such embodiments, the present invention provides compound 2, wherein said compound has at least two peaks in its XRPD selected from those at about 6.8, about 10.1, and about 20.8 degrees 2-theta. In some such embodiments, the present invention provides compound 2, wherein said compound is of Form A.

In some embodiments, the present invention provides compound 2, wherein said compound has an XRPD substantially similar to that depicted in FIG. 13.

In some embodiments, the present invention provides compound 2, wherein said compound has one or more peaks in its XRPD selected from those at about 3.6, about 7.3, and about 15.0 degrees 2-theta. In some such embodiments, the present invention provides compound 2, wherein said compound has at least two peaks in its XRPD selected from those at about 3.6, about 7.3, and about 15.0 degrees 2-theta. In some such embodiments, the present invention provides compound 2, wherein said compound is of Form B.

In some embodiments, the present invention provides compound 2, wherein said compound has an XRPD substantially similar to that depicted in FIG. 17.

In some embodiments, the present invention provides compound 2, wherein said compound has one or more peaks in its XRPD selected from those at about 8.4, about 9.3, and about 16.5 degrees 2-theta. In some such embodiments, the present invention provides compound 2, wherein said compound has at least two peaks in its XRPD selected from those at about 8.4, about 9.3, and about 16.5 degrees 2-theta. In some such embodiments, the present invention provides compound 2, wherein said compound is of Form C.

In some embodiments, the present invention provides compound 2, wherein said compound has an XRPD substantially similar to that depicted in FIG. 21.

In some embodiments, the present invention provides compound 2, wherein said compound has one or more peaks in its XRPD selected from those at about 9.1, about 10.4, and about 25.1 degrees 2-theta. In some such embodiments, the present invention provides compound 2, wherein said compound has at least two peaks in its XRPD selected from those at about 9.1, about 10.4, and about 25.1 degrees 2-theta. In some such embodiments, the present invention provides compound 2, wherein said compound is of Form D.

In some embodiments, the present invention provides compound 2, wherein said compound has an XRPD substantially similar to that depicted in FIG. 25.

In some embodiments, the present invention provides a composition comprising compound 2 and a pharmaceutically acceptable carrier or excipient.

In some embodiments, the present invention provides a method of inhibiting one or both of ERK1 and ERK2 in a patient comprising administering to said patient compound 2 or composition thereof.

In some embodiments, the present invention provides a method of treating an ERK1- or ERK2-mediated disorder in a patient, comprising administering to said compound 2 or composition thereof. In some such embodiments, the ERK1- or ERK2-mediated disorder the disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Compound 3 (Bisphosphate Complexes of Compound 1)

According to one embodiment, the present invention provides a bisphosphate complex of compound 1, represented by compound 3:

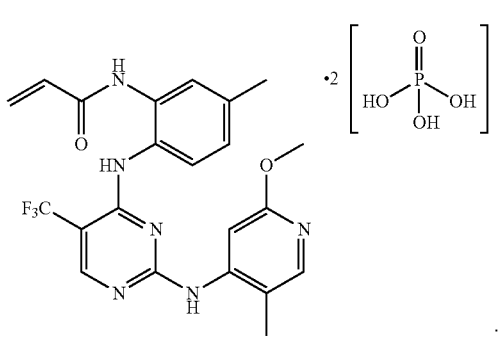

It will be appreciated by one of ordinary skill in the art that one molecule of phosphoric acid and compound 1 are ionically bonded, while the second molecule of phosphoric acid and compound 1 are likely hydrogen bonded, to form compound 3. It is contemplated that compound 3 can exist in a variety of physical forms. For example, compound 3 can be in solution, suspension, or in solid form. In certain embodiments, compound 3 is in solid form. When compound 3 is in solid form, said compound may be amorphous, crystalline, or a mixture thereof. Exemplary solid forms are described in more detail below. For purposes of clarity, it will be understood that compound 3, a bisphosphate complex of compound 1, comprises two molecules of phosphoric acid per molecule of compound 1.

In some embodiments, the present invention provides compound 3 substantially free of impurities. As used herein, the term "substantially free of impurities" means that the compound contains no significant amount of extraneous matter. Such extraneous matter may include excess phosphoric acid, excess compound 1, residual solvents, or any other impurities that may result from the preparation of, and/or isolation of, compound 3. In certain embodiments, at least about 95% by weight of compound 3 is present. In still other embodiments of the invention, at least about 99% by weight of compound 3 is present.

According to one embodiment, compound 3 is present in an amount of at least about 97, 97.5, 98.0, 98.5, 99, 99.5, 99.8 weight percent where the percentages are based on the total weight of the composition. According to another embodiment, compound 3 contains no more than about 3.0 area percent HPLC of total organic impurities and, in certain embodiments, no more than about 1.5 area percent HPLC total organic impurities relative to the total area of the HPLC chromatogram. In other embodiments, compound 3 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 3 is also meant to include all tautomeric forms of compound 3. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In certain embodiments, compound 3 is a crystalline solid. In other embodiments, compound 3 is a crystalline solid substantially free of amorphous compound 3. As used herein, the term "substantially free of amorphous compound 3" means that the compound contains no significant amount of amorphous compound 3. In certain embodiments, at least about 95% by weight of crystalline compound 3 is present. In still other embodiments of the invention, at least about 99% by weight of crystalline compound 3 is present.

It has been found that compound 3 can exist in at least one distinct crystalline form. In some embodiments, the present invention provides a crystalline form of Compound 3 referred to herein as Form A.

In some embodiments, compound 3 is amorphous. In some embodiments, compound 3 is amorphous, and is substantially free of crystalline compound 3.

Form A of Compound 3

In some embodiments, Form A of compound 3 has at least 1, 2, 3, 4 or 5 spectral peak(s) selected from the peaks listed in Table 9 below.

TABLE 9

XRPD Peak Positions for Form A of Compound 3
Position (°2 θ)

| |
|---|
| 5.7 |
| 7.1 |
| 8.9 |
| 10.3 |
| 11.0 |
| 11.4 |
| 13.2 |
| 14.2 |
| 14.5 |
| 17.2 |
| 17.7 |
| 18.4 |
| 19.4 |
| 19.9 |
| 20.6 |
| 20.8 |
| 22.1 |
| 22.5 |
| 24.3 |
| 25.5 |

[1] In this and all subsequent tables, the position 2 θ is within ±0.2.

In some embodiments, Form A of compound 3 is characterized in that it has one or more peaks in its X-ray powder diffraction pattern selected from those at about 8.9, 10.3, and 11.0. In some embodiments, Form A of compound 3 is characterized in that it has two or more peaks in its X-ray powder diffraction pattern selected from those at about 8.9, 10.3, and 11.0. In some embodiments, Form A of compound 3 is characterized in that it has all three peaks in its X-ray powder diffraction pattern selected from those at about 8.9, 10.3, and 11.0.

Figure 28:
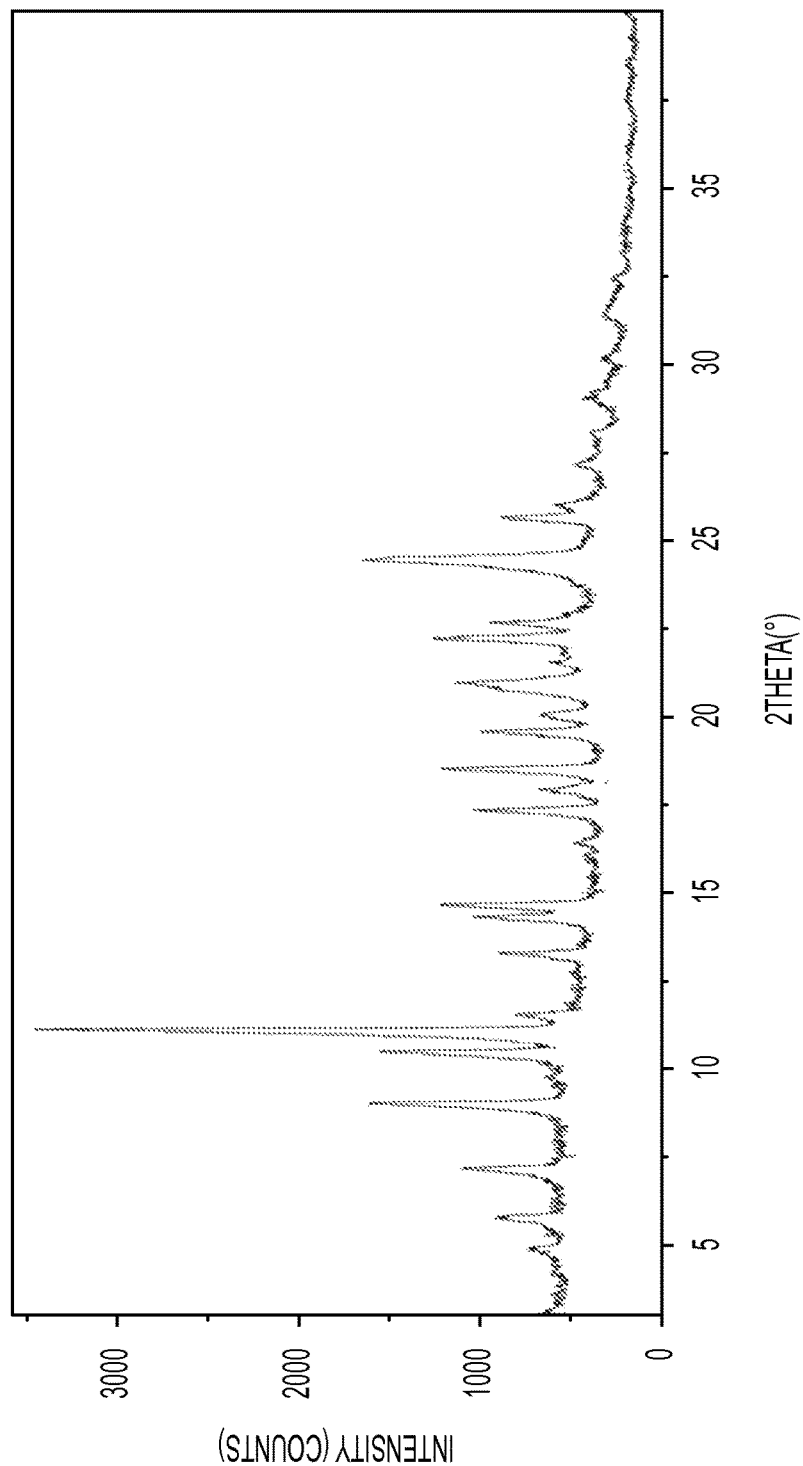
FIG. 28 depicts an XRPD pattern of Form A of compound 3.

In certain embodiments, the X-ray powder diffraction pattern is substantially similar to the XRPD provided in FIG. 28.

Methods for preparing Form A of compound 3 are described infra.

In some embodiments, the present invention provides compound 3:

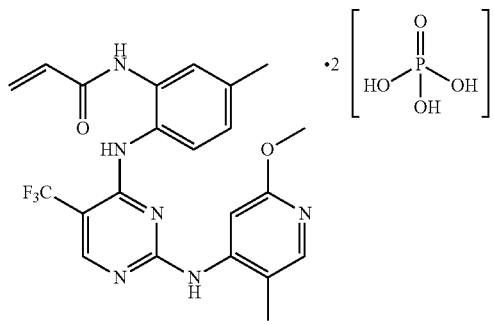

In some embodiments, the present invention provides compound 3, wherein said compound is crystalline.

In some embodiments, the present invention provides compound 3, wherein said compound is a crystalline solid substantially free of amorphous compound 3.

In some embodiments, the present invention provides compound 3, wherein said compound is substantially free of impurities.

In some embodiments, the present invention provides compound 3, wherein said compound has one or more peaks in its XRPD selected from those at about 8.9, about 10.3, and about 11.0 degrees 2-theta. In some such embodiments, the present invention provides compound 3, wherein said compound has at least two peaks in its XRPD selected from those at about 8.9, about 10.3, and about 11.0 degrees 2-theta. In some such embodiments, the present invention provides compound 3, wherein said compound is of Form A.

In some embodiments, the present invention provides compound 3, wherein said compound has an XRPD substantially similar to that depicted in FIG. 28.

In some embodiments, the present invention provides a composition comprising compound 3 and a pharmaceutically acceptable carrier or excipient.

In some embodiments, the present invention provides a method of inhibiting one or both of ERK1 and ERK2 in a patient comprising administering to said patient compound 3 or composition thereof. In some such embodiments, the present invention provides a method of treating an ERK1- or ERK2-mediated disorder in a patient, comprising administering to said patient compound 3 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Compound 4 (HCl Salts of Compound 1)

According to one embodiment, the present invention provides a hydrochloride salt of compound 1, represented by compound 4:

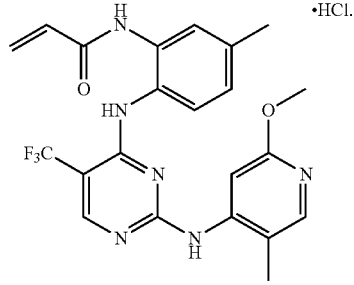

It will be appreciated by one of ordinary skill in the art that the hydrochloric acid and compound 1 are ionically bonded to form compound 4. It is contemplated that compound 4 can exist in a variety of physical forms. For example, compound 4 can be in solution, suspension, or in solid form. In certain embodiments, compound 4 is in solid form. When compound 4 is in solid form, said compound may be amorphous, crystalline, or a mixture thereof. Exemplary solid forms are described in more detail below.

In some embodiments, the present invention provides compound 4 substantially free of impurities. As used herein, the term "substantially free of impurities" means that the compound contains no significant amount of extraneous matter. Such extraneous matter may include excess hydrochloric acid, excess compound 1, residual solvents, or any other impurities that may result from the preparation of, and/or isolation of, compound 4. In certain embodiments, at least about 95% by weight of compound 4 is present. In still other embodiments of the invention, at least about 99% by weight of compound 4 is present.

According to one embodiment, compound 4 is present in an amount of at least about 97, 97.5, 98.0, 98.5, 99, 99.5, 99.8 weight percent where the percentages are based on the total weight of the composition. According to another embodiment, compound 4 contains no more than about 3.0 area percent HPLC of total organic impurities and, in certain embodiments, no more than about 1.5 area percent HPLC total organic impurities relative to the total area of the HPLC chromatogram. In other embodiments, compound 4 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 4 is also meant to include all tautomeric forms of compound 4. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 4 can exist in a variety of solid forms. Exemplary such forms include polymorphs such as those contemplated by the present invention.

In certain embodiments, compound 4 is a crystalline solid. In other embodiments, compound 4 is a crystalline solid substantially free of amorphous compound 4. As used herein, the term "substantially free of amorphous compound 4" means that the compound contains no significant amount of amorphous compound 4. In certain embodiments, at least about 95% by weight of crystalline compound 4 is present. In still other embodiments of the invention, at least about 99% by weight of crystalline compound 4 is present.

It has been found that compound 4 can exist in at least nine distinct polymorphic forms. In some embodiments, the present invention provides a polymorphic form of compound 4 referred to herein as Form A. In certain embodiments, the present invention provides a polymorphic form of compound 4 referred to herein as Form B. In certain embodiments, the present invention provides a polymorphic form of compound 4 referred to herein as Form C. In certain embodiments, the present invention provides a polymorphic form of compound 4 referred to herein as Form D. In certain embodiments, the present invention provides a polymorphic form of compound 4 referred to herein as Form E. In certain embodiments, the present invention provides a polymorphic form of compound 4 referred to herein as Form F. In certain embodiments, the present invention provides a polymorphic form of compound 4 referred to herein as Form G. In certain embodiments, the present invention provides a polymorphic form of compound 4 referred to herein as Form H. In certain embodiments, the present invention provides a polymorphic form of compound 4 referred to herein as Form I.

In some embodiments, compound 4 is amorphous. In some embodiments, compound 4 is amorphous, and is substantially free of crystalline compound 4.

Form A of Compound 4

In some embodiments, Form A of compound 4 has at least 1, 2, 3, 4 or 5 spectral peak(s) selected from the peaks listed in Table 10 below.

TABLE 10

| XRPD Peak Positions for Form A of Compound 4 Position (°2 θ) |
| --- |
| 7.5 |
| 9.3 |
| 11.2 |
| 11.9 |
| 14.2 |
| 15.0 |
| 15.3 |
| 15.7 |
| 21.4 |
| 21.9 |
| 22.6 |
| 22.8 |
| 23.4 |
| 24.6 |
| 24.8 |
| 25.2 |
| 26.4 |
| 26.8 |
| 30.5 |
| 34.1 |

[1] In this and all subsequent tables, the position 2 θ is within ±0.2.

In some embodiments, Form A of compound 4 is characterized in that it has one or more peaks in its X-ray powder diffraction pattern selected from those at about 9.3, 15.7, and 24.8. In some embodiments, Form A of compound 4 is characterized in that it has two or more peaks in its X-ray powder diffraction pattern selected from those at about 9.3, 15.7, and 24.8. In some embodiments, Form A of compound 4 is characterized in that it has all three peaks in its X-ray powder diffraction pattern selected from those at about 9.3, 15.7, and 24.8.

Figure 32:
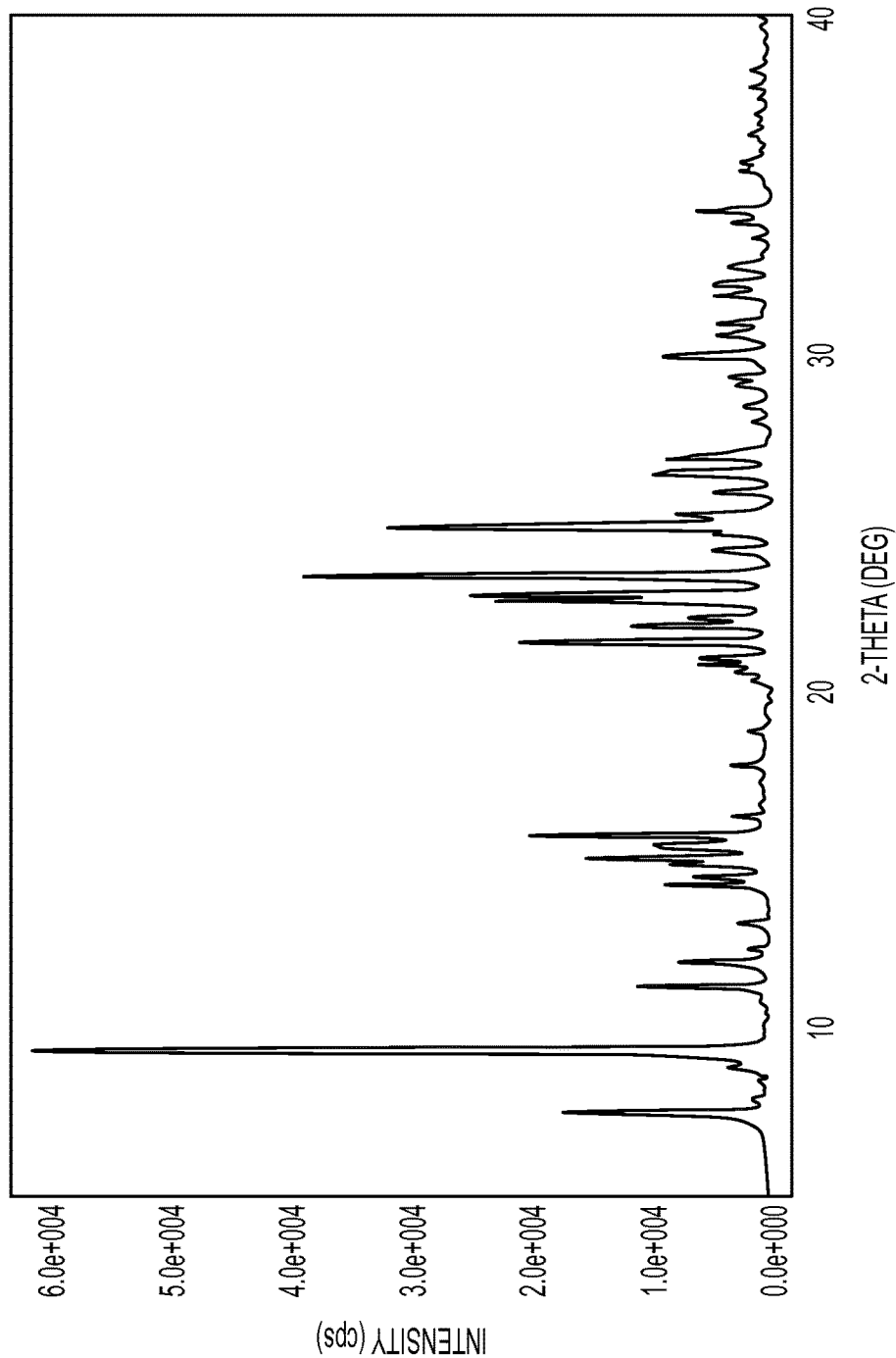
FIG. 32 depicts an XRPD pattern of Form A of compound 4.

In certain embodiments, the X-ray powder diffraction pattern is substantially similar to the XRPD provided in FIG. 32.

Methods for preparing Form A of compound 4 are described infra.

Form B of Compound 4

In some embodiments, Form B of compound 4 has at least 1, 2, 3, 4 or 5 spectral peak(s) selected from the peaks listed in Table 11 below.

TABLE 11

| XRPD Peak Positions for Form B of Compound 4 Position (°2 θ) |
| --- |
| 8.0 |
| 8.4 |
| 9.1 |
| 11.0 |
| 11.8 |
| 12.7 |
| 16.2 |
| 17.2 |
| 17.8 |
| 18.9 |
| 20.4 |
| 20.9 |
| 23.7 |
| 23.9 |
| 24.7 |
| 25.4 |
| 25.6 |
| 25.9 |
| 29.2 |
| 30.7 |

[1] In this and all subsequent tables, the position 2 θ is within ±0.2.

In some embodiments, Form B of compound 4 is characterized in that it has one or more peaks in its X-ray powder diffraction pattern selected from those at about 8.4, 12.7, and 17.8. In some embodiments, Form B of compound 4 is characterized in that it has two or more peaks in its X-ray powder diffraction pattern selected from those at about 8.4, 12.7, and 17.8. In some embodiments, Form B of compound 4 is characterized in that it has all three peaks in its X-ray powder diffraction pattern selected from those at about 8.4, 12.7, and 17.8.

Figure 36:
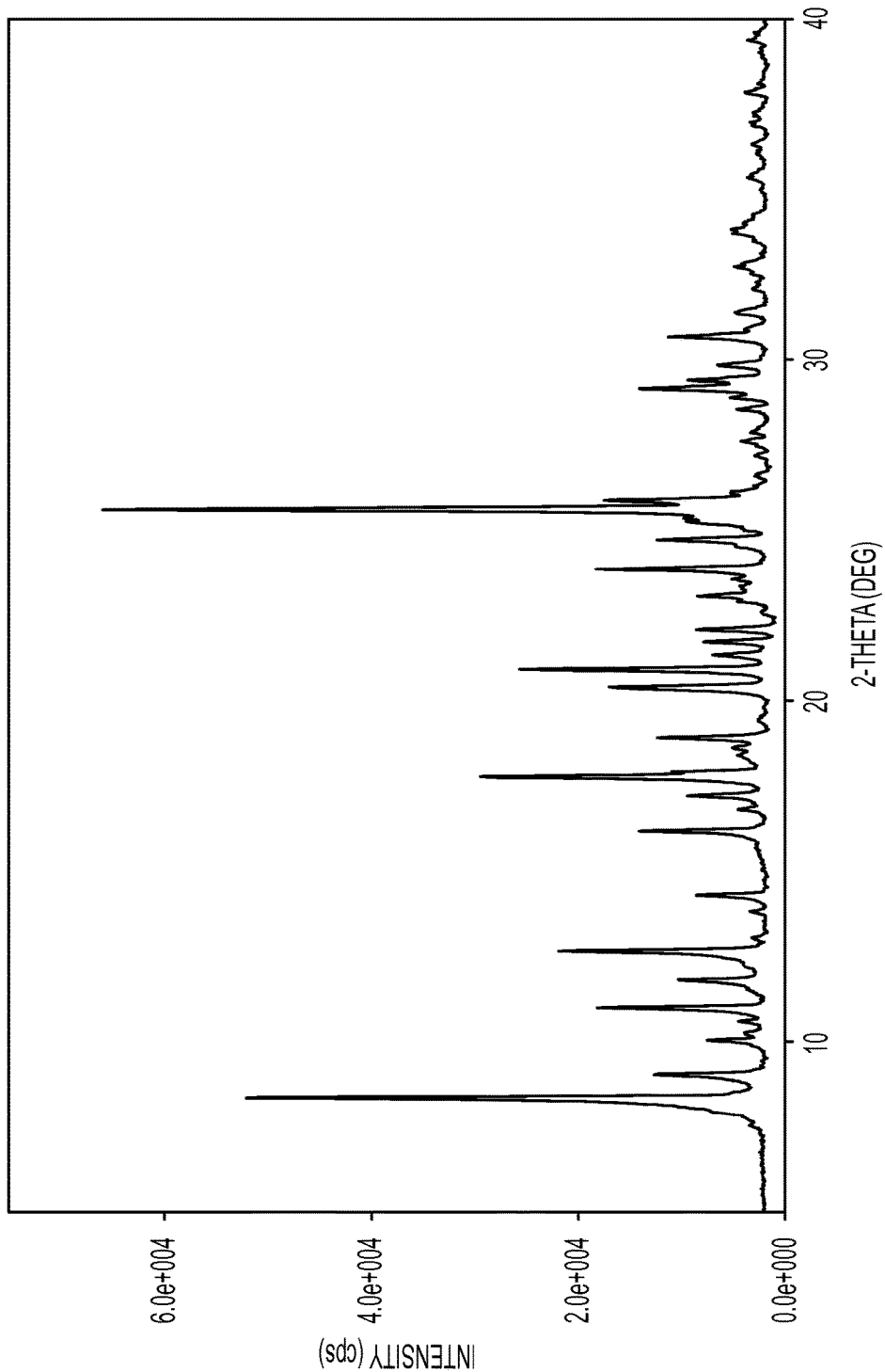
FIG. 36 depicts an XRPD pattern of Form B of compound 4.

In certain embodiments, the X-ray powder diffraction pattern is substantially similar to the XRPD provided in FIG. 36.

Methods for preparing Form B of compound 4 are described infra.

Form C of Compound 4

In some embodiments, Form C of compound 4 has at least 1, 2, 3, 4 or 5 spectral peak(s) selected from the peaks listed in Table 12 below.

TABLE 12

| XRPD Peak Positions for Form C of Compound 4 Position (°2 θ) |
| --- |
| 7.7 |
| 8.2 |
| 9.0 |
| 9.5 |
| 10.2 |
| 12.1 |
| 12.4 |
| 12.6 |
| 13.5 |
| 15.3 |
| 16.4 |
| 18.4 |
| 21.0 |
| 21.3 |
| 23.1 |

TABLE 12-continued

XRPD Peak Positions for Form C of Compound 4
Position (°2 θ)

23.4
23.7
24.2
25.5
25.7

[1] In this and all subsequent tables, the position 2 θ is within ±0.2.

In some embodiments, Form C of compound 4 is characterized in that it has one or more peaks in its X-ray powder diffraction pattern selected from those at about 7.7, 8.2, and 9.0. In some embodiments, Form C of compound 4 is characterized in that it has two or more peaks in its X-ray powder diffraction pattern selected from those at about 7.7, 8.2, and 9.0. In some embodiments, Form C of compound 4 is characterized in that it has all three peaks in its X-ray powder diffraction pattern selected from those at about 7.7, 8.2, and 9.0.

Figure 38:
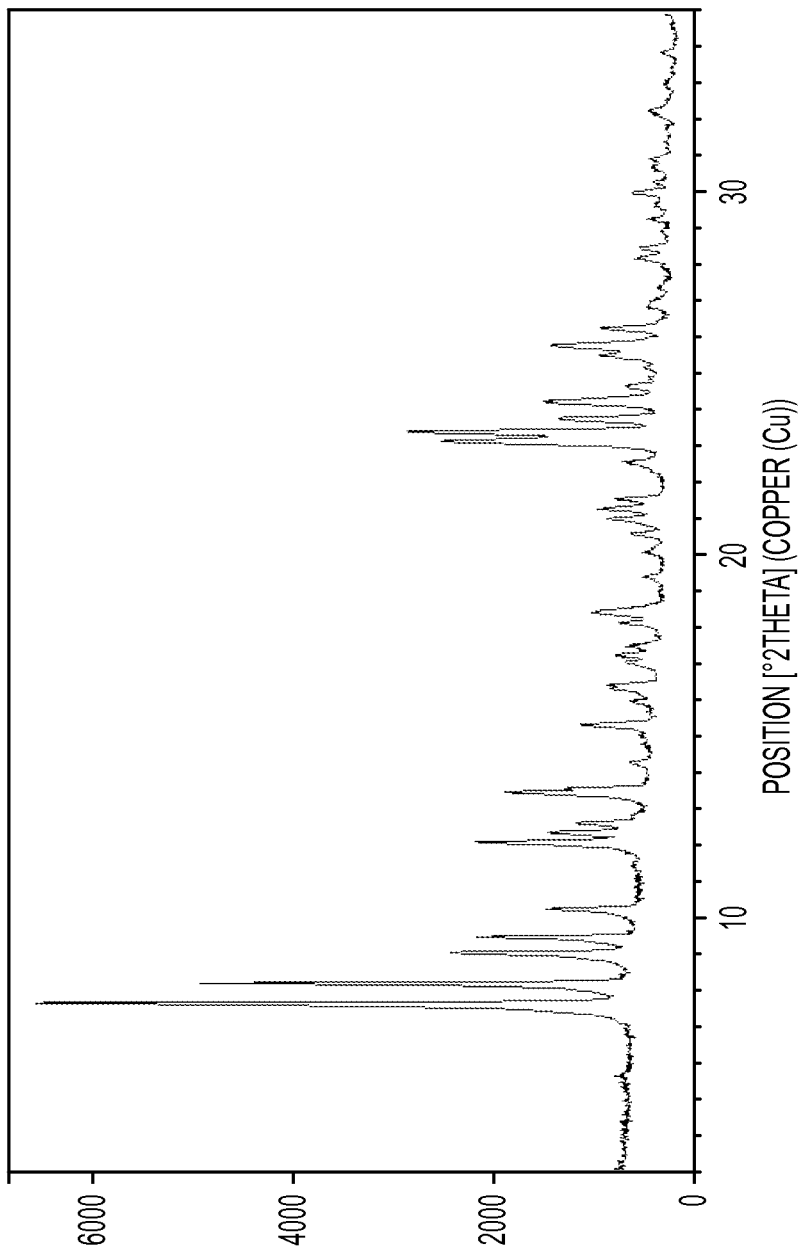
FIG. 38 depicts an XRPD pattern of Form C of compound 4.

In certain embodiments, the X-ray powder diffraction pattern is substantially similar to the XRPD provided in FIG. 38.

Methods for preparing Form C of compound 4 are described infra.

Form D of Compound 4

In some embodiments, Form D of compound 4 has at least 1, 2, 3, 4 or 5 spectral peak(s) selected from the peaks listed in Table 13 below.

TABLE 13

XRPD Peak Positions for Form D of Compound 4
Position (°2 θ)

7.1
9.1
11.2
12.7
14.0
14.4
14.6
17.0
17.2
21.7
22.0
22.4
22.8
23.7
24.8
25.3
25.5
28.0
34.2
35.7

[1] In this and all subsequent tables, the position 2 θ is within ±0.2.

In some embodiments, Form D of compound 4 is characterized in that it has one or more peaks in its X-ray powder diffraction pattern selected from those at about 7.1, 9.1, and 11.2. In some embodiments, Form D of compound 4 is characterized in that it has two or more peaks in its X-ray powder diffraction pattern selected from those at about 7.1, 9.1, and 11.2. In some embodiments, Form D of compound 4 is characterized in that it has all three peaks in its X-ray powder diffraction pattern selected from those at about 7.1, 9.1, and 11.2.

Figure 40:
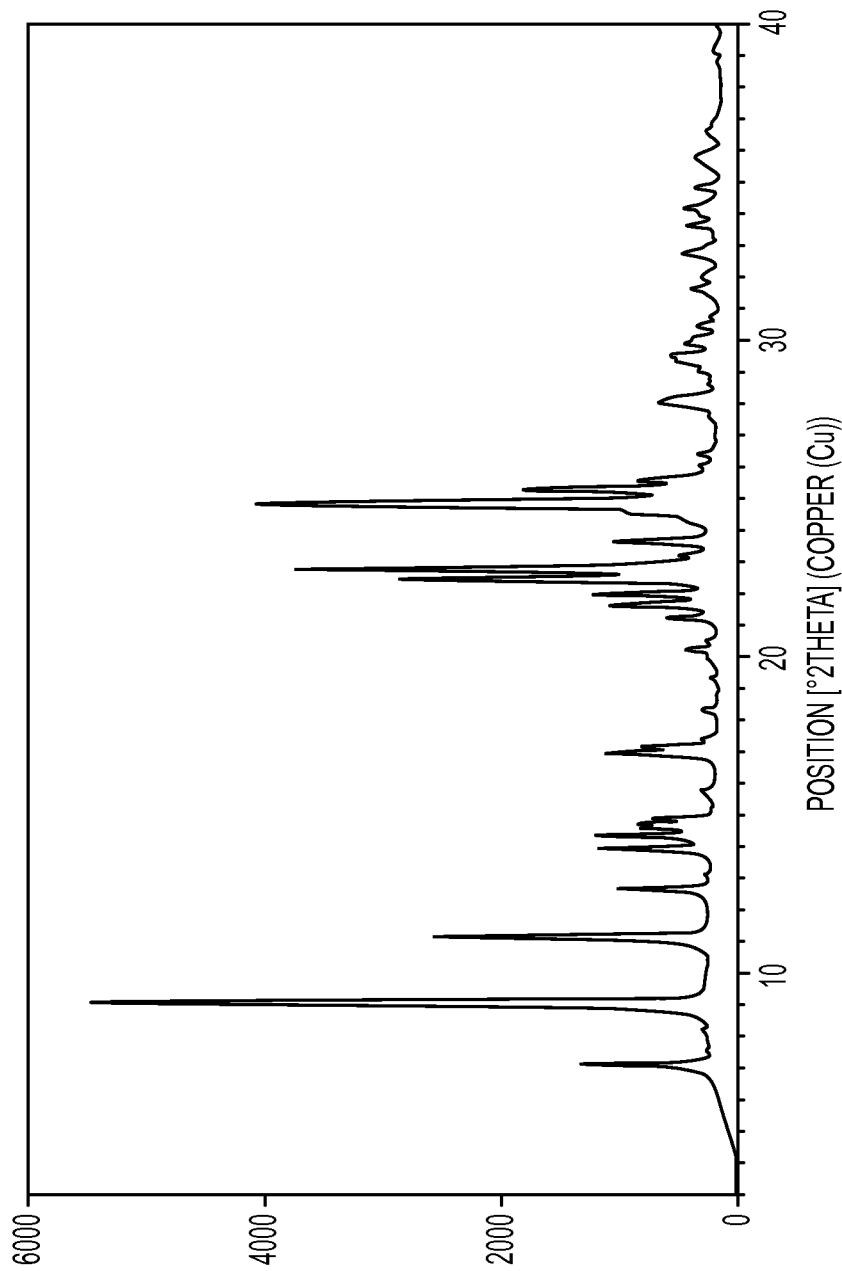
FIG. 40 depicts an XRPD pattern of Form D of compound 4.

In certain embodiments, the X-ray powder diffraction pattern is substantially similar to the XRPD provided in FIG. 40.

Methods for preparing Form D of compound 4 are described infra.

Form E of Compound 4

In some embodiments, Form E of compound 4 has at least 1, 2, 3, 4 or 5 spectral peak(s) selected from the peaks listed in Table 14 below.

TABLE 14

XRPD Peak Positions for Form E of Compound 4
Position (°2 θ)

7.7
9.0
10.7
14.4
15.5
17.1
18.2
19.8
20.4
21.5
23.1
24.4
24.6
25.0
27.0
27.3
28.1
30.9
31.2
37.6

[1] In this and all subsequent tables, the position 2 θ is within ±0.2.

In some embodiments, Form E of compound 4 is characterized in that it has one or more peaks in its X-ray powder diffraction pattern selected from those at about 7.7, 10.7, and 17.1. In some embodiments, Form E of compound 4 is characterized in that it has two or more peaks in its X-ray powder diffraction pattern selected from those at about 7.7, 10.7, and 17.1. In some embodiments, Form E of compound 4 is characterized in that it has all three peaks in its X-ray powder diffraction pattern selected from those at about 7.7, 10.7, and 17.1.

Figure 44:
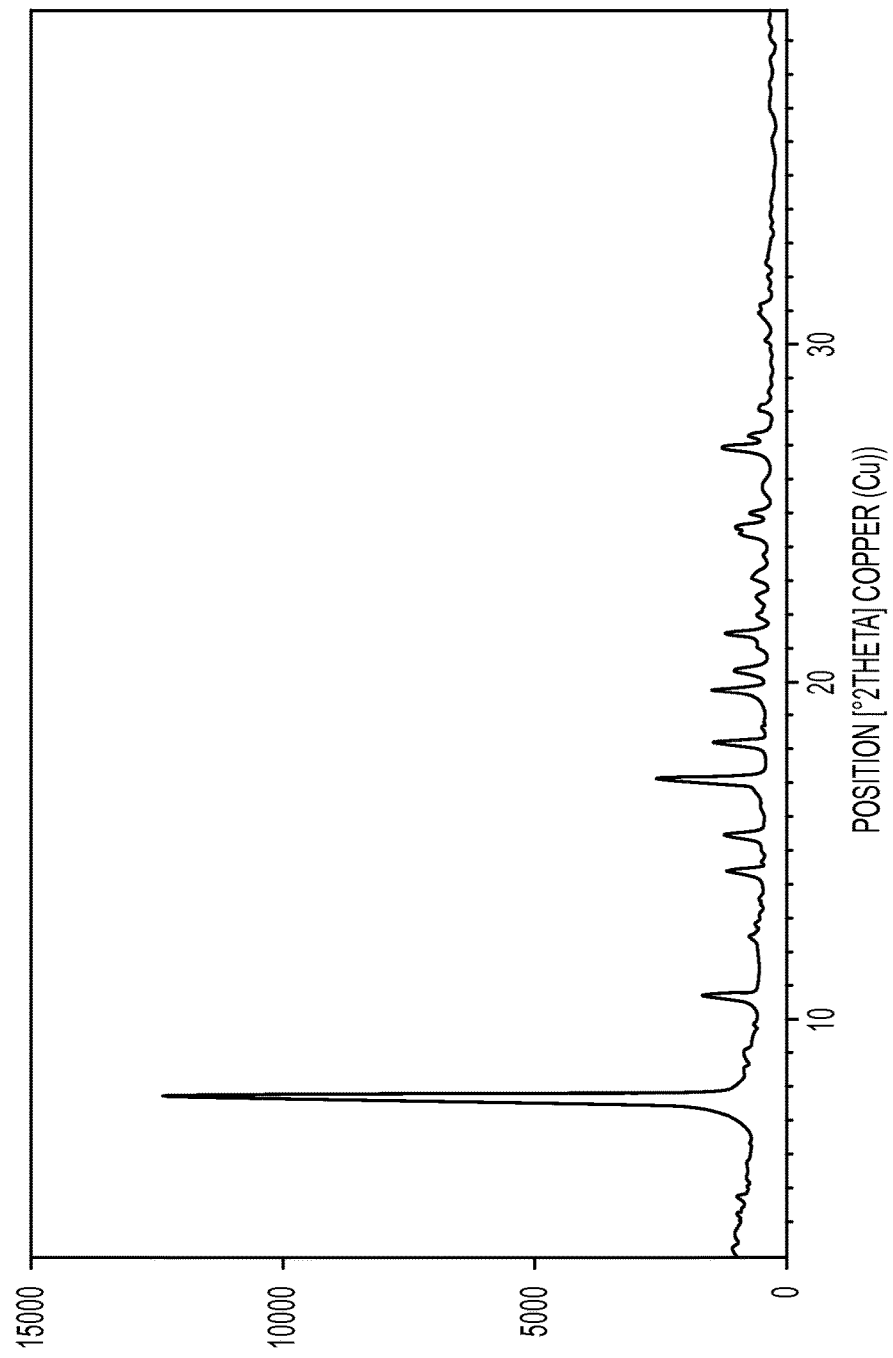
FIG. 44 depicts an XRPD pattern of Form E of compound 4.

In certain embodiments, the X-ray powder diffraction pattern is substantially similar to the XRPD provided in FIG. 44.

Methods for preparing Form E of compound 4 are described infra.

Form F of Compound 4

In some embodiments, Form F of compound 4 has at least 1, 2, 3, 4 or 5 spectral peak(s) selected from the peaks listed in Table 15 below.

TABLE 15

XRPD Peak Positions for Form F of Compound 4
Position (°2 θ)

6.1
7.7
11.3
12.4
13.8
15.4
16.9
17.7
18.6
19.5
22.6
22.9
23.1
23.6
24.9

TABLE 15-continued

XRPD Peak Positions for Form F of Compound 4
Position (°2 θ)

| |
|---|
| 25.7 |
| 26.1 |
| 30.2 |
| 34.2 |
| 35.0 |

[1] In this and all subsequent tables, the position 2 θ is within ±0.2.

In some embodiments, Form F of compound 4 is characterized in that it has one or more peaks in its X-ray powder diffraction pattern selected from those at about 6.1, 11.3, and 18.6. In some embodiments, Form F of compound 4 is characterized in that it has two or more peaks in its X-ray powder diffraction pattern selected from those at about 6.1, 11.3, and 18.6. In some embodiments, Form F of compound 4 is characterized in that it has all three peaks in its X-ray powder diffraction pattern selected from those at about 6.1, 11.3, and 18.6.

Figure 46:
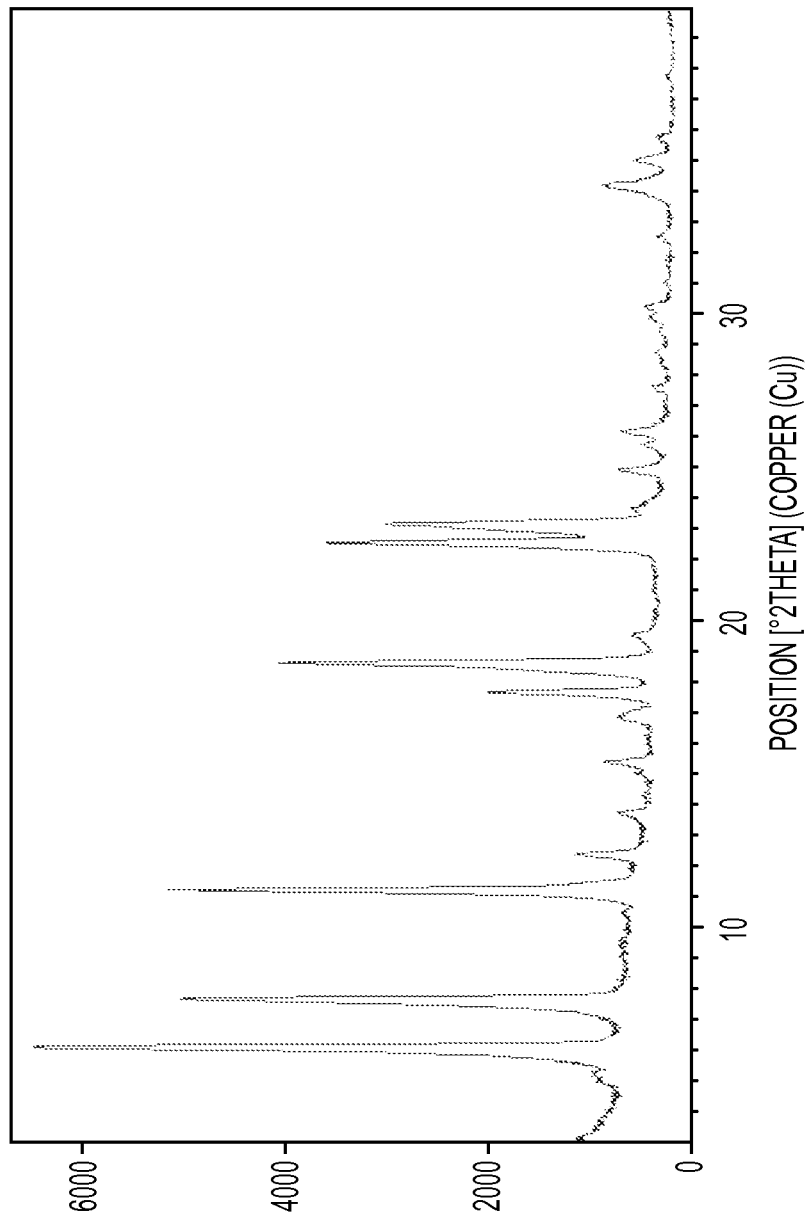
FIG. 46 depicts an XRPD pattern of Form F of compound 4.

In certain embodiments, the X-ray powder diffraction pattern is substantially similar to the XRPD provided in FIG. 46.

Methods for preparing Form F of compound 4 are described infra.

Form G of Compound 4

In some embodiments, Form G of compound 4 has at least 1, 2, 3, 4 or 5 spectral peak(s) selected from the peaks listed in Table 16 below.

TABLE 16

XRPD Peak Positions for Form G of Compound 4
Position (°2 θ)

| |
|---|
| 5.2 |
| 8.5 |
| 8.7 |
| 10.5 |
| 14.8 |
| 15.6 |
| 19.0 |
| 19.5 |
| 20.7 |
| 21.0 |
| 21.9 |
| 22.2 |
| 23.3 |
| 25.7 |
| 27.0 |
| 27.4 |
| 29.6 |
| 30.7 |
| 31.3 |

[1] In this and all subsequent tables, the position 2 θ is within ±0.2.

In some embodiments, Form G of compound 4 is characterized in that it has one or more peaks in its X-ray powder diffraction pattern selected from those at about 5.2, 8.7, and 19.5. In some embodiments, Form G of compound 4 is characterized in that it has two or more peaks in its X-ray powder diffraction pattern selected from those at about 5.2, 8.7, and 19.5. In some embodiments, Form G of compound 4 is characterized in that it has all three peaks in its X-ray powder diffraction pattern selected from those at about 5.2, 8.7, and 19.5.

Figure 48:
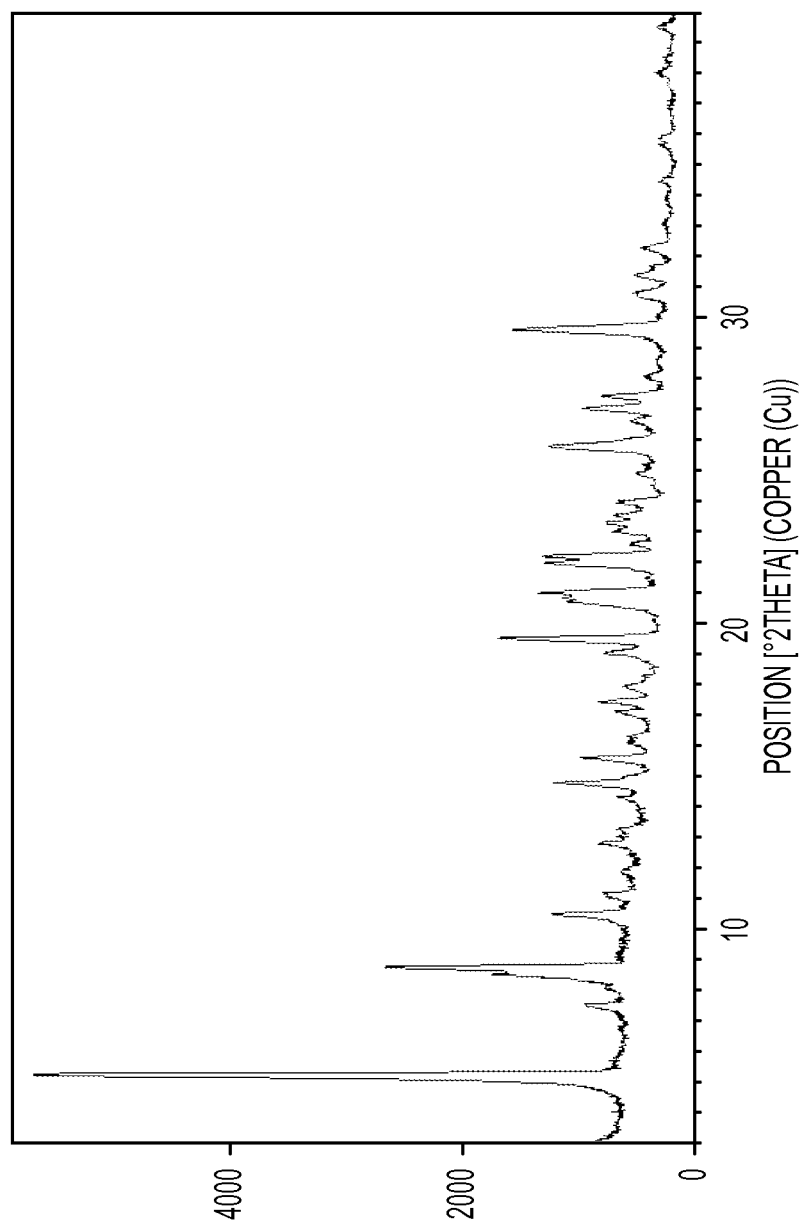
FIG. 48 depicts an XRPD pattern of Form G of compound 4.

In certain embodiments, the X-ray powder diffraction pattern is substantially similar to the XRPD provided in FIG. 48.

Methods for preparing Form G of compound 4 are described infra.

Form H of Compound 4

In some embodiments, Form H of compound 4 has at least 1, 2, 3, 4 or 5 spectral peak(s) selected from the peaks listed in Table 17 below.

TABLE 17

XRPD Peak Positions for Form H of Compound 4
Position (°2 θ)

| |
|---|
| 7.2 |
| 8.5 |
| 9.1 |
| 10.2 |
| 13.1 |
| 14.5 |
| 15.8 |
| 18.1 |
| 18.8 |
| 20.5 |
| 21.0 |
| 21.7 |
| 22.5 |
| 23.3 |
| 24.2 |
| 24.6 |
| 25.3 |
| 25.8 |
| 28.8 |
| 29.9 |

[1] In this and all subsequent tables, the position 2 θ is within ±0.2.

In some embodiments, Form H of compound 4 is characterized in that it has one or more peaks in its X-ray powder diffraction pattern selected from those at about 8.5, 9.1, and 10.2. In some embodiments, Form H of compound 4 is characterized in that it has two or more peaks in its X-ray powder diffraction pattern selected from those at about 8.5, 9.1, and 10.2. In some embodiments, Form H of compound 4 is characterized in that it has all three peaks in its X-ray powder diffraction pattern selected from those at about 8.5, 9.1, and 10.2.

Figure 50:
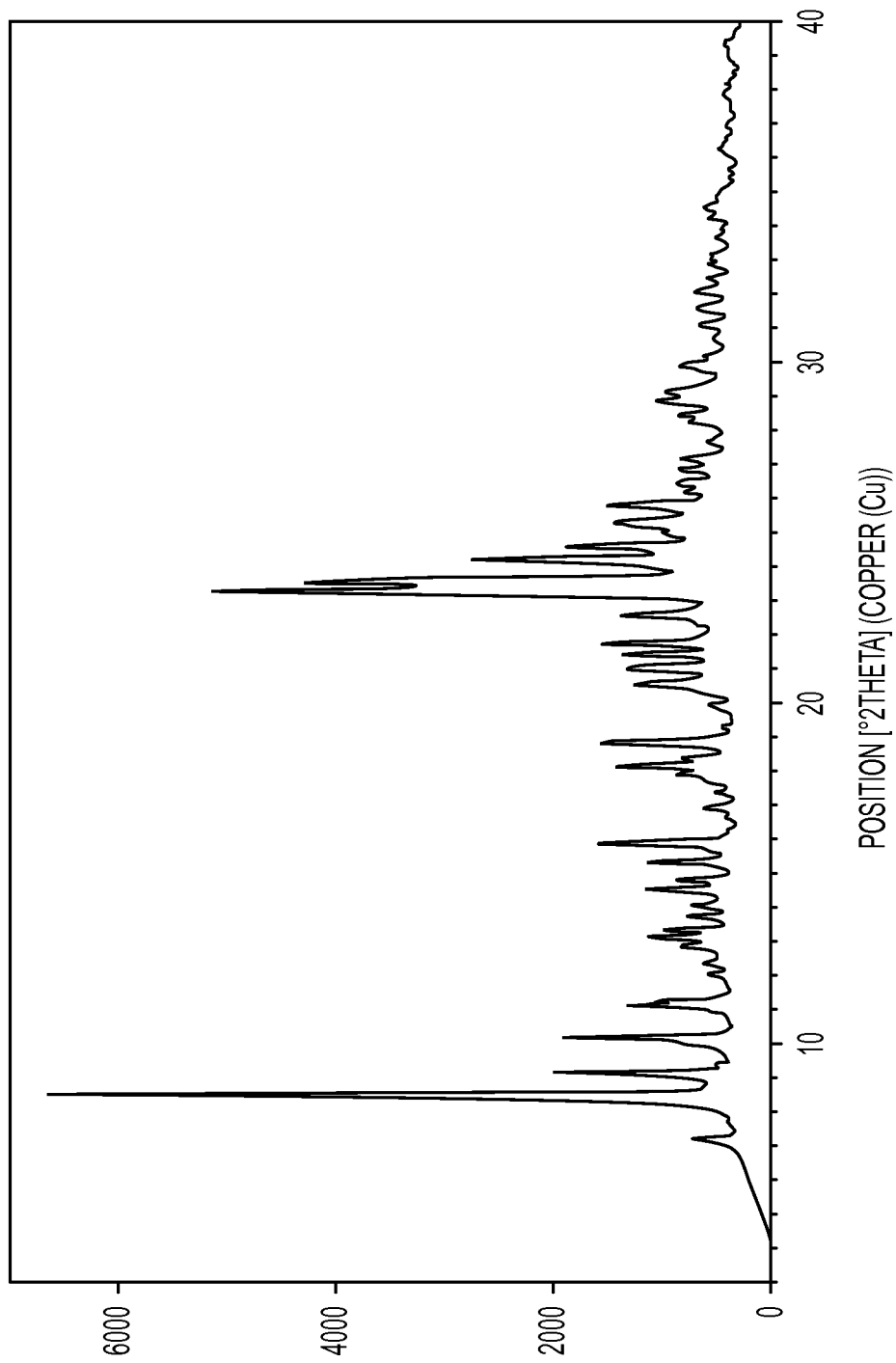
FIG. 50 depicts an XRPD pattern of Form H of compound 4.

In certain embodiments, the X-ray powder diffraction pattern is substantially similar to the XRPD provided in FIG. 50.

Methods for preparing Form H of compound 4 are described infra.

Form I of Compound 4

In some embodiments, Form I of compound 4 has at least 1, 2, 3, 4 or 5 spectral peak(s) selected from the peaks listed in Table 18 below.

TABLE 18

XRPD Peak Positions for Form I of Compound 4
Position (°2 θ)

| |
|---|
| 4.7 |
| 7.1 |
| 9.3 |
| 10.8 |
| 11.9 |
| 14.1 |
| 15.0 |
| 16.7 |
| 18.8 |
| 20.3 |
| 21.1 |
| 22.2 |
| 23.1 |
| 23.5 |
| 24.2 |

TABLE 18-continued

XRPD Peak Positions for Form I of Compound 4
Position (°2 θ)

25.4
26.0
29.1

[1] In this and all subsequent tables, the position 2 θ is within ±0.2.

In some embodiments, Form I of compound 4 is characterized in that it has one or more peaks in its X-ray powder diffraction pattern selected from those at about 4.7, 7.1, and 9.3. In some embodiments, Form I of compound 4 is characterized in that it has two or more peaks in its X-ray powder diffraction pattern selected from those at about 4.7, 7.1, and 9.3. In some embodiments, Form I of compound 4 is characterized in that it has all three peaks in its X-ray powder diffraction pattern selected from those at about 4.7, 7.1, and 9.3.

Figure 52:
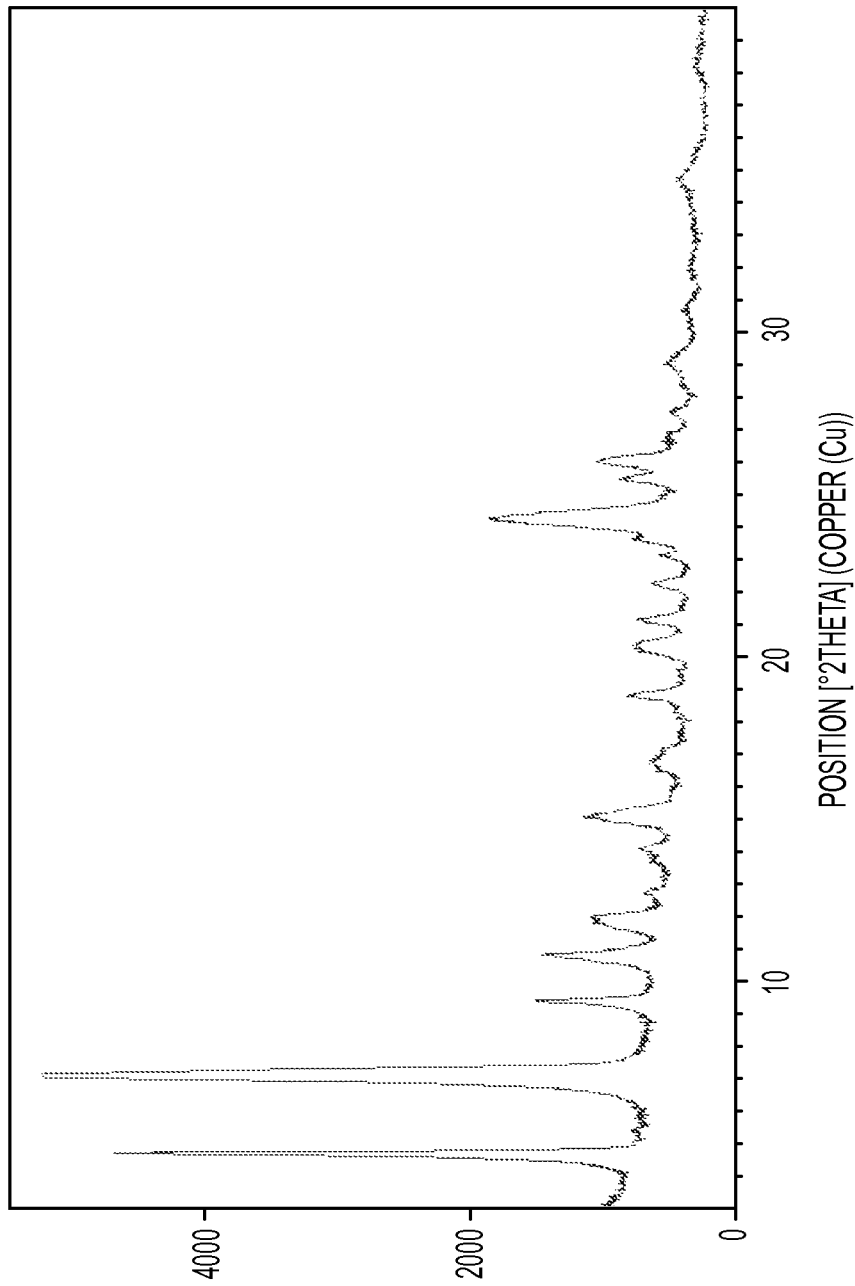
FIG. 52 depicts an XRPD pattern of Form I of compound 4.

In certain embodiments, the X-ray powder diffraction pattern is substantially similar to the XRPD provided in FIG. 52.

Methods for preparing Form I of compound 4 are described infra.

In some embodiments, the present invention provides compound 4:

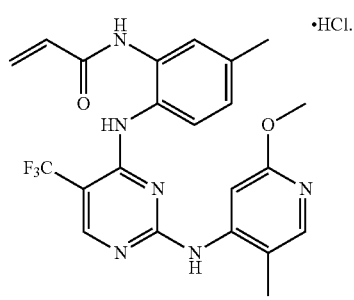

4
·HCl.

In some embodiments, the present invention provides compound 4, wherein said compound is crystalline.

In some embodiments, the present invention provides compound 4, wherein said compound is a crystalline solid substantially free of amorphous compound 4.

In some embodiments, the present invention provides compound 4, wherein said compound is substantially free of impurities.

In some embodiments, the present invention provides compound 4, wherein said compound has one or more peaks in its XRPD selected from those at about 9.3, about 15.7, and about 24.8 degrees 2-theta. In some such embodiments, the present invention provides compound 4, wherein said compound has at least two peaks in its XRPD selected from those at about 9.3, about 15.7, and about 24.8 degrees 2-theta. In some such embodiments, the present invention provides compound 4, wherein said compound is of Form A.

In some embodiments, the present invention provides compound 4, wherein said compound has an XRPD substantially similar to that depicted in FIG. 32.

In some embodiments, the present invention provides compound 4, wherein said compound has one or more peaks in its XRPD selected from those at about 8.4, about 12.7, and about 17.8 degrees 2-theta. In some such embodiments, the present invention provides compound 4, wherein said compound has at least two peaks in its XRPD selected from those at about 8.4, about 12.7, and about 17.8 degrees 2-theta. In some such embodiments, the present invention provides compound 4, wherein said compound is of Form B.

In some embodiments, the present invention provides compound 4, wherein said compound has an XRPD substantially similar to that depicted in FIG. 36.

In some embodiments, the present invention provides compound 4, wherein said compound has one or more peaks in its XRPD selected from those at about 7.7, about 8.2, and about 9.0 degrees 2-theta. In some such embodiments, the present invention provides compound 4, wherein said compound has at least two peaks in its XRPD selected from those at about 7.7, about 8.2, and about 9.0 degrees 2-theta. In some such embodiments, the present invention provides compound 4, wherein said compound is of Form C.

In some embodiments, the present invention provides compound 4, wherein said compound has an XRPD substantially similar to that depicted in FIG. 38.

In some embodiments, the present invention provides compound 4, wherein said compound has one or more peaks in its XRPD selected from those at about 7.1, about 9.1, and about 11.2 degrees 2-theta. In some such embodiments, the present invention provides compound 4, wherein said compound has at least two peaks in its XRPD selected from those at about 7.1, about 9.1, and about 11.2 degrees 2-theta. In some such embodiments, the present invention provides compound 4, wherein said compound is of Form D.

In some embodiments, the present invention provides compound 4, wherein said compound has an XRPD substantially similar to that depicted in FIG. 40.

In some embodiments, the present invention provides compound 4, wherein said compound has one or more peaks in its XRPD selected from those at about 7.7, about 10.7, and about 17.1 degrees 2-theta. In some such embodiments, the present invention provides compound 4, wherein said compound has at least two peaks in its XRPD selected from those at about 7.7, about 10.7, and about 17.1 degrees 2-theta. In some such embodiments, the present invention provides compound 4, wherein said compound is of Form E.

In some embodiments, the present invention provides compound 4, wherein said compound has an XRPD substantially similar to that depicted in FIG. 44.

In some embodiments, the present invention provides compound 4, wherein said compound has one or more peaks in its XRPD selected from those at about 6.1, about 11.3, and about 18.6 degrees 2-theta. In some such embodiments, the present invention provides compound 4, wherein said compound has at least two peaks in its XRPD selected from those at about 6.1, about 11.3, and about 18.6 degrees 2-theta. In some such embodiments, the present invention provides compound 4, wherein said compound is of Form F.

In some embodiments, the present invention provides compound 4, wherein said compound has an XRPD substantially similar to that depicted in FIG. 46.

In some embodiments, the present invention provides compound 4, wherein said compound has one or more peaks in its XRPD selected from those at about 5.2, about 8.7, and about 19.5 degrees 2-theta. In some such embodiments, the present invention provides compound 4, wherein said compound has at least two peaks in its XRPD selected from those at about 5.2, about 8.7, and about 19.5 degrees 2-theta. In some such embodiments, the present invention provides compound 4, wherein said compound is of Form G.

In some embodiments, the present invention provides compound 4, wherein said compound has an XRPD substantially similar to that depicted in FIG. 48.

In some embodiments, the present invention provides compound 4, wherein said compound has one or more peaks in its XRPD selected from those at about 8.5, about 9.1, and about 10.2 degrees 2-theta. In some such embodiments, the present invention provides compound 4, wherein said compound has at least two peaks in its XRPD selected from those at about 8.5, about 9.1, and about 10.2 degrees 2-theta. In some such embodiments, the present invention provides compound 4, wherein said compound is of Form H.

In some embodiments, the present invention provides compound 4, wherein said compound has an XRPD substantially similar to that depicted in FIG. 50.

In some embodiments, the present invention provides compound 4, wherein said compound has one or more peaks in its XRPD selected from those at about 4.7, about 7.1, and about 9.3 degrees 2-theta. In some such embodiments, the present invention provides compound 4, wherein said compound has at least two peaks in its XRPD selected from those at about 4.7, about 7.1, and about 9.3 degrees 2-theta. In some such embodiments, the present invention provides compound 4, wherein said compound is of Form I.

In some embodiments, the present invention provides compound 4, wherein said compound has an XRPD substantially similar to that depicted in FIG. 52.

In some embodiments, the present invention provides a composition comprising compound 4 and a pharmaceutically acceptable carrier or excipient.

In some embodiments, the present invention provides a method of inhibiting one or both of ERK1 and ERK2 in a patient comprising administering to said patient compound 4 or composition thereof.

In some embodiments, the present invention provides a method of treating an ERK1- or ERK2-mediated disorder in a patient, comprising administering to said patient compound 4 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Compound 5 (HBr Salts of Compound 1)

According to one embodiment, the present invention provides a hydrobromide salt of compound 1, represented by compound 5:

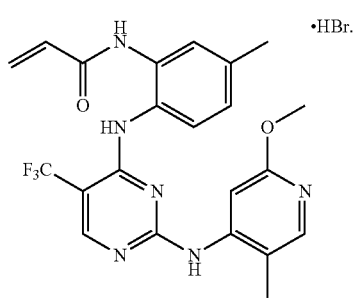

5

It will be appreciated by one of ordinary skill in the art that the hydrobromic acid and compound 1 are ionically bonded to form compound 5. It is contemplated that compound 5 can exist in a variety of physical forms. For example, compound 5 can be in solution, suspension, or in solid form. In certain embodiments, compound 5 is in solid form. When compound 5 is in solid form, said compound may be amorphous, crystalline, or a mixture thereof. Exemplary solid forms are described in more detail below.

In some embodiments, the present invention provides compound 5 substantially free of impurities. As used herein, the term "substantially free of impurities" means that the compound contains no significant amount of extraneous matter. Such extraneous matter may include excess hydrobromic acid, excess compound 1, residual solvents, or any other impurities that may result from the preparation of, and/or isolation of, compound 5. In certain embodiments, at least about 95% by weight of compound 5 is present. In still other embodiments of the invention, at least about 99% by weight of compound 5 is present.

According to one embodiment, compound 5 is present in an amount of at least about 97, 97.5, 98.0, 98.5, 99, 99.5, 99.8 weight percent where the percentages are based on the total weight of the composition. According to another embodiment, compound 5 contains no more than about 3.0 area percent HPLC of total organic impurities and, in certain embodiments, no more than about 1.5 area percent HPLC total organic impurities relative to the total area of the HPLC chromatogram. In other embodiments, compound 5 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 5 is also meant to include all tautomeric forms of compound 5. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 5 can exist in a variety of solid forms. Exemplary such forms include polymorphs such as those contemplated by the present invention.

In certain embodiments, compound 5 is a crystalline solid. In other embodiments, compound 5 is a crystalline solid substantially free of amorphous compound 5. As used herein, the term "substantially free of amorphous compound 5" means that the compound contains no significant amount of amorphous compound 5. In certain embodiments, at least about 95% by weight of crystalline compound 5 is present. In still other embodiments of the invention, at least about 99% by weight of crystalline compound 5 is present.

It has been found that compound 5 can exist in at least five distinct polymorphic forms. In some embodiments, the present invention provides a polymorphic form of compound 5 referred to herein as Form A. In certain embodiments, the present invention provides a polymorphic form of compound 5 referred to herein as Form B. In certain embodiments, the present invention provides a polymorphic form of compound 5 referred to herein as Form C. In certain embodiments, the present invention provides a polymorphic form of compound 5 referred to herein as Form D. In certain embodiments, the present invention provides a polymorphic form of compound 5 referred to herein as Form E.

In some embodiments, compound 5 is amorphous. In some embodiments, compound 5 is amorphous, and is substantially free of crystalline compound 5.

Form A of Compound 5

In some embodiments, Form A of compound 5 has at least 1, 2, 3, 4 or 5 spectral peak(s) selected from the peaks listed in Table 19 below.

TABLE 19

| XRPD Peak Positions for Form A of Compound 5 Position (°2 θ) |
|---|
| 7.5 |
| 9.5 |
| 11.3 |
| 13.0 |
| 14.3 |
| 14.7 |
| 15.0 |
| 15.7 |
| 17.3 |
| 20.3 |
| 20.9 |
| 21.6 |
| 22.6 |
| 23.2 |
| 23.7 |
| 24.8 |
| 26.0 |
| 28.8 |
| 30.5 |
| 33.8 |

[1] In this and all subsequent tables, the position 2 θ is within ±0.2.

In some embodiments, Form A of compound 5 is characterized in that it has one or more peaks in its X-ray powder diffraction pattern selected from those at about 9.5, 22.6, and 24.8. In some embodiments, Form A of compound 5 is characterized in that it has two or more peaks in its X-ray powder diffraction pattern selected from those at about 9.5, 22.6, and 24.8. In some embodiments, Form A of compound 5 is characterized in that it has all three peaks in its X-ray powder diffraction pattern selected from those at about 9.5, 22.6, and 24.8.

Figure 53:
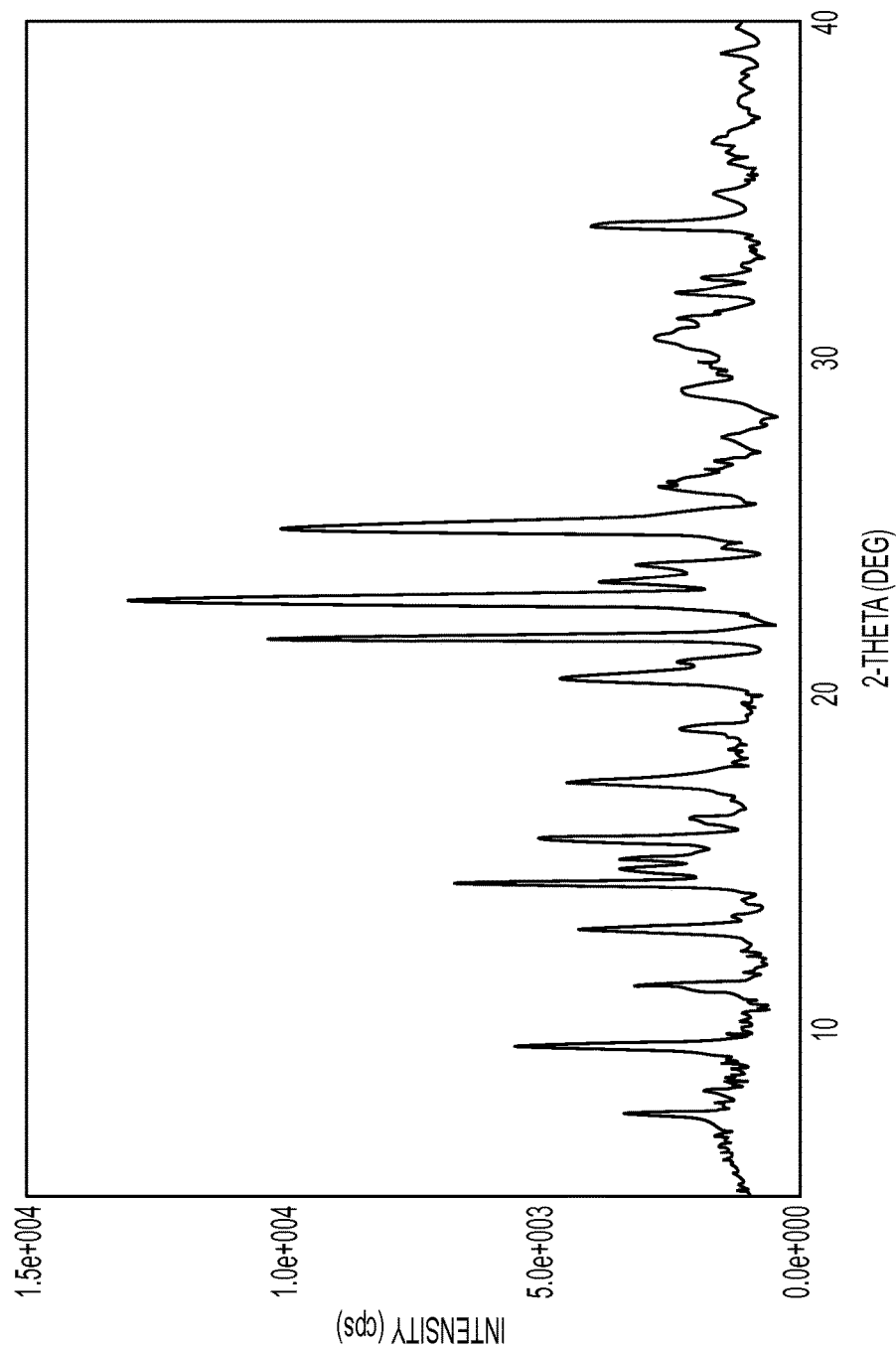
FIG. 53 depicts an XRPD pattern of Form A of compound 5.

In certain embodiments, the X-ray powder diffraction pattern is substantially similar to the XRPD provided in FIG. 53.

Methods for preparing Form A of compound 5 are described infra.

Form B of Compound 5

In some embodiments, Form B of compound 5 has at least 1, 2, 3, 4 or 5 spectral peak(s) selected from the peaks listed in Table 20 below.

TABLE 20

| XRPD Peak Positions for Form B of Compound 5 Position (°2 θ) |
|---|
| 8.3 |
| 11.8 |
| 12.3 |
| 14.2 |
| 16.2 |
| 17.9 |
| 18.7 |
| 18.9 |
| 20.3 |
| 20.5 |
| 20.8 |
| 21.1 |
| 23.8 |
| 24.5 |
| 25.5 |
| 25.7 |
| 26.3 |
| 29.2 |

TABLE 20-continued

| XRPD Peak Positions for Form B of Compound 5 Position (°2 θ) |
|---|
| 30.7 |
| 31.9 |

[1] In this and all subsequent tables, the position 2 θ is within ±0.2.

In some embodiments, Form B of compound 5 is characterized in that it has one or more peaks in its X-ray powder diffraction pattern selected from those at about 8.3, 17.9, and 25.5. In some embodiments, Form B of compound 5 is characterized in that it has two or more peaks in its X-ray powder diffraction pattern selected from those at about 8.3, 17.9, and 25.5. In some embodiments, Form B of compound 5 is characterized in that it has all three peaks in its X-ray powder diffraction pattern selected from those at about 8.3, 17.9, and 25.5.

Figure 57:
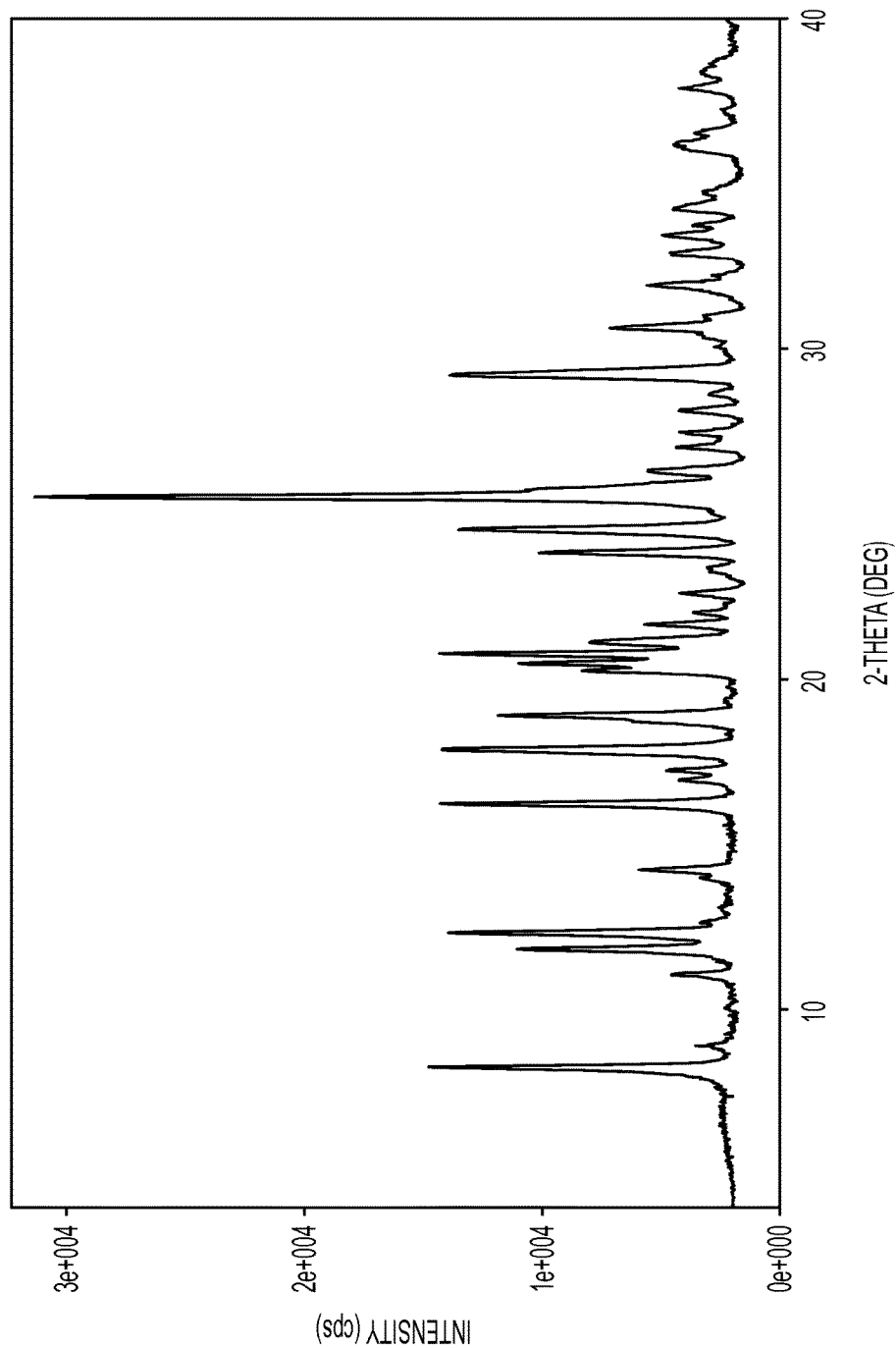
FIG. 57 depicts an XRPD pattern of Form B of compound 5.

In certain embodiments, the X-ray powder diffraction pattern is substantially similar to the XRPD provided in FIG. 57.

Methods for preparing Form B of compound 5 are described infra.

Form C of Compound 5

In some embodiments, Form C of compound 5 has at least 1, 2, 3, 4 or 5 spectral peak(s) selected from the peaks listed in Table 21 below.

TABLE 21

| XRPD Peak Positions for Form C of Compound 5 Position (°2 θ) |
|---|
| 7.4 |
| 8.4 |
| 10.5 |
| 15.4 |
| 15.8 |
| 17.4 |
| 20.1 |
| 20.8 |
| 22.1 |
| 22.3 |
| 22.6 |
| 23.2 |
| 24.2 |
| 24.5 |
| 25.9 |
| 26.6 |
| 29.0 |
| 31.8 |
| 33.8 |
| 37.7 |

[1] In this and all subsequent tables, the position 2 θ is within ±0.2.

In some embodiments, Form C of compound 5 is characterized in that it has one or more peaks in its X-ray powder diffraction pattern selected from those at about 7.4, 8.4, and 10.5. In some embodiments, Form C of compound 5 is characterized in that it has two or more peaks in its X-ray powder diffraction pattern selected from those at about 7.4, 8.4, and 10.5. In some embodiments, Form C of compound 5 is characterized in that it has all three peaks in its X-ray powder diffraction pattern selected from those at about 7.4, 8.4, and 10.5.

Figure 59:
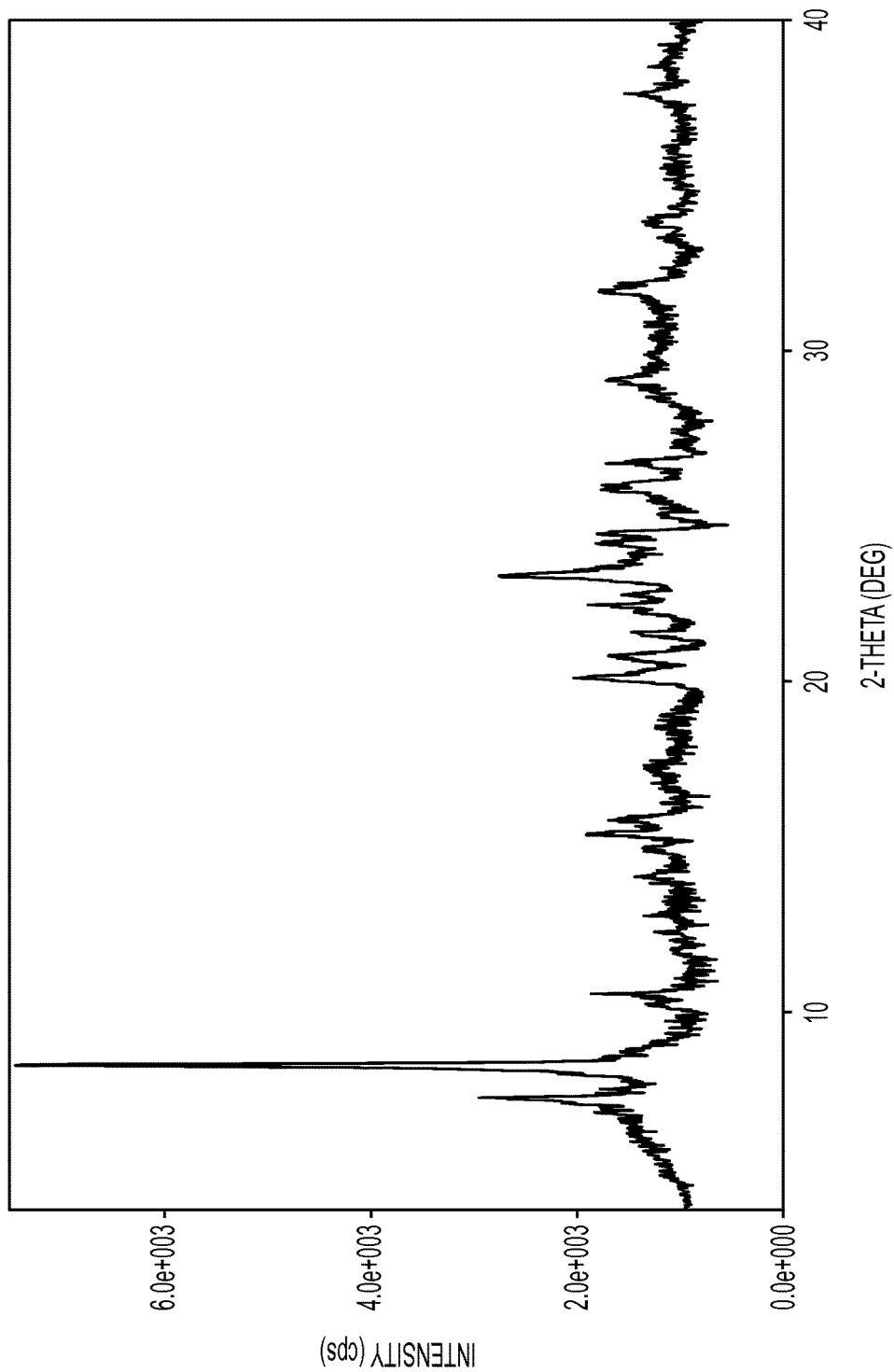
FIG. 59 depicts an XRPD pattern of Form C of compound 5.

In certain embodiments, the X-ray powder diffraction pattern is substantially similar to the XRPD provided in FIG. 59.

Methods for preparing Form C of compound 5 are described infra.

Form D of Compound 5

In some embodiments, Form D of compound 5 has at least 1, 2, 3, 4 or 5 spectral peak(s) selected from the peaks listed in Table 22 below.

TABLE 22

XRPD Peak Positions for Form D of Compound 5
Position (°2 θ)

| |
|---|
| 7.2 |
| 9.4 |
| 10.8 |
| 11.8 |
| 15.1 |
| 16.9 |
| 18.9 |
| 20.4 |
| 21.6 |
| 22.3 |
| 23.7 |
| 24.3 |
| 24.7 |
| 25.5 |
| 26.1 |
| 29.0 |
| 30.3 |
| 30.6 |
| 32.1 |
| 35.2 |

[1] In this and all subsequent tables, the position 2 θ is within ±0.2.

In some embodiments, Form D of compound 5 is characterized in that it has one or more peaks in its X-ray powder diffraction pattern selected from those at about 7.2, 10.8, and 24.3. In some embodiments, Form D of compound 5 is characterized in that it has two or more peaks in its X-ray powder diffraction pattern selected from those at about 7.2, 10.8, and 24.3. In some embodiments, Form D of compound 5 is characterized in that it has all three peaks in its X-ray powder diffraction pattern selected from those at about 7.2, 10.8, and 24.3.

Figure 61:
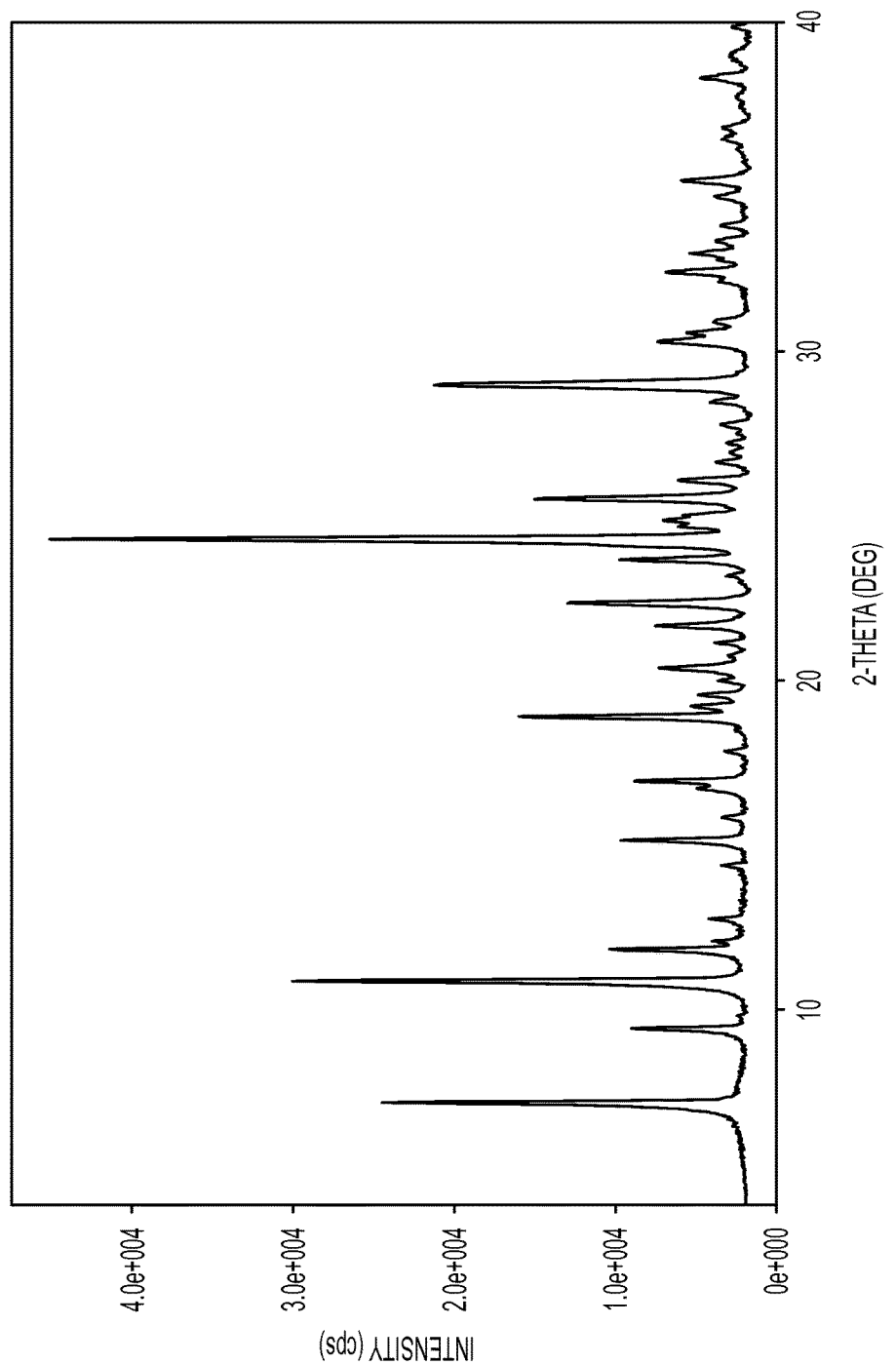
FIG. 61 depicts an XRPD pattern of Form D of compound 5.

In certain embodiments, the X-ray powder diffraction pattern is substantially similar to the XRPD provided in FIG. 61.

Methods for preparing Form D of compound 5 are described infra.

Form E of Compound 5

In some embodiments, Form E of compound 5 has at least 1, 2, 3, 4 or 5 spectral peak(s) selected from the peaks listed in Table 23 below.

TABLE 23

XRPD Peak Positions for Form E of Compound 5
Position (°2 θ)

| |
|---|
| 7.8 |
| 8.7 |
| 10.0 |
| 11.6 |
| 15.0 |
| 16.4 |
| 17.5 |
| 18.7 |
| 21.5 |
| 22.8 |
| 23.8 |
| 24.3 |
| 25.2 |
| 25.8 |
| 28.8 |
| 29.1 |
| 30.3 |
| 31.7 |

TABLE 23-continued

XRPD Peak Positions for Form E of Compound 5
Position (°2 θ)

| |
|---|
| 33.7 |
| 36.8 |

[1] In this and all subsequent tables, the position 2 θ is within ±0.2.

In some embodiments, Form E of compound 5 is characterized in that it has one or more peaks in its X-ray powder diffraction pattern selected from those at about 7.8, 8.7, and 16.4. In some embodiments, Form E of compound 5 is characterized in that it has two or more peaks in its X-ray powder diffraction pattern selected from those at about 7.8, 8.7, and 16.4. In some embodiments, Form E of compound 5 is characterized in that it has all three peaks in its X-ray powder diffraction pattern selected from those at about 7.8, 8.7, and 16.4.

Figure 63:
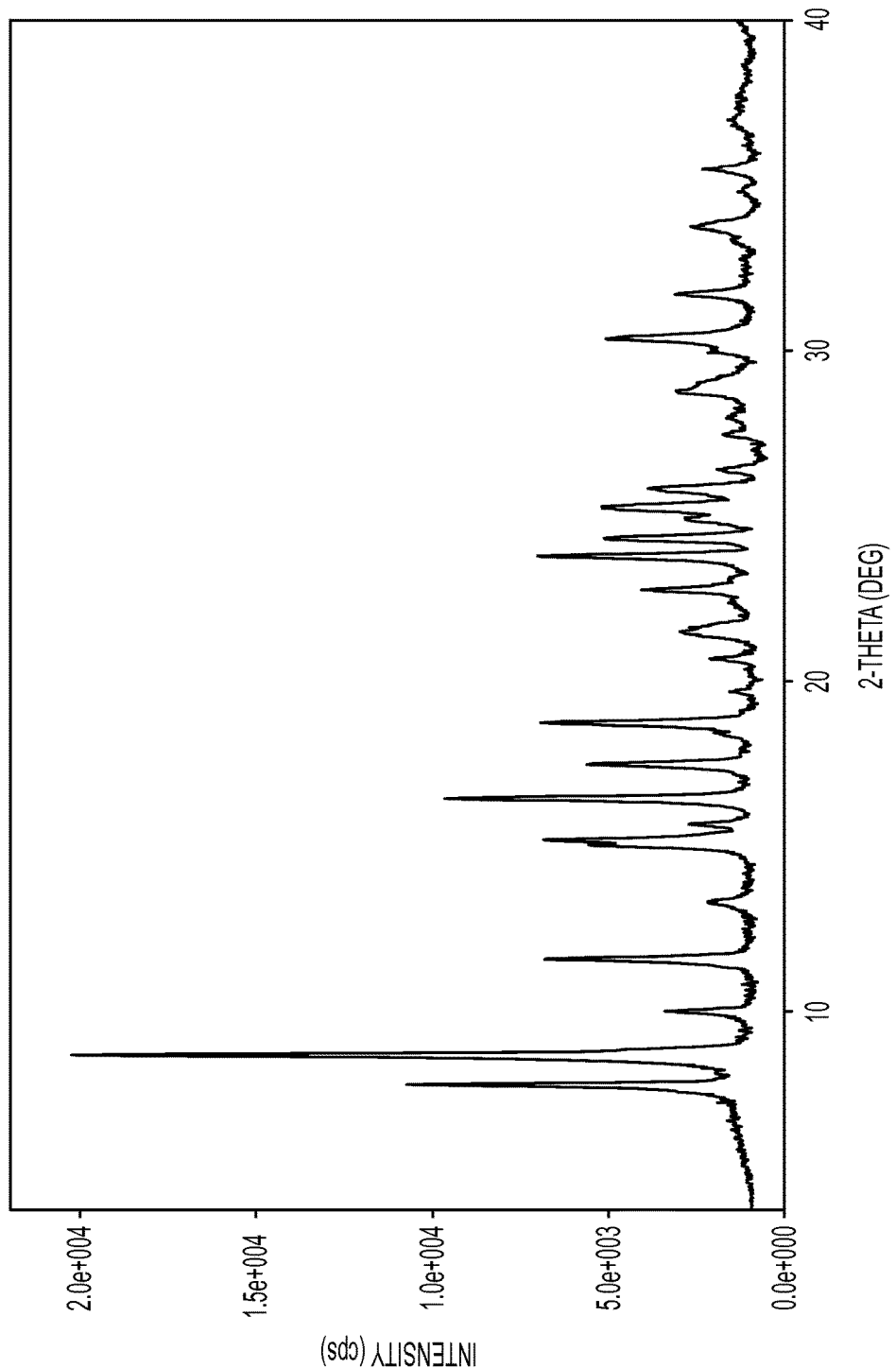
FIG. 63 depicts an XRPD pattern of Form E of compound 5.

In certain embodiments, the X-ray powder diffraction pattern is substantially similar to the XRPD provided in FIG. 63.

Methods for preparing Form E of compound 5 are described infra.

In some embodiments, the present invention provides compound 5:

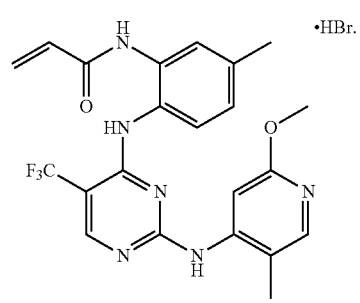

5

In some embodiments, the present invention provides compound 5, wherein said compound is crystalline.

In some embodiments, the present invention provides compound 5, wherein said compound is a crystalline solid substantially free of amorphous compound 5.

In some embodiments, the present invention provides compound 5, wherein said compound is substantially free of impurities.

In some embodiments, the present invention provides compound 5, wherein said compound has one or more peaks in its XRPD selected from those at about 9.5 about 22.6, and about 24.8 degrees 2-theta. In some such embodiments, the present invention provides compound 5, wherein said compound has at least two peaks in its XRPD selected from those at about 9.5, about 22.6, and about 24.8 degrees 2-theta. In some such embodiments, the present invention provides compound 5, wherein said compound is of Form A.

In some embodiments, the present invention provides compound 5, wherein said compound has an XRPD substantially similar to that depicted in FIG. 53.

In some embodiments, the present invention provides compound 5, wherein said compound has one or more peaks in its XRPD selected from those at about 8.3, about 17.9, and about 25.5 degrees 2-theta. In some such embodiments, the present invention provides compound 5, wherein said compound has at least two peaks in its XRPD selected from those at about 8.3, about 17.9, and about 25.5 degrees 2-theta. In some such embodiments, the present invention provides compound 5, wherein said compound is of Form B.

In some embodiments, the present invention provides compound 5, wherein said compound has an XRPD substantially similar to that depicted in FIG. 57.

In some embodiments, the present invention provides compound 5, wherein said compound has one or more peaks in its XRPD selected from those at about 7.4, about 8.4, and about 10.5 degrees 2-theta. In some such embodiments, the present invention provides compound 5, wherein said compound has at least two peaks in its XRPD selected from those at about 7.4, about 8.4, and about 10.5 degrees 2-theta. In some such embodiments, the present invention provides compound 5, wherein said compound is of Form C.

In some embodiments, the present invention provides compound 5, wherein said compound has an XRPD substantially similar to that depicted in FIG. 59.

In some embodiments, the present invention provides compound 5, wherein said compound has one or more peaks in its XRPD selected from those at about 7.2, about 10.8, and about 24.3 degrees 2-theta. In some such embodiments, the present invention provides compound 5, wherein said compound has at least two peaks in its XRPD selected from those at about 7.2, about 10.8, and about 24.3 degrees 2-theta. In some such embodiments, the present invention provides compound 5, wherein said compound is of Form D.

In some embodiments, the present invention provides compound 5, wherein said compound has an XRPD substantially similar to that depicted in FIG. 61.

In some embodiments, the present invention provides compound 5, wherein said compound has one or more peaks in its XRPD selected from those at about 7.8, about 8.7, and about 16.4 degrees 2-theta. In some such embodiments, the present invention provides compound 5, wherein said compound has at least two peaks in its XRPD selected from those at about 7.8, about 8.7, and about 16.4 degrees 2-theta. In some such embodiments, the present invention provides compound 5, wherein said compound is of Form E.

In some embodiments, the present invention provides compound 5, wherein said compound has an XRPD substantially similar to that depicted in FIG. 63.

In some embodiments, the present invention provides a composition comprising compound 5 and a pharmaceutically acceptable carrier or excipient.

In some embodiments, the present invention provides a method of inhibiting one or both of ERK1 and ERK2 in a patient comprising administering to said patient compound 5 or composition thereof.

In some embodiments, the present invention provides a method of treating an ERK1- or ERK2-mediated disorder in a patient, comprising administering to said patient compound 5 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Compound 6 (Sulfate Salts of Compound 1)

According to one embodiment, the present invention provides a sulfate salt of compound 1, represented by compound 6:

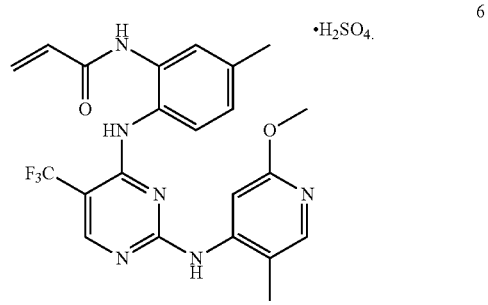

It will be appreciated by one of ordinary skill in the art that the sulfuric acid and compound 1 are ionically bonded to form compound 6. It is contemplated that compound 6 can exist in a variety of physical forms. For example, compound 6 can be in solution, suspension, or in solid form. In certain embodiments, compound 6 is in solid form. When compound 6 is in solid form, said compound may be amorphous, crystalline, or a mixture thereof. Exemplary solid forms are described in more detail below.

In some embodiments, the present invention provides compound 5 substantially free of impurities. As used herein, the term "substantially free of impurities" means that the compound contains no significant amount of extraneous matter. Such extraneous matter may include excess sulfuric acid, excess compound 1, residual solvents, or any other impurities that may result from the preparation of, and/or isolation of, compound 6. In certain embodiments, at least about 95% by weight of compound 6 is present. In still other embodiments of the invention, at least about 99% by weight of compound 6 is present.

According to one embodiment, compound 6 is present in an amount of at least about 97, 97.5, 98.0, 98.5, 99, 99.5, 99.8 weight percent where the percentages are based on the total weight of the composition. According to another embodiment, compound 6 contains no more than about 3.0 area percent HPLC of total organic impurities and, in certain embodiments, no more than about 1.5 area percent HPLC total organic impurities relative to the total area of the HPLC chromatogram. In other embodiments, compound 6 contains no more than about a percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 6 is also meant to include all tautomeric forms of compound 6. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that compound 6 can exist in a variety of solid forms. Exemplary such forms include polymorphs such as those contemplated by the present invention.

In certain embodiments, compound 6 is a crystalline solid. In other embodiments, compound 6 is a crystalline solid substantially free of amorphous compound 6. As used herein, the term "substantially free of amorphous compound 6" means that the compound contains no significant amount of amorphous compound 6. In certain embodiments, at least about 95% by weight of crystalline compound 6 is present. In still other embodiments of the invention, at least about 99% by weight of crystalline compound 6 is present.

It has been found that compound 6 can exist in at least three distinct polymorphic forms. In some embodiments, the present invention provides a polymorphic form of compound 6 referred to herein as Form A. In certain embodiments, the present invention provides a polymorphic form of compound 6 referred to herein as Form B. In certain embodiments, the present invention provides a polymorphic form of compound 6 referred to herein as Form C.

In some embodiments, compound 6 is amorphous. In some embodiments, compound 6 is amorphous, and is substantially free of crystalline compound 6.

Form A of Compound 6

In some embodiments, Form A of compound 6 has at least 1, 2, 3, 4 or 5 spectral peak(s) selected from the peaks listed in Table 24 below.

TABLE 24

XRPD Peak Positions for Form A of Compound 6
Position (°2 θ)

| |
|---|
| 6.2 |
| 7.1 |
| 9.9 |
| 14.2 |
| 14.7 |
| 19.4 |
| 19.5 |
| 20.1 |
| 20.2 |
| 20.7 |
| 21.4 |
| 23.4 |
| 23.9 |
| 24.3 |
| 24.8 |
| 25.3 |
| 26.0 |
| 26.9 |
| 28.7 |
| 29.8 |

[1] In this and all subsequent tables, the position 2 θ is within ±0.2.

In some embodiments, Form A of compound 6 is characterized in that it has one or more peaks in its X-ray powder diffraction pattern selected from those at about 6.2, 7.1, and 21.4. In some embodiments, Form A of compound 6 is characterized in that it has two or more peaks in its X-ray powder diffraction pattern selected from those at about 6.2, 7.1, and 21.4. In some embodiments, Form A of compound 6 is characterized in that it has all three peaks in its X-ray powder diffraction pattern selected from those at about 6.2, 7.1, and 21.4.

Figure 66:
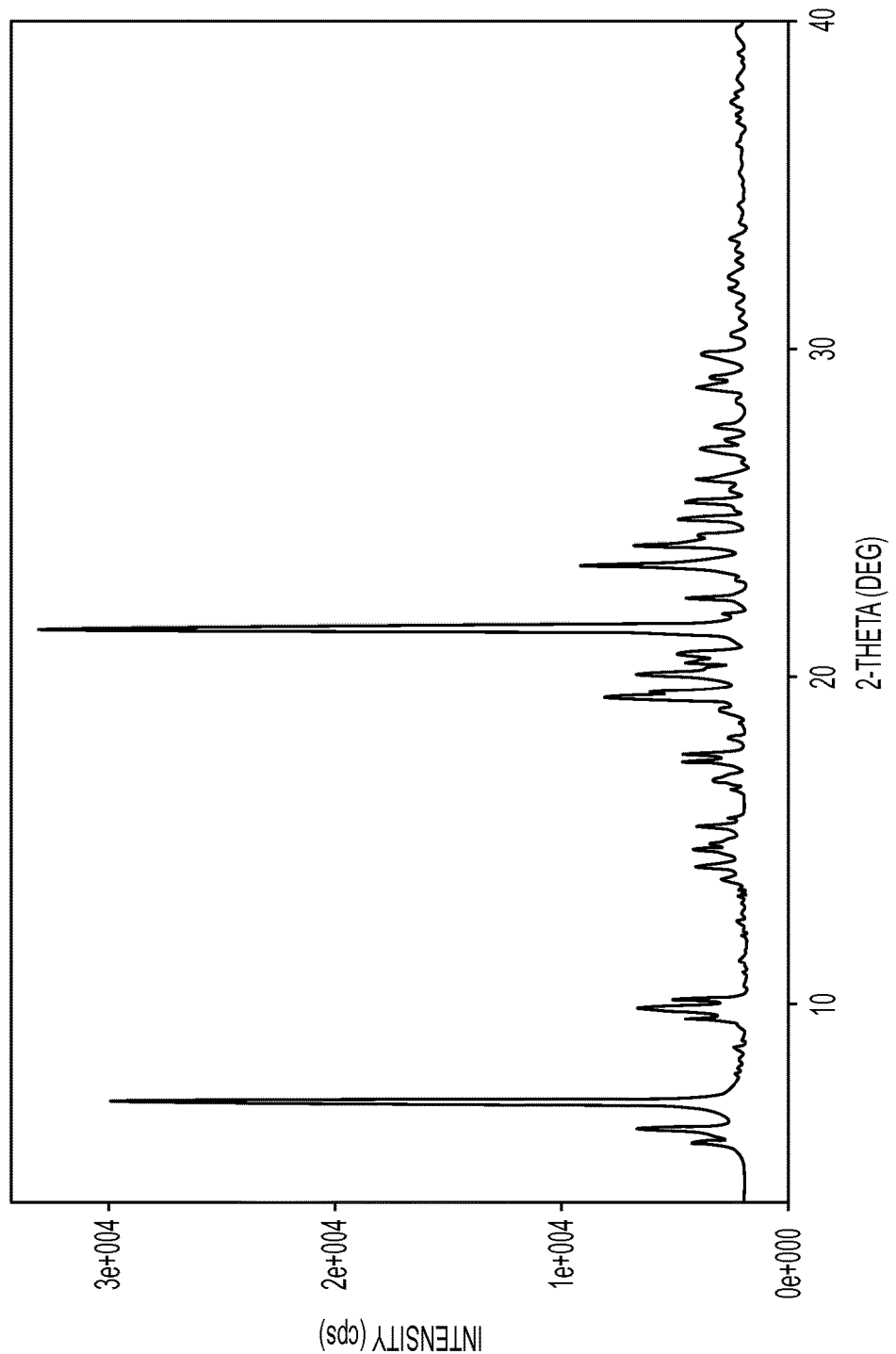
FIG. 66 depicts an XRPD pattern of Form A of compound 6.

In certain embodiments, the X-ray powder diffraction pattern is substantially similar to the XRPD provided in FIG. 66.

Methods for preparing Form A of compound 6 are described infra.

Form B of Compound 6

In some embodiments, Form B of compound 6 has at least 1, 2, 3, 4 or 5 spectral peak(s) selected from the peaks listed in Table 25 below.

TABLE 25

XRPD Peak Positions for Form B of Compound 6
Position (°2 θ)

| |
|---|
| 7.1 |
| 7.6 |

TABLE 25-continued

XRPD Peak Positions for Form B of Compound 6
Position (°2 θ)

| |
|---|
| 10.1 |
| 11.4 |
| 11.6 |
| 12.4 |
| 13.7 |
| 15.2 |
| 17.3 |
| 17.8 |
| 18.7 |
| 18.7 |
| 20.3 |
| 21.7 |
| 22.9 |
| 24.1 |
| 25.4 |
| 26.0 |
| 29.7 |
| 34.7 |

[1] In this and all subsequent tables, the position 2 θ is within ±0.2.

In some embodiments, Form B of compound 6 is characterized in that it has one or more peaks in its X-ray powder diffraction pattern selected from those at about 7.6, 15.2, and 22.9. In some embodiments, Form B of compound 6 is characterized in that it has two or more peaks in its X-ray powder diffraction pattern selected from those at about 7.6, 15.2, and 22.9. In some embodiments, Form B of compound 6 is characterized in that it has all three peaks in its X-ray powder diffraction pattern selected from those at about 7.6, 15.2, and 22.9.

Figure 70:
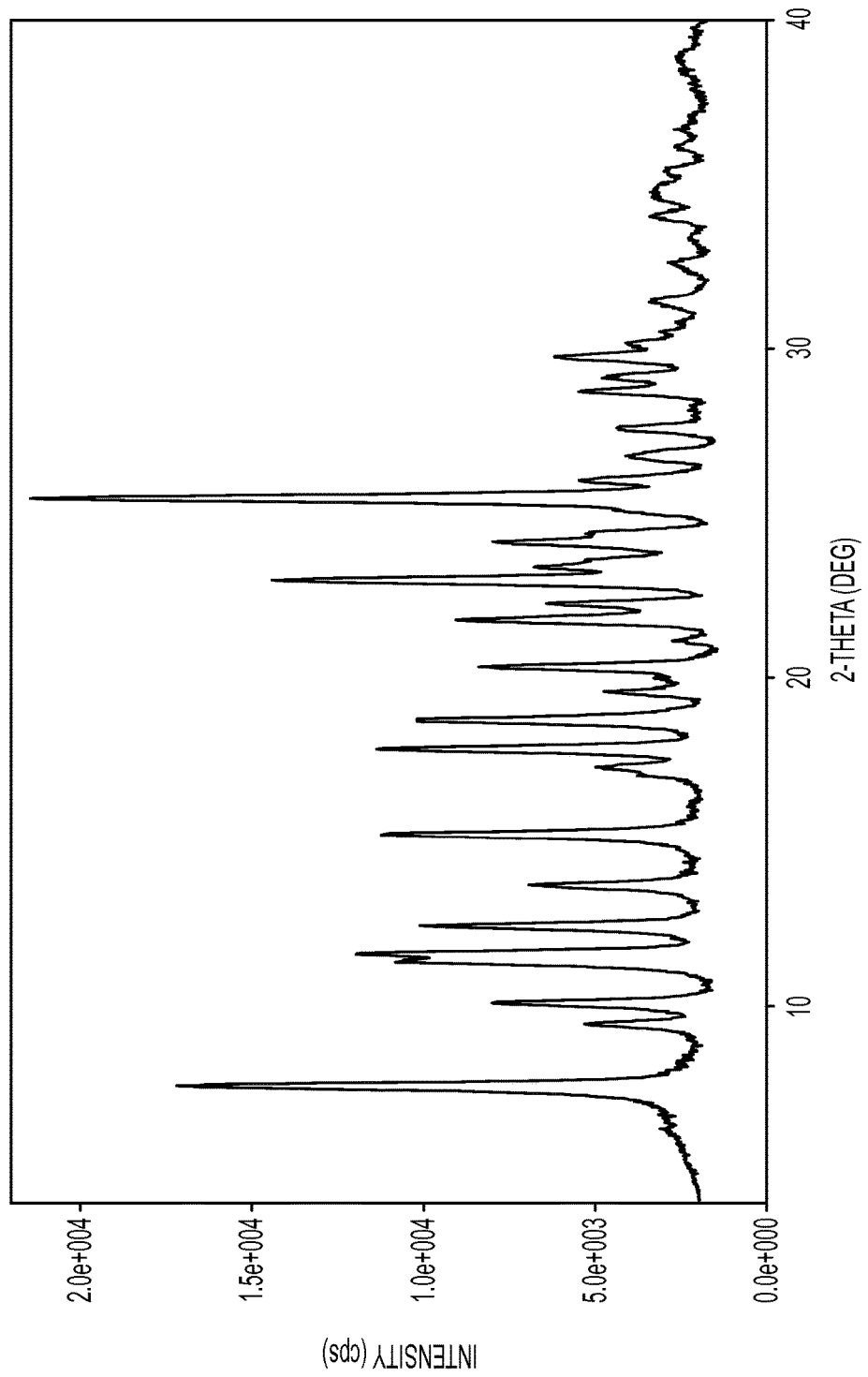
FIG. 70 depicts an XRPD pattern of Form B of compound 6.

In certain embodiments, the X-ray powder diffraction pattern is substantially similar to the XRPD provided in FIG. 70.

Methods for preparing Form B of compound 6 are described infra.

Form C of Compound 6

In some embodiments, Form C of compound 6 has at least 1, 2, 3, 4 or 5 spectral peak(s) selected from the peaks listed in Table 26 below.

TABLE 26

XRPD Peak Positions for Form C of Compound 6
Position (°2 θ)

| |
|---|
| 7.1 |
| 7.6 |
| 8.3 |
| 9.3 |
| 12.6 |
| 13.5 |
| 14.2 |
| 17.4 |
| 18.1 |
| 19.6 |
| 20.2 |
| 20.5 |
| 20.9 |
| 21.2 |
| 23.1 |
| 24.4 |
| 25.1 |
| 26.2 |
| 27.9 |
| 29.9 |

[1] In this and all subsequent tables, the position 2 θ is within ±0.2.

In some embodiments, Form C of compound 6 is characterized in that it has one or more peaks in its X-ray powder diffraction pattern selected from those at about 7.1, 7.6, and 23.1. In some embodiments, Form C of compound 6 is characterized in that it has two or more peaks in its X-ray powder diffraction pattern selected from those at about 7.1, 7.6, and 23.1. In some embodiments, Form C of compound 6 is characterized in that it has all three peaks in its X-ray powder diffraction pattern selected from those at about 7.1, 7.6, and 23.1.

Figure 72:
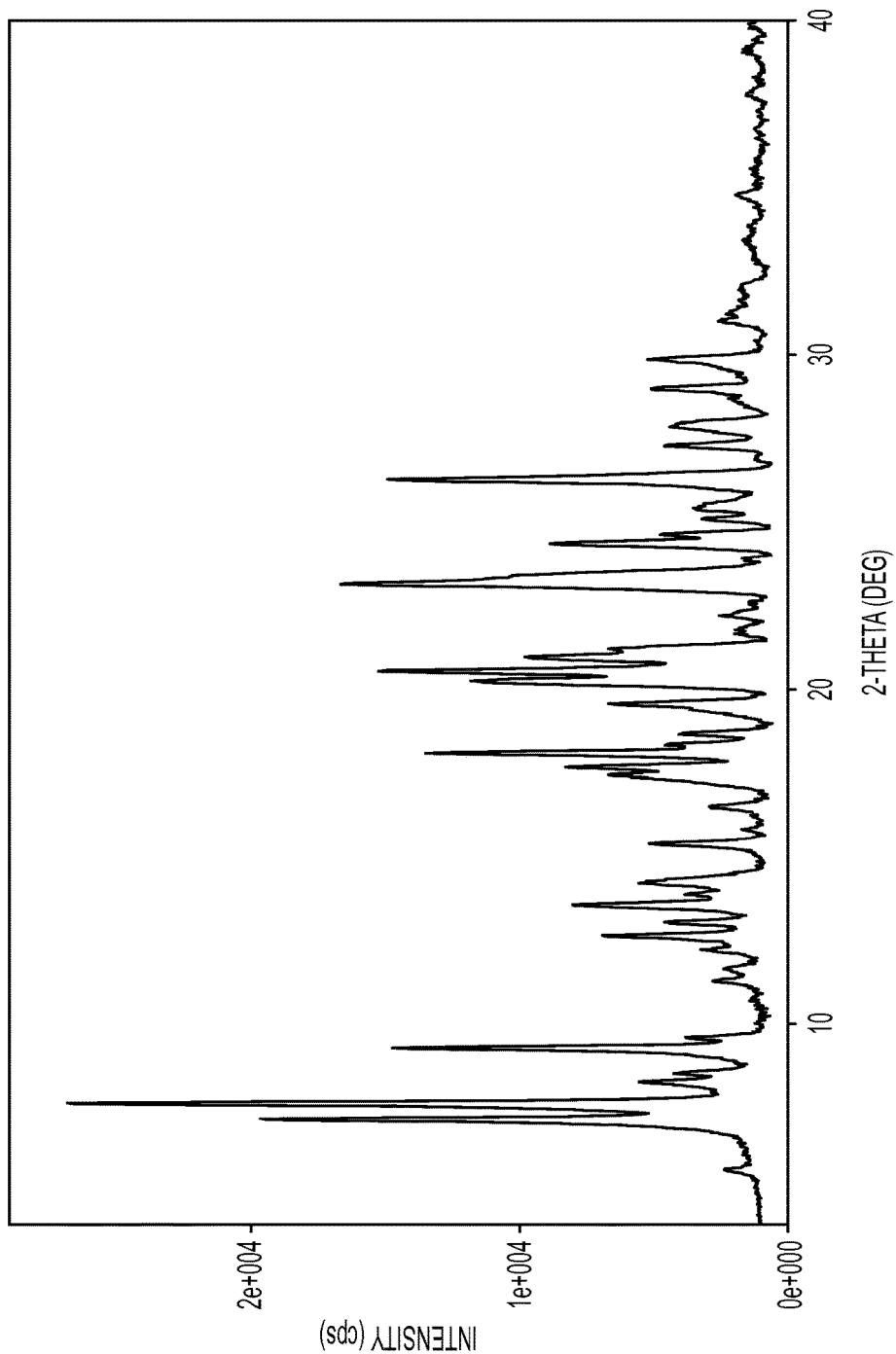
FIG. 72 depicts an XRPD pattern of Form C of compound 6.

In certain embodiments, the X-ray powder diffraction pattern is substantially similar to the XRPD provided in FIG. 72.

Methods for preparing Form C of compound 6 are described infra.

In some embodiments, the present invention provides compound 6:

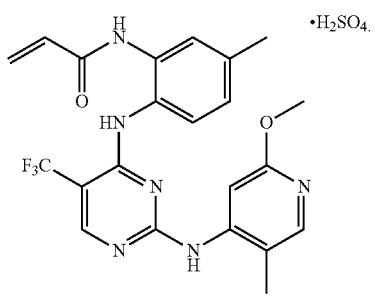

In some embodiments, the present invention provides compound 6, wherein said compound is crystalline.

In some embodiments, the present invention provides compound 6, wherein said compound is a crystalline solid substantially free of amorphous compound 6.

In some embodiments, the present invention provides compound 6, wherein said compound is substantially free of impurities.

In some embodiments, the present invention provides compound 6, wherein said compound has one or more peaks in its XRPD selected from those at about 6.2, 7.1, about and about 21.4 degrees 2-theta. In some such embodiments, the present invention provides compound 6, wherein said compound has at least two peaks in its XRPD selected from those at about 6.2, 7.1, about and about 21.4 degrees 2-theta. In some such embodiments, the present invention provides compound 6, wherein said compound is of Form A.

In some embodiments, the present invention provides compound 6, wherein said compound has an XRPD substantially similar to that depicted in FIG. 66.

In some embodiments, the present invention provides compound 6, wherein said compound has one or more peaks in its XRPD selected from those at about 7.6, about 15.2, and about 22.9 degrees 2-theta. In some such embodiments, the present invention provides compound 6, wherein said compound has at least two peaks in its XRPD selected from those at about 7.6, about 15.2, and about 22.9 degrees 2-theta. In some such embodiments, the present invention provides compound 6, wherein said compound is of Form B.

In some embodiments, the present invention provides compound 6, wherein said compound has an XRPD substantially similar to that depicted in FIG. 70.

In some embodiments, the present invention provides compound 6, wherein said compound has one or more peaks in its XRPD selected from those at about 7.1, about 7.6, and about 23.1 degrees 2-theta. In some such embodiments, the present invention provides compound 6, wherein said compound has at least two peaks in its XRPD selected from those at about 7.1, about 7.6, and about 23.1 degrees 2-theta. In some such embodiments, the present invention provides compound 6, wherein said compound is of Form C.

In some embodiments, the present invention provides compound 6, wherein said compound has an XRPD substantially similar to that depicted in FIG. 72.

In some embodiments, the present invention provides a composition comprising compound 6 and a pharmaceutically acceptable carrier or excipient.

In some embodiments, the present invention provides a method of inhibiting one or both of ERK1 and ERK2 in a patient comprising administering to said patient compound 6 or composition thereof.

In some embodiments, the present invention provides a method of treating an ERK1- or ERK2-mediated disorder in a patient, comprising administering to said patient compound 6 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Compound 7 (Bis-Sulfate Salts of Compound 1)

According to one embodiment, the present invention provides a bis-sulfate salt of compound 1, represented by compound 7:

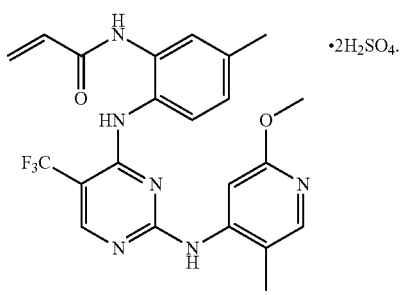

It will be appreciated by one of ordinary skill in the art that sulfuric acid and compound 1 are ionically bonded to form compound 7. It is contemplated that compound 7 can exist in a variety of physical forms. For example, compound 7 can be in solution, suspension, or in solid form. In certain embodiments, compound 7 is in solid form. When compound 7 is in solid form, said compound may be amorphous, crystalline, or a mixture thereof. Exemplary solid forms are described in more detail below.

In some embodiments, the present invention provides compound 7 substantially free of impurities. As used herein, the term "substantially free of impurities" means that the compound contains no significant amount of extraneous matter. Such extraneous matter may include excess sulfuric acid, excess compound 1, residual solvents, or any other impurities that may result from the preparation of, and/or isolation of, compound 7. In certain embodiments, at least about 95% by weight of compound 7 is present. In still other embodiments of the invention, at least about 99% by weight of compound 7 is present.

According to one embodiment, compound 7 is present in an amount of at least about 97, 97.5, 98.0, 98.5, 99, 99.5, 99.8 weight percent where the percentages are based on the total weight of the composition. According to another embodiment, compound 7 contains no more than about 3.0 area percent HPLC of total organic impurities and, in certain embodiments, no more than about 1.5 area percent HPLC total organic impurities relative to the total area of the HPLC chromatogram. In other embodiments, compound 7 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 7 is also meant to include all tautomeric forms of compound 7. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

In certain embodiments, compound 7 is a crystalline solid. In other embodiments, compound 7 is a crystalline solid substantially free of amorphous compound 7. As used herein, the term "substantially free of amorphous compound 7" means that the compound contains no significant amount of amorphous compound 7. In certain embodiments, at least about 95% by weight of crystalline compound 7 is present. In still other embodiments of the invention, at least about 99% by weight of crystalline compound 7 is present.

It has been found that compound 7 can exist in at least one distinct crystalline form. In some embodiments, the present invention provides a crystalline form of compound 7 referred to herein as Form A.

In some embodiments, compound 7 is amorphous. In some embodiments, compound 7 is amorphous, and is substantially free of crystalline compound 7.

Form A of Compound 7

In some embodiments, Form A of compound 7 has at least 1, 2, 3, 4 or 5 spectral peak(s) selected from the peaks listed in Table 27 below.

TABLE 27

XRPD Peak Positions for Form A of Compound 7
Position (°2 θ)

| |
|---|
| 7.3 |
| 8.7 |
| 9.6 |
| 11.4 |
| 11.5 |
| 14.1 |
| 17.9 |
| 18.2 |
| 19.0 |
| 19.2 |
| 20.5 |
| 20.7 |
| 21.0 |
| 22.2 |
| 23.5 |
| 24.3 |
| 24.3 |
| 27.5 |
| 28.6 |
| 31.1 |

[1] In this and all subsequent tables, the position 2 θ is within ±0.2.

In some embodiments, Form A of compound 7 is characterized in that it has one or more peaks in its X-ray powder diffraction pattern selected from those at about 7.3, 8.7, and 23.5. In some embodiments, Form A of compound 7 is characterized in that it has two or more peaks in its X-ray powder diffraction pattern selected from those at about 7.3, 8.7, and 23.5. In some embodiments, Form A of compound 7 is characterized in that it has all three peaks in its X-ray powder diffraction pattern selected from those at about 7.3, 8.7, and 23.5.

Figure 74:
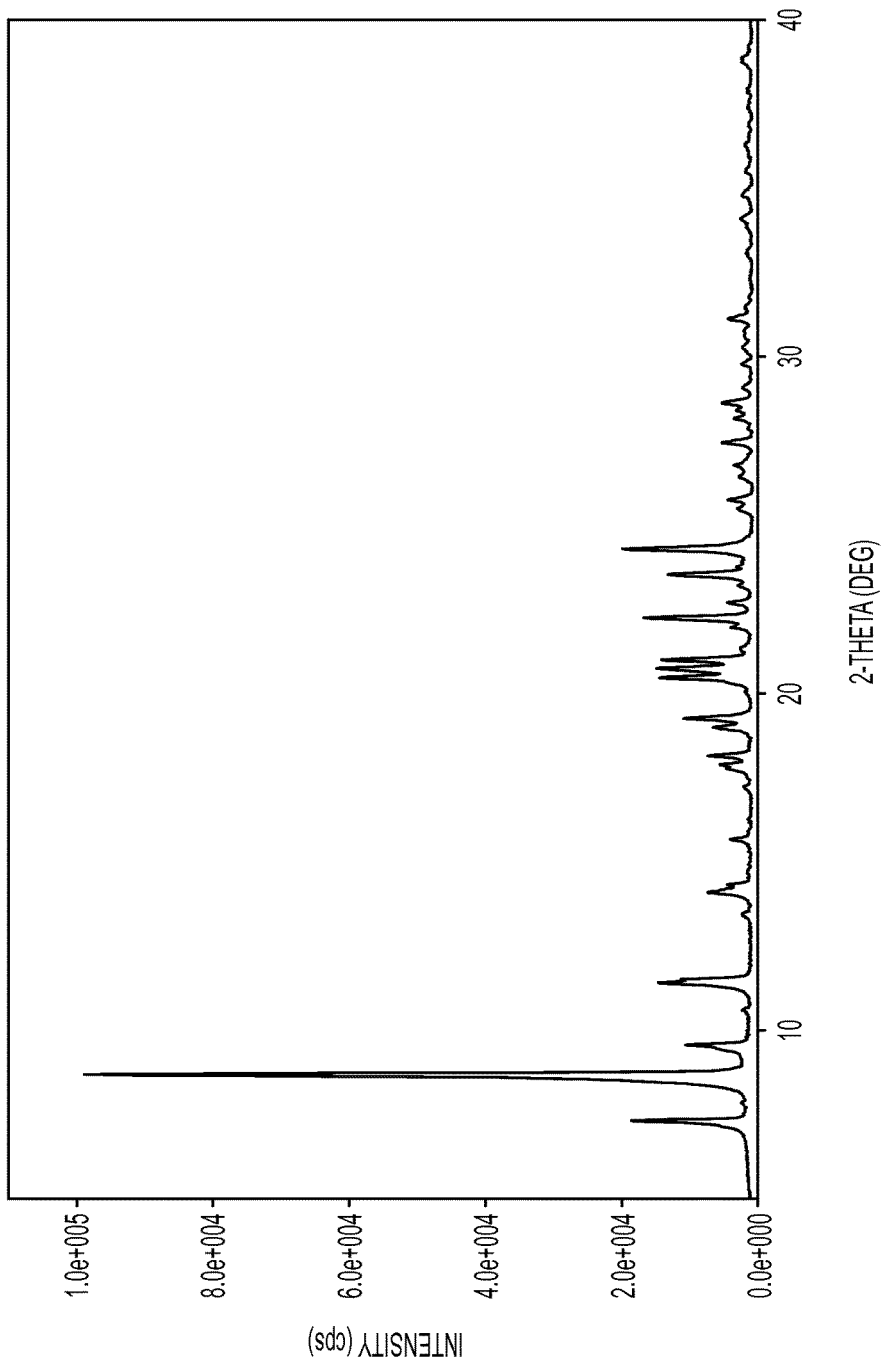
FIG. 74 depicts an XRPD pattern of Form A of compound 7.

In certain embodiments, the X-ray powder diffraction pattern is substantially similar to the XRPD provided in FIG. 74.

Methods for preparing Form A of compound 7 are described infra.

In some embodiments, the present invention provides compound 7:

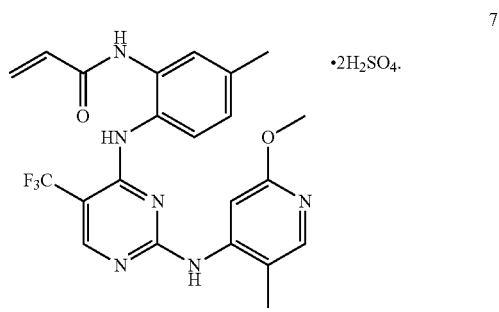 [SMILES: C=CC(=O)Nc1cc(C)ccc1Nc1nc(Nc2cc(OC)ncc2C)ncc1C(F)(F)F]

In some embodiments, the present invention provides compound 7, wherein said compound is crystalline.

In some embodiments, the present invention provides compound 7, wherein said compound is a crystalline solid substantially free of amorphous compound 7.

In some embodiments, the present invention provides compound 7, wherein said compound is substantially free of impurities.

In some embodiments, the present invention provides compound 7, wherein said compound has one or more peaks in its XRPD selected from those at about 7.3, about 8.7, and about 23.5 degrees 2-theta. In some such embodiments, the present invention provides compound 7, wherein said compound has at least two peaks in its XRPD selected from those at about 7.3, about 8.7, and about 23.5 degrees 2-theta. In some such embodiments, the present invention provides compound 7, wherein said compound is of Form A.

In some embodiments, the present invention provides compound 7, wherein said compound has an XRPD substantially similar to that depicted in FIG. 74.

In some embodiments, the present invention provides a composition comprising the compound 7 and a pharmaceutically acceptable carrier or excipient.

In some embodiments, the present invention provides a method of inhibiting one or both of ERK1 and ERK2 in a patient comprising administering to said patient compound 7 or composition thereof.

In some embodiments, the present invention provides a method of treating an ERK1- or ERK2-mediated disorder in a patient, comprising administering to said patient compound 7 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Compound 8 (Tosylate Salts of Compound 1)

According to one embodiment, the present invention provides a tosylate salt of compound 1, represented by compound 8:

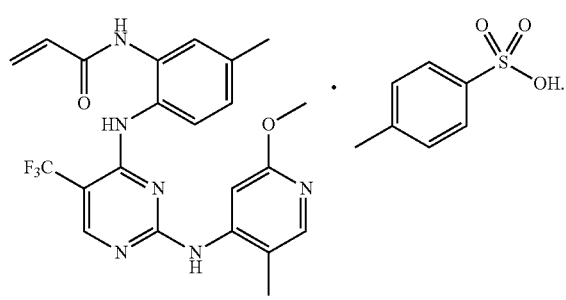

By "tosylate" is meant p-toluene sulfonate, i.e., the ionic form of p-toluenesulfonic acid. It will be appreciated by one of ordinary skill in the art that p-toluenesulfonic acid and compound 1 are ionically bonded to form compound 8. It is contemplated that compound 8 can exist in a variety of physical forms. For example, compound 8 can be in solution, suspension, or in solid form. In certain embodiments, compound 8 is in solid form. When compound 8 is in solid form, said compound may be amorphous, crystalline, or a mixture thereof. Exemplary solid forms are described in more detail below.

In some embodiments, the present invention provides compound 8 substantially free of impurities. As used herein, the term "substantially free of impurities" means that the compound contains no significant amount of extraneous matter. Such extraneous matter may include excess p-toluenesulfonic acid, excess compound 1, residual solvents, or any other impurities that may result from the preparation of, and/or isolation of, compound 8. In certain embodiments, at least about 95% by weight of compound 8 is present. In still other embodiments of the invention, at least about 99% by weight of compound 8 is present.

According to one embodiment, compound 8 is present in an amount of at least about 97, 97.5, 98.0, 98.5, 99, 99.5, 99.8 weight percent where the percentages are based on the total weight of the composition. According to another embodiment, compound 8 contains no more than about 3.0 area percent HPLC of total organic impurities and, in certain embodiments, no more than about 1.5 area percent HPLC total organic impurities relative to the total area of the HPLC chromatogram. In other embodiments, compound 8 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 8 is also meant to include all tautomeric forms of compound 8. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that compound 8 can exist in a variety of solid forms. Exemplary such forms include polymorphs and amorphous forms such as those contemplated by the present invention.

In certain embodiments, compound 8 is a crystalline solid. In other embodiments, compound 8 is a crystalline solid substantially free of amorphous compound 8. As used herein, the term "substantially free of amorphous compound 8" means that the compound contains no significant amount of amorphous compound 8. In certain embodiments, at least about 95% by weight of crystalline compound 8 is present. In still other embodiments of the invention, at least about 99% by weight of crystalline compound 8 is present.

In certain embodiments, compound 8 is an amorphous solid. In certain embodiments, at least about 95% by weight of amorphous compound 8 is present. In still other embodiments of the invention, at least about 99% by weight of amorphous compound 8 is present.

It has been found that compound 8 can exist in at least four distinct forms, three of which are polymorphic and one of which is amorphous. In some embodiments, the present invention provides a polymorphic form of compound 8 referred to herein as Form A. In some embodiments, the present invention provides a polymorphic form of compound 8 referred to herein as Form B. In some embodiments, the present invention provides a polymorphic form of compound 8 referred to herein as Form C. In some embodiments, the present invention provides an amorphous form of compound 8 referred to herein as Form D.

In some embodiments, compound 8 is amorphous. In some embodiments, compound 8 is amorphous, and is substantially free of crystalline compound 8.

Form A of Compound 8

In some embodiments, Form A of compound 8 has at least 1, 2, 3, 4 or 5 spectral peak(s) selected from the peaks listed in Table 28 below.

TABLE 28

| XRPD Peak Positions for Form A of Compound 8 Position (°2 θ) |
| --- |
| 8.6 |
| 9.0 |
| 12.4 |
| 12.8 |
| 13.4 |
| 16.1 |
| 16.4 |
| 16.6 |
| 17.0 |
| 17.9 |
| 19.1 |
| 20.0 |
| 20.5 |
| 22.9 |
| 23.5 |
| 23.7 |
| 23.8 |
| 24.8 |
| 27.8 |
| 30.7 |

[1] In this and all subsequent tables, the position 2 θ is within ±0.2.

In some embodiments, Form A of compound 8 is characterized in that it has one or more peaks in its X-ray powder diffraction pattern selected from those at about 9.0, 23.8, and 24.8. In some embodiments, Form A of compound 8 is characterized in that it has two or more peaks in its X-ray powder diffraction pattern selected from those at about 9.0, 23.8, and 24.8. In some embodiments, Form A of compound 8 is characterized in that it has all three peaks in its X-ray powder diffraction pattern selected from those at about 9.0, 23.8, and 24.8.

Figure 77:
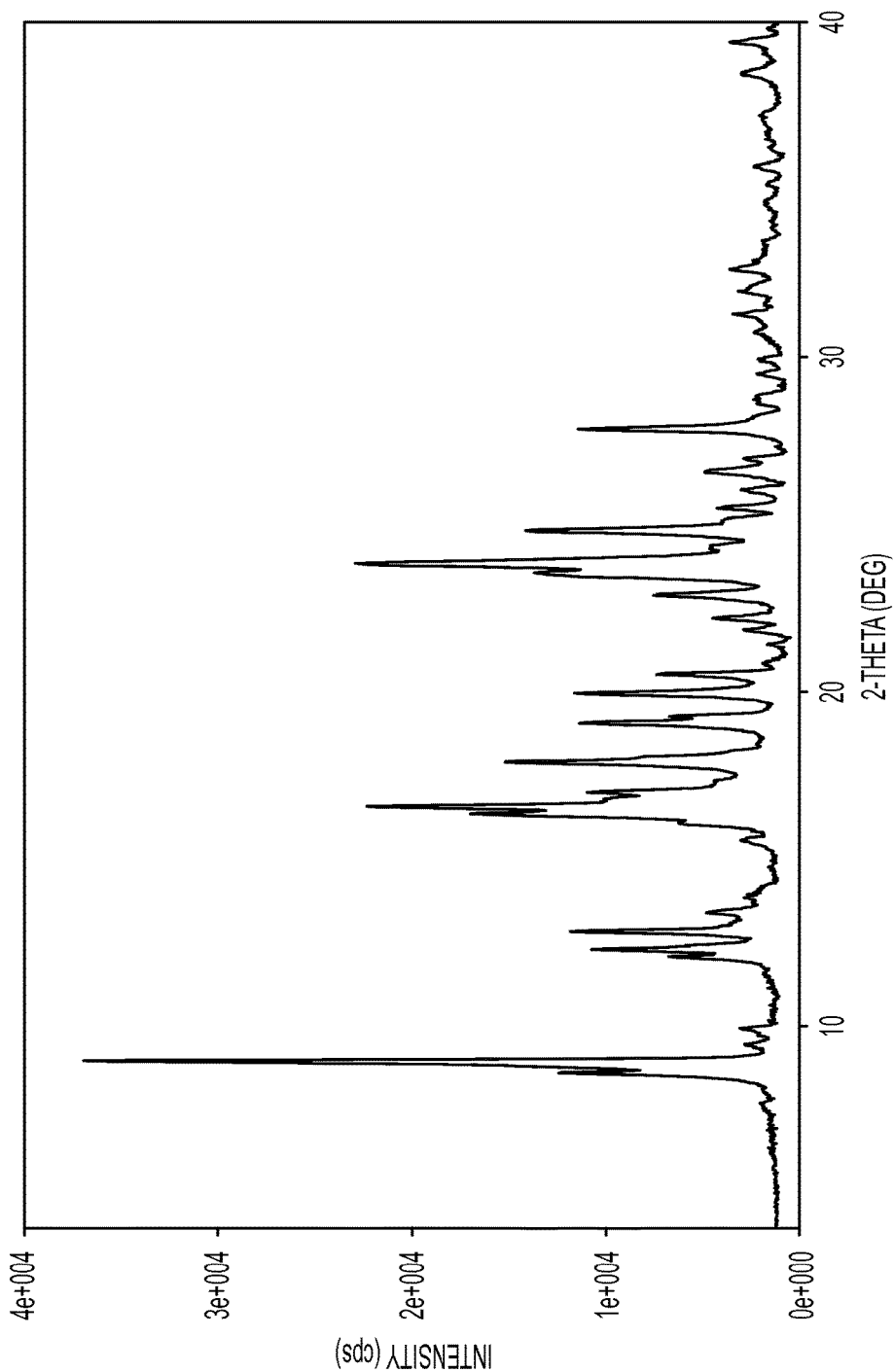
FIG. 77 depicts an XRPD pattern of Form A of compound 8.

In certain embodiments, the X-ray powder diffraction pattern is substantially similar to the XRPD provided in FIG. 77.

Methods for preparing Form A of compound 8 are described infra.

Form B of Compound 8

In some embodiments, Form B of compound 8 has at least 1, 2, 3, 4 or 5 spectral peak(s) selected from the peaks listed in Table 29 below.

TABLE 29

| XRPD Peak Positions for Form B of Compound 8 Position (°2 θ) |
|---|
| 8.6 |
| 8.9 |
| 12.2 |
| 16.2 |
| 16.5 |
| 16.9 |
| 17.2 |
| 17.9 |
| 19.0 |
| 19.1 |
| 20.1 |
| 23.1 |
| 23.4 |
| 23.6 |
| 24.6 |
| 24.7 |
| 25.1 |
| 26.3 |
| 27.6 |
| 28.2 |

[1] In this and all subsequent tables, the position 2 θ is within ±0.2.

In some embodiments, Form B of compound 8 is characterized in that it has one or more peaks in its X-ray powder diffraction pattern selected from those at about 8.9, 23.4, and 27.6. In some embodiments, Form B of compound 8 is characterized in that it has two or more peaks in its X-ray powder diffraction pattern selected from those at about 8.9, 23.4, and 27.6. In some embodiments, Form B of compound 8 is characterized in that it has all three peaks in its X-ray powder diffraction pattern selected from those at about 8.9, 23.4, and 27.6.

Figure 79:
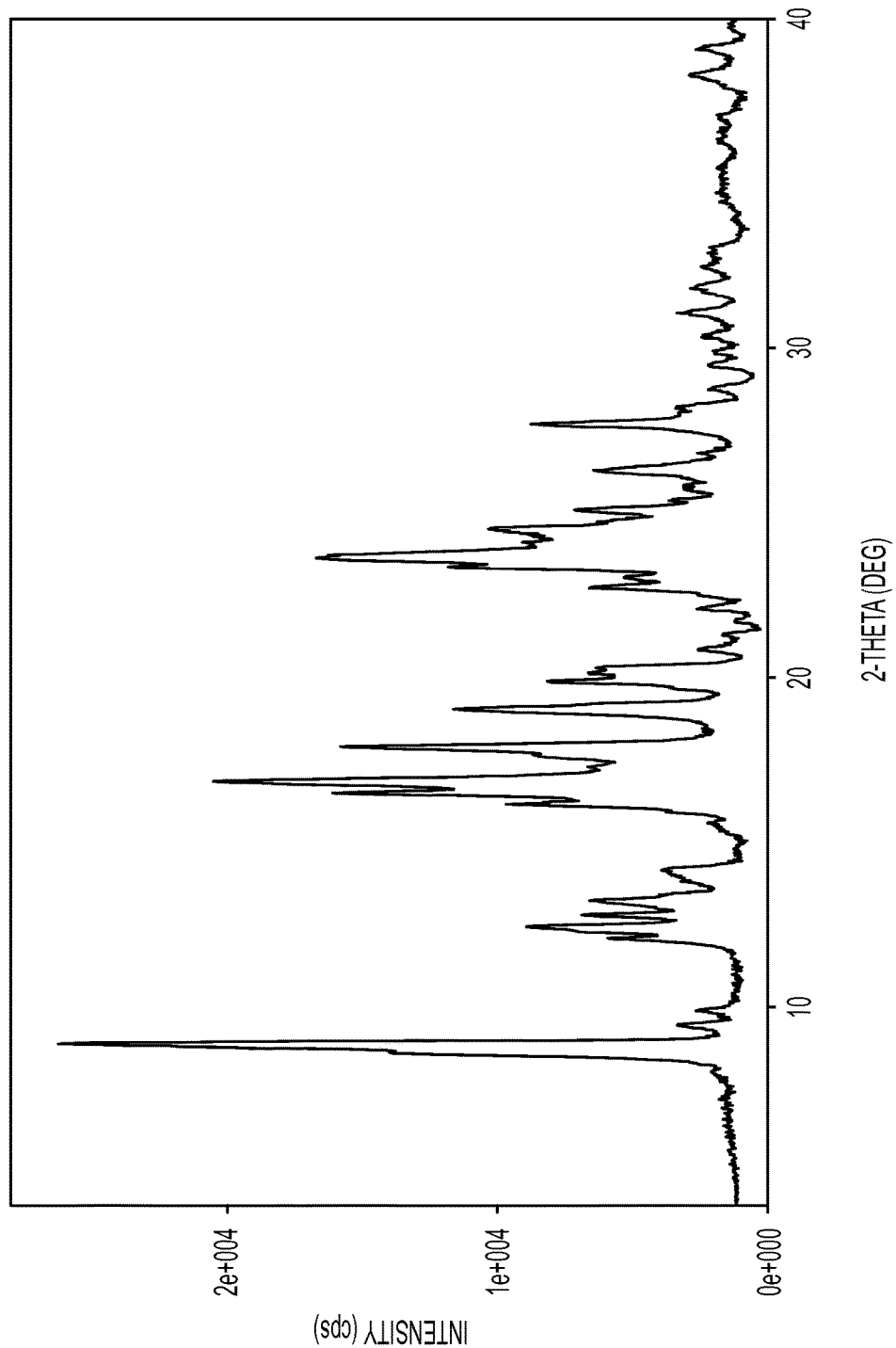
FIG. 79 depicts an XRPD pattern of Form B of compound 8.

In certain embodiments, the X-ray powder diffraction pattern is substantially similar to the XRPD provided in FIG. 79.

Methods for preparing Form B of compound 8 are described infra.

Form C of Compound 8

In some embodiments, Form C of compound 8 has at least 1, 2, 3, 4 or 5 spectral peak(s) selected from the peaks listed in Table 30 below.

TABLE 30

| XRPD Peak Positions for Form C of Compound 8 | |
|---|---|
| Peak No. | Position (°2 θ) |
| 8.8 | 23.1 |
| 9.5 | 23.8 |
| 12.5 | 24.2 |
| 13.3 | 24.6 |
| 14.2 | 25.2 |
| 16.9 | 26.3 |
| 17.4 | 30.3 |

TABLE 30-continued

| XRPD Peak Positions for Form C of Compound 8 | |
|---|---|
| Peak No. | Position (°2 θ) |
| 17.8 | 31.1 |
| 18.9 | 31.8 |
| 20.1 | 38.0 |

[1] In this and all subsequent tables, the position 2 θ is within ±0.2.

In some embodiments, Form C of compound 8 is characterized in that it has one or more peaks in its X-ray powder diffraction pattern selected from those at about 8.8, 16.9, and 24.2. In some embodiments, Form C of compound 8 is characterized in that it has two or more peaks in its X-ray powder diffraction pattern selected from those at about 8.8, 16.9, and 24.2. In some embodiments, Form C of compound 8 is characterized in that it has all three peaks in its X-ray powder diffraction pattern selected from those at about 8.8, 16.9, and 24.2.

Figure 81:
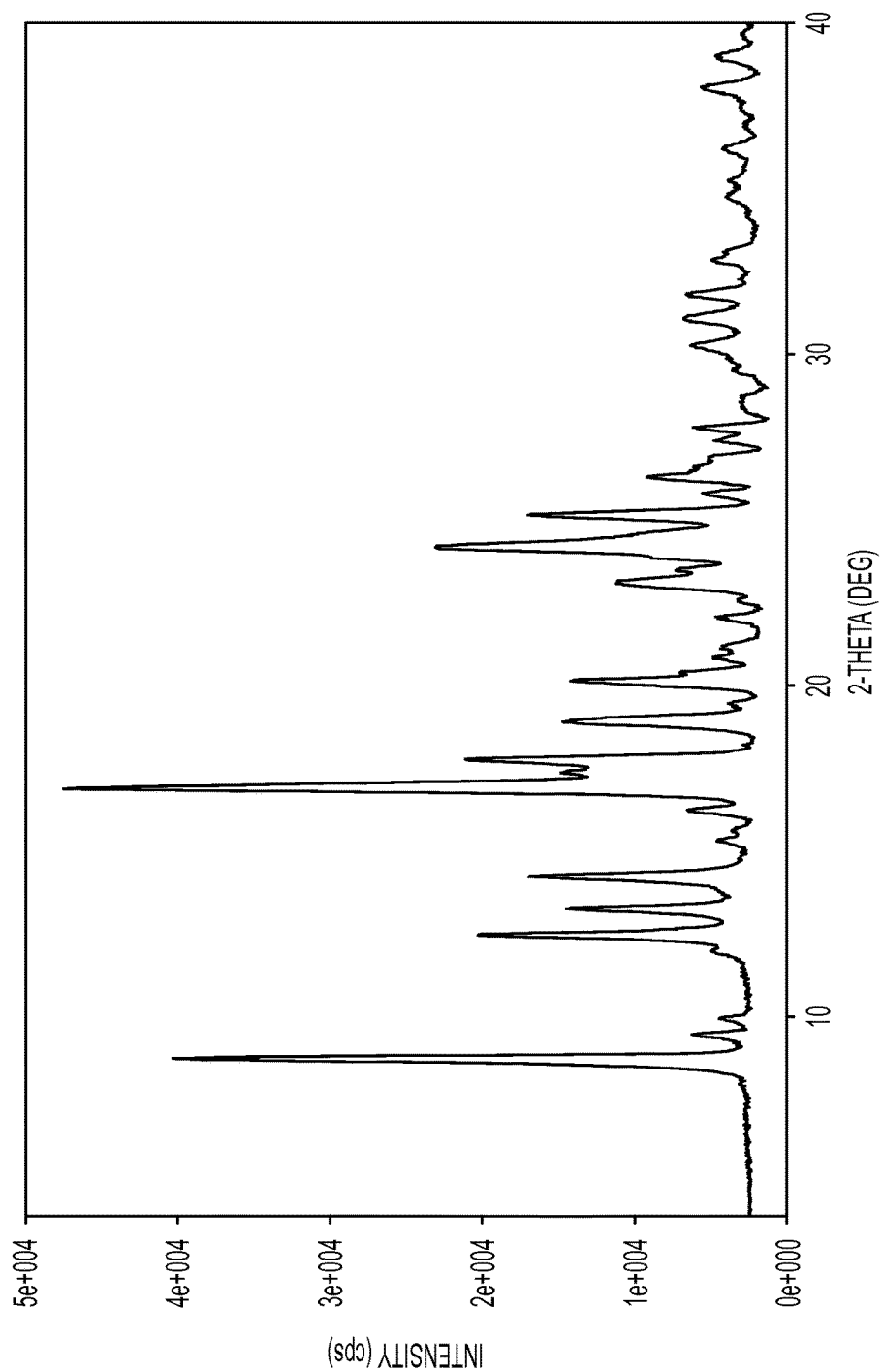
FIG. 81 depicts an XRPD pattern of Form C of compound 8.

In certain embodiments, the X-ray powder diffraction pattern is substantially similar to the XRPD provided in FIG. 81.

Methods for preparing Form C of compound 8 are described infra.

Form D of Compound 8

In some embodiments, compound 8 is an amorphous solid. For instance, in some embodiments, compound 8 is of Form D.

Figure 84:
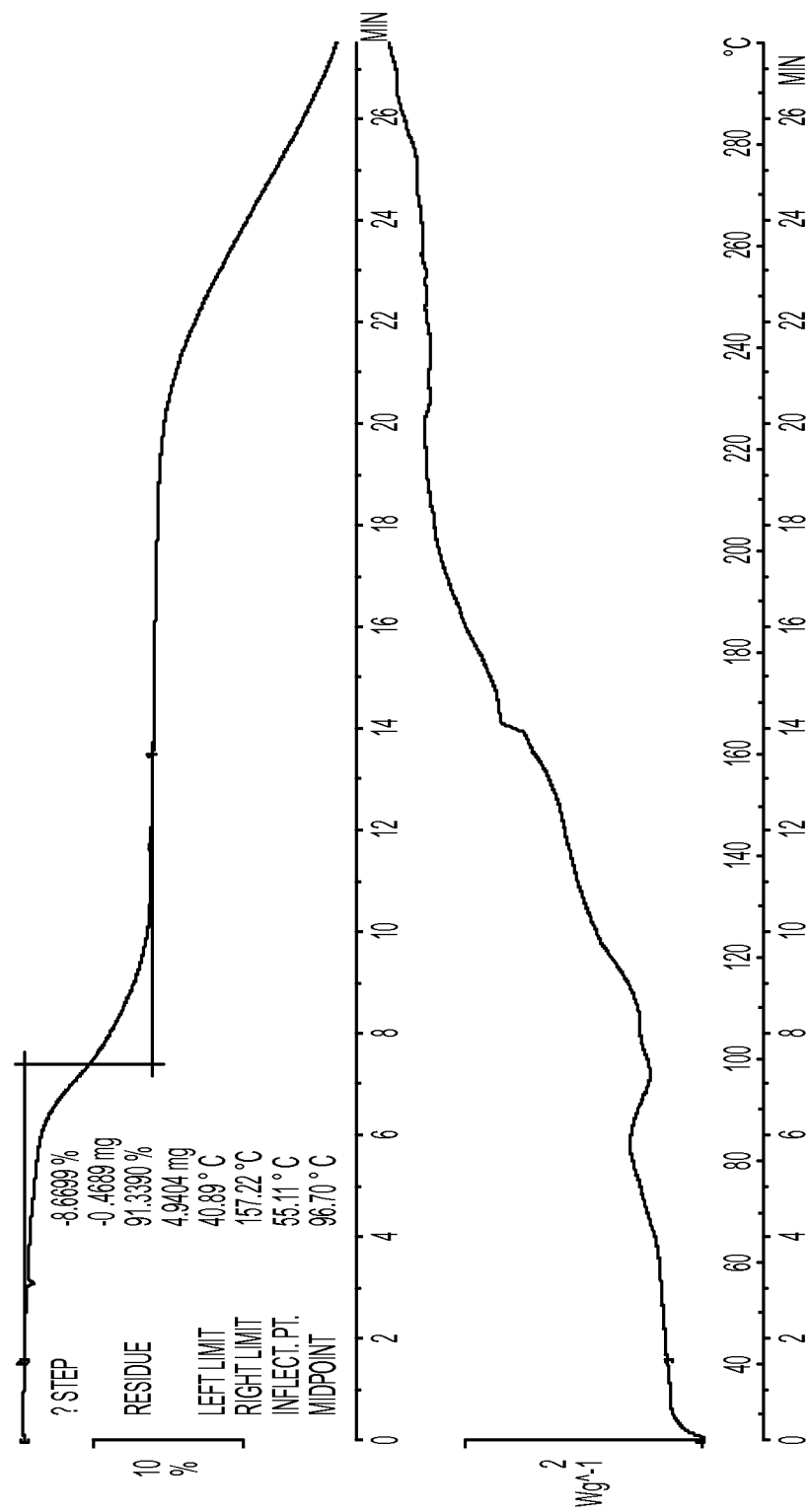
FIG. 84 depicts a DSC thermogram and TGA trace of Form D of compound 8.

In certain embodiments, Form D of compound 8 is characterized by having a DSC thermogram substantially similar to that of FIG. 84.

In certain embodiments, Form D of compound 8 is characterized by having a TGA trace substantially similar to that of FIG. 84.

Methods for preparing Form D of compound 8 are described infra.

In some embodiments, the present invention provides compound 8:

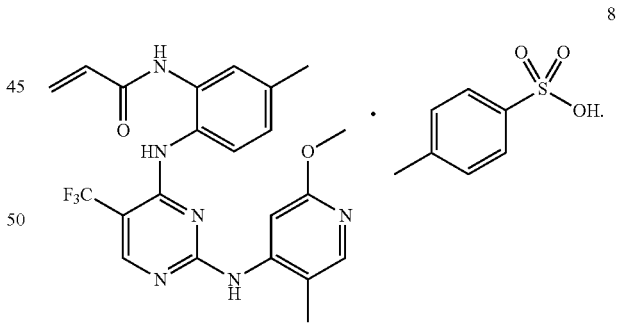

8

In some embodiments, the present invention provides compound 8, wherein said compound is crystalline.

In some embodiments, the present invention provides compound 8, wherein said compound is a crystalline solid substantially free of amorphous compound 8.

In some embodiments, the present invention provides compound 8, wherein said compound is substantially free of impurities.

In some embodiments, the present invention provides compound 8, wherein said compound has one or more peaks in its XRPD selected from those at about 9.0, about 23.8, and about 24.8 degrees 2-theta. In some such embodiments, the present invention provides compound 8, wherein said compound has at least two peaks in its XRPD selected from those at about 9.0, about 23.8, and about 24.8 degrees 2-theta. In some such embodiments, the present invention provides compound 8, wherein said compound is of Form A.

In some embodiments, the present invention provides compound 8, wherein said compound has an XRPD substantially similar to that depicted in FIG. 77.

In some embodiments, the present invention provides compound 8, wherein said compound has one or more peaks in its XRPD selected from those at about 8.9, about 23.4, and about 27.6 degrees 2-theta. In some such embodiments, the present invention provides compound 8, wherein said compound has at least two peaks in its XRPD selected from those at about 8.9, about 23.4, and about 27.6 degrees 2-theta. In some such embodiments, the present invention provides compound 8, wherein said compound is of Form B.

In some embodiments, the present invention provides compound 8, wherein said compound has an XRPD substantially similar to that depicted in FIG. 79.

In some embodiments, the present invention provides compound 8, wherein said compound has one or more peaks in its XRPD selected from those at about 8.8, about 16.9, and about 24.2 degrees 2-theta. In some such embodiments, the present invention provides compound 8, wherein said compound has at least two peaks in its XRPD selected from those at about 8.8, about 16.9, and about 24.2 degrees 2-theta. In some such embodiments, the present invention provides compound 8, wherein said compound is of Form C.

In some embodiments, the present invention provides compound 8, wherein said compound has a XRPD substantially similar to that depicted in FIG. 81.

In some embodiments, the present invention provides compound 8, wherein said compound has a DSC thermogram substantially similar to that depicted in FIG. 84. In some such embodiments, the present invention provides compound 8, wherein said compound is of Form D.

In some embodiments, the present invention provides a composition comprising compound 8 and a pharmaceutically acceptable carrier or excipient.

In some embodiments, the present invention provides a method of inhibiting one or both of ERK1 and ERK2 in a patient comprising administering to said patient compound 8 or composition thereof.

In some embodiments, the present invention provides a method of treating an ERK1- or ERK2-mediated disorder in a patient, comprising administering to said patient compound 8 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Compound 9 (Besylate Salts of Compound 1)

According to one embodiment, the present invention provides a besylate salt of compound 1, represented by compound 9:

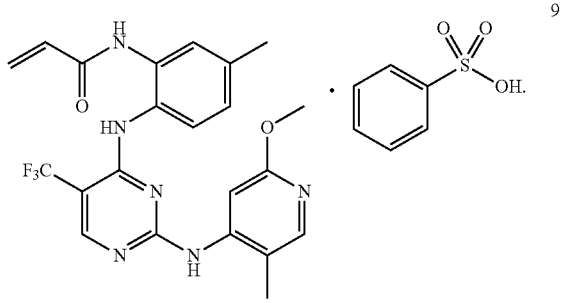

It will be appreciated by one of ordinary skill in the art that benzenesulfonic acid and compound 1 are ionically bonded to form compound 9. It is contemplated that compound 9 can exist in a variety of physical forms. For example, compound 9 can be in solution, suspension, or in solid form. In certain embodiments, compound 9 is in solid form. When compound 9 is in solid form, said compound may be amorphous, crystalline, or a mixture thereof. Exemplary solid forms are described in more detail below.

In some embodiments, the present invention provides compound 9 substantially free of impurities. As used herein, the term "substantially free of impurities" means that the compound contains no significant amount of extraneous matter. Such extraneous matter may include excess benzenesulfonic acid, excess compound 1, residual solvents, or any other impurities that may result from the preparation of, and/or isolation of, compound 9. In certain embodiments, at least about 95% by weight of compound 9 is present. In still other embodiments of the invention, at least about 99% by weight of compound 9 is present.

According to one embodiment, compound 9 is present in an amount of at least about 97, 97.5, 98.0, 98.5, 99, 99.5, 99.8 weight percent where the percentages are based on the total weight of the composition. According to another embodiment, compound 9 contains no more than about 3.0 area percent HPLC of total organic impurities and, in certain embodiments, no more than about 1.5 area percent HPLC total organic impurities relative to the total area of the HPLC chromatogram. In other embodiments, compound 9 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 9 is also meant to include all tautomeric forms of compound 9. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 9 can exist in a variety of solid forms. Exemplary such forms include polymorphs and amorphous forms such as those contemplated by the present invention.

In certain embodiments, compound 9 is a crystalline solid. In other embodiments, compound 9 is a crystalline solid substantially free of amorphous compound 9. As used herein, the term "substantially free of amorphous compound 9" means that the compound contains no significant amount of amorphous compound 9. In certain embodiments, at about 95% by weight of crystalline compound 9 is present. In still other embodiments of the invention, at least about 99% by weight of crystalline compound 9 is present.

In certain embodiments, compound 9 is an amorphous solid. In certain embodiments, at least about 95% by weight of amorphous compound 9 is present. In still other embodiments of the invention, at least about 99% by weight of amorphous compound 9 is present.

It has been found that compound 9 can exist in at least two distinct forms, one of which is crystalline and one of which is amorphous. In some embodiments, the present invention provides a crystalline form of compound 9 referred to herein as Form A. In some embodiments, the present invention provides an amorphous form of compound 9 referred to herein as Form B.

In some embodiments, compound 9 is amorphous. In some embodiments, compound 9 is amorphous, and is substantially free of crystalline compound 9.

Form A of Compound 9

In some embodiments, Form A of compound 9 has at least 1, 2, 3, 4 or 5 spectral peak(s) selected from the peaks listed in Table 31 below.

TABLE 31

XRPD Peak Positions for Form A of Compound 9

| Peak No. | Position (°2 θ) |
|---|---|
| 8.9 | 23.6 |
| 12.5 | 24.0 |
| 13.2 | 25.2 |
| 15.6 | 25.5 |
| 17.6 | 26.1 |
| 18.0 | 27.0 |
| 18.5 | 27.9 |
| 19.1 | 29.6 |
| 20.6 | 30.3 |
| 21.7 | 39.5 |

[1] In this and all subsequent tables, the position 2 θ is within ±0.2.

In some embodiments, Form A of compound 9 is characterized in that it has one or more peaks in its X-ray powder diffraction pattern selected from those at about 8.9, 18.5, and 25.2. In some embodiments, Form A of compound 9 is characterized in that it has two or more peaks in its X-ray powder diffraction pattern selected from those at about 8.9, 18.5, and 25.2. In some embodiments, Form A of compound 9 is characterized in that it has all three peaks in its X-ray powder diffraction pattern selected from those at about 8.9, 18.5, and 25.2.

Figure 85:
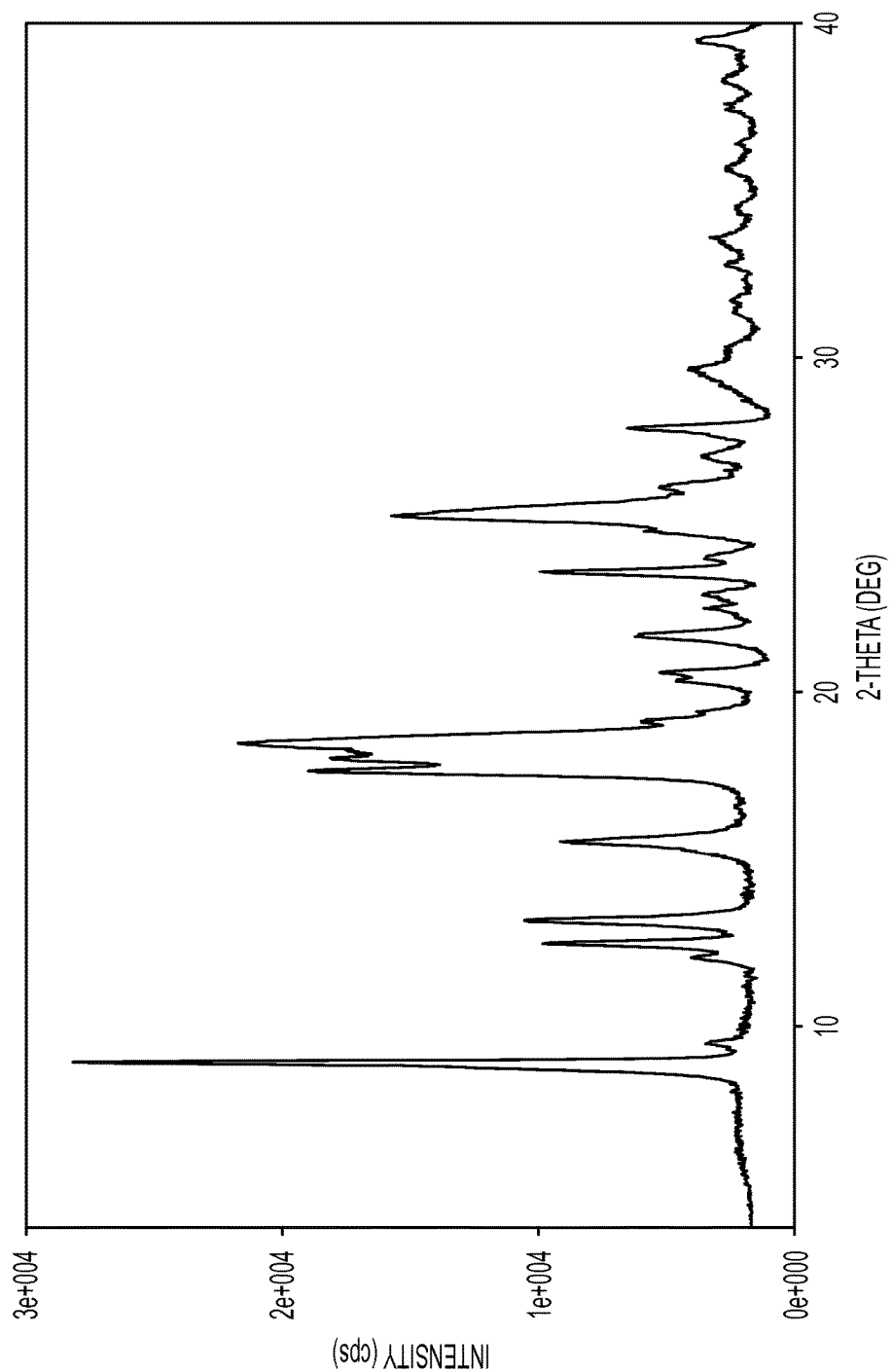
FIG. 85 depicts an XRPD pattern of Form A of compound 9.

In certain embodiments, the X-ray powder diffraction pattern is substantially similar to the XRPD provided in FIG. 85.

Methods for preparing Form A of compound 9 are described infra.

Form B of Compound 9

In some embodiments, compound 9 is an amorphous solid. For instance, in some embodiments, compound 9 is of Form B.

Figure 88:
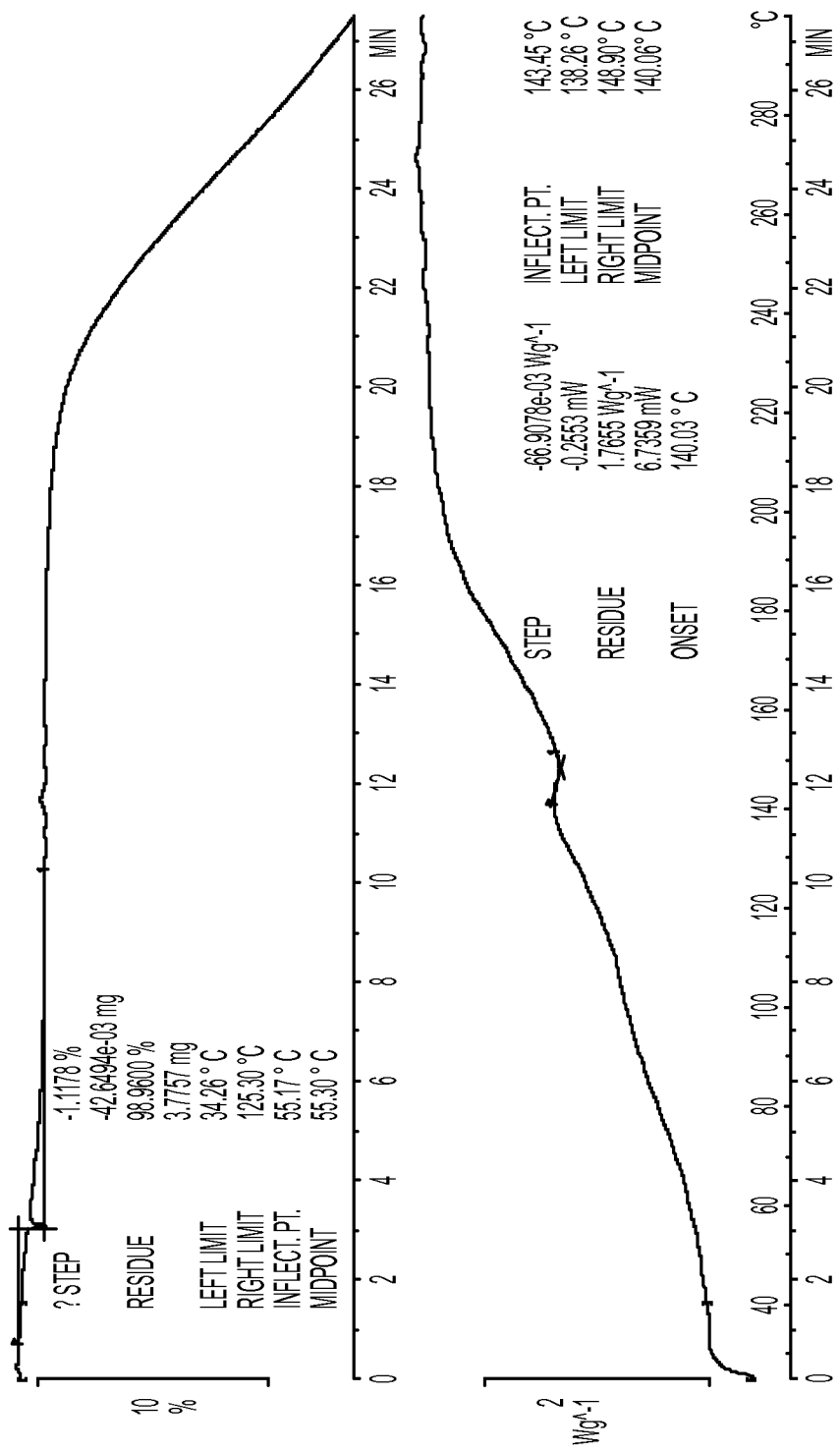
FIG. 88 depicts a DSC thermogram and TGA trace of Form B of compound 9.

In certain embodiments, Form B of compound 9 is characterized by having a DSC thermogram substantially similar to that of FIG. 88.

In certain embodiments, Form B of compound 9 is characterized by having a TGA trace substantially similar to that of FIG. 88.

Methods for preparing Form B of compound 9 are described infra.

In some embodiments, the present invention provides compound 9:

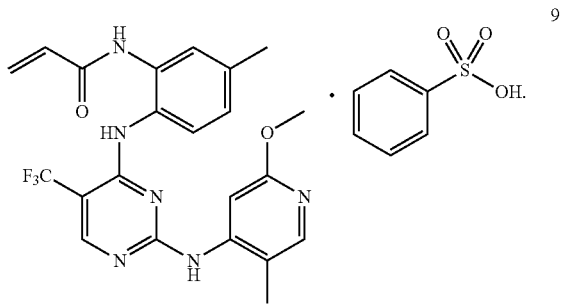

In some embodiments, the present invention provides compound 9, wherein said compound is crystalline.

In some embodiments, the present invention provides compound 9, wherein said compound is a crystalline solid substantially free of amorphous compound 9.

In some embodiments, the present invention provides compound 9, wherein said compound is substantially free of impurities.

In some embodiments, the present invention provides compound 9, wherein said compound has one or more peaks in its XRPD selected from those at about 8.9, about 18.5, and about 25.2 degrees 2-theta. In some such embodiments, the present invention provides compound 9, wherein said compound has at least two peaks in its XRPD selected from those at about 8.9, about 18.5, and about 25.2 degrees 2-theta. In some such embodiments, the present invention provides compound 9, wherein said compound is of Form A.

In some embodiments, the present invention provides compound 9, wherein said compound has a XRPD substantially similar to that depicted in FIG. 85.

In some embodiments, the present invention provides compound 9, wherein said compound has a DSC thermogram substantially similar to that depicted in FIG. 88. In some such embodiments, the present invention provides compound 9, wherein said compound is of Form B.

In some embodiments, the present invention provides a composition comprising compound 9 and a pharmaceutically acceptable carrier or excipient.

In some embodiments, the present invention provides a method of inhibiting one or both of ERK1 and ERK2 in a patient comprising administering to said patient compound 9 or composition thereof.

In some embodiments, the present invention provides a method of treating an ERK1- or ERK2-mediated disorder in a patient, comprising administering to said patient compound 9 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Compound 10 (Mesylate Salts of Compound 1)

According to one embodiment, the present invention provides a mesylate salt of compound 1, represented by compound 10:

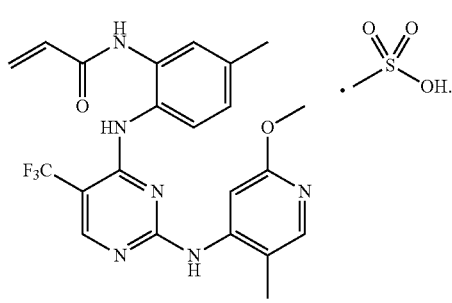

It will be appreciated by one of ordinary skill in the art that methanesulfonic acid and compound 1 are ionically bonded to form compound 10. It is contemplated that compound 10 can exist in a variety of physical forms. For example, compound 10 can be in solution, suspension, or in solid form. In certain embodiments, compound 10 is in solid form. When compound 10 is in solid form, said compound may be amorphous, crystalline, or a mixture thereof. Exemplary solid forms are described in more detail below.

In some embodiments, the present invention provides compound 10 substantially free of impurities. As used herein, the term "substantially free of impurities" means that the compound contains no significant amount of extraneous matter. Such extraneous matter may include excess methanesulfonic acid, excess compound 1, residual solvents, or any other impurities that may result from the preparation of, and/or isolation of, compound 10. In certain embodiments, at least about 95% by weight of compound 10 is present. In still other embodiments of the invention, at least about 99% by weight of compound 10 is present.

According to one embodiment, compound 10 is present in an amount of at least about 97, 97.5, 98.0, 98.5, 99, 99.5, 99.8 weight percent where the percentages are based on the total weight of the composition. According to another embodiment, compound 10 contains no more than about 3.0 area percent HPLC of total organic impurities and, in certain embodiments, no more than about 1.5 area percent HPLC total organic impurities relative to the total area of the HPLC chromatogram. In other embodiments, compound 10 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 10 is also meant to include all tautomeric forms of compound 10. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 10 can exist in a variety of solid forms. Exemplary such forms include partially crystalline forms and amorphous forms such as those contemplated by the present invention.

In certain embodiments, compound 10 is a crystalline solid. In other embodiments, compound 10 is a crystalline solid substantially free of amorphous compound 10. As used herein, the term "substantially free of amorphous compound 10" means that the compound contains no significant amount of amorphous compound 10. In certain embodiments, at least about 95% by weight of crystalline compound 10 is present. In still other embodiments of the invention, at least about 99% by weight of crystalline compound 10 is present.

In some embodiments, compound 10 is a partially crystalline solid.

In certain embodiments, compound 10 is an amorphous solid. In certain embodiments, at least about 95% by weight of amorphous compound 10 is present. In still other embodiments of the invention, at least about 99% by weight of amorphous compound 10 is present.

It has been found that compound 10 can exist in at least two forms, one of which is amorphous and the other of which is partially crystalline. In some embodiments, the present invention provides an amorphous form of compound 10 referred to herein as Form A. In some embodiments, the present invention provides a partially crystalline form of compound 10 referred to herein as Form B.

In some embodiments, compound 10 is amorphous. In some embodiments, compound 10 is amorphous, and is substantially free of crystalline compound 10.

Form A of Compound 10

In some embodiments, compound 10 is an amorphous solid. For instance, in some embodiments, compound 10 is of Form A.

Figure 89:
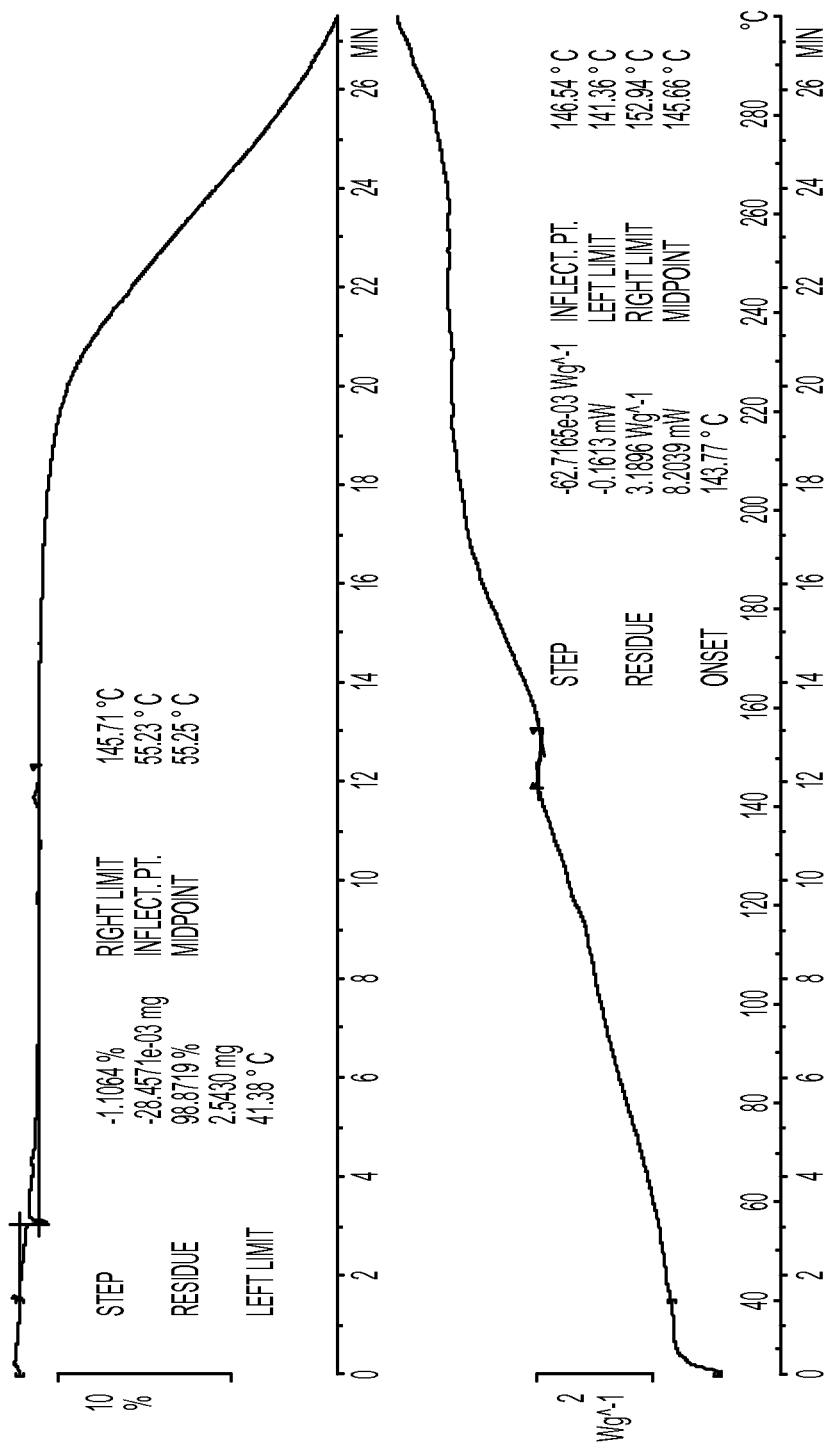
FIG. 89 depicts a DSC thermogram and TGA trace of Form A of compound 10.

In certain embodiments, Form A of compound 10 is characterized by having a DSC thermogram substantially similar to that of FIG. 89.

In certain embodiments, Form A of compound 10 is characterized by having a TGA trace substantially similar to that of FIG. 89.

Methods for preparing Form A of compound 10 are described infra.

Form B of Compound 10

In some embodiments, Form B of compound 10 has at least 1, 2, 3, 4 or 5 spectral peak(s) selected from the peaks listed in Table 32 below.

TABLE 32

| XRPD Peak Positions for Form B of Compound 10 Position (°2 θ) |
|---|
| 6.1 |
| 7.9 |
| 8.3 |
| 16.3 |
| 22.6 |

[1] In this and all subsequent tables, the position 2 θ is within ±0.2.

In some embodiments, Form B of compound 10 is characterized in that it has one or more peaks in its X-ray powder diffraction pattern selected from those at about 6.1, 8.3, and 22.6. In some embodiments, Form B of compound 10 is characterized in that it has two or more peaks in its X-ray powder diffraction pattern selected from those at about 6.1, 8.3, and 22.6. In some embodiments, Form B of compound 10 is characterized in that it has all three peaks in its X-ray powder diffraction pattern selected from those at about 6.1, 8.3, and 22.6.

Figure 90:
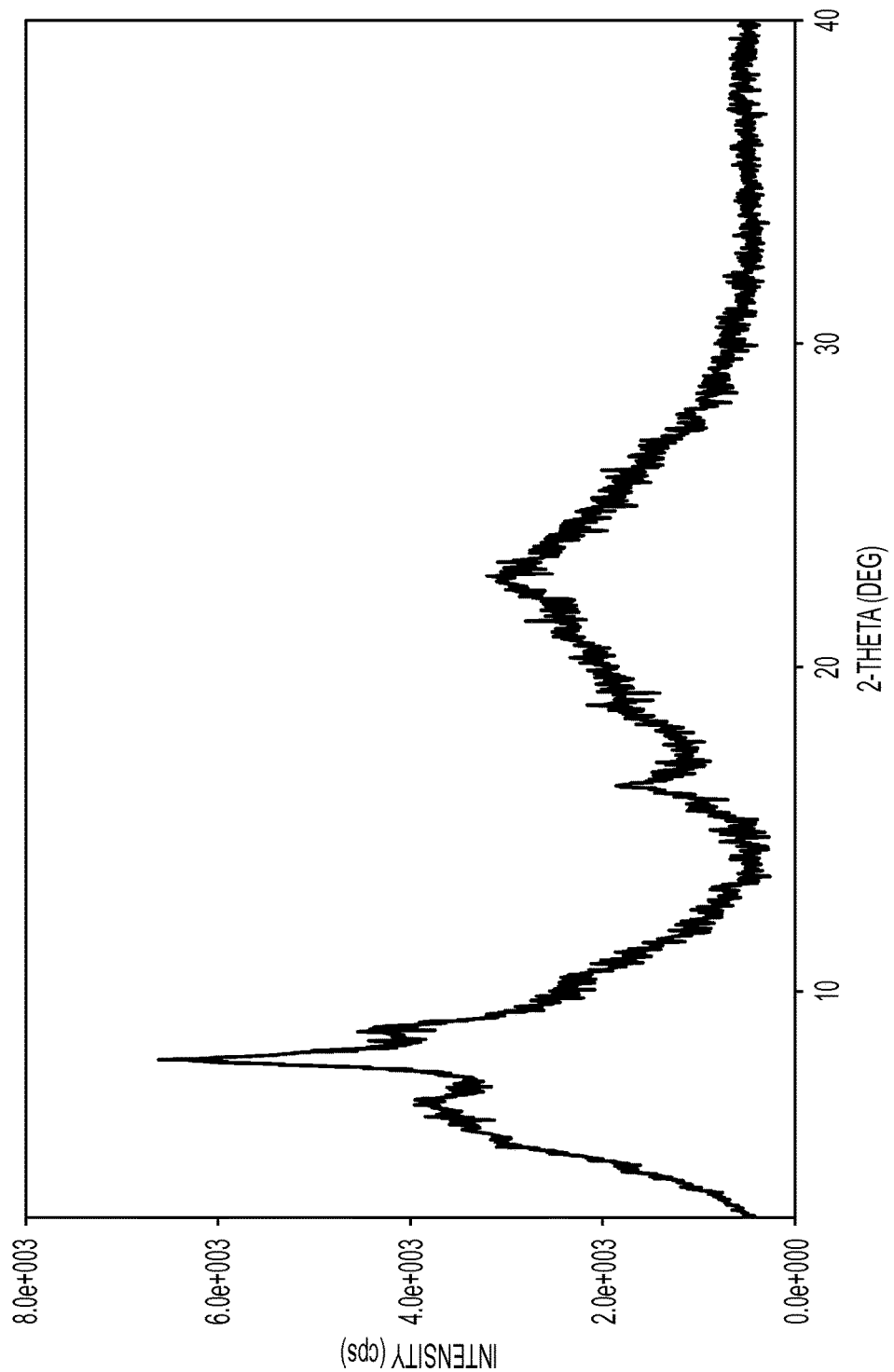
FIG. 90 depicts an XRPD pattern of Form B of compound 10.

In certain embodiments, the X-ray powder diffraction pattern is substantially similar to the XRPD provided in FIG. 90.

Methods for preparing Form B of compound 10 are described infra.

In some embodiments, the present invention provides compound 10:

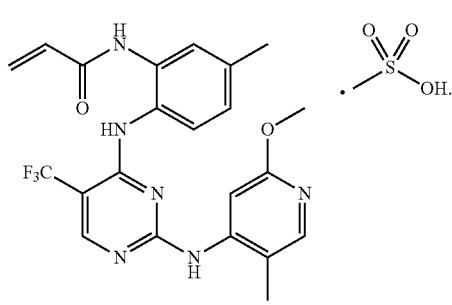

10

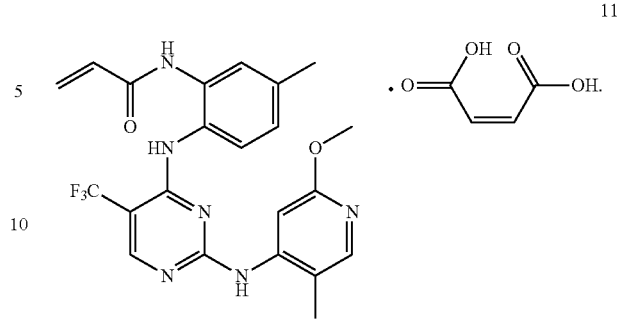

11

In some embodiments, the present invention provides compound 10, wherein said compound is crystalline. In some embodiments, the present invention provides compound 10, wherein said compound is partially crystalline.

In some embodiments, the present invention provides compound 10, wherein said compound is a crystalline solid substantially free of amorphous compound 10.

In some embodiments, the present invention provides compound 10, wherein said compound is substantially free of impurities.

In some embodiments, the present invention provides compound 10, wherein said compound has a DSC thermogram substantially similar to that depicted in FIG. 89. In some such embodiments, the present invention provides compound 10, wherein said compound is of Form A.

In some embodiments, the present invention provides compound 10, wherein said compound has one or more peaks in its XRPD selected from those at about 6.1, about 8.3, and about 22.6 degrees 2-theta. In some such embodiments, the present invention provides compound 10, wherein said compound has at least two peaks in its XRPD selected from those at about 6.1, about 8.3, and about 22.6 degrees 2-theta. In some such embodiments, the present invention provides compound 10, wherein said compound is of Form B.

In some embodiments, the present invention provides compound 10, wherein said compound has an XRPD substantially similar to that depicted in FIG. 90.

Figure 91:
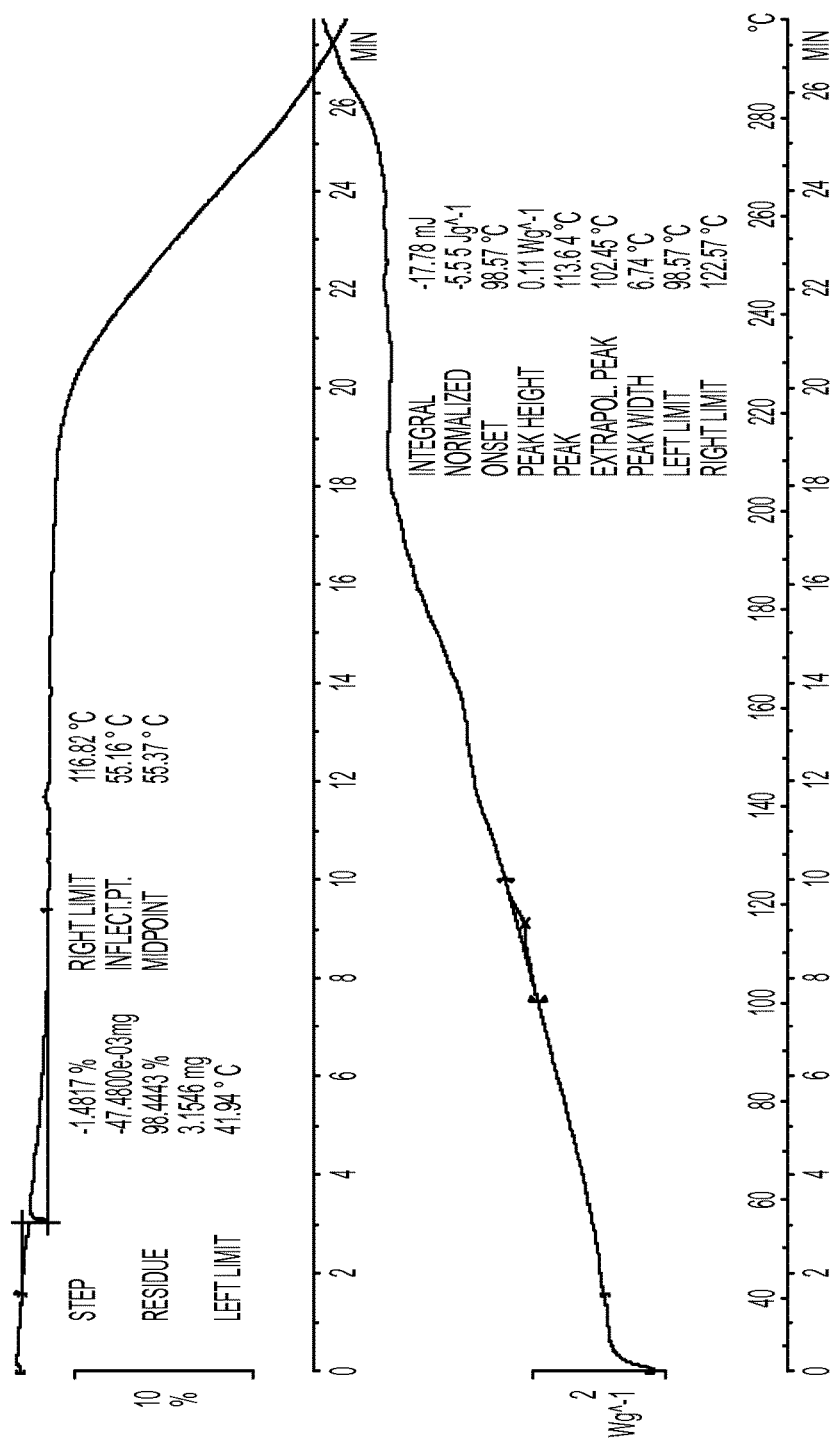
FIG. 91 depicts a DSC thermogram and TGA trace of Form B of compound 10.

In some embodiments, the present invention provides compound 10, wherein said compound has a DSC thermogram substantially similar to that depicted in FIG. 91.

In some embodiments, the present invention provides a composition comprising compound 10 and a pharmaceutically acceptable carrier or excipient.

In some embodiments, the present invention provides a method of inhibiting one or both of ERK1 and ERK2 in a patient comprising administering to said patient compound 10 or composition thereof.

In some embodiments, the present invention provides a method of treating an ERK1- or ERK2-mediated disorder in a patient, comprising administering to said patient compound 10 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Compound 11 (Maleate Salts of Compound 1)

According to one embodiment, the present invention provides a maleate salt of compound 1, represented by compound 11:

It will be appreciated by one of ordinary skill in the art that maleic acid and compound 1 are ionically bonded to form compound 11. It is contemplated that compound 11 can exist in a variety of physical forms. For example, compound 11 can be in solution, suspension, or in solid form. In certain embodiments, compound 11 is in solid form. When compound 11 is in solid form, said compound may be amorphous, crystalline, or a mixture thereof. Exemplary solid forms are described in more detail below.

In some embodiments, the present invention provides compound 11 substantially free of impurities. As used herein, the term "substantially free of impurities" means that the compound contains no significant amount of extraneous matter. Such extraneous matter may include excess maleic acid, excess compound 1, residual solvents, or any other impurities that may result from the preparation of, and/or isolation of, compound 11. In certain embodiments, at least about 95% by weight of compound 11 is present. In still other embodiments of the invention, at least about 99% by weight of compound 11 is present.

According to one embodiment, compound 11 is present in an amount of at least about 97, 97.5, 98.0, 98.5, 99, 99.5, 99.8 weight percent where the percentages are based on the total weight of the composition. According to another embodiment, compound 11 contains no more than about 3.0 area percent HPLC of total organic impurities and, in certain embodiments, no more than about 1.5 area percent HPLC total organic impurities relative to the total area of the HPLC chromatogram. In other embodiments, compound 11 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 11 is also meant to include all tautomeric forms of compound 11. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

In certain embodiments, compound 11 is a crystalline solid. In other embodiments, compound 11 is a crystalline solid substantially free of amorphous compound 11. As used herein, the term "substantially free of amorphous compound 11" means that the compound contains no significant amount of amorphous compound 11. In certain embodiments, at least about 95% by weight of crystalline compound 11 is present. In still other embodiments of the invention, at least about 99% by weight of crystalline compound 11 is present.

It has been found that compound 11 can exist in at least one distinct crystalline form. In some embodiments, the present invention provides a crystalline form of compound 11 referred to herein as Form A.

In some embodiments, compound 11 is amorphous. In some embodiments, compound 11 is amorphous, and is substantially free of crystalline compound 11.

Form A of Compound 11

In some embodiments, Form A of compound 11 has at least 1, 2, 3, 4 or 5 spectral peak(s) is or are selected from the peaks listed in Table 33 below.

TABLE 33

XRPD Peak Positions for Form A of Compound 11
Position (°2 θ)

| |
|---|
| 5.2 |
| 8.9 |
| 9.2 |
| 10.4 |
| 12.0 |
| 13.3 |
| 13.4 |
| 15.3 |
| 16.1 |
| 18.7 |
| 20.9 |
| 23.0 |
| 23.2 |
| 23.9 |
| 24.6 |
| 25.6 |
| 26.1 |
| 26.3 |
| 26.7 |
| 27.0 |

[1] In this and all subsequent tables, the position 2 θ is within ±0.2.

In some embodiments, Form A of compound 11 is characterized in that it has one or more peaks in its X-ray powder diffraction pattern selected from those at about 8.9, 9.2, and 16.1. In some embodiments, Form A of compound 11 is characterized in that it has two or more peaks in its X-ray powder diffraction pattern selected from those at about 8.9, 9.2, and 16.1. In some embodiments, Form A of compound 11 is characterized in that it has all three peaks in its X-ray powder diffraction pattern selected from those at about 8.9, 9.2, and 16.1.

Figure 92:
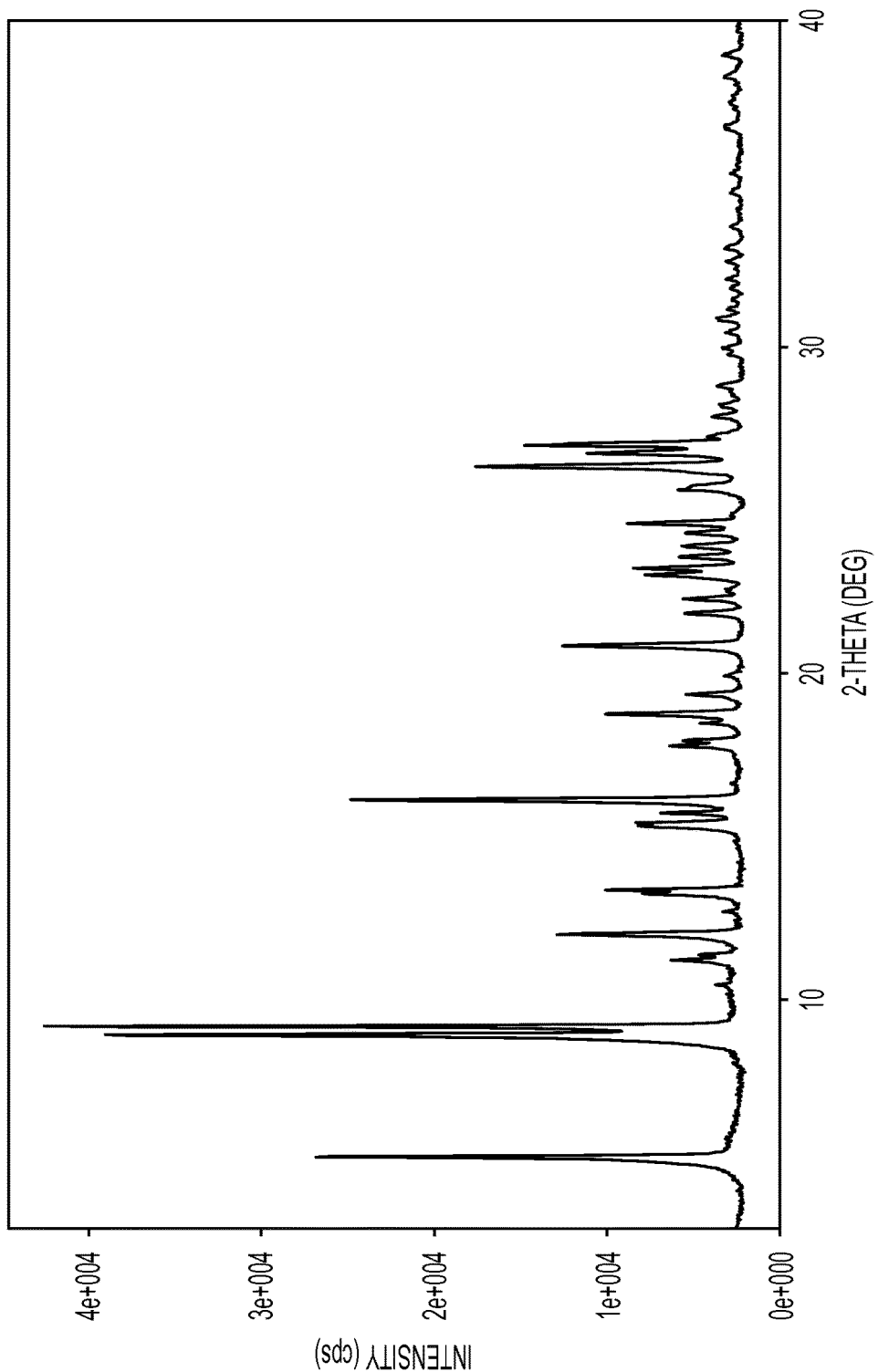
FIG. 92 depicts an XRPD pattern of Form A of compound 11.

In certain embodiments, the X-ray powder diffraction pattern is substantially similar to the XRPD provided in FIG. 92.

Methods for preparing Form A of compound 11 are described infra.

In some embodiments, the present invention provides compound 11:

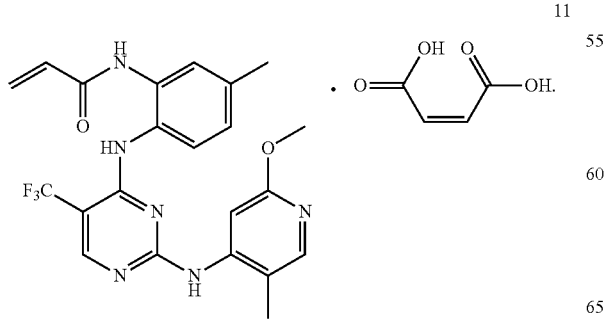

In some embodiments, the present invention provides compound 11, wherein said compound is crystalline.

In some embodiments, the present invention provides compound 11, wherein said compound is a crystalline solid substantially free of amorphous compound 11.

In some embodiments, the present invention provides compound 11, wherein said compound is substantially free of impurities.

In some embodiments, the present invention provides compound 11, wherein said compound has one or more peaks in its XRPD selected from those at about 8.9, about 9.2, and about 16.1 degrees 2-theta. In some such embodiments, the present invention provides compound 11, wherein said compound has at least two peaks in its XRPD selected from those at about 8.9, about 9.2, and about 16.1 degrees 2-theta. In some such embodiments, the present invention provides compound 11, wherein said compound is of Form A.

In some embodiments, the present invention provides compound 11, wherein said compound has an XRPD substantially similar to that depicted in FIG. 92.

In some embodiments, the present invention provides a composition comprising compound 11 and a pharmaceutically acceptable carrier or excipient.

In some embodiments, the present invention provides a method of inhibiting one or both of ERK1 and ERK2 in a patient comprising administering to said patient compound 11 or composition thereof.

In some embodiments, the present invention provides a method of treating an ERK1- or ERK2-mediated disorder in a patient, comprising administering to said patient compound 11 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

Compound 12 (Oxalate Salts of Compound 1)

According to one embodiment, the present invention provides an oxalate salt of compound 1, represented by compound 12:

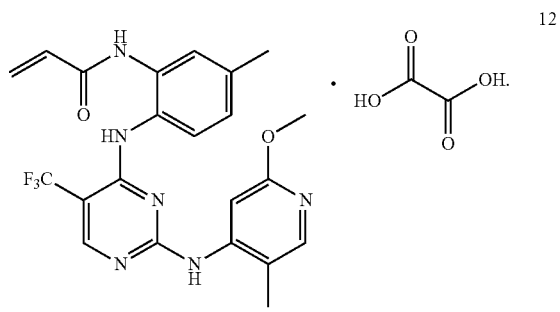 [SMILES: C=CC(=O)Nc1cc(C)ccc1Nc1nc(Nc2cc(OC)ncc2C)ncc1C(F)(F)F ; O=C(O)C(=O)O]

It will be appreciated by one of ordinary skill in the art that oxalic acid and compound 1 are ionically bonded to form compound 12. It is contemplated that compound 12 can exist in a variety of physical forms. For example, compound 12 can be in solution, suspension, or in solid form. In certain embodiments, compound 12 is in solid form. When compound 12 is in solid form, said compound may be amorphous, crystalline, or a mixture thereof. Exemplary solid forms are described in more detail below.

In some embodiments, the present invention provides compound 12 substantially free of impurities. As used herein, the term "substantially free of impurities" means that the compound contains no significant amount of extraneous matter. Such extraneous matter may include excess oxalic acid, excess compound 1, residual solvents, or any other impurities that may result from the preparation of, and/or isolation of, compound 12. In certain embodiments, at least about 95% by weight of compound 12 is present. In still other embodiments of the invention, at least about 99% by weight of compound 12 is present.

According to one embodiment, compound 12 is present in an amount of at least about 97, 97.5, 98.0, 98.5, 99, 99.5, 99.8 weight percent where the percentages are based on the total weight of the composition. According to another embodiment, compound 12 contains no more than about 3.0 area percent HPLC of total organic impurities and, in certain embodiments, no more than about 1.5 area percent HPLC total organic impurities relative to the total area of the HPLC chromatogram. In other embodiments, compound 12 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 12 is also meant to include all tautomeric forms of compound 12. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 12 can exist in a variety of solid forms. Exemplary such forms include polymorphs forms such as those contemplated by the present invention.

In certain embodiments, compound 12 is a crystalline solid. In other embodiments, compound 12 is a crystalline solid substantially free of amorphous compound 12. As used herein, the term "substantially free of amorphous compound 12" means that the compound contains no significant amount of amorphous compound 12. In certain embodiments, at least about 95% by weight of crystalline compound 12 is present. In still other embodiments of the invention, at least about 99% by weight of crystalline compound 12 is present.

It has been found that compound 12 can exist in at least three distinct polymorphic forms. In some embodiments, the present invention provides a polymorphic form of compound 12 referred to herein as Form A. In some embodiments, the present invention provides a polymorphic form of compound 12 referred to herein as Form B. In some embodiments, the present invention provides a polymorphic form of compound 12 referred to herein as Form C.

In some embodiments, compound 12 is amorphous. In some embodiments, compound 12 is amorphous, and is substantially free of crystalline compound 12.

Form A of Compound 12

In some embodiments, Form A of compound 12 has at least 1, 2, 3, 4 or 5 spectral peak(s) selected from the peaks listed in Table 34 below.

TABLE 34

XRPD Peak Positions for Form A of Compound 12
Position (°2 θ)

| |
|---|
| 5.4 |
| 5.8 |
| 6.8 |
| 9.7 |
| 10.3 |
| 12.3 |
| 13.4 |
| 14.4 |
| 16.4 |
| 17.4 |
| 17.7 |
| 20.3 |
| 22.0 |
| 23.4 |
| 23.7 |
| 24.9 |
| 25.2 |
| 26.9 |
| 30.2 |
| 35.4 |

[1] In this and all subsequent tables, the position 2 θ is within ±0.2.

In some embodiments, Form A of compound 12 is characterized in that it has one or more peaks in its X-ray powder diffraction pattern selected from those at about 5.4, 5.8, and 22.0. In some embodiments, Form A of compound 12 is characterized in that it has two or more peaks in its X-ray powder diffraction pattern selected from those at about 5.4, 5.8, and 22.0. In some embodiments, Form A of compound 12 is characterized in that it has all three peaks in its X-ray powder diffraction pattern selected from those at about 5.4, 5.8, and 22.0.

Figure 94:
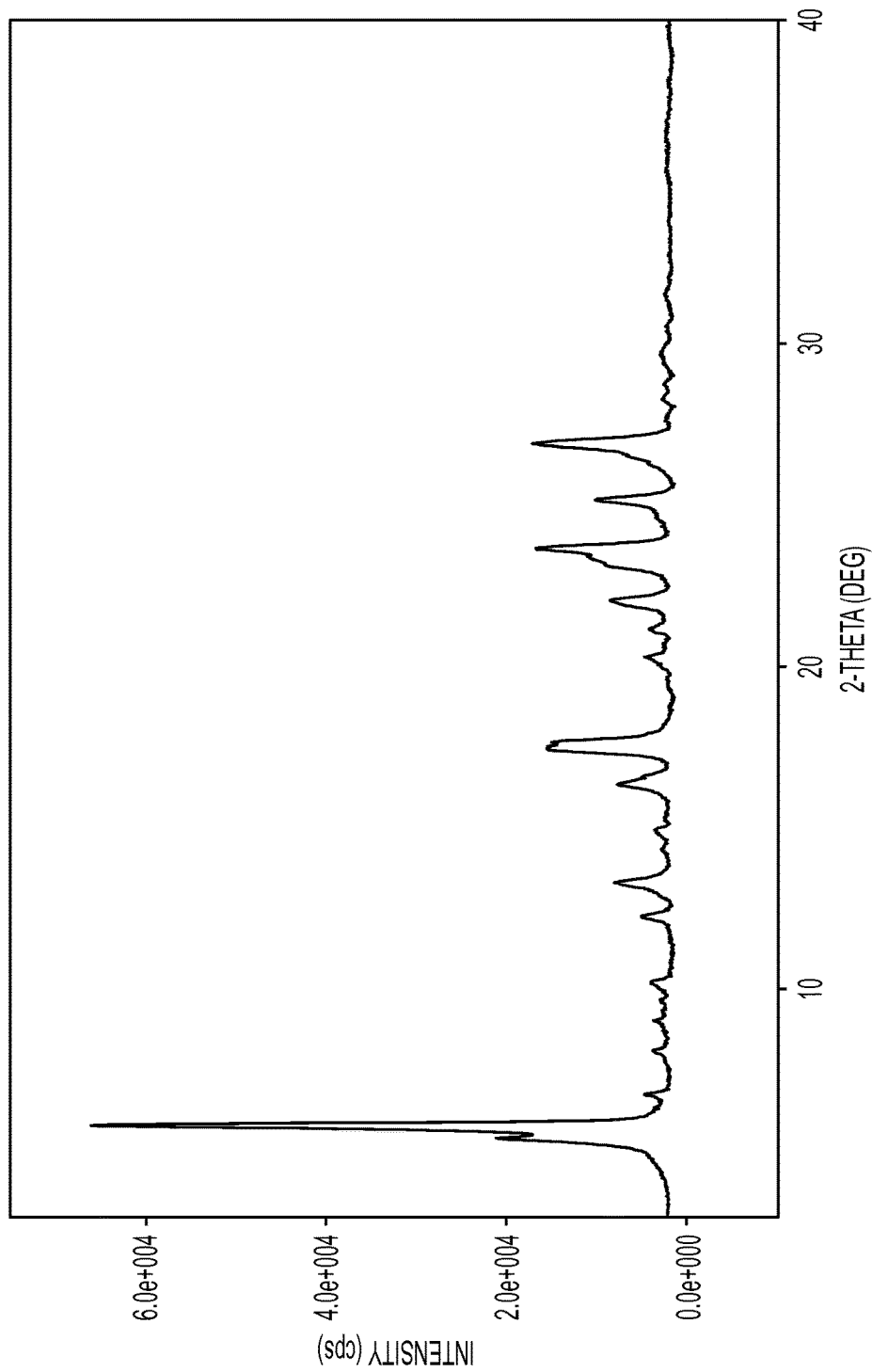
FIG. 94 depicts an XRPD pattern of Form A of compound 12.

In certain embodiments, the X-ray powder diffraction pattern is substantially similar to the XRPD provided in FIG. 94.

Methods for preparing Form A of compound 12 are described infra.

Form B of Compound 12

In some embodiments, Form B of compound 12 has at least 1, 2, 3, 4 or 5 spectral peak(s) selected from the peaks listed in Table 35 below.

TABLE 35

XRPD Peak Positions for Form B of Compound 12
Position (°2 θ)

| |
|---|
| 5.0 |
| 5.8 |
| 8.3 |
| 9.1 |
| 9.9 |
| 12.5 |
| 13.4 |
| 14.8 |
| 15.2 |
| 16.7 |
| 17.4 |
| 20.3 |
| 21.7 |
| 24.8 |
| 25.3 |
| 26.3 |
| 26.8 |
| 28.1 |
| 29.2 |
| 30.6 |

[1] In this and all subsequent tables, the position 2 θ is within ±0.2.

In some embodiments, Form B of compound 12 is characterized in that it has one or more peaks in its X-ray powder diffraction pattern selected from those at about 5.0, 9.9, and 26.3. In some embodiments, Form B of compound 12 is characterized in that it has two or more peaks in its X-ray powder diffraction pattern selected from those at about 5.0, 9.9, and 26.3. In some embodiments, Form B of compound 12 is characterized in that it has all three peaks in its X-ray powder diffraction pattern selected from those at about 5.0, 9.9, and 26.3.

Figure 96:
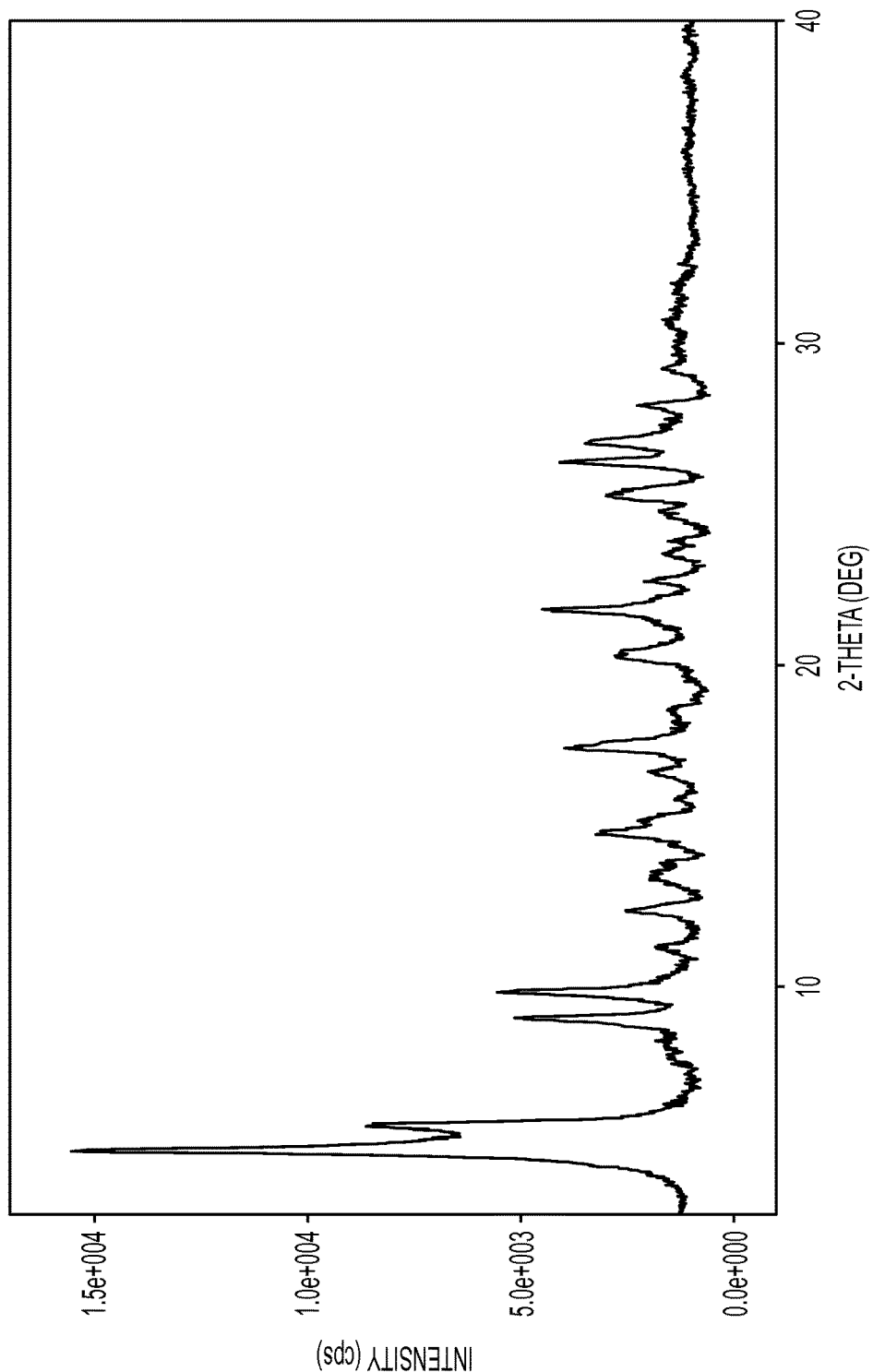
FIG. 96 depicts an XRPD pattern of Form B of compound 12.

In certain embodiments, the X-ray powder diffraction pattern is substantially similar to the XRPD provided in FIG. 96.

Methods for preparing Form B of compound 12 are described infra.

Form C of Compound 12

In some embodiments, Form C of compound 12 has at least 1, 2, 3, 4 or 5 spectral peak(s) is or are selected from the peaks listed in Table 36 below.

TABLE 36

| XRPD Peak Positions for Form C of Compound 12 Position (°2 θ) |
| --- |
| 5.6 |
| 5.8 |
| 8.4 |
| 9.3 |
| 10.1 |
| 12.4 |
| 13.4 |
| 14.9 |
| 16.2 |
| 16.6 |
| 17.5 |
| 18.5 |
| 21.8 |
| 22.2 |
| 23.4 |
| 25.2 |
| 25.9 |
| 26.3 |
| 26.9 |
| 36.5 |

[1] In this and all subsequent tables, the position 2 θ is within ±0.2.

In some embodiments, Form C of compound 12 is characterized in that it has one or more peaks in its X-ray powder diffraction pattern selected from those at about 5.6, 5.8, and 8.4. In some embodiments, Form C of compound 12 is characterized in that it has two or more peaks in its X-ray powder diffraction pattern selected from those at about 5.6, 5.8, and 8.4. In some embodiments, Form C of compound 12 is characterized in that it has all three peaks in its X-ray powder diffraction pattern selected from those at about 5.6, 5.8, and 8.4.

Figure 98:
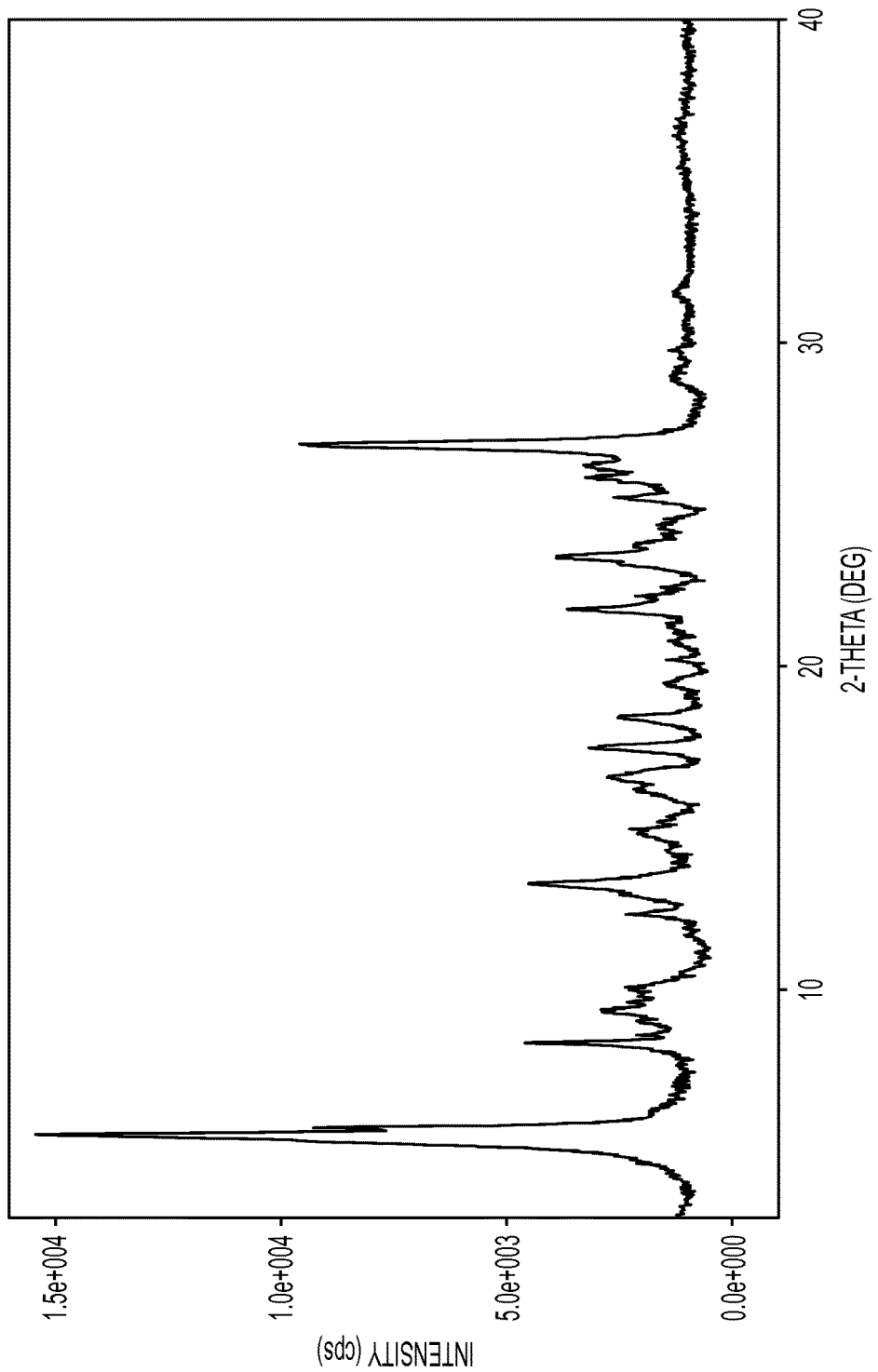
FIG. 98 depicts an XRPD pattern of Form C of compound 12.

In certain embodiments, the X-ray powder diffraction pattern is substantially similar to the XRPD provided in FIG. 98.

Methods for preparing Form C of compound 12 are described infra.

In some embodiments, the present invention provides compound 12:

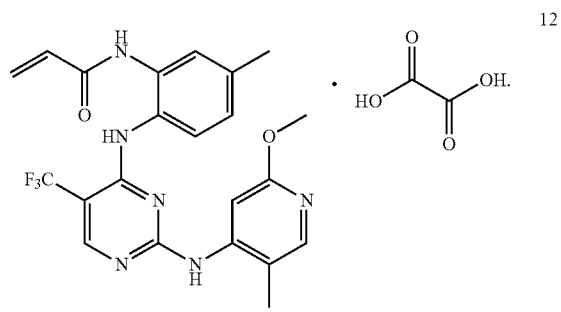 [SMILES: C=CC(=O)Nc1cc(C)ccc1Nc1nc(Nc2cc(OC)ncc2C)ncc1C(F)(F)F ; O=C(O)C(=O)O]

In some embodiments, the present invention provides compound 12, wherein said compound is crystalline.

In some embodiments, the present invention provides compound 12, wherein said compound is a crystalline solid substantially free of amorphous compound 12.

In some embodiments, the present invention provides compound 12, wherein said compound is substantially free of impurities.

In some embodiments, the present invention provides compound 12, wherein said compound has one or more peaks in its XRPD selected from those at about 5.4, about 5.8, and about 22.0 degrees 2-theta. In some such embodiments, the present invention provides compound 12, wherein said compound has at least two peaks in its XRPD selected from those at about 5.4, about 5.8, and about 22.0 degrees 2-theta. In some such embodiments, the present invention provides compound 12, wherein said compound is of Form A.

In some embodiments, the present invention provides compound 12, wherein said compound has an XRPD substantially similar to that depicted in FIG. 94.

In some embodiments, the present invention provides compound 12, wherein said compound has one or more peaks in its XRPD selected from those at about 5.0, about 9.9, and about 26.3 degrees 2-theta. In some such embodiments, the present invention provides compound 12, wherein said compound has at least two peaks in its XRPD selected from those at about 5.0, about 9.9, and about 26.3 degrees 2-theta. In some such embodiments, the present invention provides compound 12, wherein said compound is of Form B.

In some embodiments, the present invention provides compound 12, wherein said compound has a XRPD substantially similar to that depicted in FIG. 96.

In some embodiments, the present invention provides compound 12, wherein said compound has one or more peaks in its XRPD selected from those at about 5.6, about 5.8, and about 8.4 degrees 2-theta. In some such embodiments, the present invention provides compound 12, wherein said compound has at least two peaks in its XRPD selected from those at about 5.6, about 5.8, and about 8.4 degrees 2-theta. In some such embodiments, the present invention provides compound 12, wherein said compound is of Form C.

In some embodiments, the present invention provides compound 12, wherein said compound has an XRPD substantially similar to that depicted in FIG. 98.

In some embodiments, the present invention provides a composition comprising compound 12 and a pharmaceutically acceptable carrier or excipient.

In some embodiments, the present invention provides a method of inhibiting one or both of ERK1 and ERK2 in a patient comprising administering to said patient compound 12 or composition thereof.

In some embodiments, the present invention provides a method of treating an ERK1- or ERK2-mediated disorder in a patient, comprising administering to said patient compound 12 or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

In some embodiments, the present invention provides a compound selected from: compound 1, Form A, compound 1, Form B, compound 1, Form C, compound 1, Form D, compound 2, Form A, compound 2, Form B, compound 2, Form C, compound 2, Form D, compound 3, Form A, compound 4, Form A, compound 4, Form B, compound 4, Form C, compound 4, Form D, compound 4, Form E, compound 4, Form F, compound 4, Form G, compound 4, Form H, compound 4, Form I, compound 5, Form A, compound 5, Form B, compound 5, Form C, compound 5, Form D, compound 5, Form E, compound 6, Form A, compound 6, Form B, compound 6, Form C, compound 7, Form A, compound 8, Form A, compound 8, Form B, compound 8, Form C, compound 8, Form D, compound 9, Form A, compound 9, Form B, compound 10, Form A, compound 10, Form B, compound 11, Form A, compound 12, Form A, compound 12, Form B, and compound 12, Form C. In some such embodiments, the present invention provides a composition comprising one of the above compound forms and a pharmaceutically acceptable carrier or excipient. In some such embodiments, the present invention provides a method of inhibiting one or both of ERK1 and ERK2 in a patient comprising administering to said patient one of the above compound forms or composition thereof. In some such embodiments, the present invention provides a method of treating an ERK1- or ERK2-mediated disorder in a patient, comprising administering to said patient one of the above compound forms or composition thereof. In some such embodiments, the ERK1- or ERK2-mediated disorder is selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases.

General Methods of Providing a Salt Compound

Compound 1 is prepared according to the methods described in detail in the '230 publication, the entirety of which is hereby incorporated herein by reference. Salt compounds of general formula A, which formula encompasses, inter alia, salt compounds 2 through 12, and/or particular forms thereof, are prepared from compound 1, according to the general Scheme below.

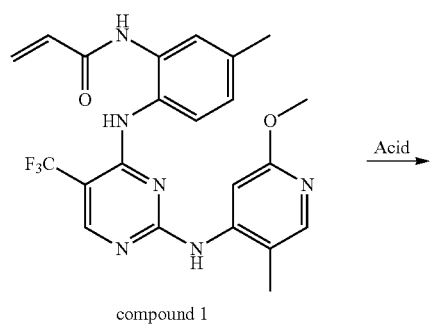

compound 1

Acid →

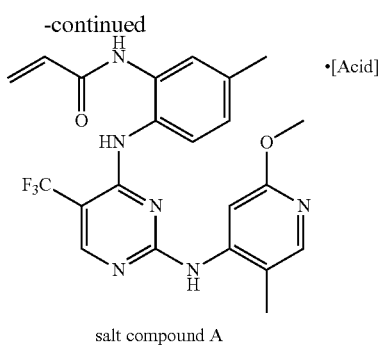

salt compound A

For instance, each of compounds 2 through 12, and forms thereof, are prepared from compound 1 by combining compound 1 with an appropriate acid to form a salt of that acid. Thus, another aspect of the present invention provides a method for preparing compounds 2 through 12, and forms thereof.

As described generally above, in some embodiments, the present invention provides a method for preparing a salt compound of the general formula A:

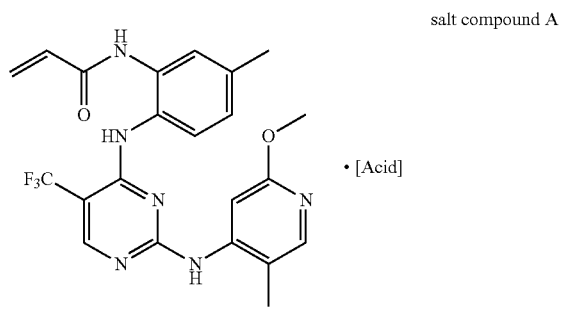

salt compound A comprising steps of:
combining compound 1:

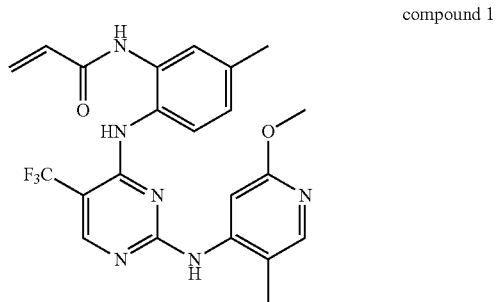 [SMILES: C=CC(=O)Nc1cc(C)ccc1Nc1nc(Nc2cc(OC)ncc2C)ncc1C(F)(F)F]

compound 1 with a suitable acid and optionally a suitable solvent under conditions suitable for forming a salt compound of general formula A.

In some embodiments, a suitable acid is phosphoric acid. In some embodiments, the present invention provides a method of making a phosphate salt of compound 1. In some embodiments, the phosphate salt of compound 1 is a monophosphate salt. In certain embodiments, the phosphate salt of compound 1 is compound 2. In certain embodiments, the phosphate salt of compound 1 is Form A of compound 2. In certain embodiments, the phosphate salt of compound 1 is Form B of compound 2. In certain embodiments, the phosphate salt of compound 1 is Form C of compound 2. In certain embodiments, the phosphate salt of compound 1 is Form D of compound 2. In some embodiments, the phosphate salt of compound 1 is a bisphosphate complex In certain embodiments, the phosphate complex of compound 1 is compound 3. In certain embodiments, the phosphate complex of compound 1 is Form A of compound 3.

In some embodiments, a suitable acid is hydrochloric acid. In some embodiments, the present invention provides a method of making a hydrochloride salt of compound 1. In certain embodiments, the hydrochloride salt of compound 1 is compound 4. In certain embodiments, the hydrochloride salt of compound 1 is Form A of compound 4. In certain embodiments, the hydrochloride salt of compound 1 is Form B of compound 4. In certain embodiments, the hydrochloride salt of compound 1 is Form C of compound 4. In certain embodiments, the hydrochloride salt of compound 1 is Form D of compound 4. In certain embodiments, the hydrochloride salt of compound 1 is Form E of compound 4. In certain embodiments, the hydrochloride salt of compound 1 is Form F of compound 4. In certain embodiments, the hydrochloride salt of compound 1 is Form G of compound 4. In certain embodiments, the hydrochloride salt of compound 1 is Form H of compound 4. In certain embodiments, the hydrochloride salt of compound 1 is Form I of compound 4.

In some embodiments, a suitable acid is hydrobromic acid. In some embodiments, the present invention provides a method of making a hydrobromide salt of compound 1. In certain embodiments, the hydrobromide salt of compound 1 is compound 5. In certain embodiments, the hydrobromide salt of compound 1 is Form A of compound 5. In certain embodiments, the hydrobromide salt of compound 1 is Form B of compound 5. In certain embodiments, the hydrobromide salt of compound 1 is Form C of compound 5. In certain embodiments, the hydrobromide salt of compound 1 is Form D of compound 5. In certain embodiments, the hydrobromide salt of compound 1 is Form E of compound 5.

In some embodiments, a suitable acid is sulfuric acid. In some embodiments, the present invention provides a method of making a sulfate salt of compound 1. In some embodiments, the sulfate salt of compound 1 is a monosulfate salt. In certain embodiments, the sulfate salt of compound 1 is compound 6. In certain embodiments, the sulfate salt of compound 1 is Form A of compound 6. In certain embodiments, the sulfate salt of compound 1 is Form B of compound 6. In certain embodiments, the sulfate salt of compound 1 is Form C of compound 6. In some embodiments, the sulfate salt of compound 1 is a bis-sulfate salt. In certain embodiments, the sulfate salt of compound 1 is compound 7. In certain embodiments, the phosphate salt of compound 1 is Form A of compound 7.

In some embodiments, a suitable acid is p-toluenesulfonic acid. In some embodiments, the present invention provides a method of making a tosylate salt of compound 1. In certain embodiments, the tosylate salt of compound 1 is compound 8. In certain embodiments, the tosylate salt of compound 1 is Form A of compound 8. In certain embodiments, the tosylate salt of compound 1 is Form B of compound 8. In certain embodiments, the tosylate salt of compound 1 is Form C of compound 8. In certain embodiments, the tosylate salt of compound 1 is Form D of compound 8.

In some embodiments, a suitable acid is benzenesulfonic acid. In some embodiments, the present invention provides a method of making a besylate salt of compound 1. In certain embodiments, the besylate salt of compound 1 is compound 9. In certain embodiments, the besylate salt of compound 1 is Form A of compound 9. In certain embodiments, the besylate salt of compound 1 is Form B of compound 9.

In some embodiments, a suitable acid is methanesulfonic acid. In some embodiments, the present invention provides a method of making a mesylate salt of compound 1. In certain embodiments, the mesylate salt of compound 1 is compound 10. In certain embodiments, the mesylate salt of compound 1 is Form A of compound 10. In certain embodiments, the mesylate salt of compound 1 is Form B of compound 10.

In some embodiments, a suitable acid is maleic acid. In some embodiments, the present invention provides a method of making a maleate salt of compound 1. In certain embodiments, the maleate salt of compound 1 is compound 11. In certain embodiments, the maleate salt of compound 1 is Form A of compound 11.

In some embodiments, a suitable acid is oxalic acid. In some embodiments, the present invention provides a method of making an oxalate salt of compound 1. In certain embodiments, the oxalate salt of compound 1 is compound 12. In certain embodiments, the oxalate salt of compound 1 is Form A of compound 12. In certain embodiments, the oxalate salt of compound 1 is Form B of compound 12. In certain embodiments, the oxalate salt of compound 1 is Form C of compound 12.

A suitable solvent may be any solvent system (e.g., one solvent or a mixture of solvents) in which compound 1 and/or an acid are soluble, or are at least partially soluble.

Examples of suitable solvents useful in the present invention include, but are not limited to protic solvents, aprotic solvents, polar aprotic solvent, or mixtures thereof. In certain embodiments, suitable solvents include an ether, an ester, an alcohol, a ketone, or a mixture thereof. In some embodiments, the solvent is one or more organic alcohols. In some embodiments, the solvent is chlorinated. In some embodiments, the solvent is an aromatic solvent.

In certain embodiments, a suitable solvent is methanol, ethanol, isopropanol, or acetone wherein said solvent is anhydrous or in combination with water or heptane. In some embodiments, suitable solvents include tetrahydrofuran, dimethylformamide, dimethylsulfoxide, glyme, diglyme, methyl t-butyl ether, t-butanol, n-butanol, and acetonitrile. In some embodiments, a suitable solvent is ethanol. In some embodiments, a suitable solvent is anhydrous ethanol. In some embodiments, the suitable solvent is MTBE.

In some embodiments, a suitable solvent is ethyl acetate. In some embodiments, a suitable solvent is a mixture of methanol and methylene chloride. In some embodiments, a suitable solvent is a mixture of acetonitrile and water. In certain embodiments, a suitable solvent is methyl acetate, isopropyl acetate, acetone, or tetrahydrofuran. In certain embodiments, a suitable solvent is diethylether. In certain embodiments, a suitable solvent is water. In certain embodiments, a suitable solvent is methyl ethyl ketone. In certain embodiments, a suitable solvent is toluene.

In some embodiments, the present invention provides a method for preparing a salt compound of the general formula A, comprising one or more steps of removing a solvent and adding a solvent. In some embodiments, an added solvent is the same as the solvent removed. In some embodiments, an added solvent is different from the solvent removed. Means of solvent removal are known in the synthetic and chemical arts and include, but are not limited to, any of those described herein and in the Exemplification.

In some embodiments, a method for preparing a salt compound of the general formula A comprises one or more steps of heating or cooling a preparation.

In some embodiments, a method for preparing a salt compound of the general formula A comprises one or more steps of agitating or stirring a preparation.

In some embodiments, a method for preparing a salt compound of the general formula A comprises a step of adding a suitable acid to a solution or slurry of compound 1.

In some embodiments, a method for preparing a salt compound of the general formula A comprises a step of heating.

In certain embodiments, a salt compound of formula A precipitates from the mixture. In another embodiment, a salt compound of formula A crystallizes from the mixture. In other embodiments, a salt compound of formula A crystallizes from solution following seeding of the solution (i.e., adding crystals of a salt compound of formula A to the solution).

A salt compound of formula A can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, a salt compound of formula A is optionally isolated. It will be appreciated that a salt compound of formula A may be isolated by any suitable physical means known to one of ordinary skill in the art. In certain embodiments, precipitated solid salt compound of formula A is separated from the supernatant by filtration. In other embodiments, precipitated solid salt compound of formula A is separated from the supernatant by decanting the supernatant.

In certain embodiments, a salt compound of formula A is separated from the supernatant by filtration.

In certain embodiments, an isolated salt compound of formula A is dried in air. In other embodiments isolated Compound 2 is dried under reduced pressure, optionally at elevated temperature.

Uses of Compounds and Pharmaceutically Acceptable Compositions

As described generally above, compound 1, and pharmaceutically acceptable salts thereof described herein, is an inhibitor of one or both of ERK1 and ERK2. One of ordinary skill in the art will recognize that ERK is one of the key components in the RAS-RAF-MEK-ERK MAPK pathway and that ERK1 and ERK2 are downstream nodes within the MAPK pathway. Without wishing to be bound by theory, because of the downstream location of ERK1 and ERK1 in the MAPK pathway, an ERK inhibitor can treat disease or disorders in which activation of the MAPK pathway at any level (Ras-Raf-Mek-ERK) is known or suspected to play a role, including one or both of ERK1 and ERK2 as well as other nodes in the MAPK pathway upstream from ERK (such as Ras, Raf and Mek). Furthermore, because ERK is a downstream target, ERK inhibitors are believed to be able to overcome, in some instances, drug resistance induced by inhibitors of targets upstream of ERK within the MAPK pathway. For example, small molecule inhibitors of RAF or MEK utilized in the treatment of K-RAS and B-RAF mutant tumors have resulted in such drug resistance. Similarly, drug resistance has been associated with other tumors driven by hyperactivation of the MAPK pathway (such as NF 1 mutant tumors). Kinase selectivity was achieved through silencing the selective Cys in a combination of the interactions between the covalent inhibitors of the invention and unique amino acids in the ATP binding pocket. Targeting the selective Cys provides for prolonged pharmacodynamics in silencing ERK activity, as well as potential lower doses in cancer treatment, compared to reversible inhibitors.

The activity of compound 1, and pharmaceutically acceptable salts thereof, as an inhibitor of one or both of an ERK1 and ERK2 kinase, or a mutant thereof, may be assayed in vitro, in vivo or in a cell line. In vitro assays include assays that determine inhibition of downstream phosphorylation, changes in gene expression, subsequent functional markers and consequences, and/or kinase activity of one or both of activated ERK1 and ERK2 kinase, or a mutant thereof. Alternate in vitro assays quantitate the ability of the test compound to bind to one or both of ERK1 and ERK2. Test compound binding may be measured by radiolabeling the test compound prior to binding, isolating one or both of the compound/ERK1 complex and the compound/ERK2 complex, and determining the amount of radiolabel bound. Alternatively, test compound binding may be determined by running a competition experiment where test compounds are incubated with one or both of ERK1 and ERK2 kinase bound to known radioligands. Test compound binding may be determined by competition with an ERK covalent probe that is amenable to further functionalization with a detection probe, such as, for example, a fluorophore, biotin conjugate, radiolabel, or any other probe that facilitates its quantification. Detailed conditions for assaying a compound utilized in this invention as an inhibitor of one or both of ERK1 and ERK2, or a mutant thereof, are also set forth below and/or in the Examples of the '230 publication.

The term "measurably inhibit", as used herein means a measurable change in one or both of ERK1 and ERK2 protein kinase activity between a sample comprising a provided composition, and one or both of an ERK1 and ERK2 protein kinase and an equivalent sample comprising one or both of ERK1 and ERK2 protein kinase in the absence of a provided composition. Such measurements of protein kinase activity are known to one of ordinary skill in the art and include those methods set forth herein below and/or in the Examples of the '230 publication.

As described above, in some embodiments, compound 1, and pharmaceutically acceptable salts thereof, is an inhibitor of one or both of ERK1 and ERK2 protein kinases, and ERK1 and ERK2 are downstream targets within the MAPK pathway. Without wishing to be bound by any particular theory, such compounds and compositions are particularly useful for treating or lessening the severity of a disease, condition, or disorder in which activation of the MAPK pathway at any level (Ras-Raf-Mek-ERK) is known or suspected to play a role. Such disease, condition, or disorder may be referred to herein as associated with the MAPK pathway or alternatively as associated with one or both of ERK1 and ERK2. Such diseases, conditions, or disorders may also be referred to herein as an "ERK1- or ERK2-mediated disease, condition, or disorder."

In some embodiments, the present invention provides a method for treating or lessening the severity of a disease, condition, or disorder where activation of the MAPK pathway (at any level in Ras-Raf-Mek-ERK), including one or both of ERK1 and ERK2 protein kinases, is implicated in said disease, condition, or disorder, wherein said method comprises administering to a patient in need thereof a compound of the present invention.

In some embodiments, the present invention relates to a method of inhibiting one or both of ERK1 and ERK2 protein kinase activity in a patient comprising the step of administering to said patient a composition comprising a compound of the present invention.

In other embodiments, the present invention provides a method for treating a disease, condition, or disorder mediated by one or both of ERK1 and ERK2 kinase, or a mutant thereof, in a patient in need thereof, comprising the step of administering to said patient a compound of the present invention.

In certain embodiments, the present invention provides a method for overcoming drug resistance to Raf or MEK inhibitors, comprising the step of administering to a patient an inhibitor compound of one or both of ERK1 and ERK2, such as a compound of the present invention. In certain embodiments, the mechanism of drug resistance is through mutation of a target protein or reactivation of the MAPK pathway.

As used herein, the term "resistance" may refer to changes in a wild-type nucleic acid sequence coding a target protein, and/or to the amino acid sequence of the target protein and/or to the amino acid sequence of another protein, which changes, decreases or abolishes the inhibitory effect of the inhibitor on the target protein. The term "resistance" may also refer to overexpression or silencing of a protein differing from a target protein that can reactivate the MAPK pathway or other survival pathways.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent, delay or lessen the severity of their recurrence.

In some embodiments, the present invention provides a method of treating, stabilizing or lessening the severity or progression of one or more diseases or disorders associated with one or both of ERK1 and ERK2 comprising administering to a patient in need thereof a composition comprising a compound of the present invention.

General diseases, conditions, or disorders treated by a compound of the present invention include cancer, an autoimmune disorder, a neurodegenerative or neurological disorder, liver disease, a cardiac disorder, schizophrenia, or a bone-related disorder.

In some embodiments, the present invention relates to a method of treating or lessening the severity of a disease, condition, or disorder selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases, wherein the method comprises administering to a patient in need thereof a composition comprising a compound of the present invention.

In some embodiments, the present invention relates to a method of treating a cancer wherein the method comprises administering to a patient in need thereof a composition comprising a compound of the present invention. In some embodiments, the cancer is recurring. In certain embodiments, the cancer is refractory. In some embodiments, the cancer is metastatic. In some embodiments, the cancer is locally advanced.

In certain embodiments, the cancer is a RAF inhibitor-resistant cancer. In some such embodiments, the RAF inhibitor-resistant cancer is a BRAF inhibitor-resistant cancer.

In certain embodiments, the cancer is a MEK inhibitor-resistant cancer.

In certain embodiments, the cancer is a MAPK pathway-mediated cancer.

In some embodiments, the cancer is a BRAF-mutated cancer. In certain embodiments, the BRAF-mutated cancer is a $BRAF^{V600}$-mutated cancer, such as $BRAF^{V600E}$ $BRAF^{V600K}$, $BRAF^{V600R}$, and $BRAF^{V600D}$.

In some embodiments, the cancer is a RAS-mutated cancer. In certain embodiments, the RAS-mutated involves codons 12, 13, or 61. In certain embodiments, the RAS-mutated cancer is a KRAS-mutated cancer, including, but not limited to, $KRAS^{G12C/D/V}$, $KRAS^{G13C/D}$, or $KRAS^{Q61L/H/R}$. In certain embodiments, the RAS-mutated cancer is an NRAS-mutated cancer, including, but not limited to, $NRAS^{Q61R}$, $NRAS^{Q61K}$, $NRAS^{Q61L}$, or $NRAS^{Q61H}$. In certain embodiments, the RAS-mutated cancer is an HRAS-mutated cancer, including, but not limited to, $HRAS^{G12V}$, $HRAS^{Q61R}$, and $HRAS^{G12S}$.

In some embodiments, the present invention relates to a method of treating a cancer wherein the method comprises administering to a patient in need thereof a composition comprising a compound of the present invention, wherein the cancer is selected from multiple myeloma, breast, ovary, cervix, prostate, testis, genitourinary tract, esophagus, larynx, glioblastoma, neuroblastoma, stomach (gastric), skin, keratoacanthoma, lung, epidermoid carcinoma, large cell carcinoma, small cell carcinoma, lung, bone, colon, thyroid, adenoma, pancreas, adenocarcinoma, thyroid, follicular carcinoma, undifferentiated carcinoma, papillary carcinoma, seminoma, melanoma (including uveal melanoma) sarcoma, bladder carcinoma, liver carcinoma (e.g., hepatocellular carcinoma (HCC)) and biliary passage carcinoma), kidney carcinoma, myeloid disorders, lymphoid disorders, Hodgkin's, hairy cells, buccal cavity and pharynx (oral), lip, tongue, mouth, pharynx, small intestine, colorectal carcinoma, large intestine, rectum, brain and central nervous system, endometrial, multiple myeloma (MM), prostate, AML, and leukemia. In some such embodiments, the cancer is relapsed. In some embodiments, the cancer is refractory. In some embodiments, the cancer is locally advanced. In some embodiments, the cancer is metastatic.

In some embodiments, the present invention relates to a method of treating a cancer wherein the method comprises administering to a patient in need thereof a composition comprising a compound of the present invention, wherein the cancer is selected from carcinoma, lymphoma, blastoma, sarcoma, and leukemia. In some embodiments, a sarcoma is a soft tissue sarcoma. In some embodiments, a lymphoma is non-hodgkins lymphoma. In some embodiments, a lymphoma is large cell immunoblastic lymphoma. In some embodiments, the cancer is selected from adenocarcinoma; adenoma; adrenocortical cancer; bladder cancer; bone cancer; brain cancer; breast cancer; cancer of the buccal cavity; cervical cancer; colon cancer; colorectal cancer; endometrial or uterine carcinoma; epidermoid carcinoma; esophogeal cancer; eye cancer; follicular carcinoma; gallbladder cancer; prostate, AML, multiple myeloma (MM), gastrointestinal cancer, such as, for example, gastrointestinal stromal tumor; cancer of the genitourinary tract; glioblastoma; hairy cell carcinoma; various types of head and neck cancer; hepatic carcinoma; hepatocellular cancer; Hodgkin's disease; keratoacanthoma; kidney cancer; large cell carcinoma; cancer of the large intestine; laryngeal cancer; liver cancer; lung cancer, such as, for example, adenocarcinoma of the lung, anaplastic carcinoma of the lung, papillary lung adenocarcinoma, small-cell lung cancer, squamous carcinoma of the lung, non-small cell lung cancer; melanoma and nonmelanoma skin cancer; lymphoid disorders; myeloproliferative disorders, such as, for example, polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, chronic lymphocytic leukemia (CLL), hypereosinophilic syndrome, systematic mast cell disease, atypical CML, AML, or juvenile myelomonocytic leukemia; plasmacytoma; multiple myeloma; neuroblastoma; ovarian cancer; papillary carcinoma; pancreatic cancer; cancer of the peritoneum; prostate cancer, including benign prostatic hyperplasia; rectal cancer; salivary gland carcinoma; sarcoma; seminoma; squamous cell cancer; small cell carcinoma; cancer of the small intestine; stomach cancer; testicular cancer; thyroid cancer; undifferentiated carcinoma; and vulval cancer. In some such embodiments, the cancer is relapsed. In some embodiments, the cancer is refractory. In some embodiments, the cancer is locally advanced. In some embodiments, the cancer is metastatic.

In some embodiments, the present invention relates to a method of treating a cancer wherein the method comprises administering to a patient in need thereof a composition comprising a compound of the present invention, wherein the cancer is selected from melanoma, pancreatic cancer, thyroid cancer, colorectal cancer, lung cancer (e.g., non-small cell lung cancer), breast cancer, endometrial cancer, prostate cancer, ovarian cancer, hepatocellular carcinoma (HCC), multiple myeloma (MM), and leukemia. In some embodiments, a leukemia is an acute leukemia. In certain embodiments, a leukemia is acute myeloid leukemia. In certain embodiments, a leukemia is acute lymphoblastic leukemia.

In some embodiments, the present invention relates to a method of treating a cancer wherein the method comprises administering to a patient in need thereof a composition comprising a compound of the present invention, wherein the cancer is selected from melanoma, colorectal cancer, lung cancer, or pancreatic.

In some embodiments, the present invention relates to a method of treating a cancer wherein the method comprises administering to a patient in need thereof a composition comprising a compound of the present invention, wherein the cancer is melanoma. In certain embodiments, the melanoma is uveal melanoma. In some embodiments, the melanoma is a melanoma of the skin. In certain embodiments, the melanoma is locally advanced. In some embodiments, the melanoma is metastatic. In some embodiments, the melanoma is recurring. In some embodiments, the melanoma is $BRAF^{v600}$-mutated melanoma. In certain embodiments, the melanoma is a RAS-mutated melanoma. In some embodiments, the melanoma is NRAS-mutated melanoma. In certain embodiments, the melanoma is wild type for KRAS, NRAS or BRAF. In certain embodiments, the melanoma is a BRAF inhibitor-resistant (e.g., Vemurfenib-resistant, dabrafenib-resistant, etc.) melanoma. In certain embodiments, the cancer is a VemR (i.e., Vemurfenib-resistant) BRAF-mutated melanoma. In some embodiments, the melanoma is relapsed. In some embodiments, the melanoma is refractory.

In some embodiments, the present invention relates to a method of treating a cancer wherein the method comprises administering to a patient in need thereof a composition comprising a compound of the present invention, wherein the cancer is colorectal cancer. In certain embodiments, the colorectal cancer is locally advanced. In certain embodiments, the colorectal cancer is metastatic. In certain embodiments, the colorectal cancer is a BRAF-mutated colorectal cancer. In certain embodiments, the colorectal cancer is a $BRAF^{v600}$-mutated colorectal cancer. In certain embodiments, the colorectal cancer is a RAS-mutated colorectal cancer. In certain embodiments, the colorectal cancer is a KRAS-mutated colorectal cancer. In certain embodiments, the colorectal cancer is a NRAS-mutated colorectal cancer. In some embodiments, the colorectal cancer is relapsed. In some embodiments, the colorectal cancer is refractory.

In some embodiments, the present invention relates to a method of treating a cancer wherein the method comprises administering to a patient in need thereof a composition comprising a compound of the present invention, wherein the cancer is pancreatic cancer. In certain embodiments, the pancreatic cancer is locally advanced. In certain embodiments, the pancreatic cancer is metastatic. In certain embodiments, the pancreatic cancer is a pancreatic ductal adenocarcinoma (PDAC). In certain embodiments, the pancreatic cancer is a RAS-mutated pancreatic cancer. In certain embodiments, the pancreatic cancer is a KRAS-mutated pancreatic cancer. In certain embodiments, the pancreatic cancer is KRAS-mutated pancreatic cancer, including, but not limited to, $KRAS^{G12C/D/V}$, $KRAS^{G13C/D}$, or $KRAS^{Q61L/H/R}$. In some embodiments, the pancreatic cancer is relapsed. In some embodiments, the pancreatic cancer is refractory.

In some embodiments, the present invention relates to a method of treating a cancer wherein the method comprises administering to a patient in need thereof a composition comprising a compound of the present invention, wherein the cancer is a papillary thyroid cancer. In certain embodiments, the papillary thyroid cancer is locally advanced. In some embodiments, the papillary thyroid cancer is metastatic. In some embodiments, the papillary thyroid cancer is recurring. In some embodiments, the papillary thyroid cancer is BRAF-mutated papillary thyroid cancer. In some embodiments, the papillary thyroid cancer is $BRAF^{v600}$-mutated papillary thyroid cancer. In some embodiments, the papillary thyroid cancer is relapsed. In some embodiments, the papillary thyroid cancer is refractory. In some embodiments, the papillary thyroid cancer includes undifferentiated or dedifferentiated histology.

In some embodiments, the present invention relates to a method of treating a cancer wherein the method comprises administering to a patient in need thereof a composition comprising a compound of the present invention, wherein the cancer is lung cancer. In certain embodiments, the lung cancer is non-small cell lung cancer (NSCLC). In certain embodiments, the lung cancer is locally advanced. In certain embodiments, the lung cancer is metastatic. In certain embodiments, the lung cancer is a RAS-mutated lung cancer. In certain embodiments, the lung cancer is KRAS-mutated lung cancer. In certain embodiments, the lung cancer is a KRAS-mutated lung cancer, including, but not limited to, $KRAS^{G12C/D/V}$, $KRAS^{G13C/D}$, $KRAS^{Q61L/H/R}$. In some embodiments, the lung cancer is relapsed. In some embodiments, the lung cancer is refractory.

In some embodiments, the present invention relates to a method of treating a cancer wherein the method comprises administering to a patient in need thereof a composition comprising a compound of the present invention, wherein the cancer is a leukemia. In some embodiments, a leukemia is a chronic leukemia. In certain embodiments, a leukemia is chronic myeloid leukemia. In some embodiments, a leukemia is an acute leukemia. In certain embodiments, a leukemia is acute myeloid leukemia (AML). In certain embodiments, a leukemia is acute monocytic leukemia (AMoL, or AML-M5). In certain embodiments, a leukemia is acute lymphoblastic leukemia (ALL). In certain embodiments, a leukemia is acute T cell leukemia. In certain embodiments, a leukemia is myelomonoblastic leukemia. In certain embodiments, a leukemia is human B cell precursor leukemia. In certain embodiments, a leukemia has a Flt3 mutation or rearrangement. In some embodiments, the leukemia is relapsed. In some embodiments, the leukemia is refractory.

In some embodiments, the present invention relates to a method of treating a cancer wherein the method comprises administering to a patient in need thereof a composition comprising a compound of the present invention, wherein the cancer is a CNS cancer, for instance CNS tumors. In certain embodiments, a CNS tumor is a glioblastoma or glioblastoma multiforme (GBM). In some embodiments, the present invention relates to a method of treating stomach (gastric) and esophageal tumors and cancers.

In some embodiments, the present invention relates to a method of treating a cancer wherein the method comprises administering to a patient in need thereof a composition comprising a compound of the present invention, wherein the cancer is multiple myeloma (MM). In certain embodiments, the multiple myeloma is locally advanced. In certain embodiments, the multiple myeloma is metastatic. In certain embodiments, the multiple myeloma is a RAS-mutated multiple myeloma. In certain embodiments, the multiple myeloma is KRAS-mutated multiple myeloma. In certain embodiments, the multiple myeloma is a KRAS-mutated multiple myeloma, including, but not limited to, $KRAS^{G12C/D/V}$, $KRAS^{G13C/D}$, or $KRAS^{Q61L/H/R}$. In some embodiments, the multiple myeloma is relapsed. In some embodiments, the multiple myeloma is refractory.

In some embodiments, the present invention relates to a method of treating a cancer, wherein the method comprises administering to a patient in need thereof a composition comprising a compound of the present invention, wherein the cancer is hepatocellular carcinoma (HCC). In certain embodiments, the HCC is locally advanced. In certain embodiments, the HCC is metastatic. In certain embodiments, the HCC is a RAS-mutated HCC. In certain embodiments, the HCC is KRAS-mutated HCC. In certain embodiments, the HCC is a KRAS-mutated HCC, including, but not limited to, $KRAS^{G12C/D/V}$, $KRAS^{G13C/D}$, or $KRAS^{Q61L/H/R}$. In some embodiments, the hepatocellular carcinoma is relapsed. In some embodiments, the hepatocellular carcinoma is refractory.

In some embodiments, the present invention relates to a method of treating a cancer wherein the method comprises administering to a patient in need thereof a composition comprising a compound of the present invention, wherein the cancer is selected from breast, colorectal, endometrial, hematological, leukemia (e.g., AML), liver, lung, melanoma, ovarian, pancreatic, prostate, or thyroid.

Pharmaceutically Acceptable Compositions

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection.

This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting one or both of ERK 1 and ERK2 kinase, or a mutant thereof, activity in a biological sample comprising the step of contacting said biological sample with a compound of this invention, or a composition comprising said compound. In certain embodiments, the invention relates to a method of irreversibly inhibiting one or both of ERK1 and ERK2 kinase, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof and blood, saliva, urine, feces, semen, tears, or other body fluids or extracts thereof.

Inhibition of one or both of ERK1 and ERK2, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting one or both of ERK1 and ERK2 kinase, or a mutant thereof, activity in a patient comprising the step of administering to said patient a compound of the present invention, or a composition comprising said compound. According to certain embodiments, the invention relates to a method of irreversibly inhibiting one or both of ERK1 and ERK2 kinase, or a mutant thereof, activity in a patient comprising the step of administering to said patient a compound of the present invention, or a composition comprising said compound. In certain embodiments, the activity is inhibited irreversibly by covalently modifying Cys 183 of ERK1. In certain embodiments, the activity is inhibited irreversibly by covalently modifying Cys 166 of ERK2. In certain embodiments, the activity is inhibited irreversibly by covalently modifying Cys 183 of ERK1 and Cys 166 of ERK2. In other embodiments, the present invention provides a method for treating a disease, disorder, or condition mediated by one or both of ERK1 and ERK2 kinase, or a mutant thereof, in a patient in need thereof, comprising the step of administering to said patient a compound according to the present invention or pharmaceutically acceptable composition thereof. Such disorders are described in detail herein.

All features of each of the aspects of the invention apply to all other aspects mutatis mutandis. Each of the references referred to herein, including but not limited to patents, patent applications and journal articles, is incorporated by reference herein as though fully set forth in its entirety.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Procedures

X-ray powder diffraction patterns were collected on one of two instruments, a PANalytical Empyrean X-ray powder diffractometer or a Rigaku XRD, both with CuKα radiation. The PANalytical Empyrean instrument was equipped with a fine focus X-ray tube. The voltage and amperage of the X-ray generator were set at 45 kV and 40 mA, respectively. The divergence slits were set at $\frac{1}{16}°$ and $\frac{1}{8}°$, and the receiving slits were set at $\frac{1}{16}°$. Diffracted radiation was measured using a Pixel 2D detector. A theta-two theta continuous scan was set at step size 0.013 or 0.026 from 3° to 40° 2θ with sample spinning rate of 4. A sintered alumina standard was used to check the peak positions. The diffraction patterns measured on the Rigaku system were obtained on a Rigaku XRD; SmartLab with Cu-Kα radiation and D/teX Ultra detector.

The powder samples were deposited on a zero-background polished silicon sample holder and were spun during measurement. Measurements were performed as follows: 40 kV/44 mA tube power, 0.02° 2θ step size, 4 or 5° 2θ/min, and 3-40° 2θ scanning range.

Proton Nuclear Magnetic Resonance ($^1$H NMR) spectra were obtained on a Bruker AVANCE-300 MHz NMR spectrometer. Deuterated DMSO was used as solvent.

DSC data was obtained on a TA Instruments Q1000, Q2000, or Discover Series DSC. Samples were weighed into aluminum pans, crimped with pin hole aluminum lids, and heated at a rate of 10° C./min. Indium was used as the calibration standard.

TGA analyses were performed on a TA instruments Q500 or Discovery Series TGA. About 2 to 10 mg were added to an aluminum sample pan and heated at a rate of 10° C./min.

TGA/DSC data was obtained on a Mettler Toledo TGA/DSC 1 Star System. The samples were loaded on a aluminum sample pan and heated at a rate of 10° C./min.

Hygroscopicity was determined on a Surface Measurement Systems DVS-1 or DVS-Advantage Dynamic Vapor Sorption analyzer. A typical sample size of 5 to 20 mg was loaded into the DVS instrument sample pan and the sample was analyzed on a DVS automated sorption analyzer at room temperature. The relative humidity (RH) was increased from 0 or 5% to 90 or 95% RH at 5 or 10% RH steps. The RH was then decreased in a similar manner to accomplish a full absorption/desorption cycle. In some cases a second absorption/desorption cycle was performed.

Example A

General Preparation of Compound 1

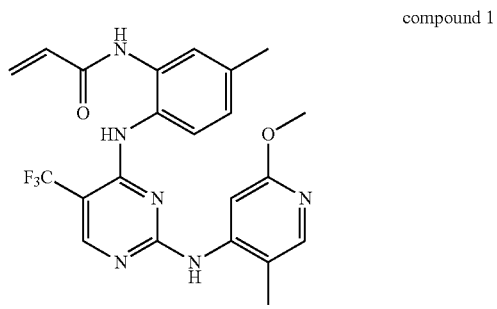 [SMILES: C=CC(=O)Nc1cc(C)ccc1Nc1nc(Nc2cc(OC)ncc2C)ncc1C(F)(F)F]

compound 1

The title compound was prepared according to the steps and intermediates described below and in the '230 publication, the entirety of which is incorporated herein by reference.

Step 1: N-(2-(2-Chloro-5-(trifluoromethyl)pyrimidin-4-ylamino)5-methylphenyl)acrylamide (Intermediate 1)

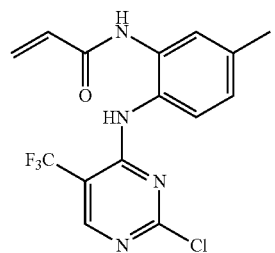 [SMILES: C=CC(=O)Nc1cc(C)ccc1Nc1nc(Cl)ncc1C(F)(F)F]

To a stirred solution of N-(2-amino-5-methylphenyl)acrylamide (22.2 mmol) in dimethyl acetamide (25 mL) was added potassium carbonate (46.0 mmol) at rt, and the mixture was stirred for 15 minutes. To this reaction mixture, 2,4-dichloro-5-trifluoromethylpyrimidine (22.2 mmol) was added, and the stirring continued at 60° C. for 1 h. Upon completion, the reaction mixture was diluted with water (2×50 mL) and extracted with EtOAc (2×100 mL). The organic layer was dried over sodium sulfate and concentrated to get the crude product. This crude was purified by silica gel column chromatography and subsequently purified by prep-HPLC to get desired intermediate 1.

Step 2: Acid Catalyzed Coupling Method

To a solution of Intermediate 1 (2.923 mmol) in 0.04 M PTSA solution in 1,4-dioxane (20 mL) was added 2-methoxy-5-methylpyridin-4-amine (3.5076 mmol), and the mixture was stirred at 95° C. for 16 h. Upon completion, the reaction mixture was directly absorbed on silica gel and purified by column chromatography. The resulting product was stirred in a mixture of DCM:EtOAc:diethyl ether (10 mL:10 mL:30 mL) for 10 min, then filtered and dried under vacuum to obtain the desired compound.

MS m/z 459.2 (ES+, M+H). $^1$HNMR (DMSO-d$_6$) δ 2.10 (s, 3H), 2.32 (s, 3H), 3.75 (s, 3H), 5.78 (dd, 1H, J=2.0, 10.0 Hz), 6.28 (dd, 1H, J=2.0, 16.8 Hz), 6.45 (dd, 1H, J=10.6, 16.8 Hz), 7.09 (br t, 3H, J=8.0 Hz), 7.50 (d, 1H, J=8.4 Hz), 7.79 (s, 1H), 8.36 (s, 2H), 8.72 (s, 1H), 10.25 (s, 1H).

Alternative Step 2: Pd-Catalyzed Coupling Method

Alternatively, Step 2 can be carried out by adding Intermediate 1 to a suitable coupling partner in the presence of Na$_2$CO$_3$, a degassed solvent (e.g., tert-amyl alcohol), a suitable palladium catalyst (e.g., tris-dibenzylamino dipalladium) and a suitable phosphine ligand (e.g., Dave Phos) under conditions suitable to effect coupling.

Example 1

Preparation of Free Base Forms A-D of Compound 1

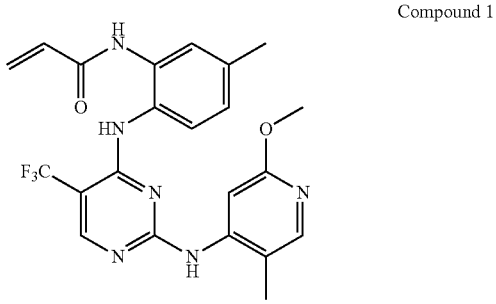 [SMILES: C=CC(=O)Nc1cc(C)ccc1Nc1nc(Nc2cc(OC)ncc2C)ncc1C(F)(F)F]

Compound 1

Compound 1 is prepared according to the method described in detail in Example 94 of the '230 publication, the entirety of which is hereby incorporated herein by reference.

Form A of Compound 1

Form A of compound 1 was prepared as follows.

Procedure A: Form B of compound 1 was slurried in ethyl acetate at 30° C. After overnight vigorous stirring, the reaction was filtered and dried.

Procedure B: Form B of compound 1 was heated to a temperature of 170° C., then cooled to room temperature. Solids converted to Form A at a temperature of 145° C.

Characterization of the resulting material demonstrated a crystalline, anhydrous Form A.

Table 1, supra, is reproduced below and sets forth the X-ray diffraction peaks observed for Form A of compound 1.

TABLE 1

| XRPD Peak Positions for Form A of Compound 1 Position (°2 θ) |
| --- |
| 8.6 |
| 9.0 |
| 11.6 |
| 14.1 |
| 15.3 |
| 15.4 |
| 17.2 |
| 18.5 |
| 20.4 |
| 20.6 |
| 21.2 |
| 21.5 |
| 21.9 |
| 22.9 |
| 23.4 |
| 23.9 |
| 25.3 |
| 25.8 |
| 26.1 |
| 27.0 |

[1] In this and all subsequent tables, the position 2 θ is within ±0.2.

FIG. 1 depicts an XRPD pattern of Form A of compound 1.

Figure 2:
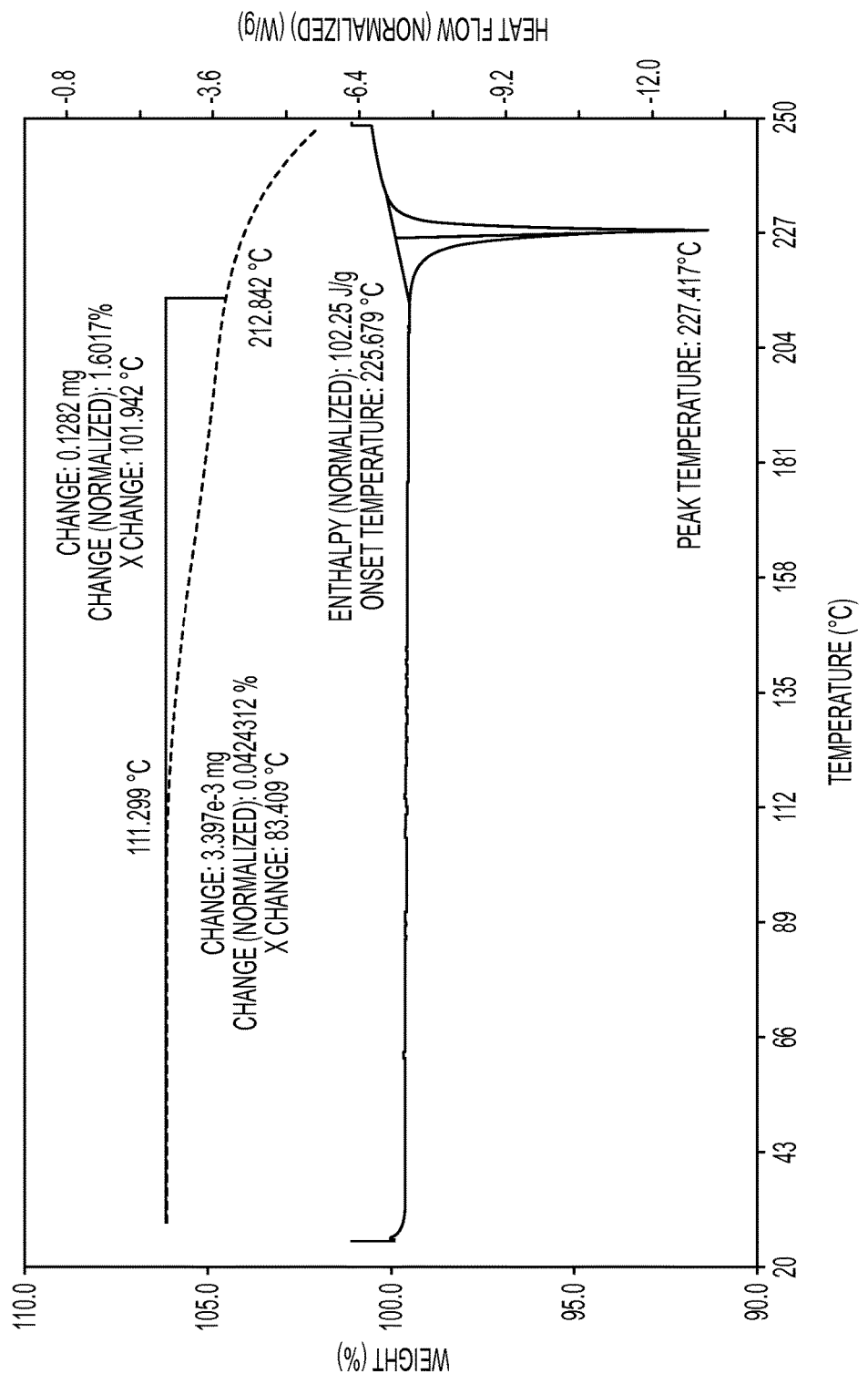
FIG. 2 depicts a DSC thermogram and TGA trace of Form A of compound 1.

FIG. 2 depicts a DSC thermogram and TGA trace of Form A of compound 1.

Figure 3:
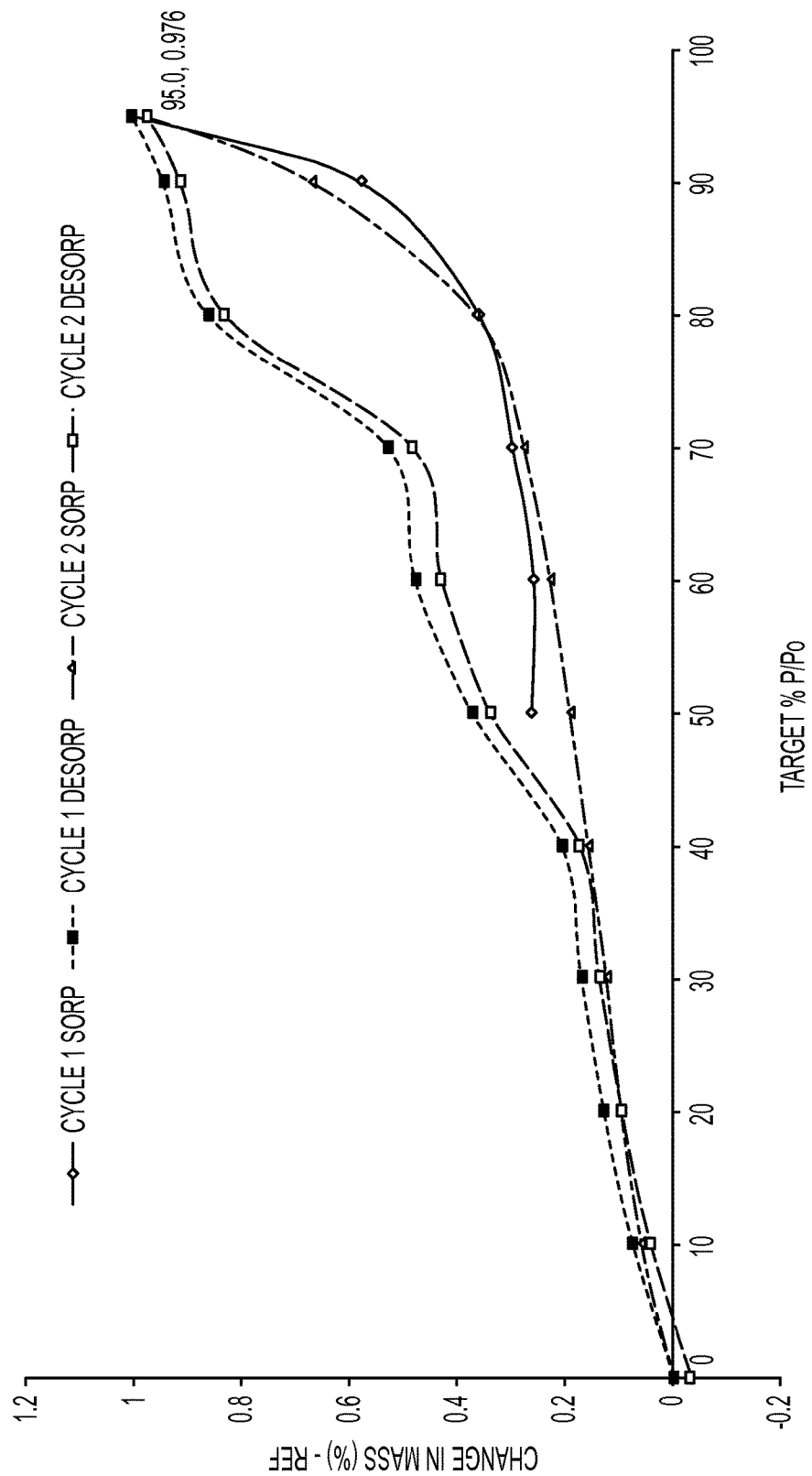
FIG. 3 depicts a DVS plot of Form A of compound 1.

FIG. 3 depicts a DVS plot of Form A of compound 1.

Form B of Compound 1

Form B of compound 1 was prepared as follows.

Procedure A: compound 1 was slurried in 10 volumes of methanol for 8 hours at 20° C., filtered, and dried.

Procedure B: compound 1 was dissolved in MeOH/CH$_2$Cl$_2$ (11.20 mg/mL), dried under nitrogen purge, then slurried in MeOH overnight, filtered and dried in a vacuum oven at ambient temperature until analysis.

Characterization of the resulting material demonstrated a crystalline Form B.

Table 2, supra, is reproduced below and sets forth the X-ray diffraction peaks observed for Form B of compound 1.

TABLE 2

| XRPD Peak Positions for Form B of Compound 1 Position (°2 θ) |
| --- |
| 4.6 |
| 7.2 |
| 8.3 |
| 9.3 |
| 11.6 |
| 13.6 |
| 14.4 |
| 16.5 |
| 17.7 |
| 18.7 |
| 21.0 |
| 21.3 |
| 23.2 |
| 23.5 |
| 24.4 |
| 27.5 |

[1] In this and all subsequent tables, the position 2 θ is within ±0.2.

FIG. 4 depicts an XRPD pattern of Form B of compound 1.

Figure 5:
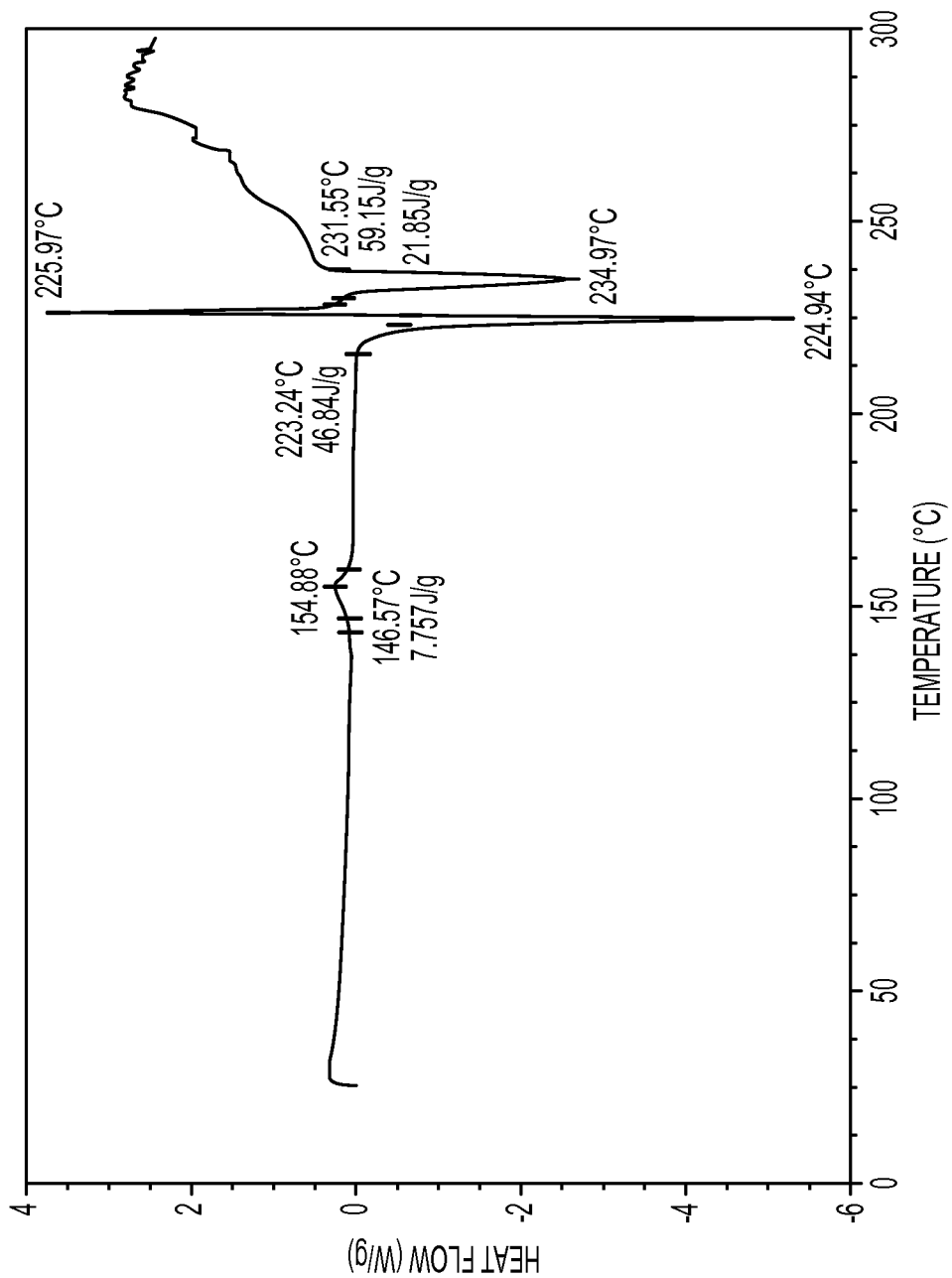
FIG. 5 depicts a DSC thermogram of Form B of compound 1.

FIG. 5 depicts a DSC thermogram of Form B of compound 1.

Figure 6:
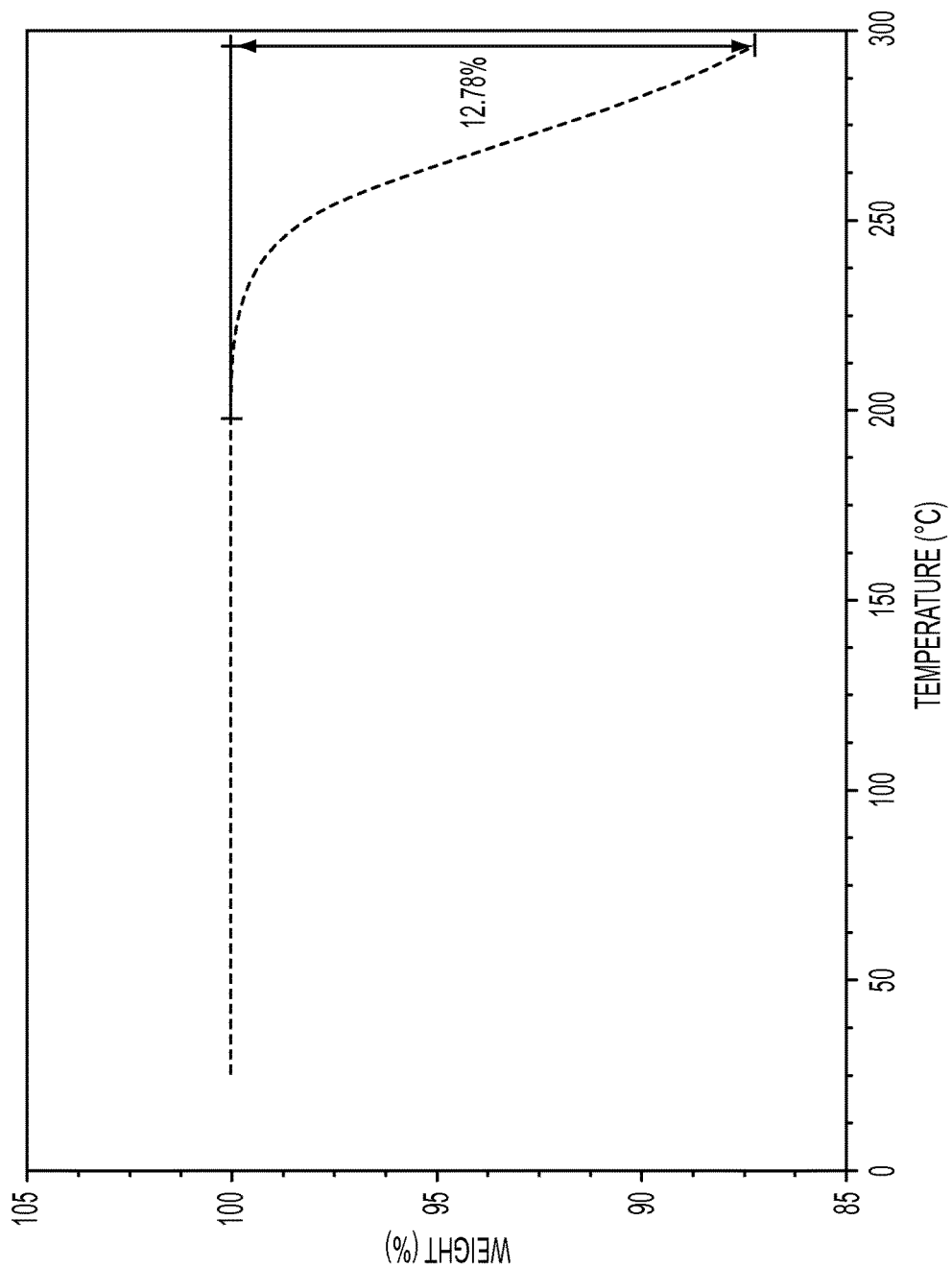
FIG. 6 depicts a TGA trace of Form B of compound 1.

FIG. 6 depicts a TGA trace of Form B of compound 1.

Elemental analysis—Calculated: C, 57.64; H, 4.62; N, 18.33; Found: C, 57.46; H, 4.58; N, 18.36.

Karl Fisher titration: 0%

Form C of Compound 1

Form C of Compound 1 was prepared as follows.

Procedure A: Form A of compound 1 was slurried in methyl acetate, acetone, or tetrahydrofuran for seven days at room temperature.

Procedure B: 6.8 g of free base Form B were charged to 41 mL isopropylacetate and slurried at 20° C. for about 1 hour. The batch was filtered, washed with 7 mL of isopropyl acetate and dried under reduced pressure to yield 6.4 g.

Characterization of the resulting material demonstrated a crystalline, anhydrous Form C.

Table 3, supra, is reproduced below and sets forth the X-ray diffraction peaks observed for Form C of compound 1.

TABLE 3

XRPD Peak Positions for Form C of Compound 1
Position (°2 θ)

| |
| --- |
| 7.6 |
| 8.8 |
| 9.6 |
| 11.7 |
| 12.3 |
| 14.5 |
| 15.3 |
| 15.9 |
| 17.5 |
| 18.0 |
| 20.1 |
| 21.0 |
| 22.8 |
| 23.4 |
| 23.8 |
| 24.7 |
| 25.2 |
| 25.5 |
| 26.4 |
| 27.7 |

[1] In this and all subsequent tables, the position 2 θ is within ±0.2.

FIG. 7 depicts an XRPD pattern of Form C of compound 1.

Figure 8:
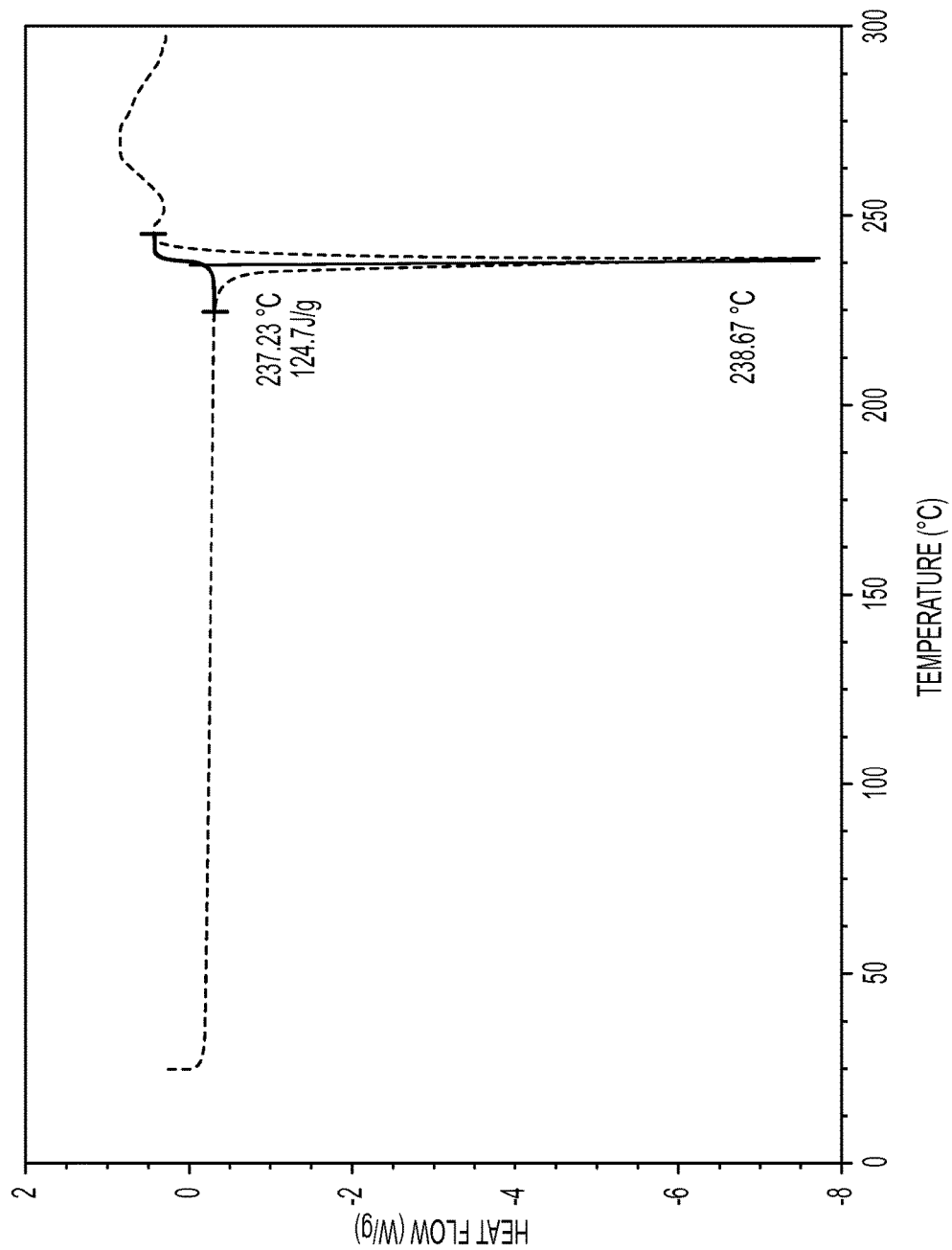
FIG. 8 depicts a DSC thermogram of Form C of compound 1.

FIG. 8 depicts a DSC thermogram of Form C of compound 1.

Figure 9:
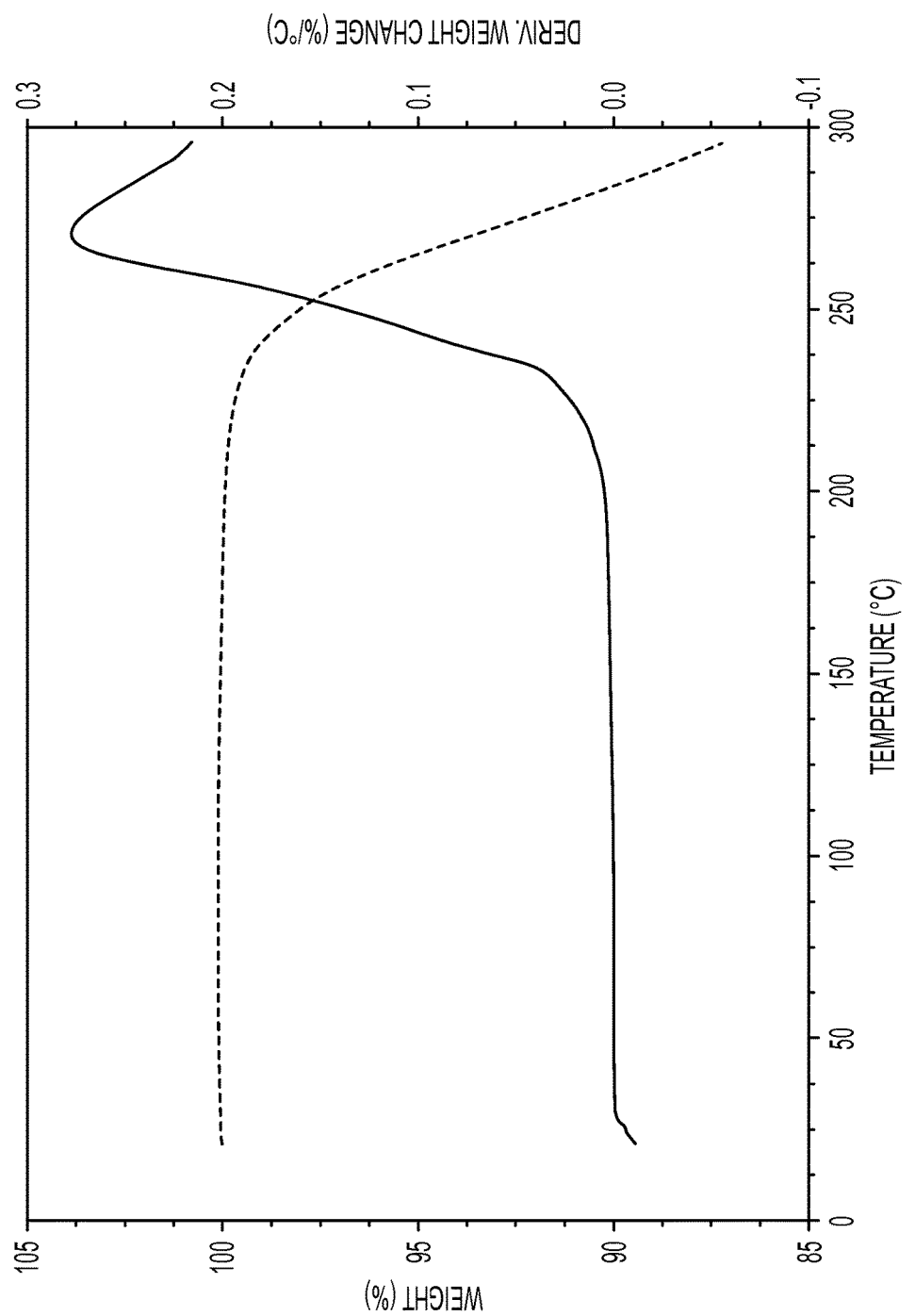
FIG. 9 depicts a TGA trace of Form C of compound 1.

FIG. 9 depicts a TGA trace of Form C of compound 1.

Form D of Compound 1

Form D of compound 1 was prepared as follows.

Procedure: Form B of Compound 1 (400 mg) was charged to a vial with 1.7 mL tetrahydrofuran and 0.3 mL water and vigorously stirred. After 24 hours, the slurry was filtered and dried in a vacuum oven at 45° C.

Characterization of the resulting material demonstrated a crystalline, anhydrous Form D.

Table 4, supra, is reproduced below and sets forth the X-ray diffraction peaks observed for Form D of compound 1.

TABLE 4

XRPD Peak Positions for Form D of Compound 1
Position (°2 θ)

| |
| --- |
| 8.2 |
| 8.9 |
| 9.5 |
| 9.6 |
| 10.6 |
| 15.0 |
| 17.3 |
| 17.7 |
| 19.1 |
| 20.2 |
| 21.1 |
| 22.0 |
| 22.4 |
| 23.7 |
| 24.7 |
| 25.2 |
| 25.9 |
| 26.5 |
| 28.6 |
| 35.1 |

[1] In this and all subsequent tables, the position 2 θ is within ±0.2.

FIG. 10 depicts an XRPD pattern of Form D of compound 1.

Figure 11:
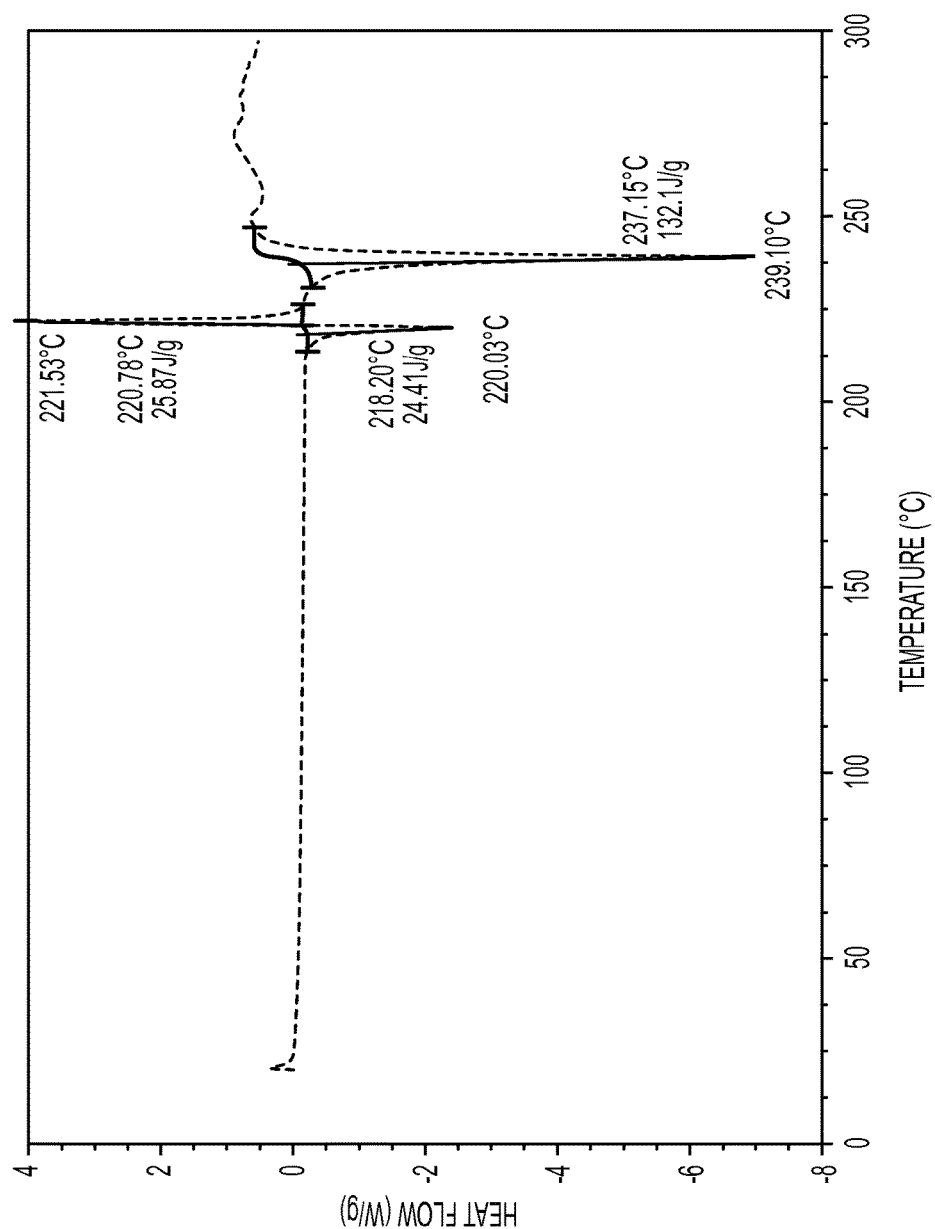
FIG. 11 depicts a DSC thermogram of Form D of compound 1.

FIG. 11 depicts a DSC thermogram of Form D of compound 1.

Figure 12:
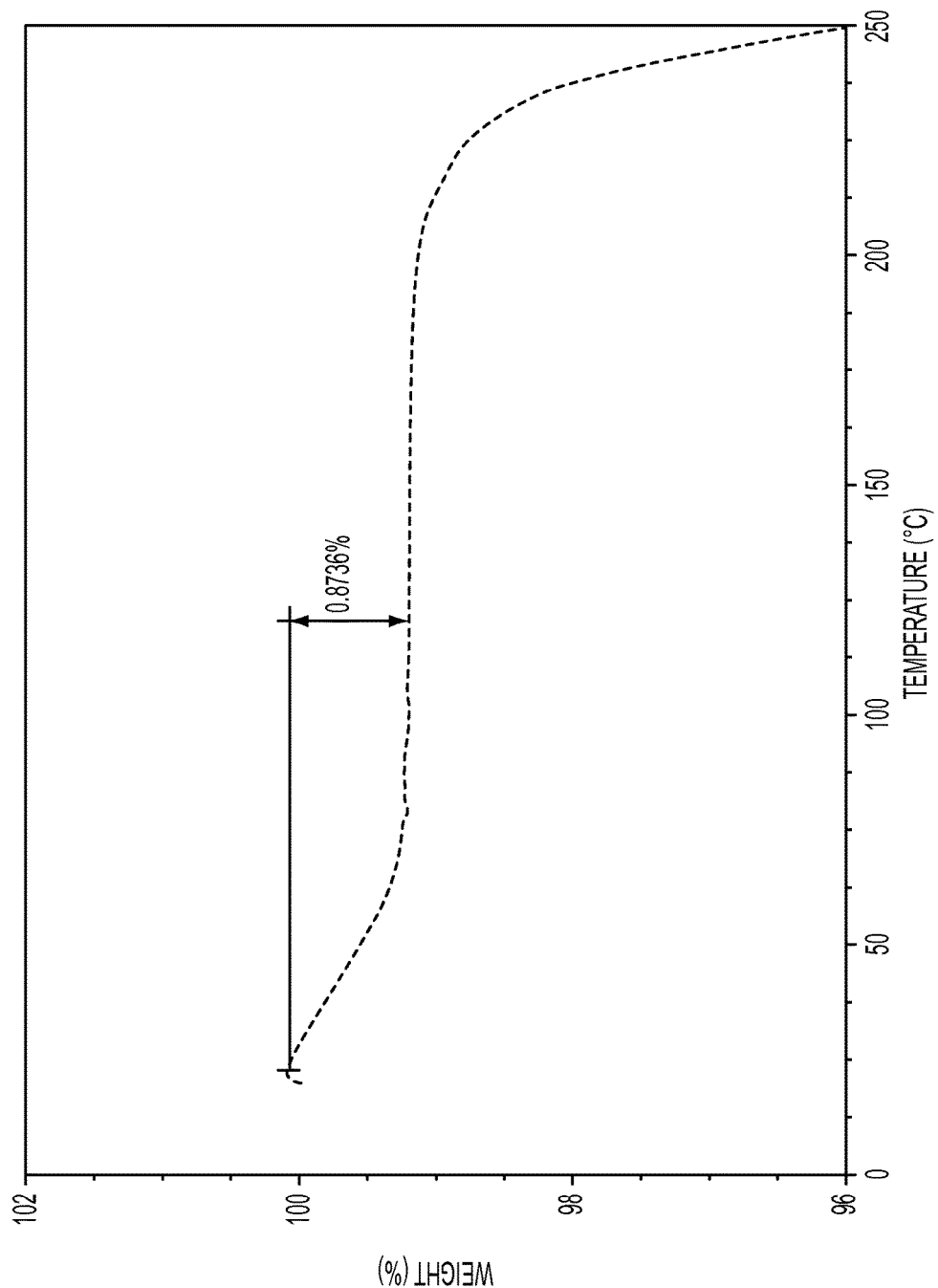
FIG. 12 depicts a TGA trace of Form D of compound 1.

FIG. 12 depicts a TGA trace of Form D of compound 1.

Free Base Competitive Slurries:

Three competitive slurry experiments were performed:

1: Form A (20.0 mg)+Form C (20.4 mg) in 0.4 ml ethyl acetate

2: Form B (15.7 mg)+Form C (15.6 mg) in 0.3 ml ethyl acetate

3: Form A (13.3 mg)+Form B (11.5 mg) in 0.3 ml ethyl acetate

The three slurries were stirred vigorously for three days. Solids were then filtered and dried. XRPD and DSC showed conversion to form C for all three experiments.

About 20 mg Form C was stirred in methanol (~2 mL) at room temperature for 24 hours. Solids were filtered and dried. XRPD and DSC showed solids converted to Form B.

Form B of compound 1 was heated at 5° C./min in an XRD-DSC instrument. Both XRPD and DSC were recorded simultaneously, indicating Form B experienced solid-solid transition between 153° C. and 160° C., resulting in Form A, which melted around 222° C. and recrystallized to become Form C, which melted around 235° C.

Example 2

Preparation of Forms A-D of Compound 2

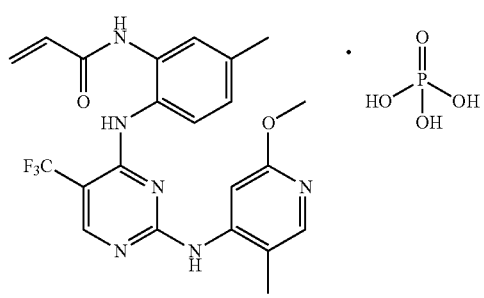

Form A of Compound 2

Form A of compound 2 was prepared as follows.

Procedure A: Compound 1 was dissolved in 15× tetrahydrofuran. One molar equivalent of 2 molar phosphoric acid in acetonitrile was charged. The batch was slurried at 20° C. for 1 to 2 hours. The solvent was removed under reduced pressure. The resulting solids were slurried in acetone for about 16 hours at 20° C., filtered and dried.

Procedure B: Compound 1 was dissolved in THF. Equal molar equivalent of 1.08 M phosphoric acid in acetonitrile was charged. The sample was shaken at ambient temperature at 200 RPM for 1 hour. The solvent was removed under nitrogen purge. The resulting solids were slurried in acetone with a stirring bar at ambient temperature overnight, then filtered and dried in vacuum oven at 30° C. overnight.

Procedure C: Compound 1 was dissolved in THF (20× vol) at 20° C. Seeds of compound 2 Form A (5% wt) were charged. A 1 M solution of phosphoric acid (1 mol eq.) in ethanol was charged. The batch was left under vigorous agitation for two hours. Solvent exchange to isopropyl acetate was carried out with a constant volume distillation under reduced pressure, with temperature not exceeding 40° C. The batch was cooled to 20° C. The solvent was removed under nitrogen purge. The batch was filtered, washed two times with isopropyl acetate and dried in a vacuum oven at ~40° C. overnight, under vacuum with nitrogen bleed.

Procedure D: Compound 1 was dissolved in 9× vol THF/H$_2$O (95:5 vol). A solution of H$_3$PO$_4$ (1.2 mol eq.) in ethanol was charged to a second flask, seeds of compound 2 form A (5%) were charged and vigorous agitation was started. The solution of compound 1 was charged to the H$_3$PO$_4$ solution (reverse addition) over one hour. The slurry was aged for one hour. Solvent exchange to ethanol was started (constant volume vacuum distillation with continuous addition of ethanol, final THF NMT 0.5%). The batch was cooled to 20° C., filtered and dried in a vacuum oven at ~40° C. overnight, under vacuum with nitrogen bleed.

Procedure E: Compound 1 was dissolved in 10× vol THF/H$_2$O (95:5 vol). Isopropyl alcohol (5× vol) was charged. Constant volume distillation, with continuous addition of isopropyl alcohol was started at atmospheric pressure. Solvent exchange was carried out until THF content was below 5%. Compound 1 recrystallized during the solvent exchange. The batch was cooled to 30° C. A 1 M solution of H$_3$PO$_4$ in IPA was charged over 2 hours. Seeds of compound 2 Form A (1%) were then charged. The batch was stirred vigorously overnight. The batch was filtered and dried in a vacuum oven at ~40° C. overnight, under vacuum with nitrogen bleed.

Procedure F: Compound 1 was dissolved in 9× vol THF/H$_2$O (95:5 vol). After polish filtration, distillation to reduce volume from 9× to 5× was performed, followed by addition of 8× ethyl acetate to bring the total volume to 13×. Solvent exchange to ethyl acetate, with constant volume distillation was carried out (final THF NMT 2%). The temperature was then reduced to 30° C. Seeds of compound 2 (1% wt) were charged. A solution of H$_3$PO$_4$ (1.2 eq.) in ethanol (5×) was then dosed in over 2 hours. The temperature was reduced to 20° C., the batch was aged for 12 hours under vigorous stirring, then filtered, washed two times with ethyl acetate and dried in a vacuum oven at ~40° C. overnight, under vacuum with nitrogen bleed.

Procedure G: Compound 1 was charged to a reactor, then ethanol (4× vol) and ethyl acetate (6×), were charged. The batch was agitated at 30° C. A solution of H$_3$PO$_4$ (1.2 mol eq.) in ethanol (2× vol) was charged over 2 hours. Seeds of compound 2 Form A (1%) were charged. The batch was filtered, washed two times with ethyl acetate, dried overnight at ~40° C., under vacuum with nitrogen bleed.

Characterization of the resulting material demonstrated a crystalline, anhydrous Form A of compound 2. Up to 3.8% water uptake was observed for this Form at 95% relative humidity.

Table 5, supra, is reproduced below and sets forth the X-ray diffraction peaks observed for Form A of compound 2.

TABLE 5

XRPD Peak Positions for Form A of Compound 2
Position (°2 θ)

| |
|---|
| 5.9 |
| 6.3 |
| 6.8 |
| 9.8 |
| 10.1 |
| 11.1 |
| 13.8 |
| 14.4 |
| 15.4 |
| 16.0 |
| 16.6 |
| 17.3 |
| 17.9 |
| 18.9 |
| 19.2 |
| 19.7 |
| 20.3 |
| 20.8 |
| 21.3 |
| 22.2 |
| 23.0 |
| 23.3 |
| 23.6 |
| 24.0 |
| 24.7 |
| 25.5 |
| 26.0 |
| 26.8 |
| 27.4 |
| 27.9 |
| 28.4 |
| 29.2 |
| 30.5 |
| 31.3 |
| 31.8 |

[1] In this and all subsequent tables, the position 2 θ is within ±0.2.

FIG. 13 depicts an XRPD pattern of Form A of compound 2.

Figure 14:
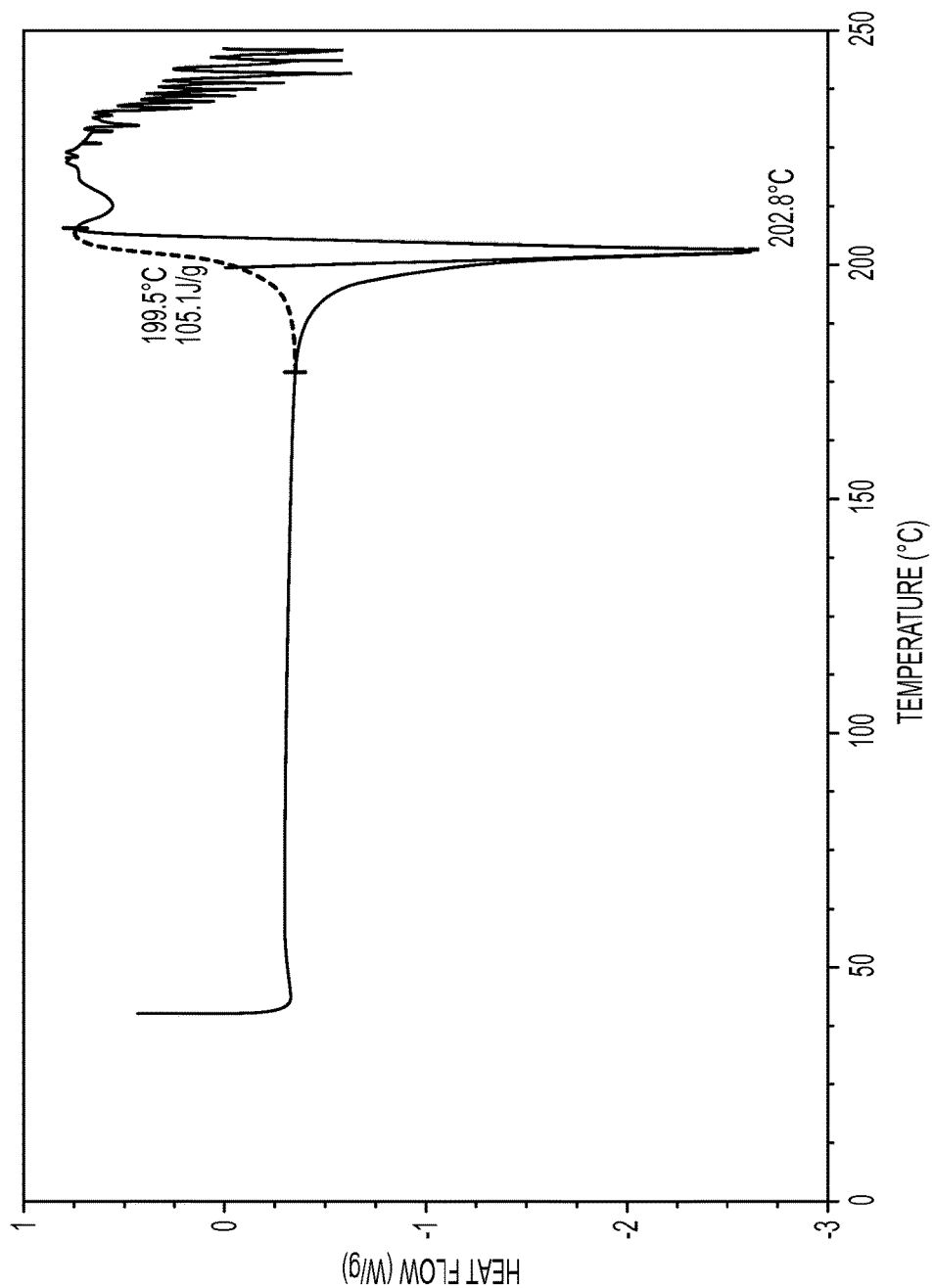
FIG. 14 depicts a DSC thermogram of Form A of compound 2.

FIG. 14 depicts a DSC thermogram of Form A of compound 2.

Figure 15:
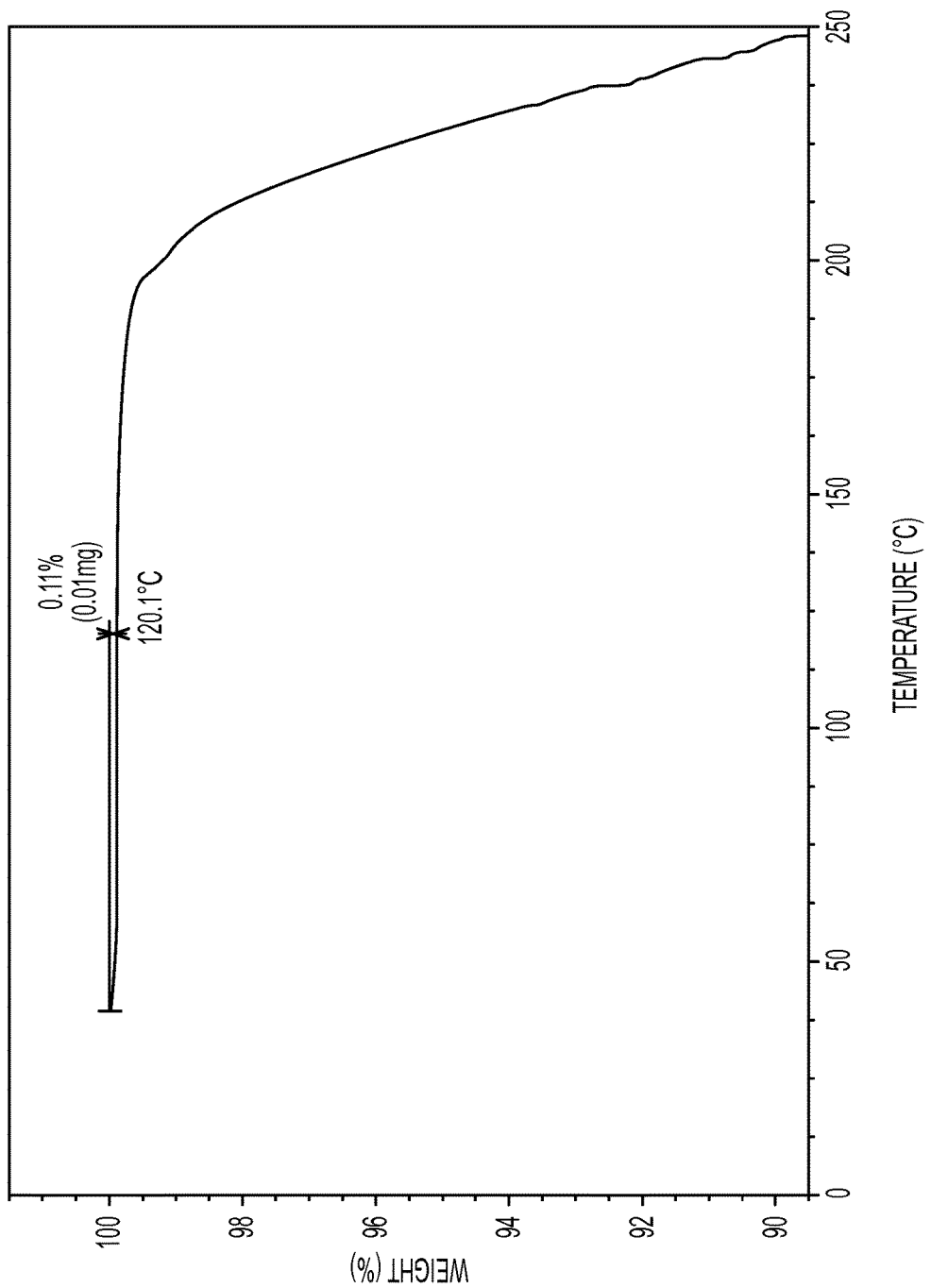
FIG. 15 depicts a TGA trace of Form A of compound 2.

FIG. 15 depicts a TGA trace of Form A of compound 2.

Figure 16:
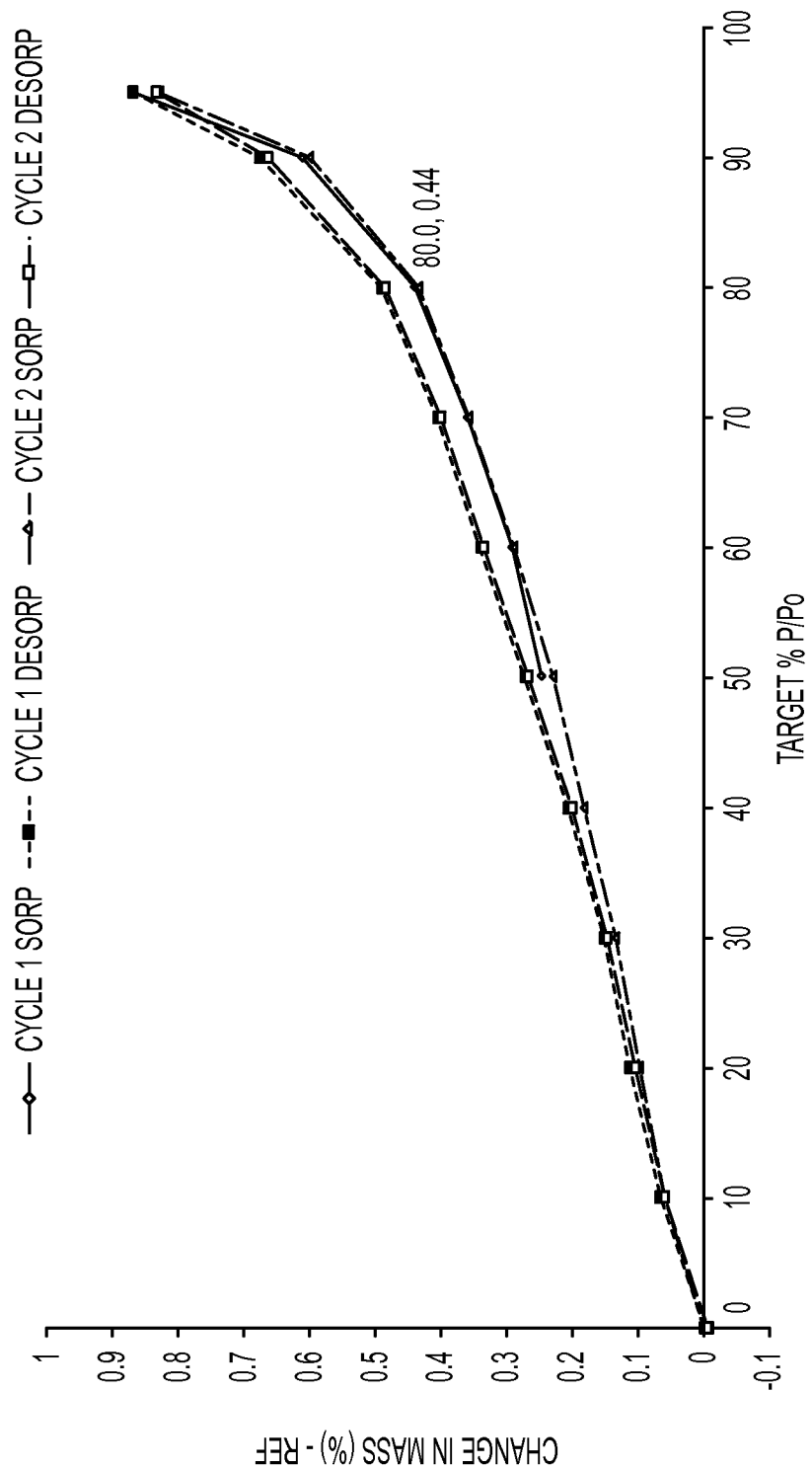
FIG. 16 depicts a DVS plot of Form A of compound 2.

FIG. 16 depicts a DVS plot of Form A of compound 2.

Elemental analysis—Calculated: C, 47.49; H, 4.35; N, 15.10; P, 5.57; Found: C, 47.09; H, 4.33; N, 14.90; P, 5.57.

Karl Fisher titration: 0.22%

Form B of Compound 2

Form B of compound 2 was prepared as follows.

Procedure: The phosphate salt of compound 1 was dissolved in tetrahydrofuran or ethanol and filtered using a syringe filter. The solution was evaporated at room temperature under a nitrogen stream.

Characterization of the resulting material demonstrated a crystalline Form B of compound 2 in the form of a hydrate.

Table 6, supra, is reproduced below and sets forth the X-ray diffraction peaks observed for Form B of compound 2.

TABLE 6

| XRPD Peak Positions for Form B of Compound 2 Position (°2 θ) |
|---|
| 3.6 |
| 7.3 |
| 8.6 |
| 9.5 |
| 10.7 |
| 12.0 |
| 13.5 |
| 14.6 |
| 15.0 |
| 15.7 |
| 16.6 |
| 18.2 |
| 19.2 |
| 19.9 |
| 20.3 |
| 21.6 |
| 22.0 |
| 22.5 |
| 22.9 |
| 23.4 |
| 24.1 |
| 24.9 |
| 25.3 |
| 25.7 |
| 26.3 |
| 26.9 |
| 27.8 |
| 28.7 |
| 29.5 |
| 30.2 |
| 31.8 |
| 34.2 |
| 36.1 |
| 37.1 |
| 38.8 |
| 39.3 |

[1] In this and all subsequent tables, the position 2 θ is within ±0.2.

FIG. 17 depicts an XRPD pattern of Form B of compound 2.

Figure 18:
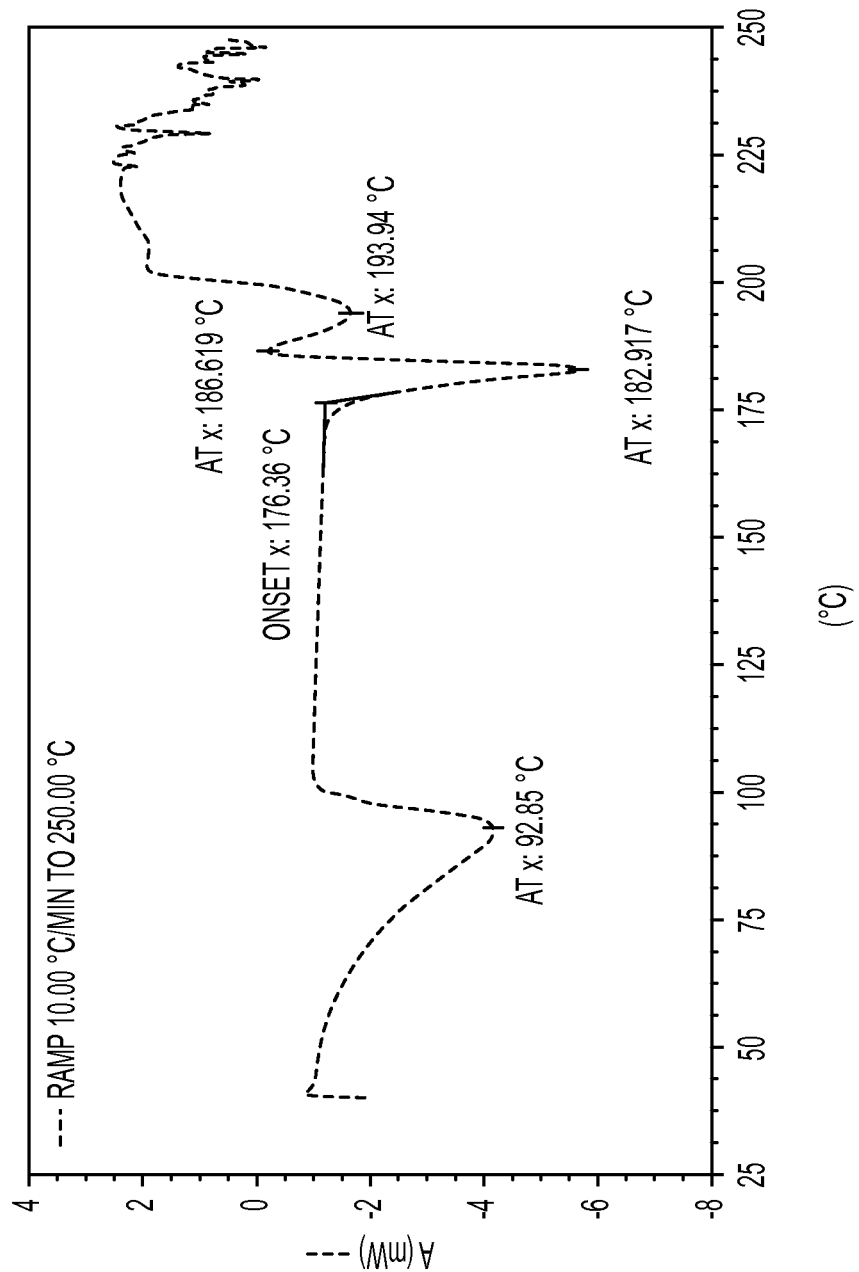
FIG. 18 depicts a DSC thermogram of Form B of compound 2.

FIG. 18 depicts a DSC thermogram of Form B of compound 2.

Figure 19:
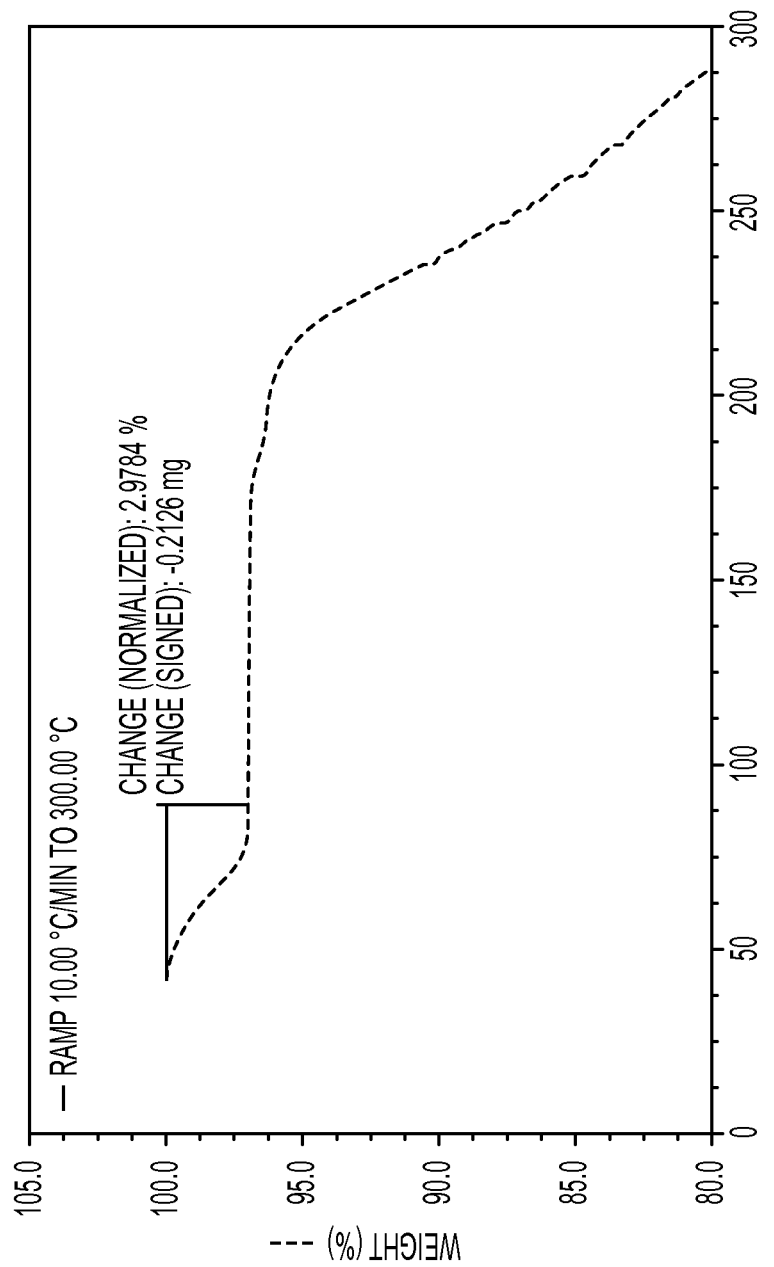
FIG. 19 depicts a TGA trace of Form B of compound 2.

FIG. 19 depicts a TGA trace of Form B of compound 2.

Figure 20:
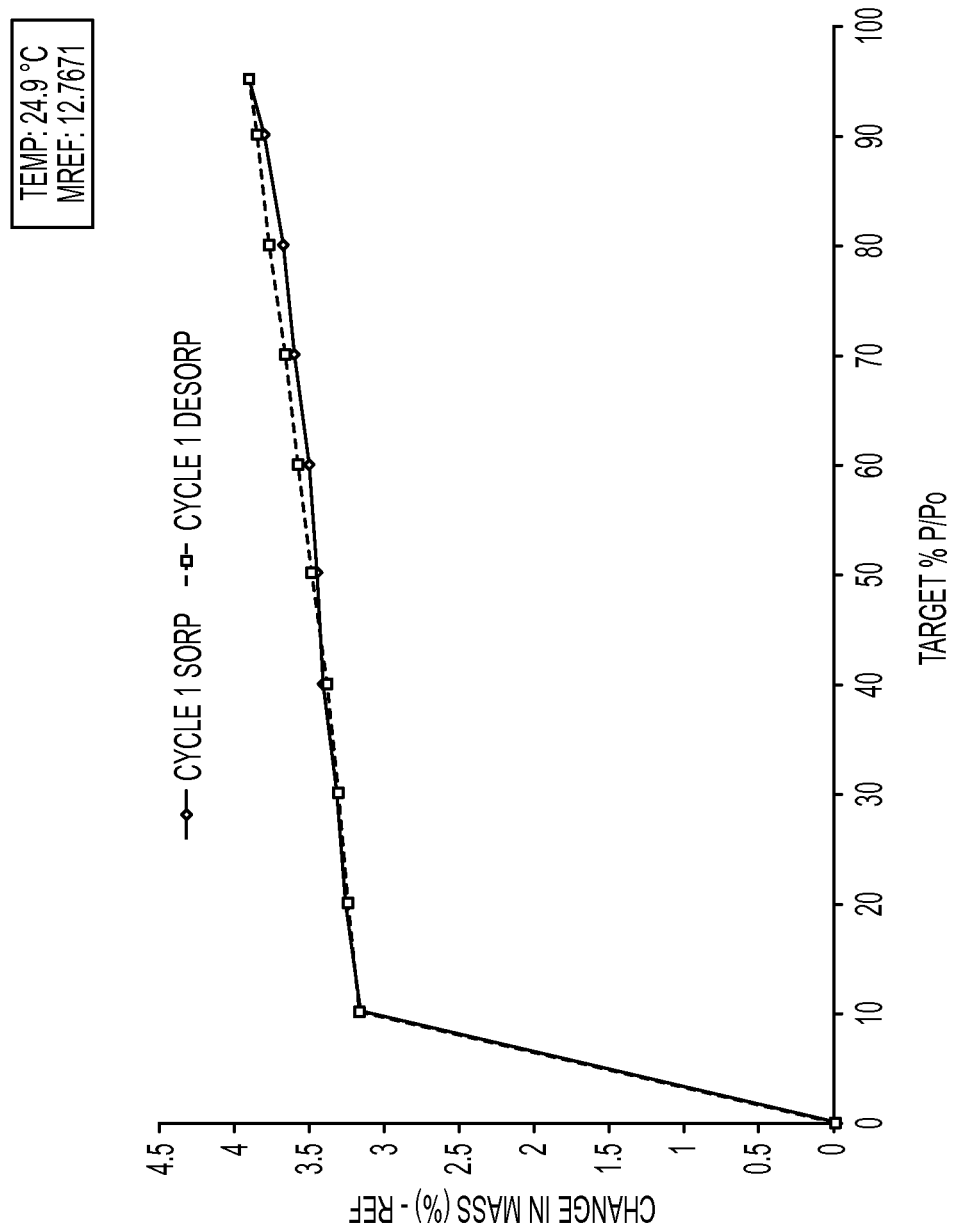
FIG. 20 depicts a DVS plot of Form B of compound 2.

FIG. 20 depicts a DVS plot of Form B of compound 2.

Phosphate content: 17.8 wt %

Karl Fisher titration: 3.1%

Form C of Compound 2

Form C of compound 2 was prepared as follows.

Procedure: The phosphate salt of compound 1 was dissolved in ethanol at room temperature and filtered using a syringe filter. Three to five volumes of acetonitrile was added as anti-solvent. The mixture was cooled in a refrigerator. Precipitated solids were isolated by filtration and air dried.

Characterization of the resulting material demonstrated a crystalline Form C of compound 2.

Table 7, supra, is reproduced below and sets forth the X-ray diffraction peaks observed for Form C of compound 2.

TABLE 7

| XRPD Peak Positions for Form C of Compound 2 Position (°2 θ) |
|---|
| 4.2 |
| 6.8 |
| 8.4 |
| 9.3 |
| 11.6 |

TABLE 7-continued

| XRPD Peak Positions for Form C of Compound 2 Position (°2 θ) |
|---|
| 12.5 |
| 12.7 |
| 13.7 |
| 15.3 |
| 15.8 |
| 16.5 |
| 18.7 |
| 19.4 |
| 20.5 |
| 22.0 |
| 22.7 |
| 24.5 |
| 25.2 |
| 26.2 |
| 32.0 |

[1] In this and all subsequent tables, the position 2 θ is within ±0.2.

FIG. 21 depicts an XRPD pattern of Form C of compound 2.

Figure 22:
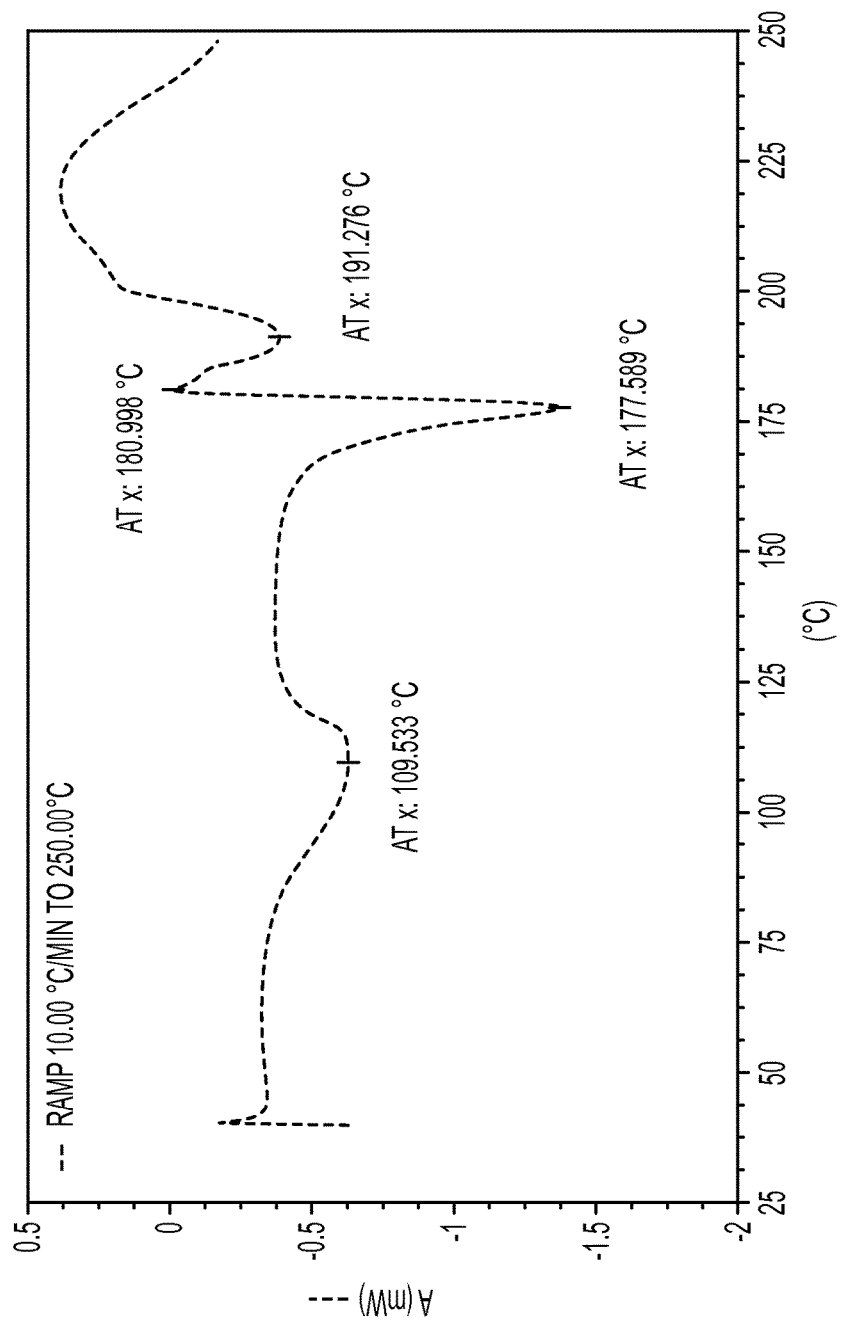
FIG. 22 depicts a DSC thermogram of Form C of compound 2.

FIG. 22 depicts a DSC thermogram of Form C of compound 2.

Figure 23:
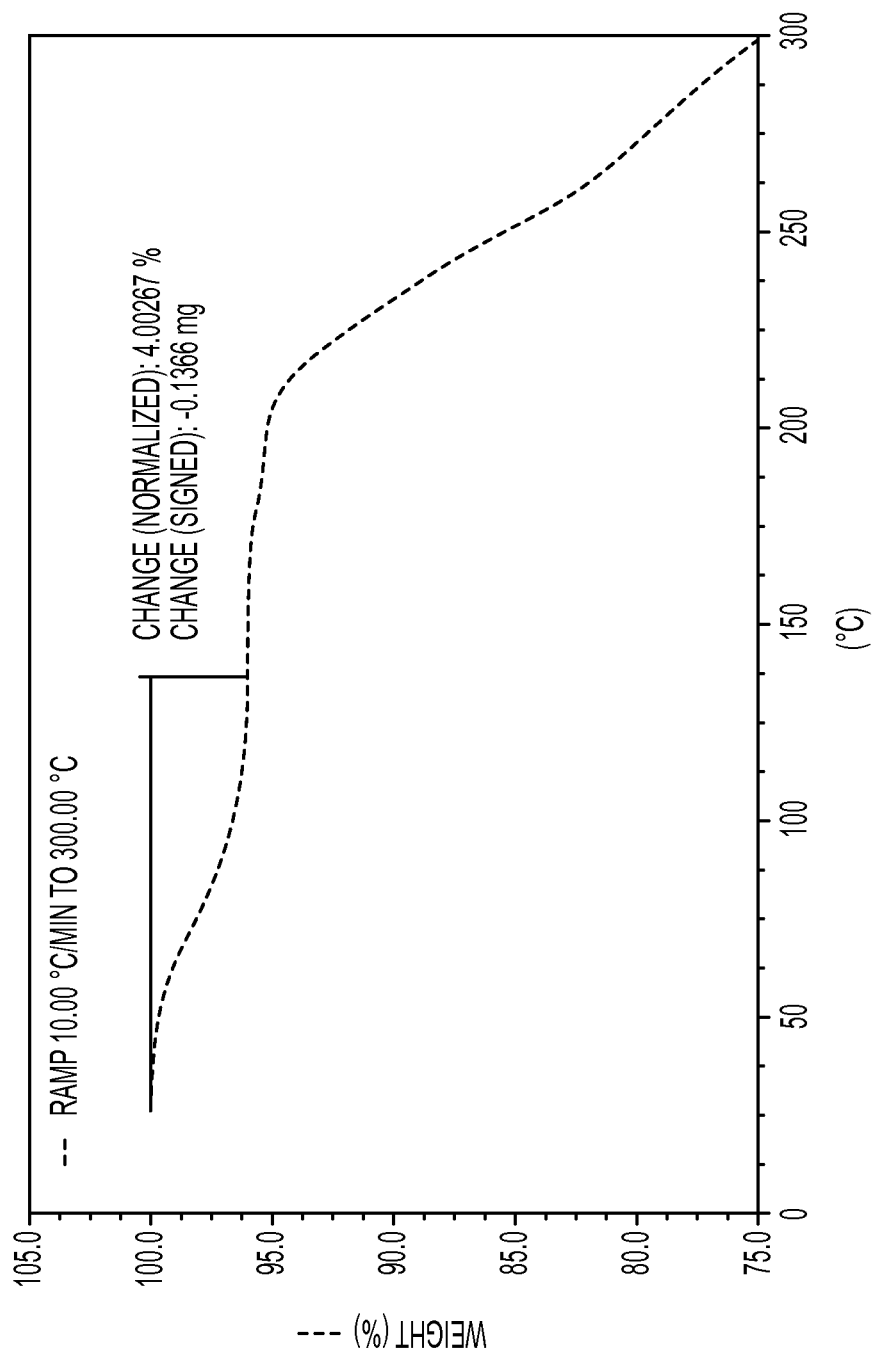
FIG. 23 depicts a TGA trace of Form C of compound 2.

FIG. 23 depicts a TGA trace of Form C of compound 2.

Figure 24:
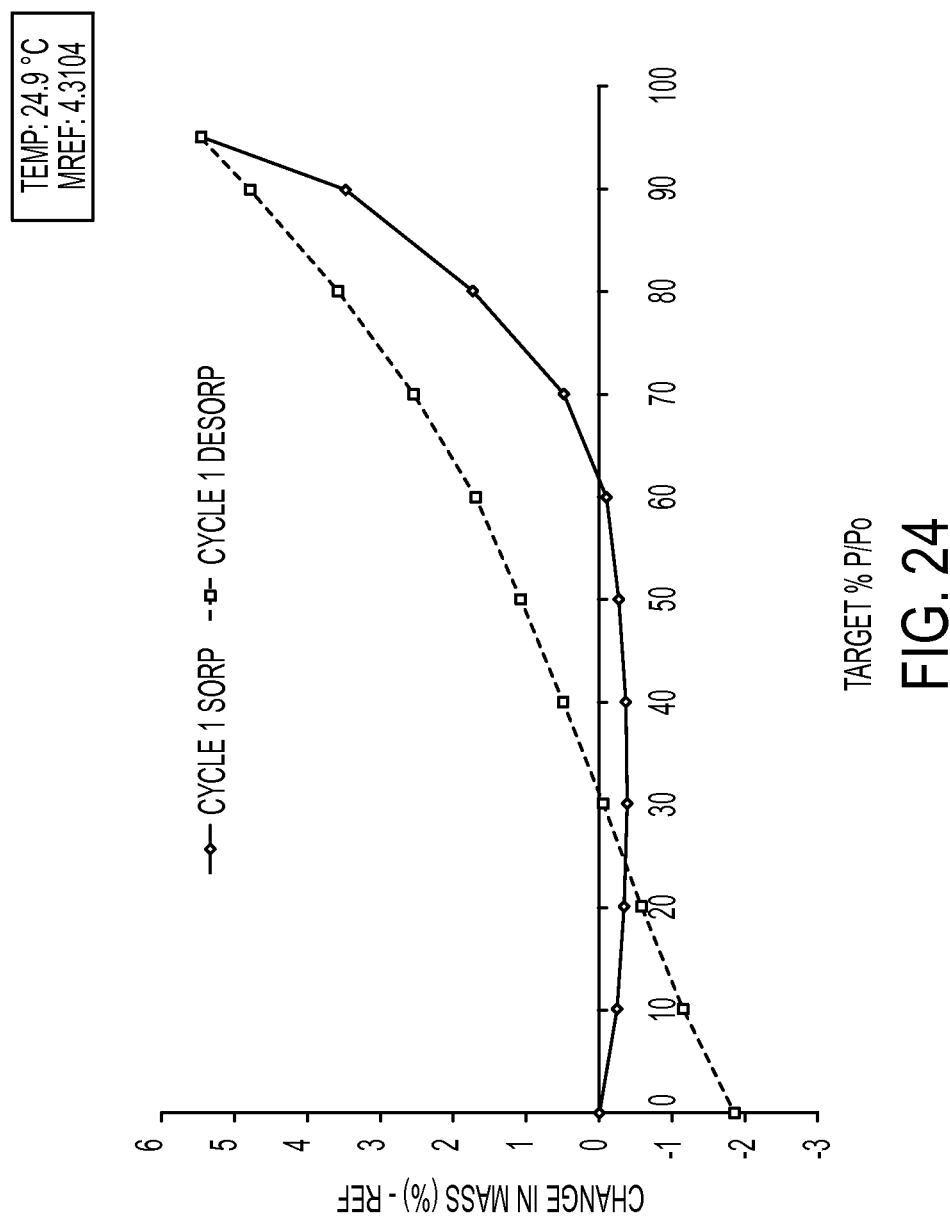
FIG. 24 depicts a DVS plot of Form C of compound 2.

FIG. 24 depicts a DVS plot of Form C of compound 2.

Phosphate content: 16.8 wt %

Karl Fisher titration: 0.14%

Form D of Compound 2

Form D of compound 2 was prepared as follows.

Procedure: The phosphate salt of compound 1 (i.e., compound 2, Form C) was heated to 140° C. to obtain Form D of compound 2. Alternatively, compound 1 free base (3 g) was dissolved in about 60 ml of THF. Phosphoric acid (1 molar equiv., 1M in water) was charged. The solution was stirred for one hour followed by removal of the solvent under reduced pressure. Acetone (10 volumes) was charged to the isolated solid and the slurry was agitated overnight after which the solids were collected and dried under reduced pressure at about 40° C.

Characterization of the resulting material demonstrated a crystalline Form D of compound 2.

Table 8, supra, is reproduced below and sets forth the X-ray diffraction peaks observed for Form D of compound 2.

TABLE 8

| XRPD Peak Positions for Form D of Compound 2 Position (°2 θ) |
|---|
| 7.1 |
| 8.1 |
| 9.1 |
| 10.4 |
| 10.6 |
| 11.2 |
| 12.9 |
| 13.9 |
| 15.8 |
| 16.4 |
| 17.2 |
| 17.7 |
| 18.7 |
| 19.0 |
| 20.2 |
| 20.7 |
| 21.0 |
| 22.1 |
| 22.7 |
| 24.5 |
| 25.1 |

TABLE 8-continued

XRPD Peak Positions for Form D of Compound 2
Position (°2 θ)

| |
|---|
| 26.4 |
| 27.4 |
| 27.8 |
| 28.7 |
| 29.1 |
| 31.0 |
| 31.5 |
| 33.8 |
| 36.3 |
| 37.0 |
| 38.0 |

[1] In this and all subsequent tables, the position 2 θ is within ±0.2.

FIG. 25 depicts an XRPD pattern of Form D of compound 2.

Figure 26:
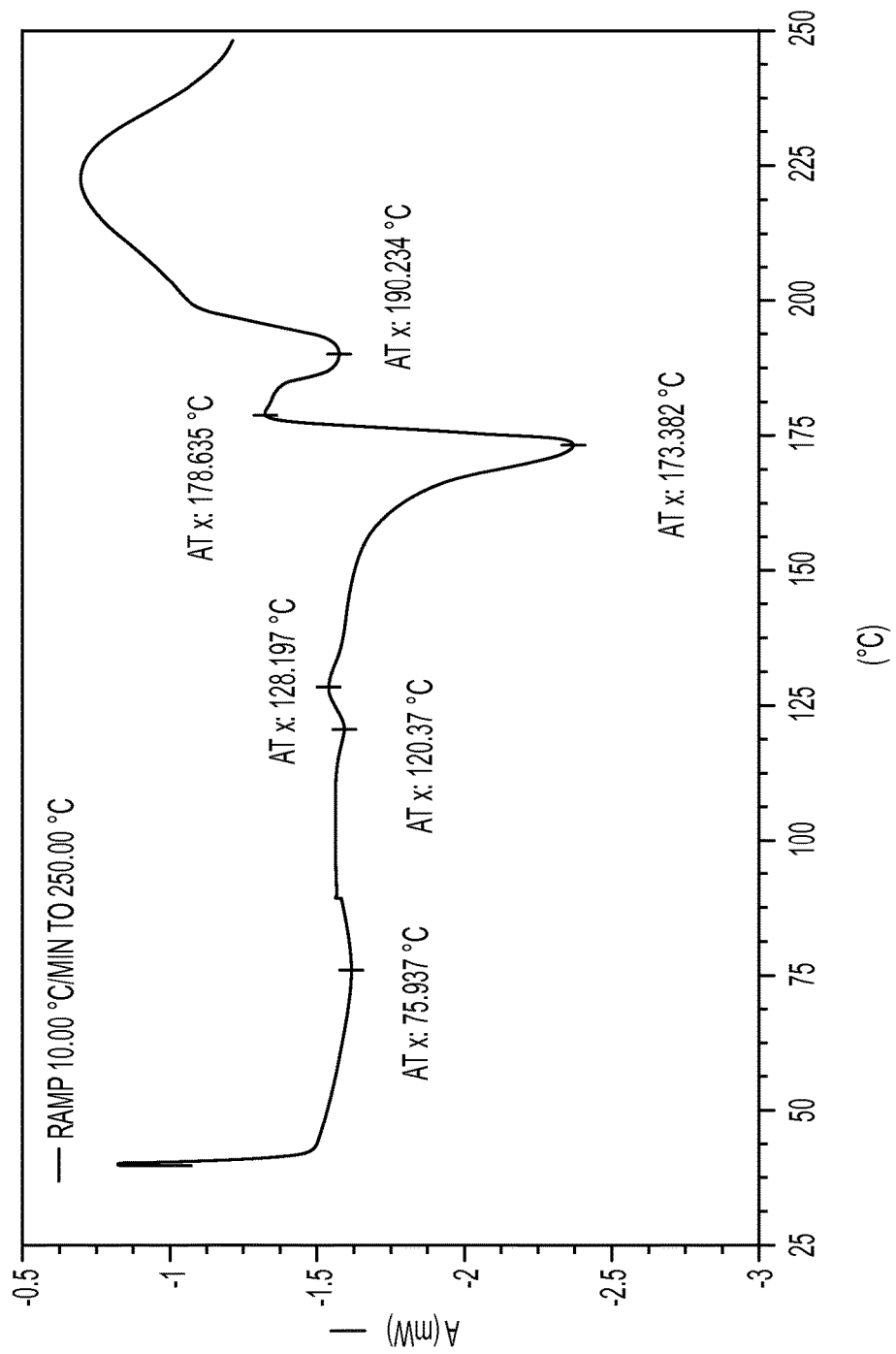
FIG. 26 depicts a DSC thermogram of Form D of compound 2.

FIG. 26 depicts a DSC thermogram of Form D of compound 2.

Figure 27:
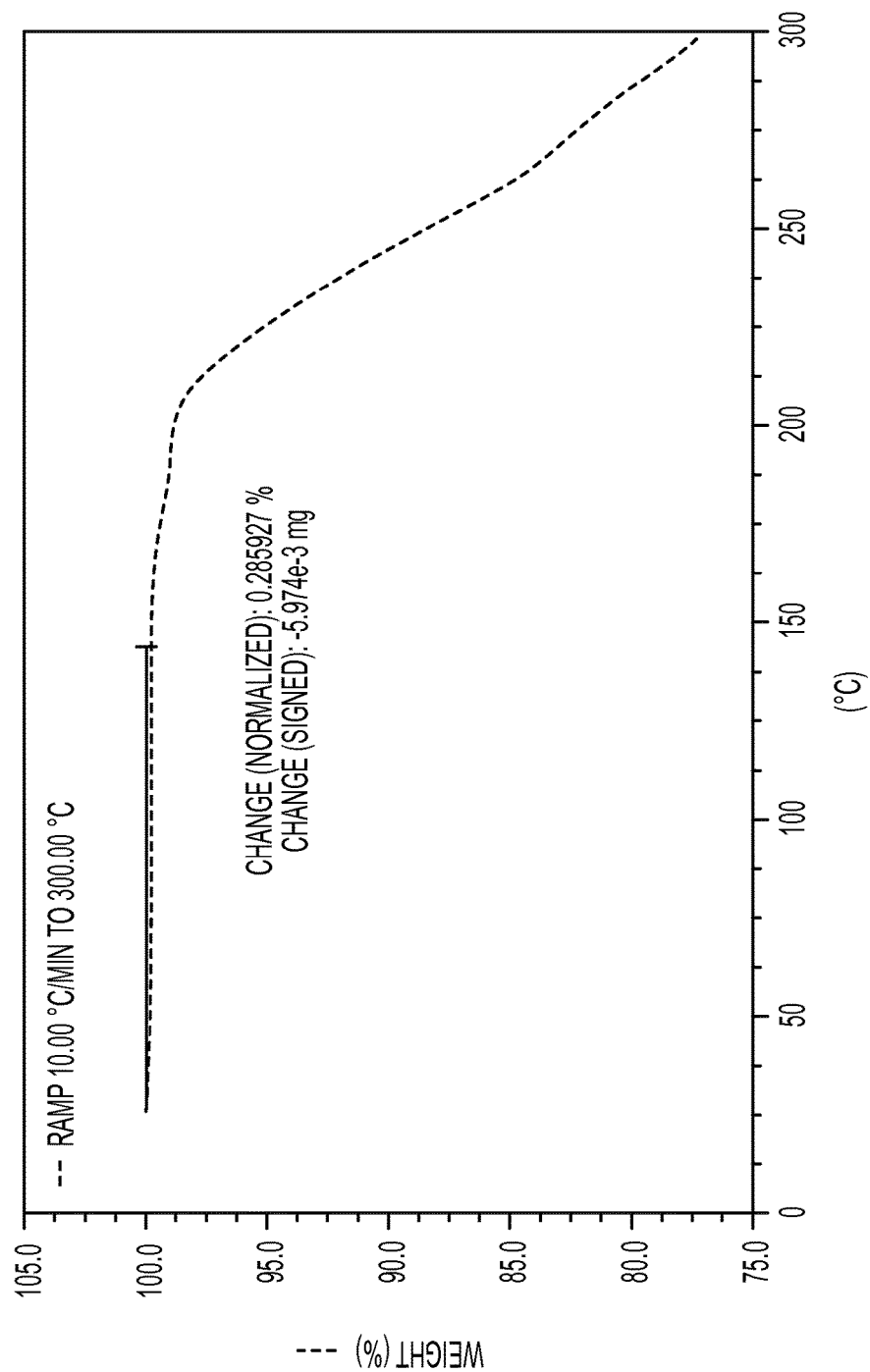
FIG. 27 depicts a TGA trace of Form D of compound 2.

FIG. 27 depicts a TGA trace of Form D of compound 2.

Phosphate Interconversions
From polymorph screen:

| Starting Form(s) | Solvent/Condition | Temperature/ Condition | XRPD Result |
|---|---|---|---|
| Form B | slurry in MeOH | RT, 5 days | free base (Form B) |
| Form B | slurry in EtOH | RT, 5 days | Form A + free base (Form C) |
| Form B | slurry in acetone | RT, 5 days | Form A |
| Form B | slurry in MeCN | RT, 5 days | Form A |
| Form B | slurry in MeCN/water (1:1) | RT, 5 days | free base (Form D) |

Example 3

Preparation of Form A of Compound 3

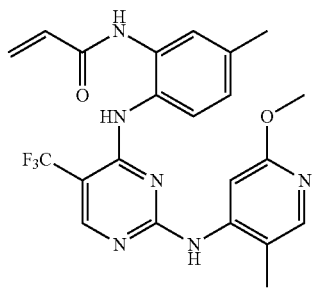

Form A of Compound 3

Form A of compound 3 was prepared as follows.

Procedure: Compound 1 was dissolved in 20 volumes of isopropanol. Eight molar equivalents of phosphoric acid were charged. The reaction was heated to 60° C. for 24 hours, then cooled to 20° C., filtered, washed with 10 volumes of isopropanol, and dried under reduced pressure at 40° C.

Characterization of the resulting material demonstrated a crystalline, anhydrous Form A of compound 3.

Table 9, supra, is reproduced below and sets forth the X-ray diffraction peaks observed for Form A of compound 3.

TABLE 9

XRPD Peak Positions for Form A of Compound 3
Position (°2θ)

| |
|---|
| 5.7 |
| 7.1 |
| 8.9 |
| 10.3 |
| 11.0 |
| 11.4 |
| 13.2 |
| 14.2 |
| 14.5 |
| 17.2 |
| 17.7 |
| 18.4 |
| 19.4 |
| 19.9 |
| 20.6 |
| 20.8 |
| 22.1 |
| 22.5 |
| 24.3 |
| 25.5 |

[1] In this and all subsequent tables, the position 2θ is within ±0.2.

FIG. 28 depicts an XRPD pattern of Form A of compound 3.

Figure 29:
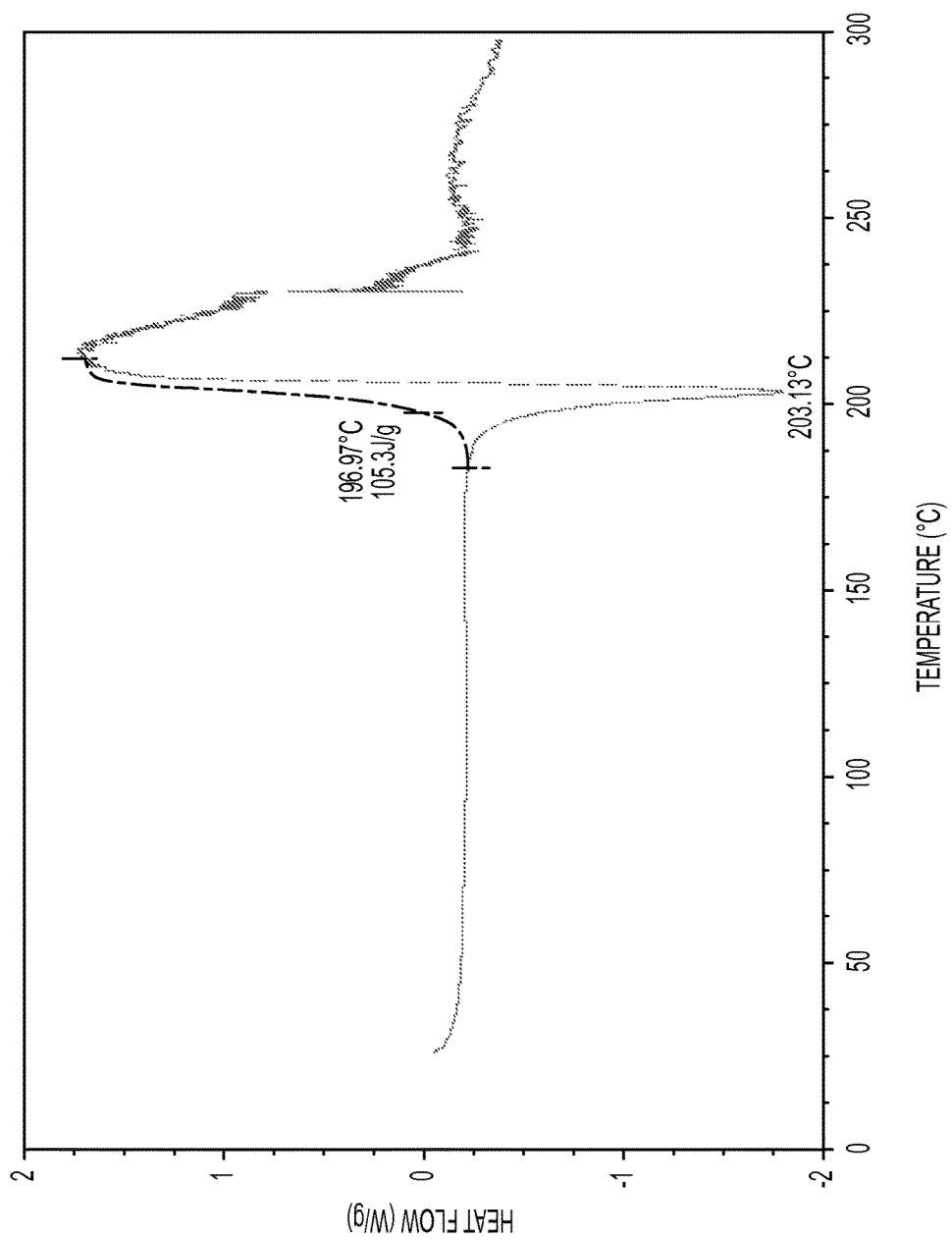
FIG. 29 depicts a DSC thermogram of Form A of compound 3.

FIG. 29 depicts a DSC thermogram of Form A of compound 3.

Figure 30:
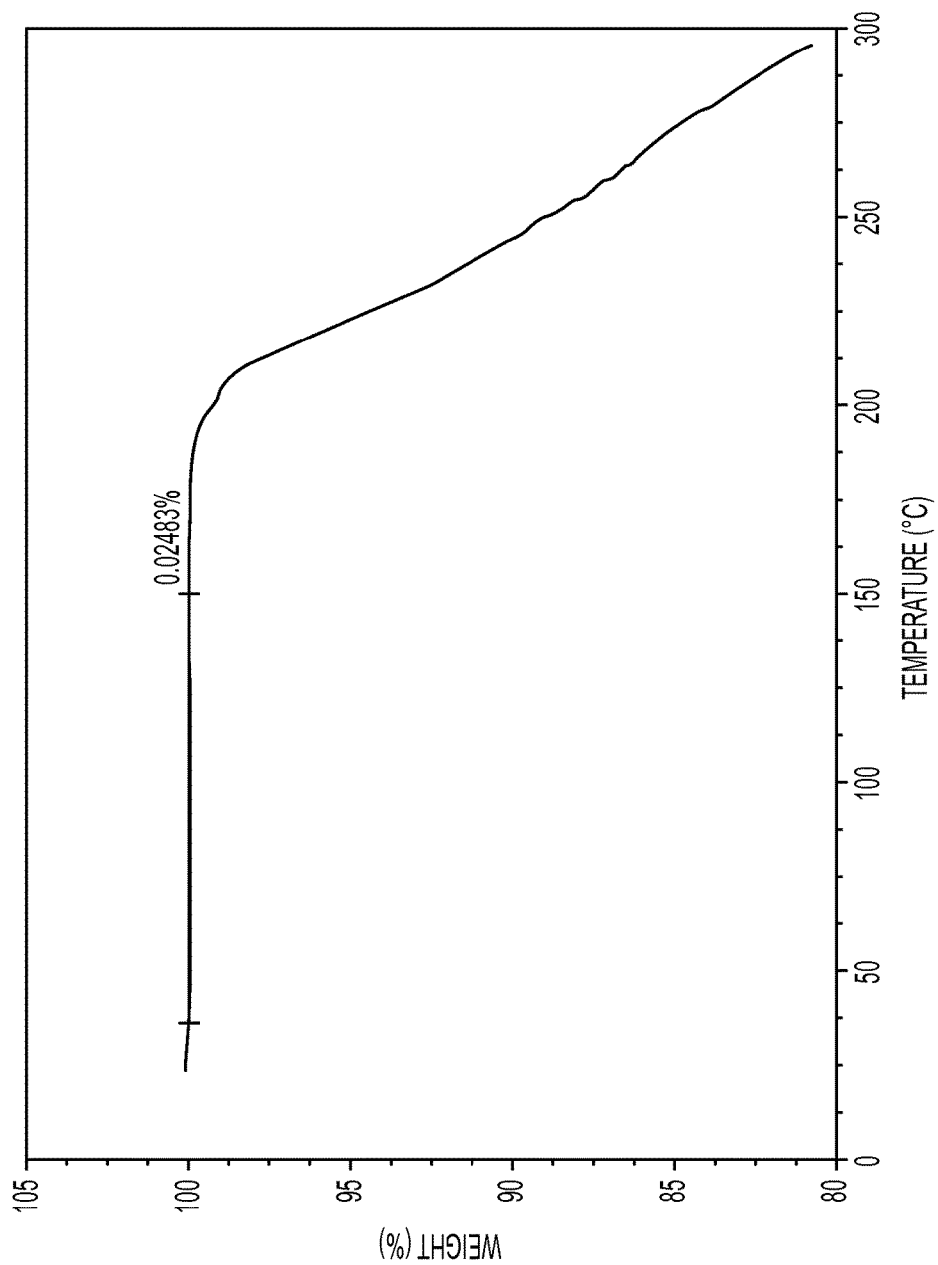
FIG. 30 depicts a TGA trace of Form A of compound 3.

FIG. 30 depicts a TGA trace of Form A of compound 3.

Figure 31:
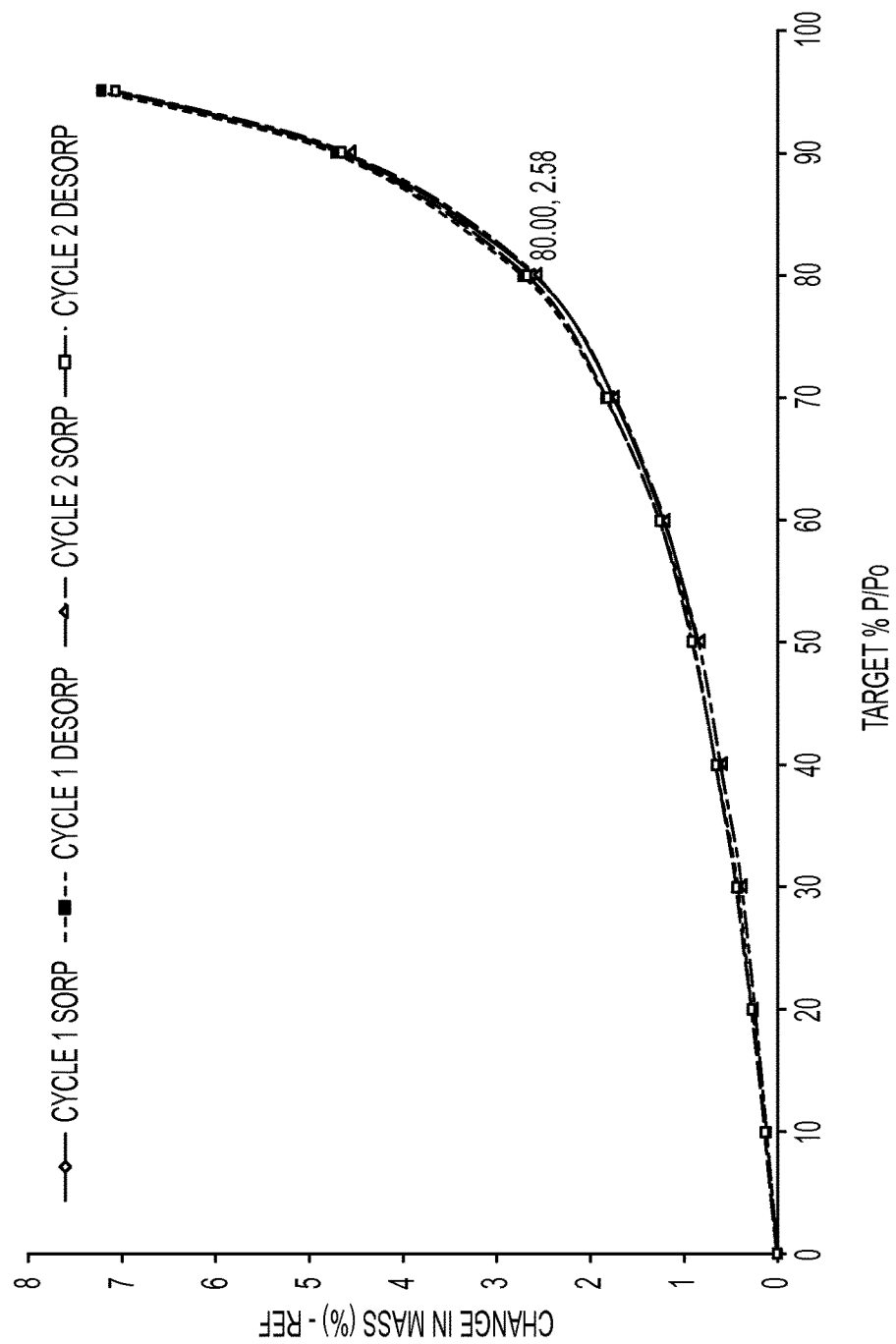
FIG. 31 depicts a DVS plot of Form A of compound 3.

FIG. 31 depicts a DVS plot of Form A of compound 3.

Elemental analysis—Calculated: C, 40.38; H, 4.16; N, 12.84; P, 9.47; Found: C, 40.01; H, 4.15; N, 12.61; P, 9.69.

Example 4

Preparation of Forms A-I of Compound 4

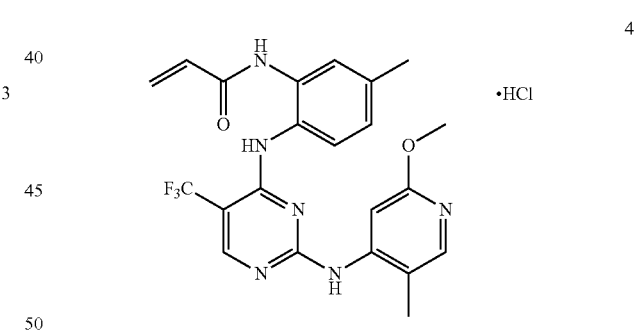

Form A of Compound 4

Form A of compound 4 was prepared as follows.

Procedure A: Two grams of the hydrochloride salt of compound 1 were dissolved in 10 mL of methanol and passed through a 0.2 uM filter. The solution was reduced in volume to about 3 mL and stirred for about 16 hours at 23° C. The resulting solids were collected by suction filtration and dried under a nitrogen stream.

Procedure B: 507 mg of compound 1 were mixed with 8 mL of MeOH/CH$_2$Cl$_2$ (1/1 v/v, premixed), followed by addition of 1.1 mL 1N HCl (in diethylether). The solution was stirred for 1 hour to become a clear solution. The solution was dried in a fume hood under nitrogen purge. Next, 1 mL of methanol was added to the vial, which was vortex agitated until precipitation was observed. The vial was capped and stirred at room temperature overnight. The solids were recovered through filtration and dried in a vacuum oven at room temperature.

Characterization of the resulting material demonstrated a crystalline Form A of compound 4 in the form of a hydrate.

Table 10, supra, is reproduced below and sets forth the X-ray diffraction peaks observed for Form A of compound 4.

TABLE 10

XRPD Peak Positions for Form A of Compound 4
Position (°2θ)

| |
| --- |
| 7.5 |
| 9.3 |
| 11.2 |
| 11.9 |
| 14.2 |
| 15.0 |
| 15.3 |
| 15.7 |
| 21.4 |
| 21.9 |
| 22.6 |
| 22.8 |
| 23.4 |
| 24.6 |
| 24.8 |
| 25.2 |
| 26.4 |
| 26.8 |
| 30.5 |
| 34.1 |

[1]In this and all subsequent tables, the position 2θ is within ±0.2.

FIG. 32 depicts an XRPD pattern of Form A of compound 4.

Figure 33:
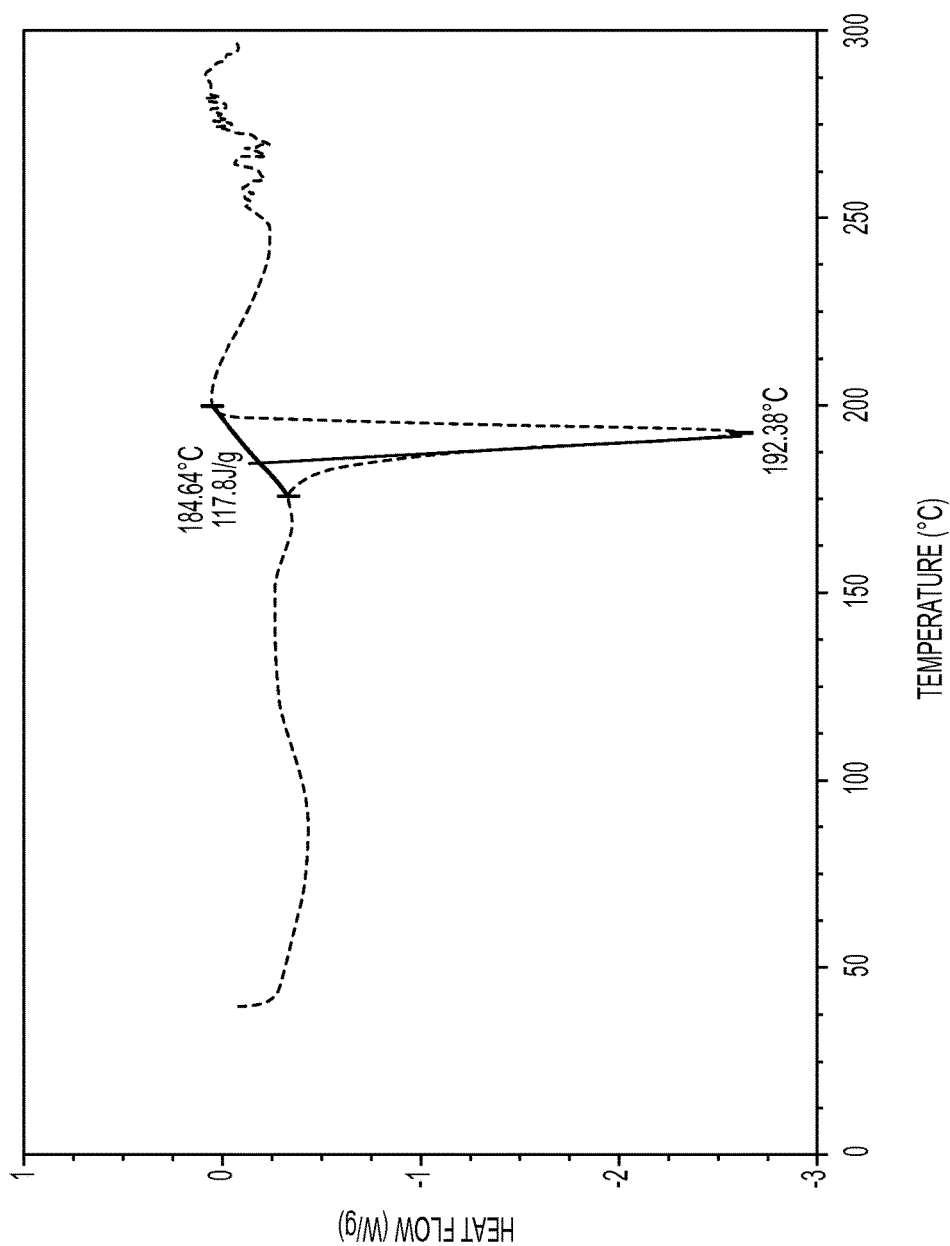
FIG. 33 depicts a DSC thermogram of Form A of compound 4.

FIG. 33 depicts a DSC thermogram of Form A of compound 4.

Figure 34:
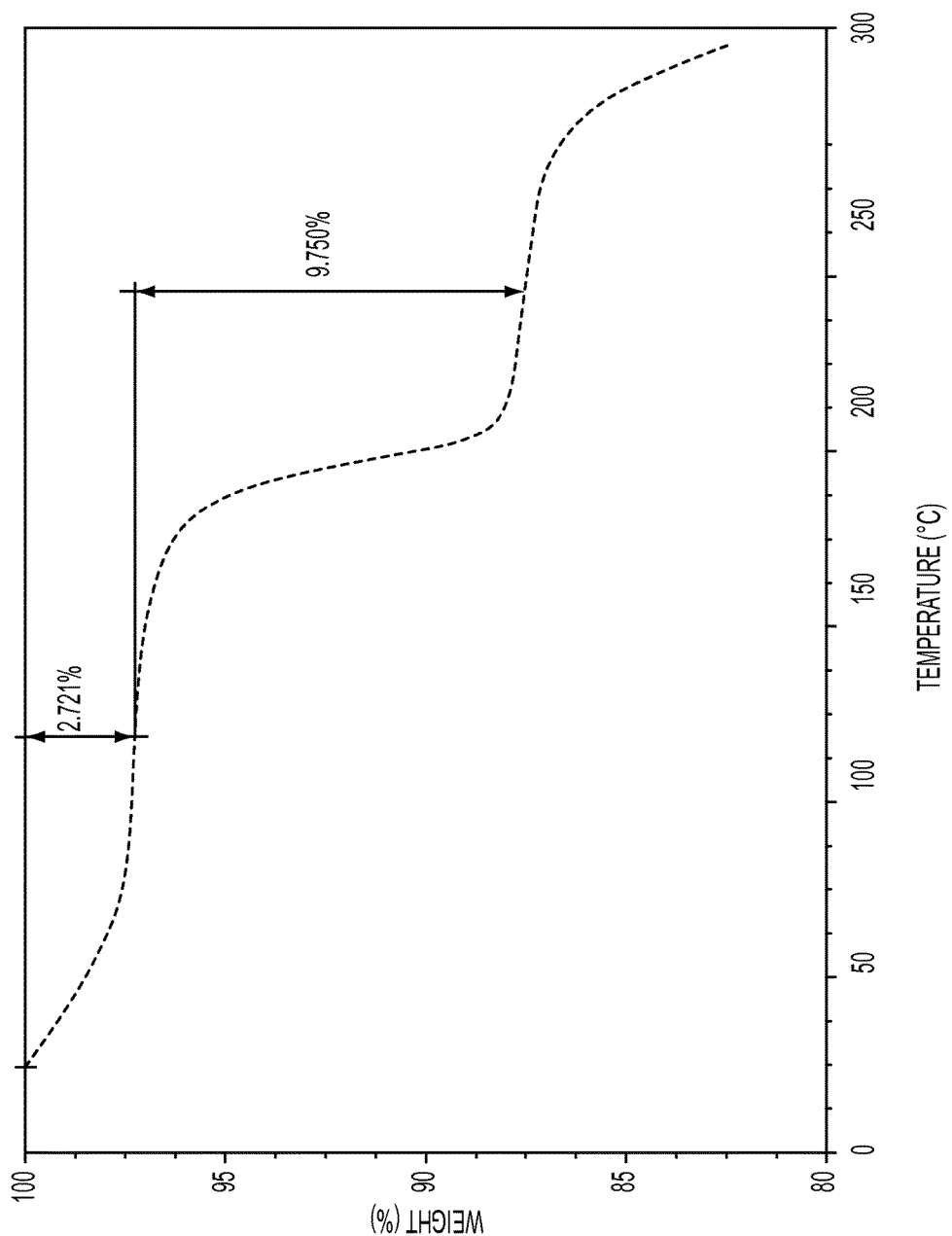
FIG. 34 depicts a TGA trace of Form A of compound 4.

FIG. 34 depicts a TGA trace of Form A of compound 4.

Figure 35:
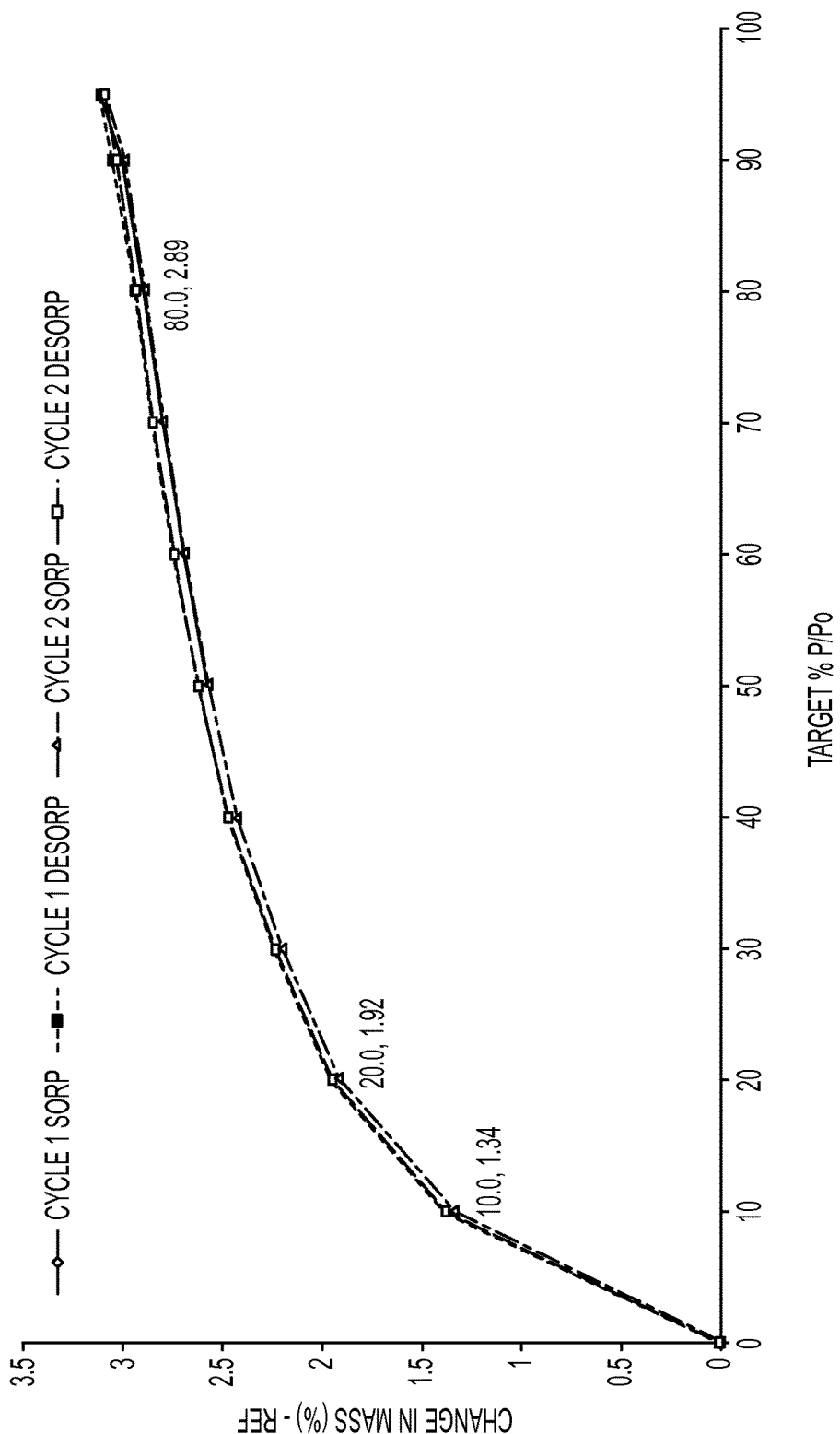
FIG. 35 depicts a DVS plot of Form A of compound 4.

FIG. 35 depicts a DVS plot of Form A of compound 4.

Elemental analysis—Calculated: C, 51.52; H, 4.72; Cl, 6.91; N, 16.38; Found: C, 51.89; H, 4.51; Cl, 7.11; N, 16.52.

Karl Fischer titration: 2.56%

Form B of Compound 4

Form B of compound 4 was prepared as follows.

Procedure: Compound 1 was dissolved in tetrahydrofuran. An equal molar equivalent of 1M HCl in diethyl ether was charged. The sample was shaken at ambient temperature at 200 RPM for 1 hour. The solvent was removed under nitrogen purge. The resulting solids were slurried in acetonitrile with a stirring bar at ambient temperature overnight, then filtered and dried in a vacuum oven at 30° C. overnight.

Characterization of the resulting material demonstrated a crystalline Form B of compound 4.

Table 11, supra, is reproduced below and sets forth the X-ray diffraction peaks observed for Form B of compound 4.

TABLE 11

XRPD Peak Positions for Form B of Compound 4
Position (°2θ)

| |
| --- |
| 8.0 |
| 8.4 |
| 9.1 |
| 11.0 |
| 11.8 |
| 12.7 |
| 16.2 |
| 17.2 |
| 17.8 |

TABLE 11-continued

XRPD Peak Positions for Form B of Compound 4
Position (°2θ)

| |
| --- |
| 18.9 |
| 20.4 |
| 20.9 |
| 23.7 |
| 23.9 |
| 24.7 |
| 25.4 |
| 25.6 |
| 25.9 |
| 29.2 |
| 30.7 |

[1]In this and all subsequent tables, the position 2θ is within ±0.2.

FIG. 36 depicts an XRPD pattern of Form B of compound 4.

Figure 37:
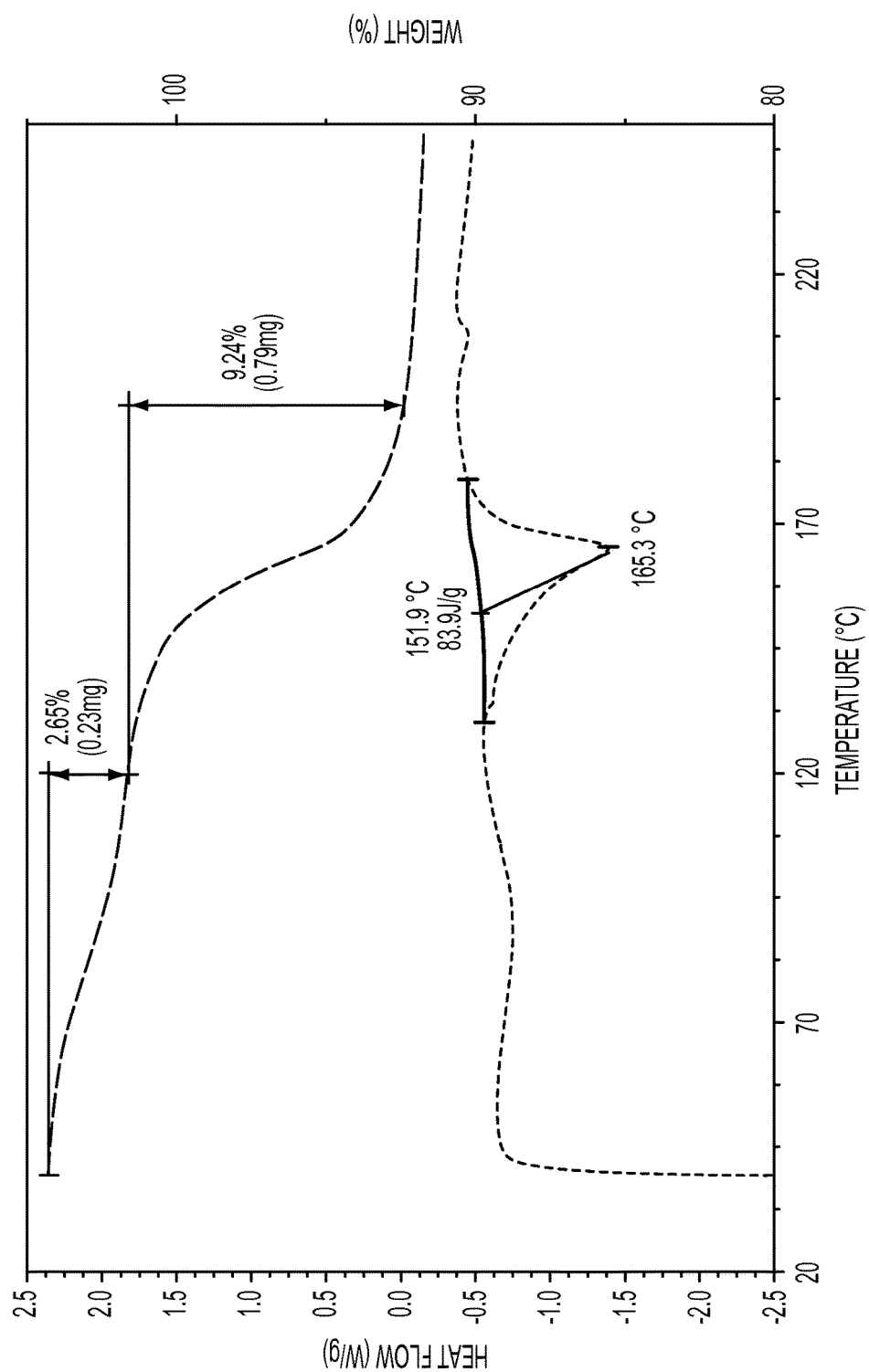
FIG. 37 depicts a DSC thermogram and TGA trace of Form B of compound 4.

FIG. 37 depicts a DSC thermogram and TGA trace of Form B of compound 4.

Form C of Compound 4

Form C of compound 4 was prepared as follows.

Procedure: Form B of compound 4 was slurried in acetone for 5 days at room temperature.

Characterization of the resulting material demonstrated a crystalline Form C of compound 4.

Table 12, supra, is reproduced below and sets forth the X-ray diffraction peaks observed for Form C of compound 4.

TABLE 12

XRPD Peak Positions for Form C of Compound 4
Position (°2θ)

| |
| --- |
| 7.7 |
| 8.2 |
| 9.0 |
| 9.5 |
| 10.2 |
| 12.1 |
| 12.4 |
| 12.6 |
| 13.5 |
| 15.3 |
| 16.4 |
| 18.4 |
| 21.0 |
| 21.3 |
| 23.1 |
| 23.4 |
| 23.7 |
| 24.2 |
| 25.5 |
| 25.7 |

[1]In this and all subsequent tables, the position 2θ is within ±0.2.

FIG. 38 depicts an XRPD pattern of Form C of compound 4.

Figure 39:
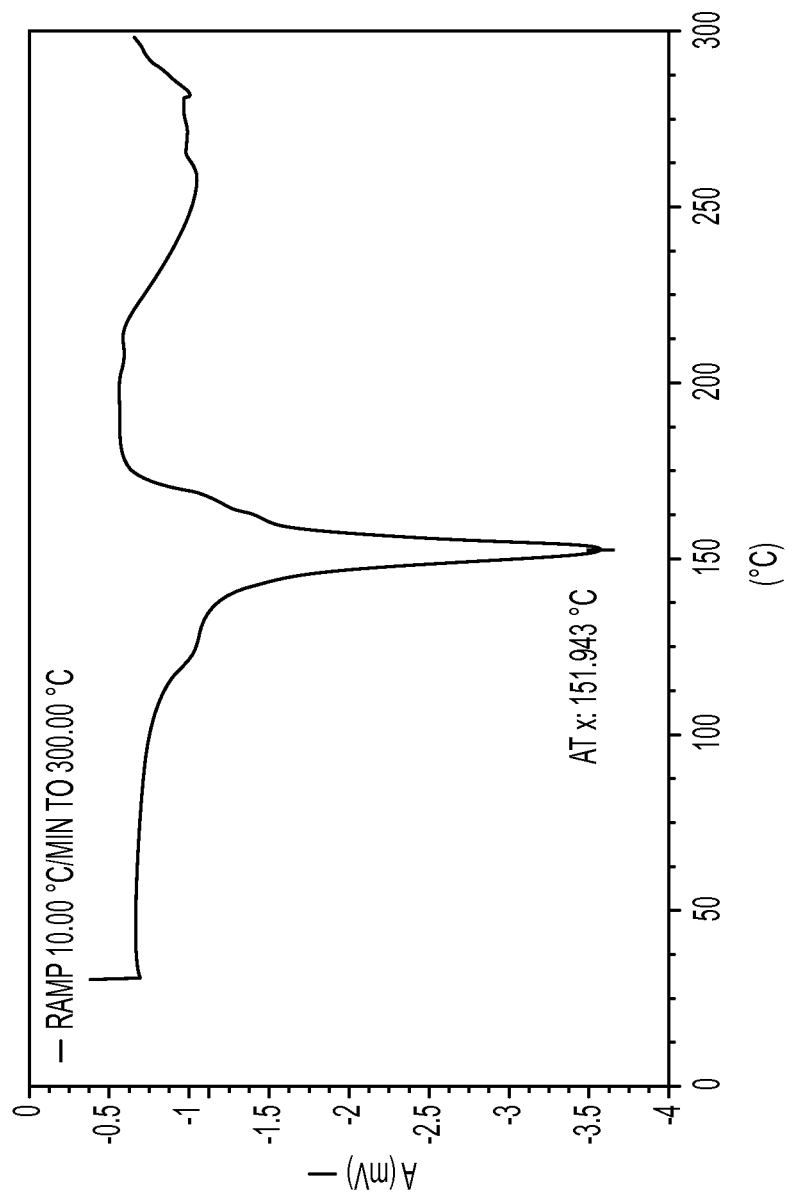
FIG. 39 depicts a DSC thermogram of Form C of compound 4.

FIG. 39 depicts a DSC thermogram of Form C of compound 4.

Form D of Compound 4

Form D of compound 4 was prepared as follows.

Procedure: Compound 1 (3 g, 6.5 mmol) was charged to a 150 mL round bottom flask. Methanol (15×) was charged. A solution of HCl (3.27 mL, 6.54 mmol; 2M in diethyl ether) was charged to the flask. The solids completely dissolved. The solution was stirred overnight, then transferred to a crystallizing dish for slow evaporation of the solvent. Solids were then placed to dry in a vacuum oven with a nitrogen bleed at 40° C.

Characterization of the resulting material demonstrated a crystalline Form D of compound 4.

Table 13, supra, is reproduced below and sets forth the X-ray diffraction peaks observed for Form D of compound 4.

TABLE 13

XRPD Peak Positions for Form D of Compound 4
Position (°2θ)

| |
|---|
| 7.1 |
| 9.1 |
| 11.2 |
| 12.7 |
| 14.0 |
| 14.4 |
| 14.6 |
| 17.0 |
| 17.2 |
| 21.7 |
| 22.0 |
| 22.4 |
| 22.8 |
| 23.7 |
| 24.8 |
| 25.3 |
| 25.5 |
| 28.0 |
| 34.2 |
| 35.7 |

[1]In this and all subsequent tables, the position 2θ is within ±0.2.

FIG. 40 depicts an XRPD pattern of Form D of compound 4.

Figure 41:
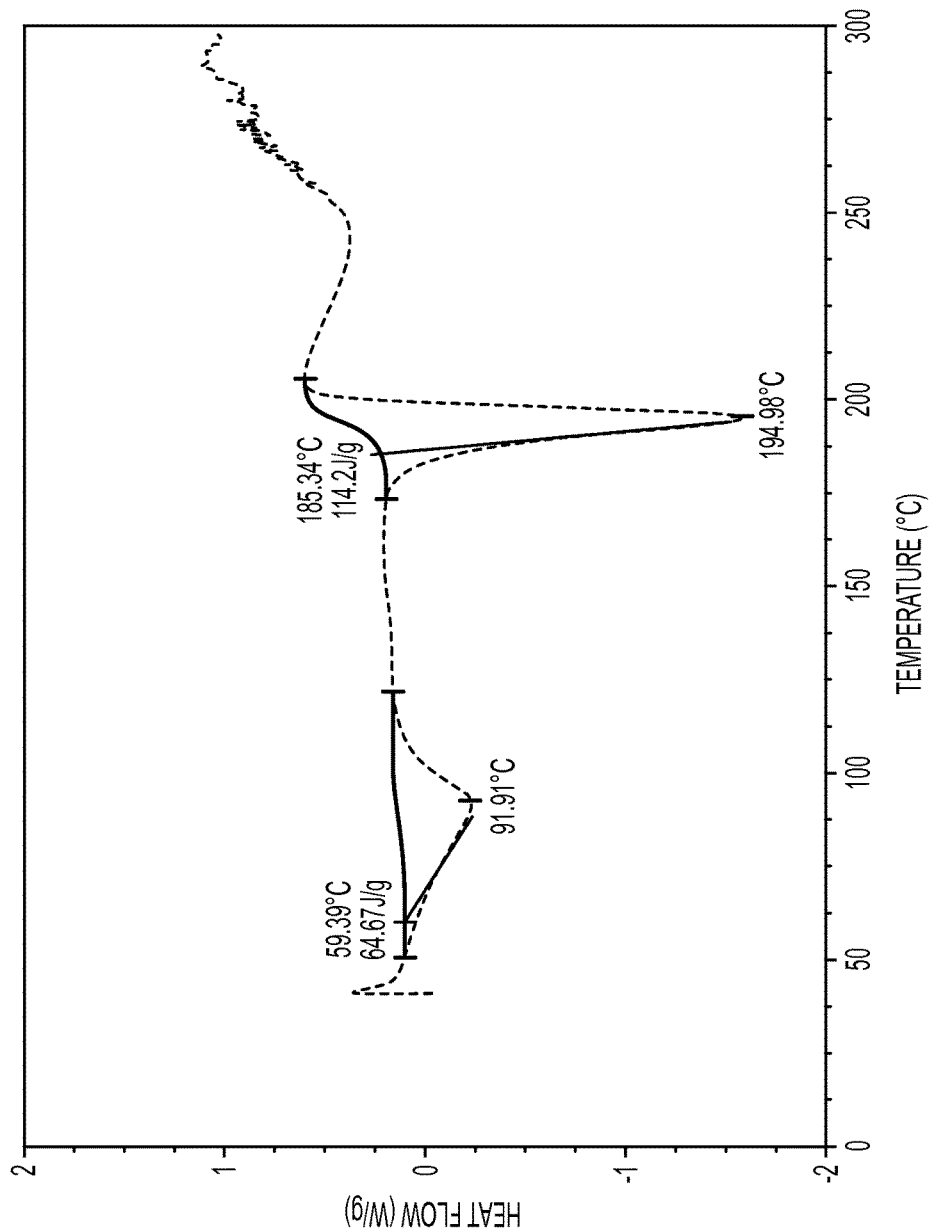
FIG. 41 depicts a DSC thermogram of Form D of compound 4.

FIG. 41 depicts a DSC thermogram of Form D of compound 4.

Figure 42:
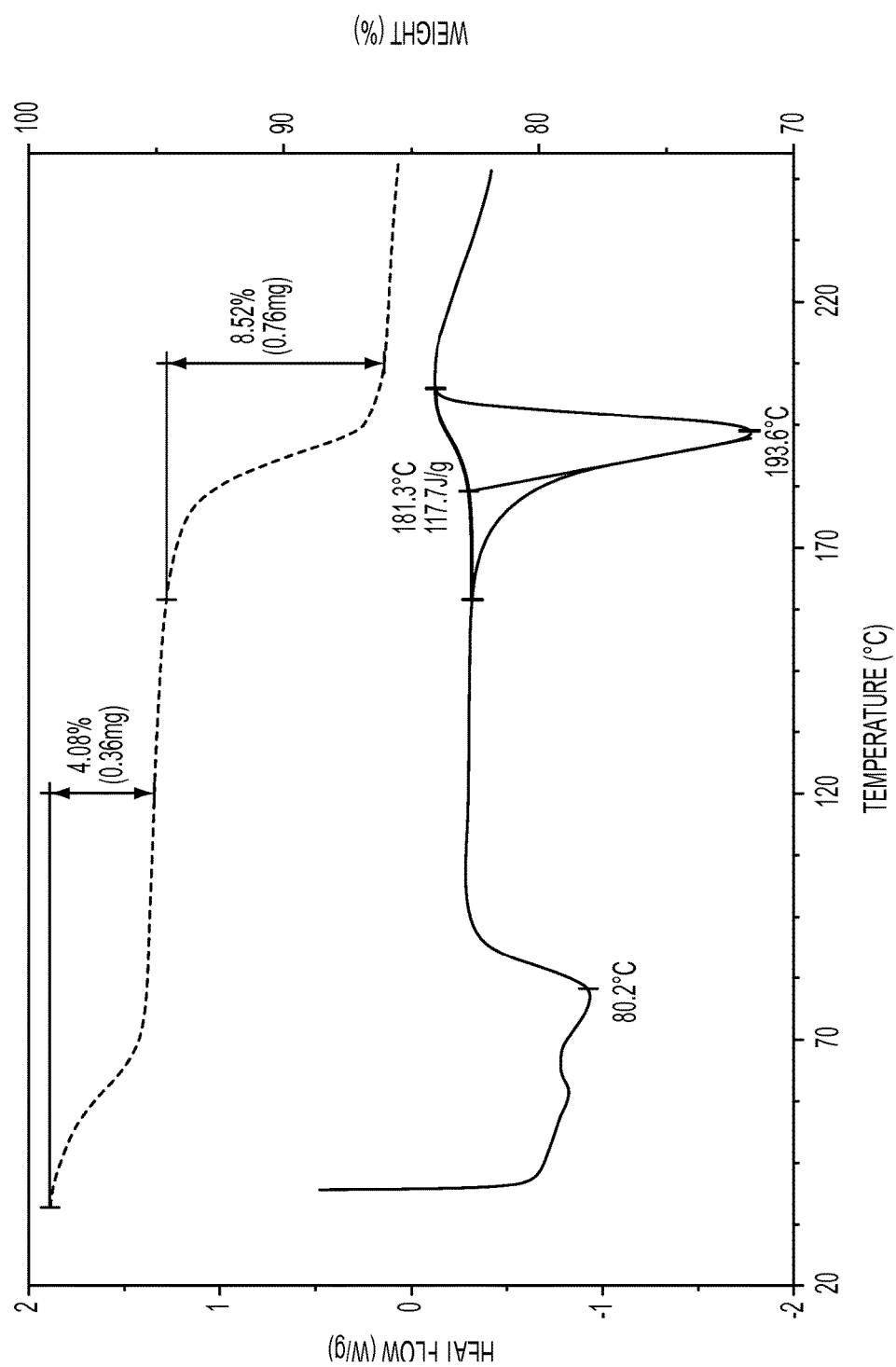
FIG. 42 depicts a DSC thermogram and TGA trace of Form D of compound 4.

FIG. 42 depicts a DSC thermogram and TGA trace of Form D of compound 4.

Figure 43:
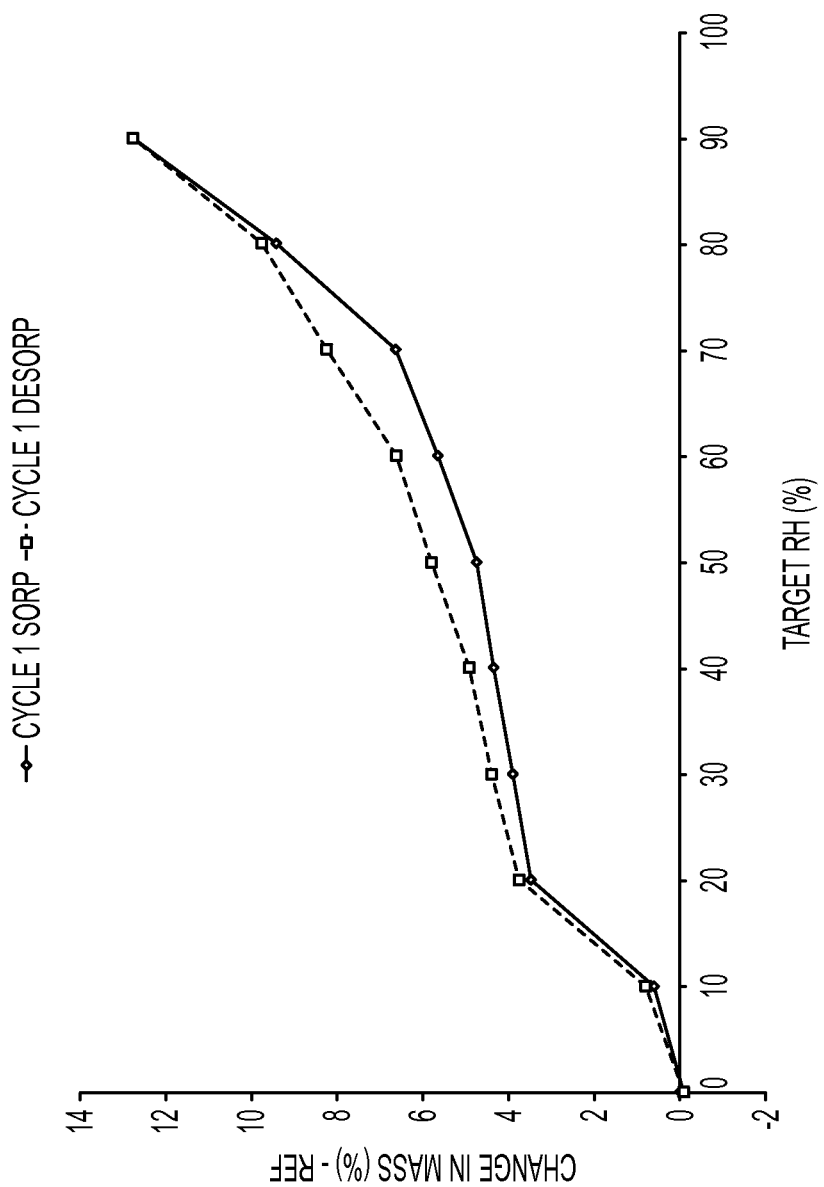
FIG. 43 depicts a DVS plot of Form D of compound 4.

FIG. 43 depicts a DVS plot of Form D of compound 4.

Karl Fischer titration: 1.21%

Form E of Compound 4

Form E of compound 4 was prepared as follows.

Procedure: Form B of compound 4 was slurried in acetonitrile/water (1:1) for five days at room temperature.

Characterization of the resulting material demonstrated a crystalline Form E of compound 4.

Table 14, supra, is reproduced below and sets forth the X-ray diffraction peaks observed for Form E of compound 4.

TABLE 14

XRPD Peak Positions for Form E of Compound 4
Position (°2θ)

| |
|---|
| 7.7 |
| 9.0 |
| 10.7 |
| 14.4 |
| 15.5 |
| 17.1 |
| 18.2 |
| 19.8 |
| 20.4 |
| 21.5 |
| 23.1 |
| 24.4 |
| 24.6 |
| 25.0 |
| 27.0 |
| 27.3 |
| 28.1 |
| 30.9 |

TABLE 14-continued

XRPD Peak Positions for Form E of Compound 4
Position (°2θ)

| |
|---|
| 31.2 |
| 37.6 |

[1]In this and all subsequent tables, the position 2θ is within ±0.2.

FIG. 44 depicts an XRPD pattern of Form E of compound 4.

Figure 45:
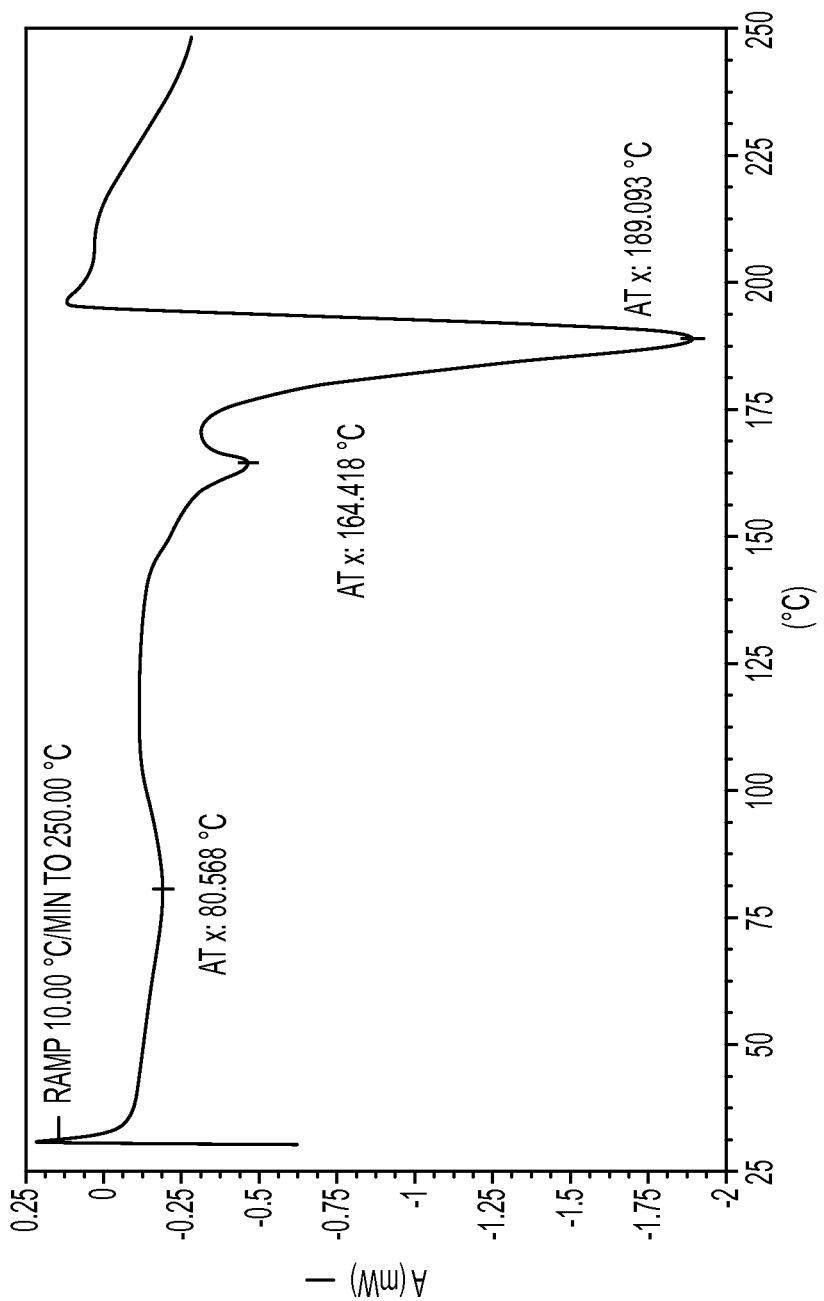
FIG. 45 depicts a DSC thermogram of Form E of compound 4.

FIG. 45 depicts a DSC thermogram of Form E of compound 4.

Form F of Compound 4

Form F of compound 4 was prepared as follows.

Procedure: Form B of compound 4 was slurried in isopropanol for five days at room temperature.

Characterization of the resulting material demonstrated a crystalline Form F of compound 4.

Table 15, supra, is reproduced below and sets forth the X-ray diffraction peaks observed for Form F of compound 4.

TABLE 15

XRPD Peak Positions for Form F of Compound 4
Position (°2θ)

| |
|---|
| 6.1 |
| 7.7 |
| 11.3 |
| 12.4 |
| 13.8 |
| 15.4 |
| 16.9 |
| 17.7 |
| 18.6 |
| 19.5 |
| 22.6 |
| 22.9 |
| 23.1 |
| 23.6 |
| 24.9 |
| 25.7 |
| 26.1 |
| 30.2 |
| 34.2 |
| 35.0 |

[1]In this and all subsequent tables, the position 2θ is within ±0.2.

FIG. 46 depicts an XRPD pattern of Form F of compound 4.

Figure 47:
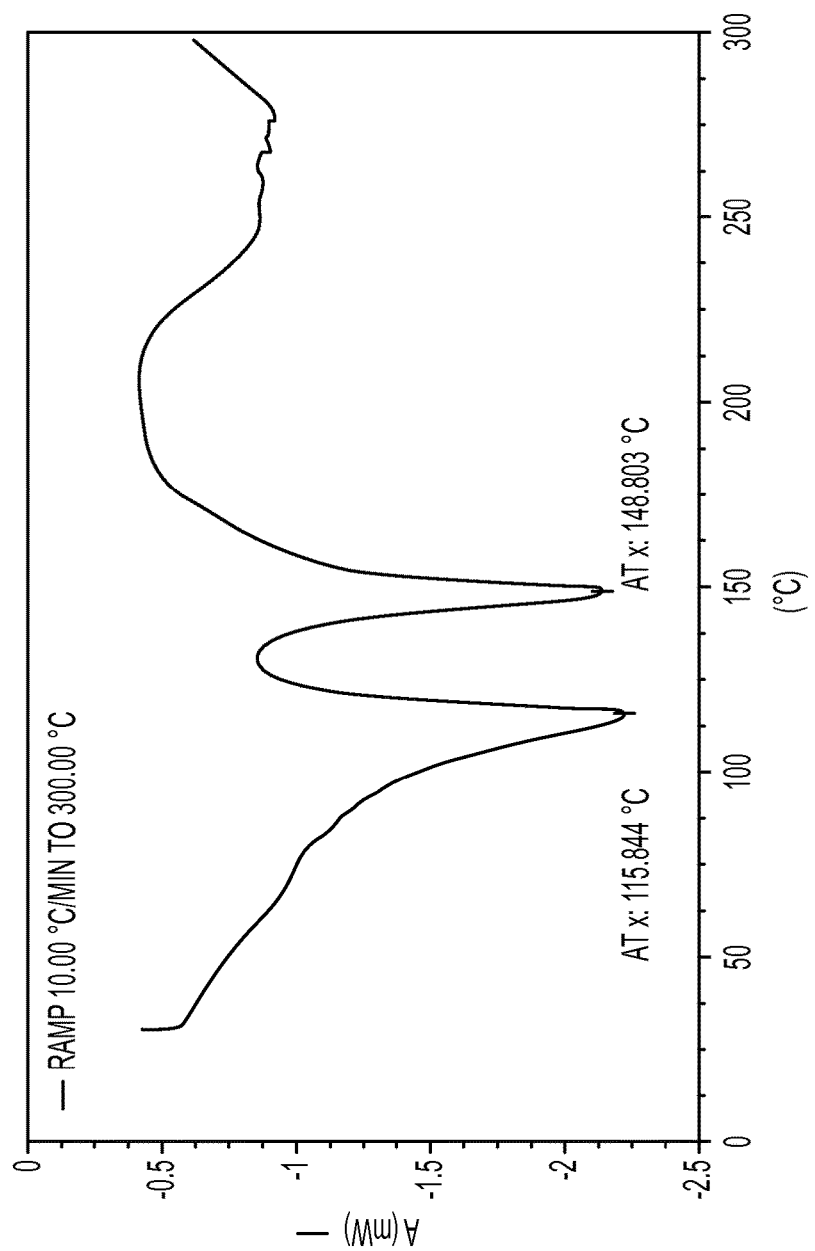
FIG. 47 depicts a DSC thermogram of Form F of compound 4.

FIG. 47 depicts a DSC thermogram of Form F of compound 4.

Form G of Compound 4

Form G of compound 4 was prepared as follows.

Procedure: Form B of compound 4 was slurried in acetonitrile for five days at room temperature.

Characterization of the resulting material demonstrated a crystalline Form G of compound 4.

Table 16, supra, is reproduced below and sets forth the X-ray diffraction peaks observed for Form G of compound 4.

TABLE 16

XRPD Peak Positions for Form G of Compound 4
Position (°2θ)

| |
|---|
| 5.2 |
| 8.5 |
| 8.7 |
| 10.5 |
| 14.8 |

TABLE 16-continued

XRPD Peak Positions for Form G of Compound 4
Position (°2θ)

15.6
19.0
19.5
20.7
21.0
21.9
22.2
23.3
25.7
27.0
27.4
29.6
30.7
31.3

[1] In this and all subsequent tables, the position 2θ is within ±0.2.

FIG. 48 depicts an XRPD pattern of Form G of compound 4.

Figure 49:
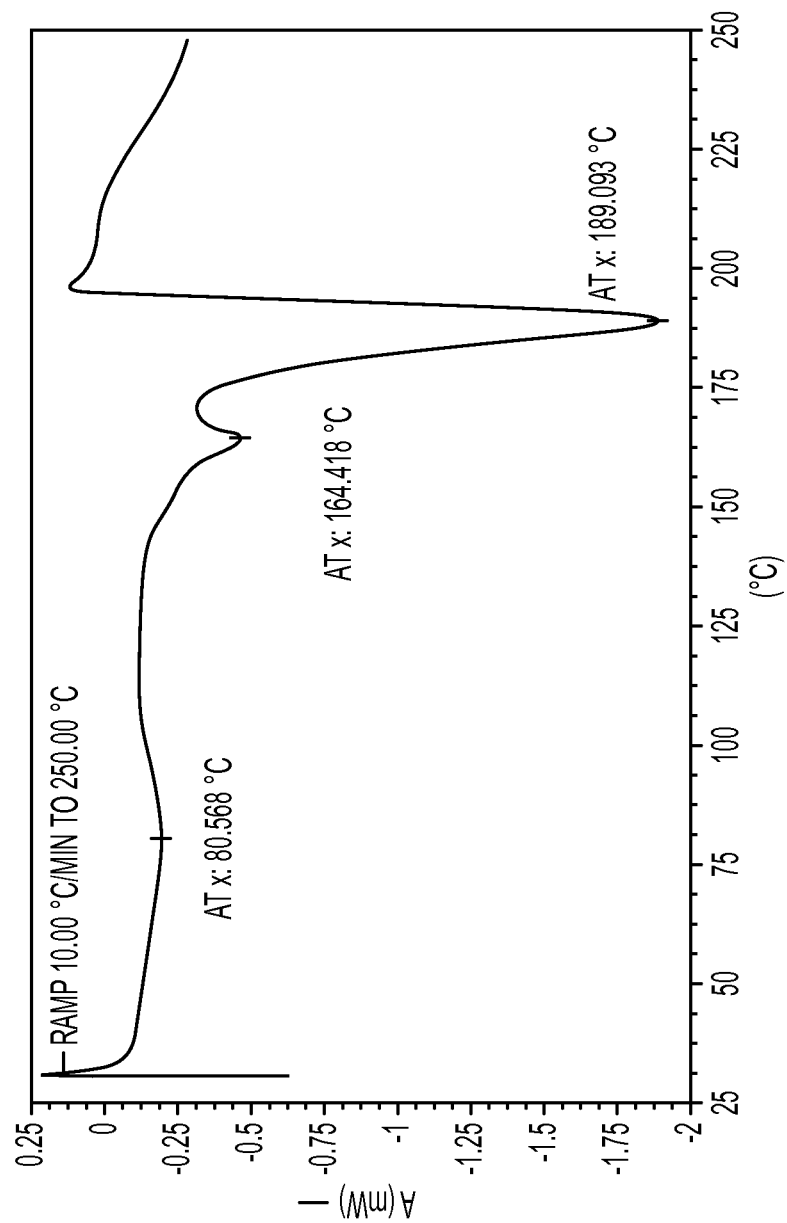
FIG. 49 depicts a DSC thermogram of Form G of compound 4.

FIG. 49 depicts a DSC thermogram of Form G of compound 4.

Form H of Compound 4

Form H of compound 4 was prepared as follows.

Procedure: 1 g of the HCl salt of compound 1 was dissolved in methanol (4 mL) and filtered through a syringe filter. The solvent was evaporated slowly under a stream of nitrogen until the reaction mixture was slightly cloudy. The salt solution was stirred at room temperature overnight, filtered, and dried at room temperature under a stream of nitrogen for 15 minutes.

Characterization of the resulting material demonstrated a crystalline Form H of compound 4.

Table 17, supra, is reproduced below and sets forth the X-ray diffraction peaks observed for Form H of compound 4.

TABLE 17

XRPD Peak Positions for Form H of Compound 4
Position (°2θ)

7.2
8.5
9.1
10.2
13.1
14.5
15.8
18.1
18.8
20.5
21.0
21.7
22.5
23.3
24.2
24.6
25.3
25.8
28.8
29.9

[1] In this and all subsequent tables, the position 2θ is within ±0.2.

FIG. 50 depicts an XRPD pattern of Form H of compound 4.

Figure 51:
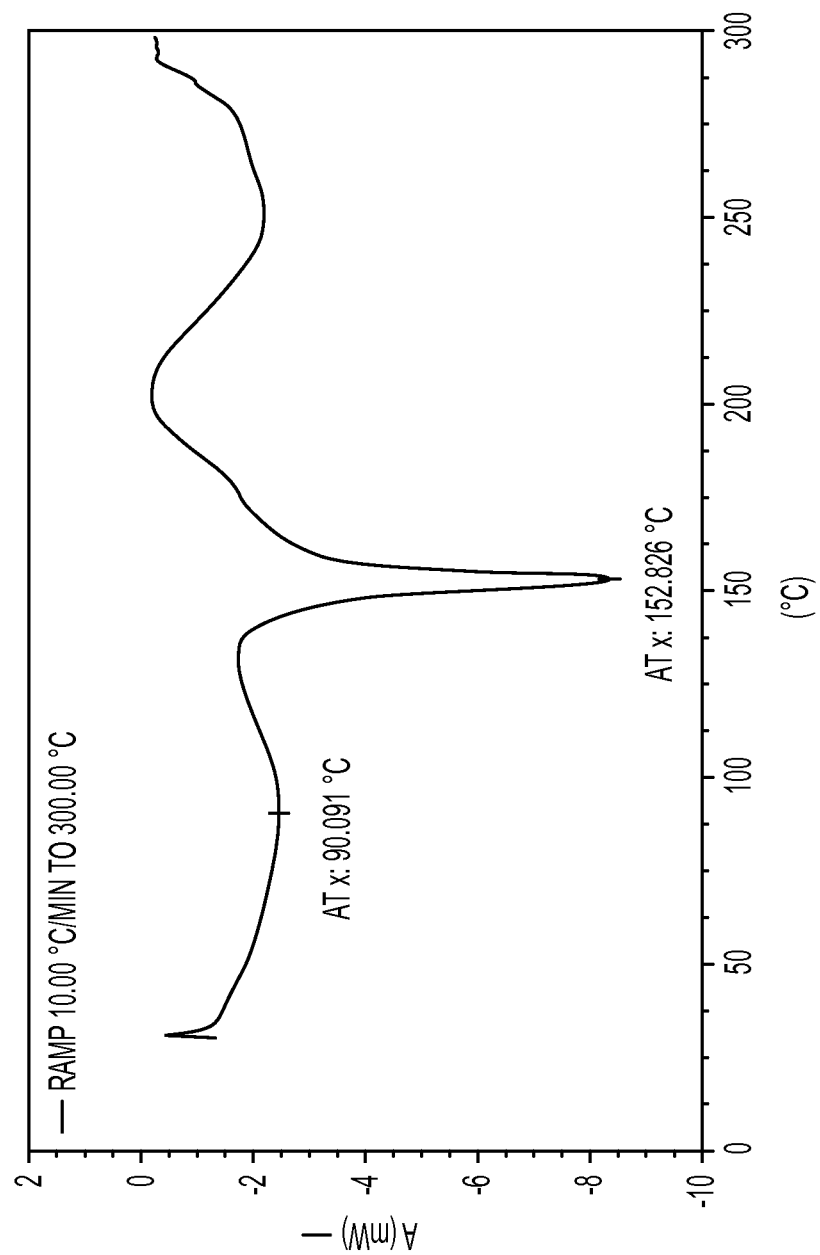
FIG. 51 depicts a DSC thermogram of Form H of compound 4.

FIG. 51 depicts a DSC thermogram of Form H of compound 4.

Form I of Compound 4

Form I of Compound 4 was prepared as follows.

Procedure: Form H of compound 4 was slurried in water for two hours at room temperature.

Characterization of the resulting material demonstrated a crystalline Form I of compound 4.

Table 18, supra, is reproduced below and sets forth the X-ray diffraction peaks observed for Form I of compound 4.

TABLE 18

XRPD Peak Positions for Form I of Compound 4
Position (°2θ)

4.7
7.1
9.3
10.8
11.9
14.1
15.0
16.7
18.8
20.3
21.1
22.2
23.1
23.5
24.2
25.4
26.0
29.1

[1] In this and all subsequent tables, the position 2θ is within ±0.2.

FIG. 52 depicts an XRPD pattern of Form I of compound 4.

Example 5

Preparation of Forms A-E of Compound 5

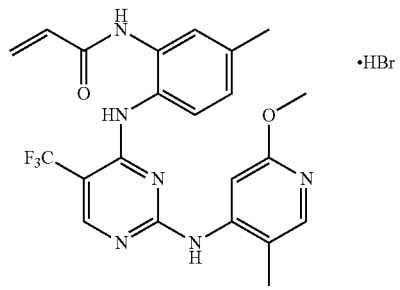

Form A of Compound 5

Form A of compound 5 was prepared as follows.

Procedure A: 4.1 g of compound 1 was dissolved in tetrahydrofuran (15×). Hydrobromic acid (1 molar equivalent of 48% HBr diluted to 2M in acetonitrile) was charged and agitated for 2 hours at 20° C. The solvent was removed under reduced pressure and the resulting solids were slurried in acetone for 16 hours at 20° C., filtered and dried to yield 4.89 g product.

Procedure B: Compound 1 was dissolved in tetrahydrofuran. Equal molar equivalent of 8.84 M HBr in water was charged. The sample was shaken at ambient temperature at 200 RPM for 1 hour. The solvent was removed under nitrogen purge. The resulting solids were slurried in acetonitrile (or acetone) with a stirring bar at ambient temperature overnight, then filtered and dried in vacuum oven at 30° C. overnight.

Characterization of the resulting material demonstrated a crystalline, anhydrous Form A of compound 5.

Table 19, supra, is reproduced below and sets forth the X-ray diffraction peaks observed for Form A of compound 5.

TABLE 19

XRPD Peak Positions for Form A of Compound 5
Position (°2θ)

| |
|---|
| 7.5 |
| 9.5 |
| 11.3 |
| 13.0 |
| 14.3 |
| 14.7 |
| 15.0 |
| 15.7 |
| 17.3 |
| 20.3 |
| 20.9 |
| 21.6 |
| 22.6 |
| 23.2 |
| 23.7 |
| 24.8 |
| 26.0 |
| 28.8 |
| 30.5 |
| 33.8 |

[1]In this and all subsequent tables, the position 2θ is within ±0.2.

FIG. 53 depicts an XRPD pattern of Form A of compound 5.

Figure 54:
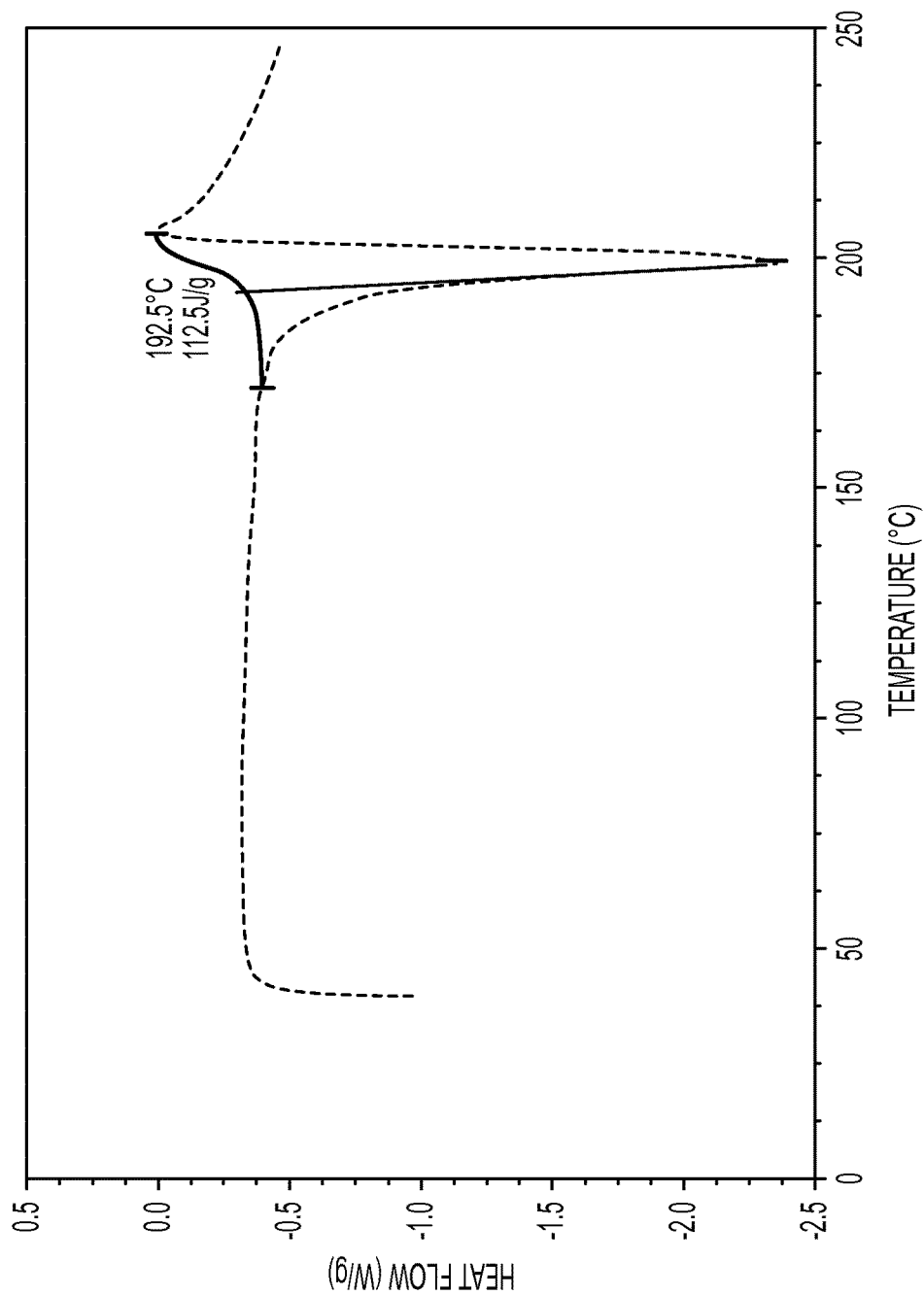
FIG. 54 depicts a DSC thermogram of Form A of compound 5.

FIG. 54 depicts a DSC thermogram of Form A of compound 5.

Figure 55:
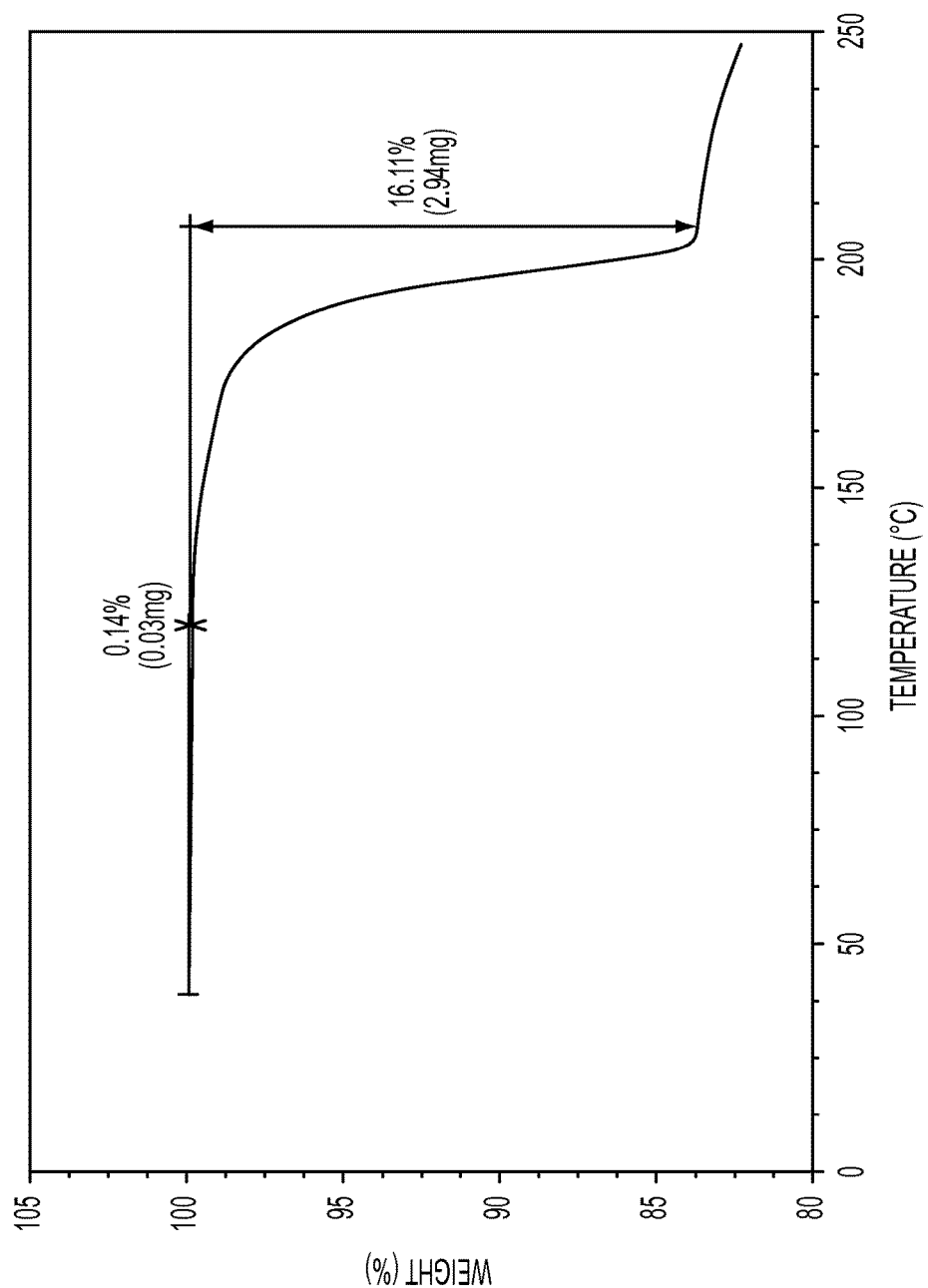
FIG. 55 depicts a TGA trace of Form A of compound 5.

FIG. 55 depicts a TGA trace of Form A of compound 5.

Figure 56:
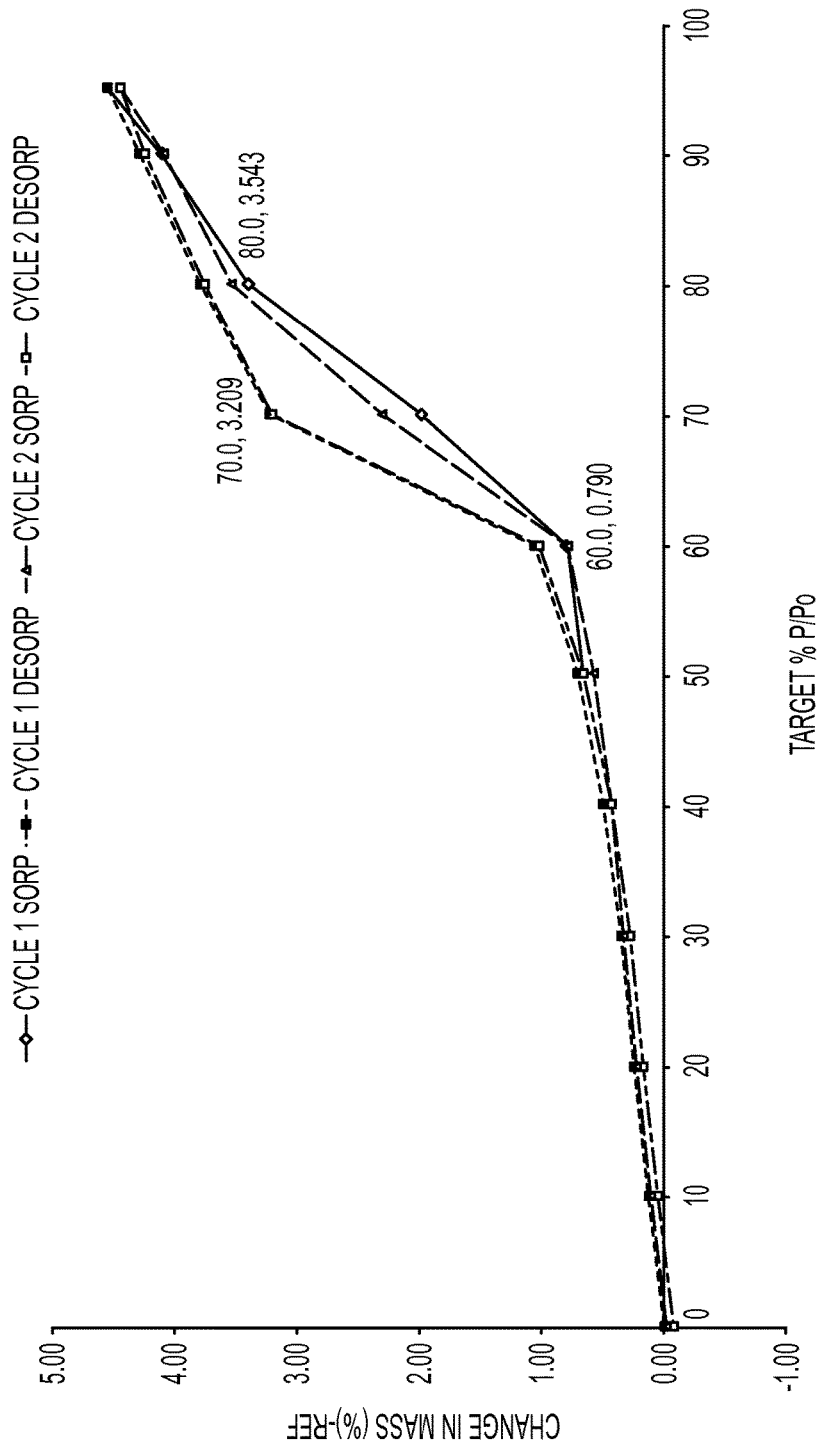
FIG. 56 depicts a DVS plot of Form A of compound 5.

FIG. 56 depicts a DVS plot of Form A of compound 5.

Elemental analysis—Calculated: C, 48.99; H, 4.11; Br, 14.81; N, 15.58; Found: C, 48.37; H, 4.19; Br, 15.34; N, 15.28.

Karl Fischer titration: 0.35%

Form B of Compound 5

Form B of compound 5 was prepared as follows.

Procedure: Compound 1 was dissolved in tetrahydrofuran. Equal molar equivalent of 8.84 M HBr in water was charged. The sample was shaken at ambient temperature at 200 RPM for 1 hour. The solvent was removed under nitrogen purge. The resulting solids were slurried in methyl ethyl ketone or toluene with magnetic stirring at ambient temperature overnight, then filtered and dried in a vacuum oven at 30° C. overnight.

Characterization of the resulting material demonstrated a crystalline Form B of compound 5.

Table 20, supra, is reproduced below and sets forth the X-ray diffraction peaks observed for Form B of compound 5.

TABLE 20

XRPD Peak Positions for Form B of Compound 5
Position (°2θ)

| |
|---|
| 8.3 |
| 11.8 |
| 12.3 |
| 14.2 |
| 16.2 |
| 17.9 |
| 18.7 |
| 18.9 |
| 20.3 |
| 20.5 |
| 20.8 |

TABLE 20-continued

XRPD Peak Positions for Form B of Compound 5
Position (°2θ)

| |
|---|
| 21.1 |
| 23.8 |
| 24.5 |
| 25.5 |
| 25.7 |
| 26.3 |
| 29.2 |
| 30.7 |
| 31.9 |

[1]In this and all subsequent tables, the position 2θ is within ±0.2.

FIG. 57 depicts an XRPD pattern of Form B of compound 5.

Figure 58:
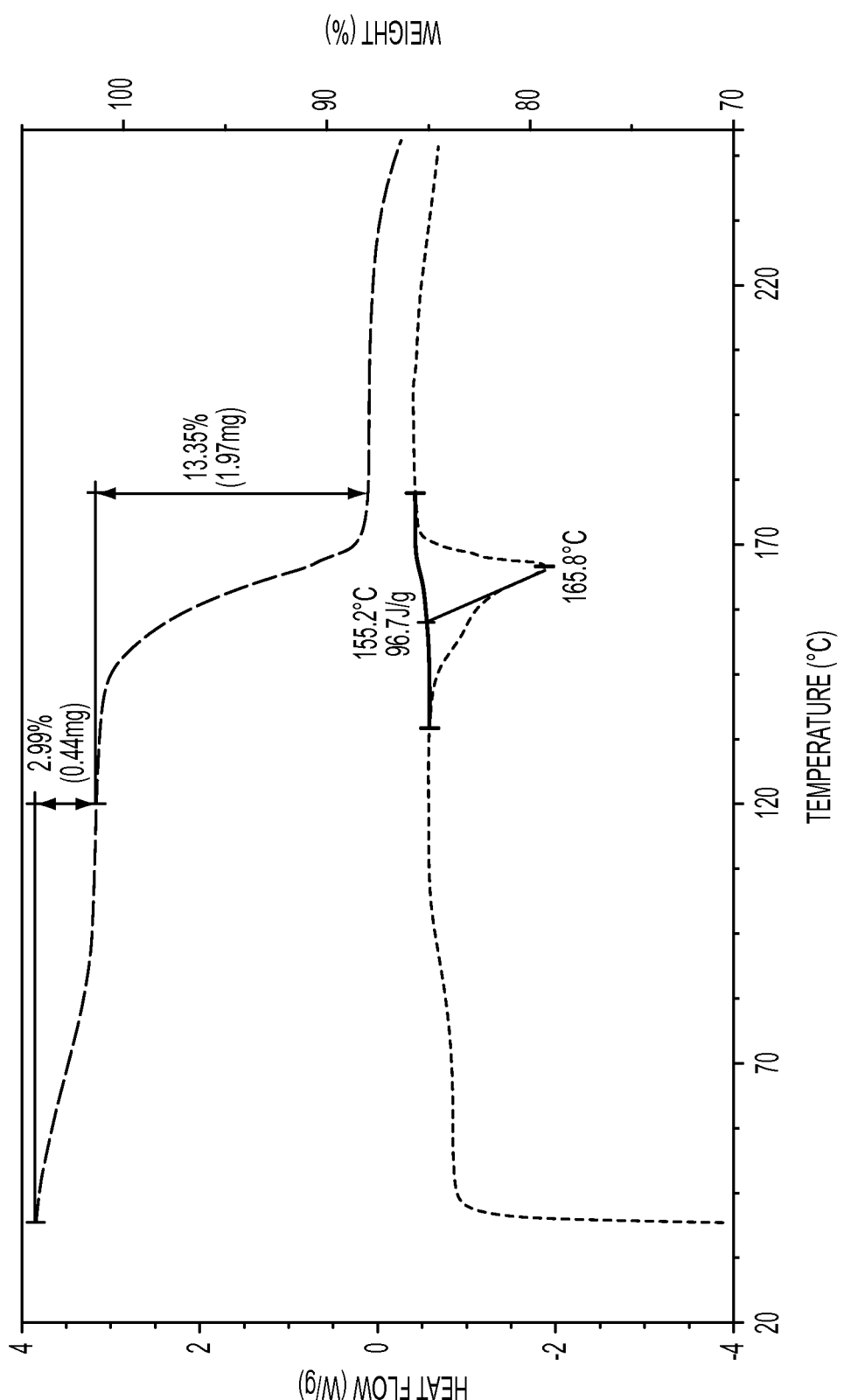
FIG. 58 depicts a DSC thermogram and TGA trace of Form B of compound 5.

FIG. 58 depicts a DSC thermogram and TGA trace of Form B of compound 5.

Form C of Compound 5

Form C of compound 5 was prepared as follows.

Procedure: Compound 1 (0.5 g, 1.091 mmol) was dissolved in THF (5 ml, 61.0 mmol) at room temperature. HBr (0.148 ml, 1.309 mmol) was added to solution to form a slightly hazy solution, which was stirred at room temperature for 15 min. Next was added acetonitrile (5 mL). Nitrogen was streamed over the hazy solution until solvent was fully evaporated. Pale yellow solid formed. The product was charged with acetonitrile (5 mL), slurried overnight, filtered, and dried.

Characterization of the resulting material demonstrated a crystalline Form C of compound 5.

Table 21, supra, is reproduced below and sets forth the X-ray diffraction peaks observed for Form C of compound 5.

TABLE 21

XRPD Peak Positions for Form C of Compound 5
Position (°2θ)

| |
|---|
| 7.46x |
| 8.4 |
| 10.5 |
| 15.4 |
| 15.8 |
| 17.4 |
| 20.1 |
| 20.8 |
| 22.1 |
| 22.3 |
| 22.6 |
| 23.2 |
| 24.2 |
| 24.5 |
| 25.9 |
| 26.6 |
| 29.0 |
| 31.8 |
| 33.8 |
| 37.7 |

[1]In this and all subsequent tables, the position 2θ is within ±0.2.

FIG. 59 depicts an XRPD pattern of Form C of compound 5.

Figure 60:
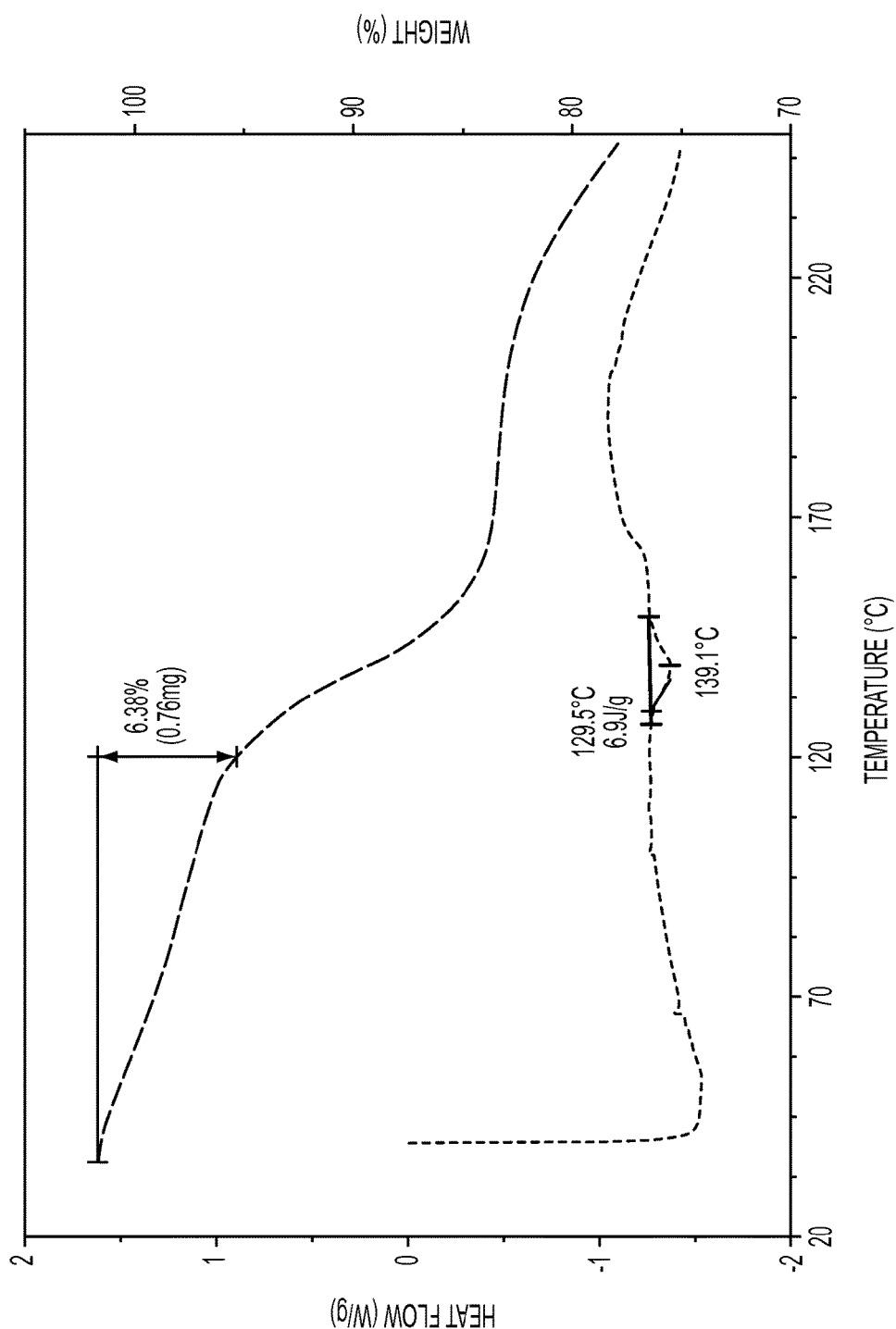
FIG. 60 depicts a DSC thermogram and TGA trace of Form C of compound 5.

FIG. 60 depicts a DSC thermogram and TGA trace of Form C of compound 5.

Form D of Compound 5

Form D of compound 5 was prepared as follows.

Procedure: Compound 1 (3.0 g, 6.54 mmol) was dissolved in 60 mL tetrahydrofuran. HBr (48% diluted to 1M with water) was charged in a 1:1 ratio. The solution was stirred for one hour after which the solvent was evaporated under reduced pressure. Acetonitrile (10x) was charged and the slurry was vigorously stirred overnight. Solids were filtered and dried in a vacuum oven at 40° C. with a nitrogen bleed.

Characterization of the resulting material demonstrated a crystalline Form D of compound 5.

Table 22, supra, is reproduced below and sets forth the X-ray diffraction peaks observed for Form D of compound 5.

TABLE 22

XRPD Peak Positions for Form D of Compound 5
Position (°2θ)

| |
|---|
| 7.2 |
| 9.4 |
| 10.8 |
| 11.8 |
| 15.1 |
| 16.9 |
| 18.9 |
| 20.4 |
| 21.6 |
| 22.3 |
| 23.7 |
| 24.3 |
| 24.7 |
| 25.5 |
| 26.1 |
| 29.0 |
| 30.3 |
| 30.6 |
| 32.1 |
| 35.2 |

[1]In this and all subsequent tables, the position 2θ is within ±0.2.

FIG. 61 depicts an XRPD pattern of Form D of compound 5.

Figure 62:
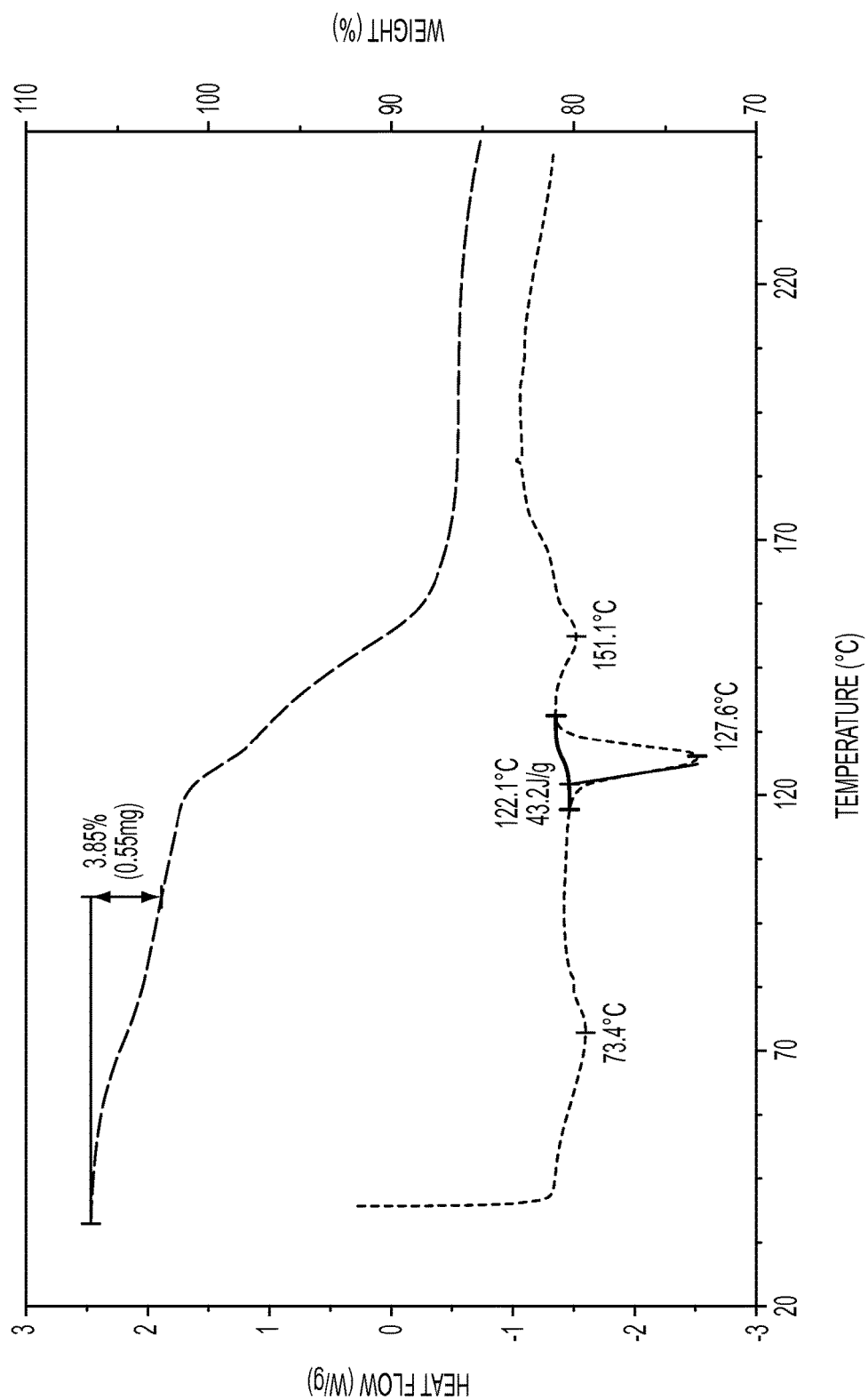
FIG. 62 depicts a DSC thermogram and TGA trace of Form D of compound 5.

FIG. 62 depicts a DSC thermogram and TGA trace of Form D of compound 5.

Form E of Compound 5

Form E of compound 5 was prepared as follows.

Procedure: Compound 1 (3 g, 6.54 mmol) was dissolved in ~60 ml tetrahydrofuran. HBr (48% diluted to ~1M with water) was charged in a 1:1 ratio. The solution was stirred for one hour, after which the solvent was evaporated under reduced pressure. Acetonitrile (10x) was charged and the slurry was vigorously stirred overnight. The solvent was removed under reduced pressure. Tetrahydrofuran (20x) was charged. The slurry was vigorously stirred, then the tetrahydrofuran was removed under reduced pressure to facilitate the removal of water. Acetonitrile (10x) was charged and the slurry was again vigorously stirred overnight. Solids were filtered and dried in a vacuum oven at 40° C., with nitrogen bleed.

Characterization of the resulting material demonstrated a crystalline Form E of compound 5.

Table 23, supra, is reproduced below and sets forth the X-ray diffraction peaks observed for Form E of compound 5.

TABLE 23

XRPD Peak Positions for Form E of Compound 5
Position (°2θ)

| |
|---|
| 7.8 |
| 8.7 |
| 10.0 |
| 11.6 |
| 15.0 |

TABLE 23-continued

XRPD Peak Positions for Form E of Compound 5
Position (°2θ)

| |
|---|
| 16.4 |
| 17.5 |
| 18.7 |
| 21.5 |
| 22.8 |
| 23.8 |
| 24.3 |
| 25.2 |
| 25.8 |
| 28.8 |
| 29.1 |
| 30.3 |
| 31.7 |
| 33.7 |
| 36.8 |

[1]In this and all subsequent tables, the position 2θ is within ±0.2.

FIG. 63 depicts an XRPD pattern of Form E of compound 5.

Figure 64:
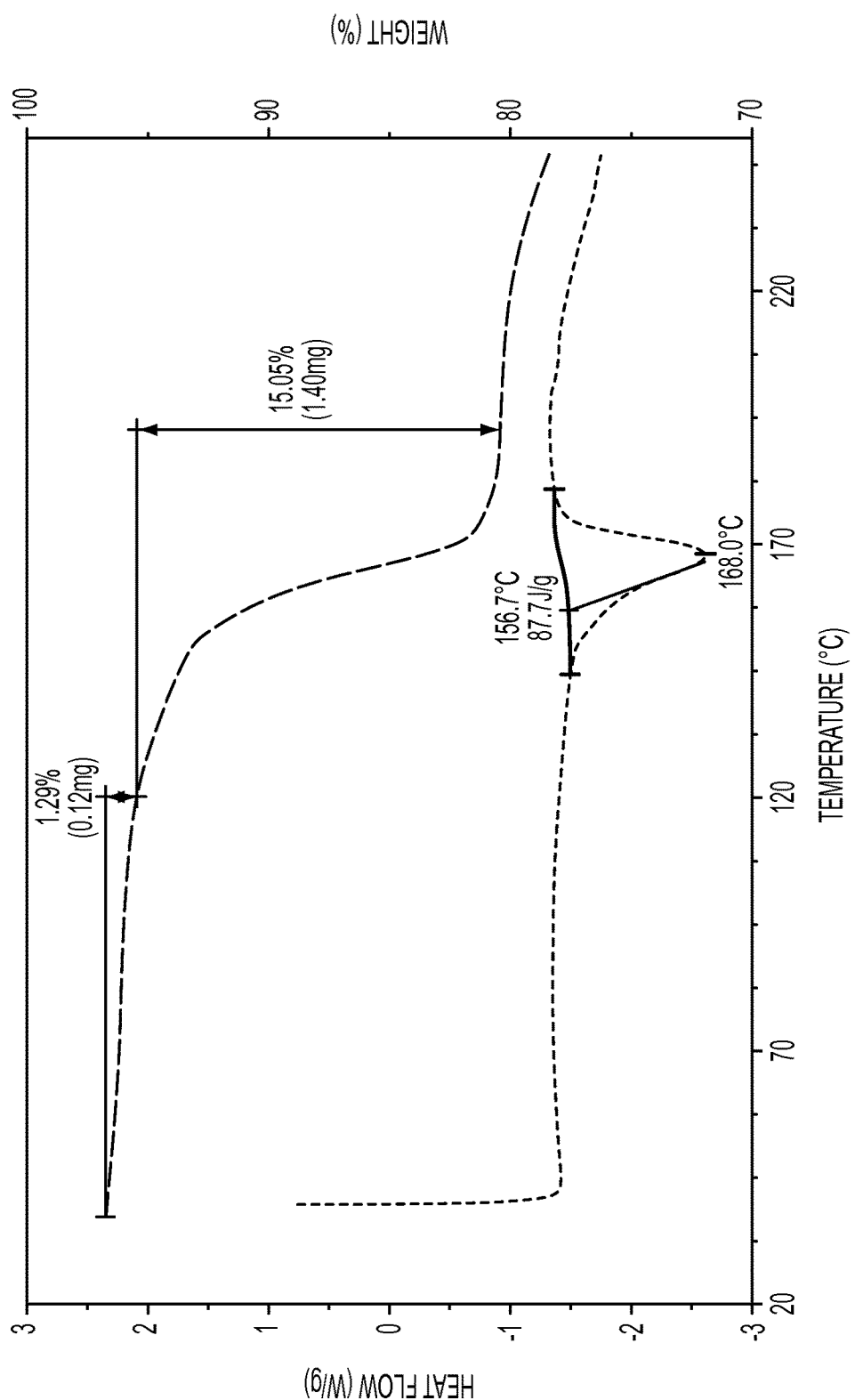
FIG. 64 depicts a DSC thermogram of Form E of compound 5.

FIG. 64 depicts a DSC thermogram of Form E of compound 5.

Figure 65:
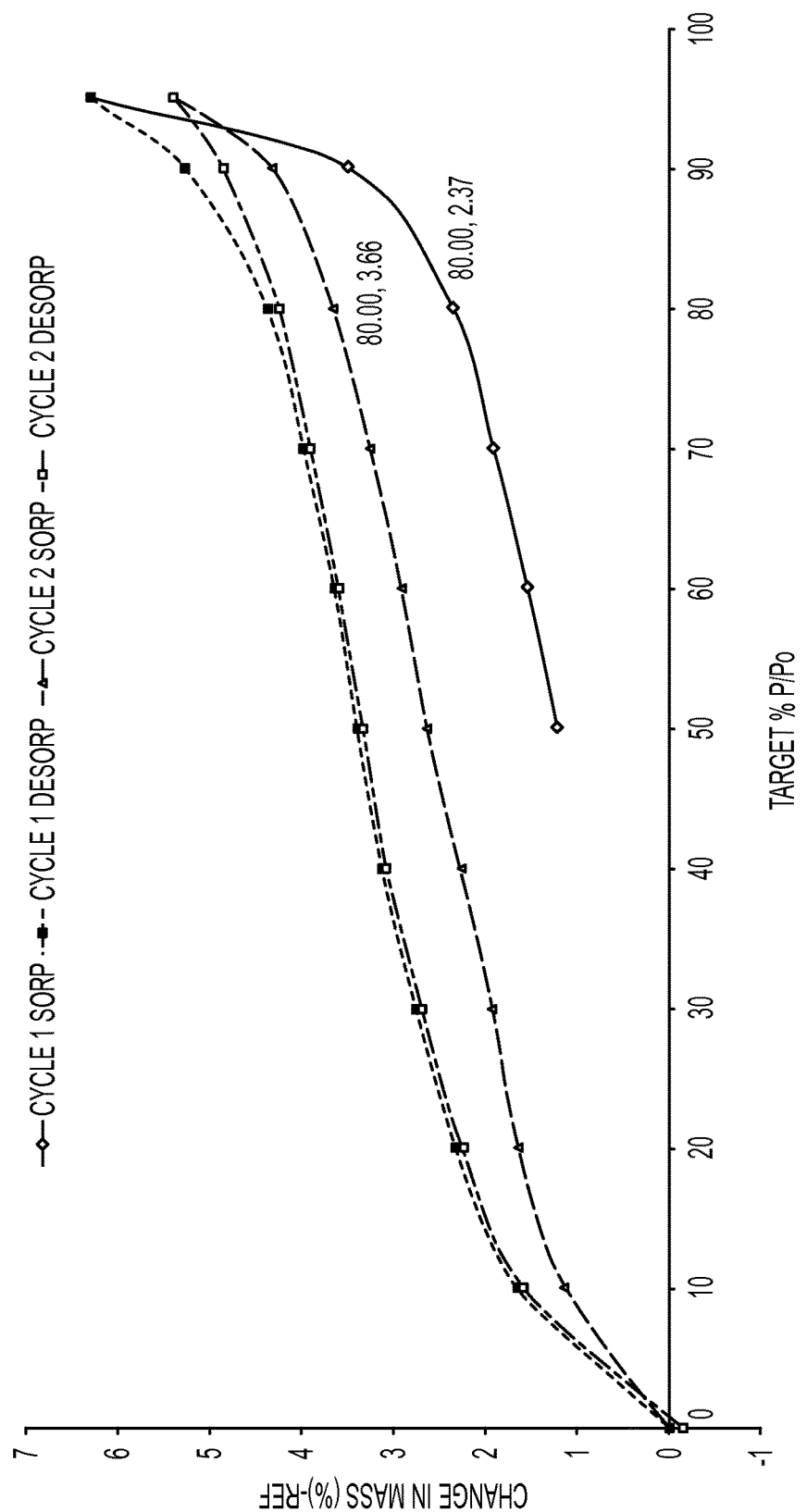
FIG. 65 depicts a DVS plot of Form E of compound 5.

FIG. 65 depicts a DVS plot of Form E of compound 5.

Example 6

Preparation of Forms A-C of Compound 6

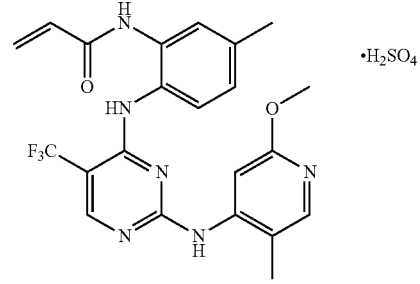

6

Form A of Compound 6

Form A of compound 6 was prepared as follows.

Procedure A: Compound 1 (4.1 g, 8.94 mmol) was dissolved in 15x tetrahydrofuran. One molar equivalent of 2 M sulfuric acid in acetonitrile was charged. Solids precipitated as the acid was charged. The slurry was stirred for 2 hours at 20° C., then the solvent was removed under reduced pressure. The resulting solids were slurried in ethyl acetate at 20° C. for about 16 hours, filtered, and dried.

Procedure B: Compound 1 was dissolved in tetrahydrofuran. Equal molar equivalent of 1.18 M $H_2SO_4$ in acetonitrile was charged. The sample was shaken at ambient temperature at 200 RPM for 1 hour. The solvent was removed under nitrogen purge. The resulting solids were slurried in ethyl acetate with a stirring bar at ambient temperature overnight, then filtered and dried in vacuum oven at 30° C. overnight.

Characterization of the resulting material demonstrated a crystalline, anhydrous Form A of compound 6.

Table 24, supra, is reproduced below and sets forth the X-ray diffraction peaks observed for Form A of compound 6.

TABLE 24

XRPD Peak Positions for Form A of Compound 6
Position (° 2θ)

| |
|---|
| 6.2 |
| 7.1 |
| 9.9 |
| 14.2 |
| 14.7 |
| 19.4 |
| 19.5 |
| 20.1 |
| 20.2 |
| 20.7 |
| 21.4 |
| 23.4 |
| 23.9 |
| 24.3 |
| 24.8 |
| 25.3 |
| 26.0 |
| 26.9 |
| 28.7 |
| 29.8 |

[1]In this and all subsequent tables, the position 2θ is within ±0.2.

FIG. 66 depicts an XRPD pattern of Form A of compound 6.

Figure 67:
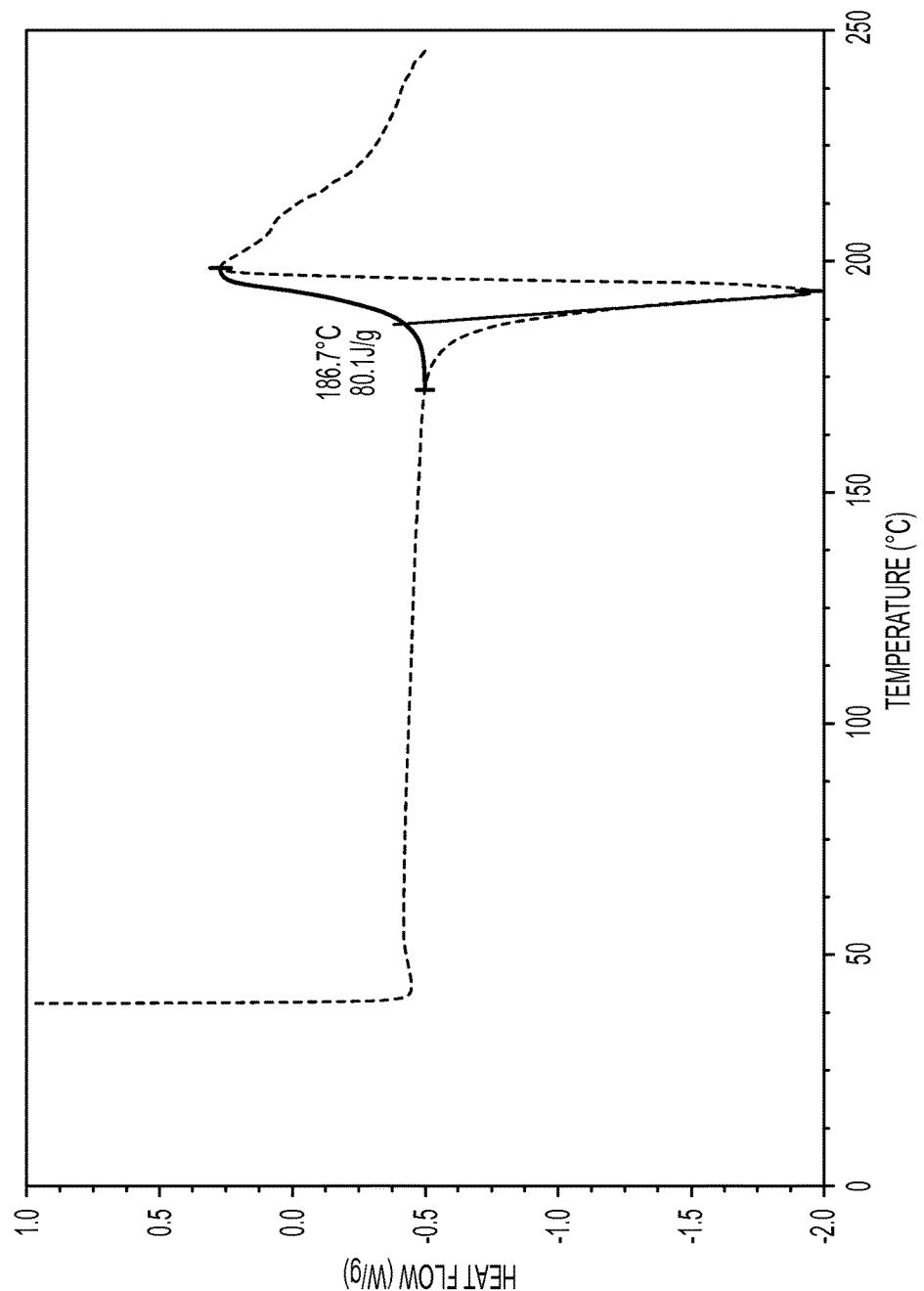
FIG. 67 depicts a DSC thermogram of Form A of compound 6.

FIG. 67 depicts a DSC thermogram of Form A of compound 6.

Figure 68:
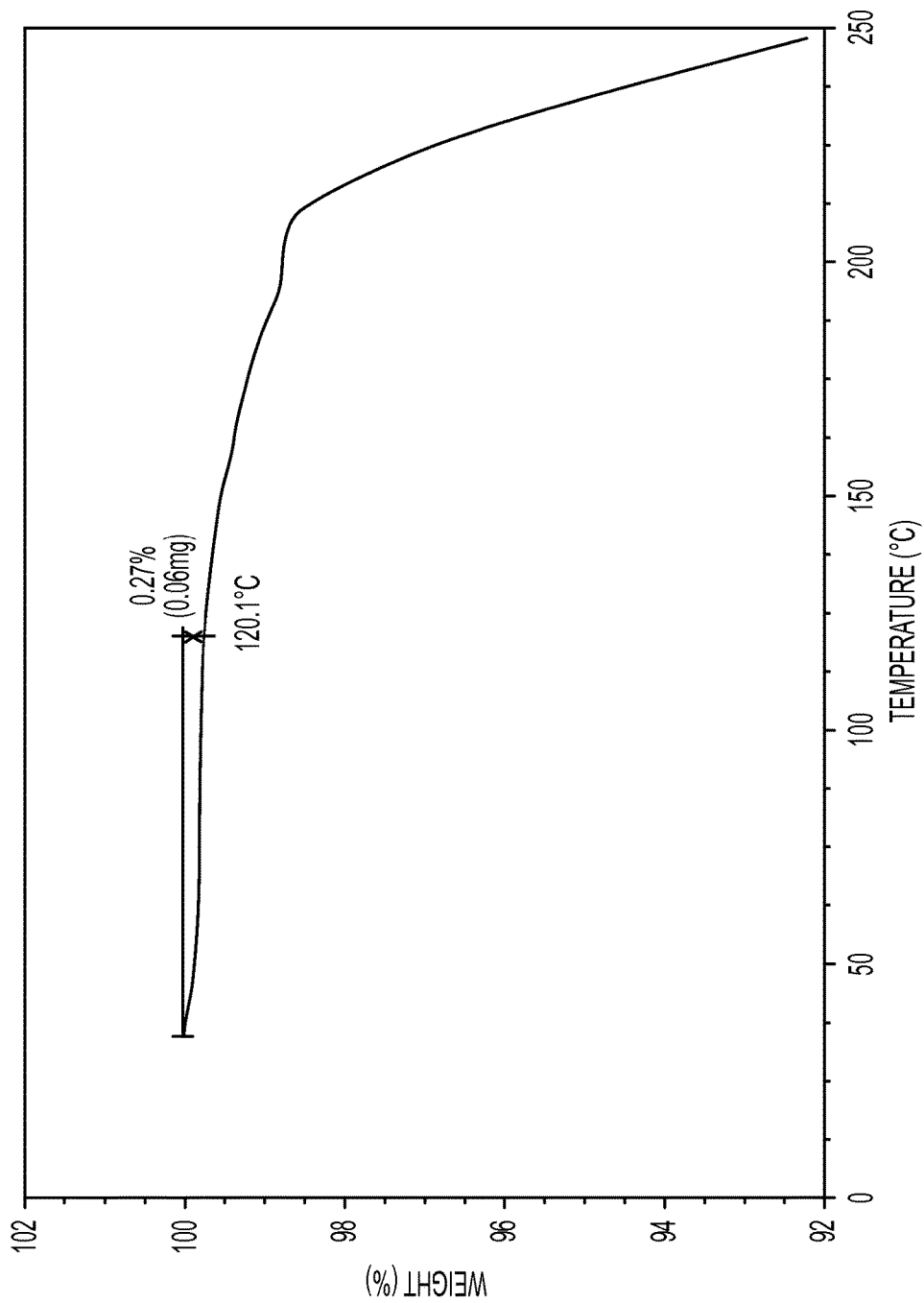
FIG. 68 depicts a TGA trace of Form A of compound 6.

FIG. 68 depicts a TGA trace of Form A of compound 6.

Figure 69:
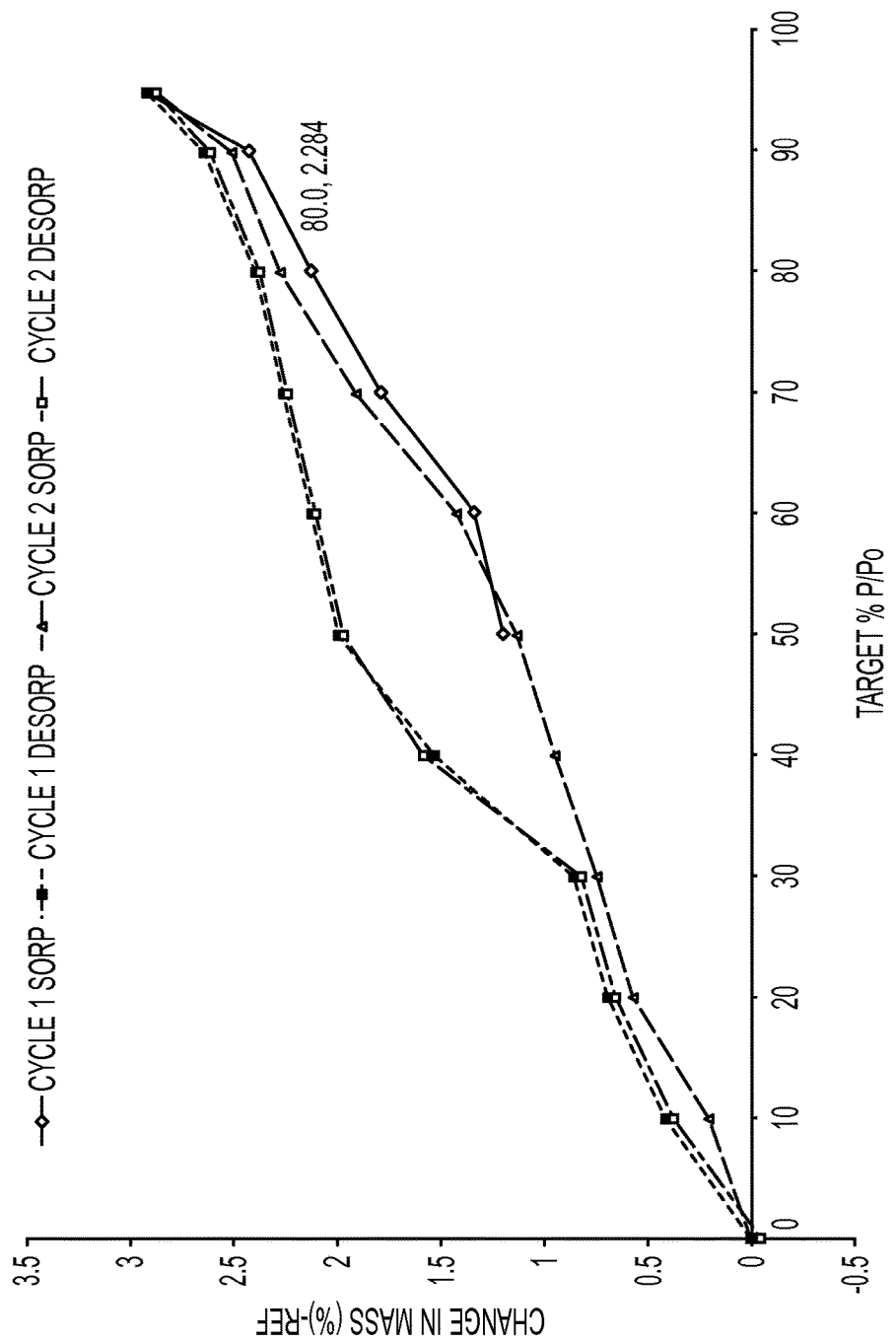
FIG. 69 depicts a DVS plot of Form A of compound 6.

FIG. 69 depicts a DVS plot of Form A of compound 6.

Elemental analysis—Calculated: C, 47.48; H, 4.17; N, 15.10; S, 5.76; Found: C, 46.89; H, 4.31; N, 14.73; S, 6.05.

Karl Fischer titration: 0.69%

Form B of Compound 6

Form B of compound 6 was prepared as follows.

Procedure A: Compound 1 (3 g, 6.54 mmol) was dissolved in ~60 ml tetrahydrofuran. H$_2$SO$_4$ (95% diluted to ~1M with water) was charged. The solution was stirred for more than one hour, after which the solvent was removed under reduced pressure. Ethyl acetate (10×) was charged. The slurry was vigorously stirred overnight, after which the solids were filtered and dried in a vacuum oven at 40° C. with nitrogen bleed.

Procedure B: Compound 1 was dissolved in tetrahydrofuran. Equal molar equivalent of 1.18 M H$_2$SO$_4$ in acetonitrile was charged. The sample was shaken at ambient temperature at 200 RPM for 1 hour. The solvent was removed under nitrogen purge. The resulting solids were slurried in acetone with a stirring bar at ambient temperature overnight, then filtered and dried in vacuum oven at 30° C. overnight.

Characterization of the resulting material demonstrated a crystalline Form B of compound 6.

Table 25, supra, is reproduced below and sets forth the X-ray diffraction peaks observed for Form B of compound 6.

TABLE 25

XRPD Peak Positions for Form B of Compound 6
Position (° 2θ)

| |
|---|
| 7.1 |
| 7.6 |
| 10.1 |
| 11.4 |
| 11.6 |
| 12.4 |
| 13.7 |
| 15.2 |
| 17.3 |

TABLE 25-continued

XRPD Peak Positions for Form B of Compound 6
Position (° 2θ)

| |
|---|
| 17.8 |
| 18.7 |
| 18.7 |
| 20.3 |
| 21.7 |
| 22.9 |
| 24.1 |
| 25.4 |
| 26.0 |
| 29.7 |
| 34.7 |

[1]In this and all subsequent tables, the position 2θ is within ±0.2.

FIG. 70 depicts an XRPD pattern of Form B of compound 6.

Figure 71:
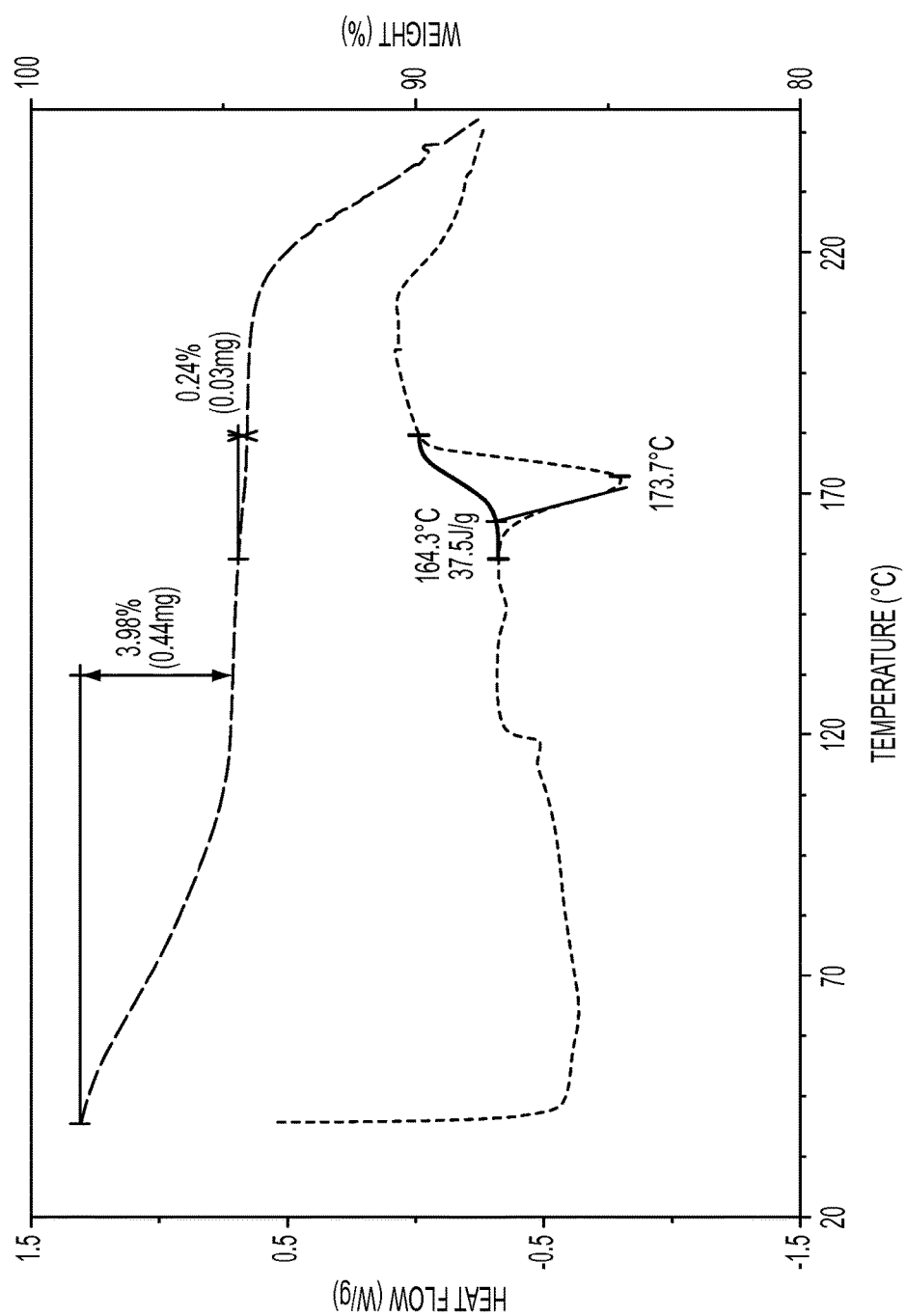
FIG. 71 depicts a DSC thermogram and TGA trace of Form B of compound 6.

FIG. 71 depicts a DSC thermogram and TGA trace of Form B of compound 6.

Form C of Compound 6

Form C of compound 6 was prepared as follows.

Procedure: Compound 1 (3 g, 6.54 mmol) was dissolved in tetrahydrofuran. Equimolar equivalent of 1.18 M H$_2$SO$_4$ in acetonitrile was charged. The sample was shaken at ambient temperature at 200 RPM for 1 hour. The solvent was removed under nitrogen purge. The resulting solids were slurried in methanol with a stirring bar at ambient temperature overnight, after which the solids were filtered and dried in a vacuum oven at 30° C. overnight.

Characterization of the resulting material demonstrated a crystalline Form C of compound 6.

Table 26, supra, is reproduced below and sets forth the X-ray diffraction peaks observed for Form C of compound 6.

TABLE 26

XRPD Peak Positions for Form C of Compound 6
Position (° 2θ)

| |
|---|
| 7.1 |
| 7.6 |
| 8.3 |
| 9.3 |
| 12.6 |
| 13.5 |
| 14.2 |
| 17.4 |
| 18.1 |
| 19.6 |
| 20.2 |
| 20.5 |
| 20.9 |
| 21.2 |
| 23.1 |
| 24.4 |
| 25.1 |
| 26.2 |
| 27.9 |
| 29.9 |

[1]In this and all subsequent tables, the position 2θ is within ±0.2.

FIG. 72 depicts an XRPD pattern of Form C of compound 6.

Figure 73:
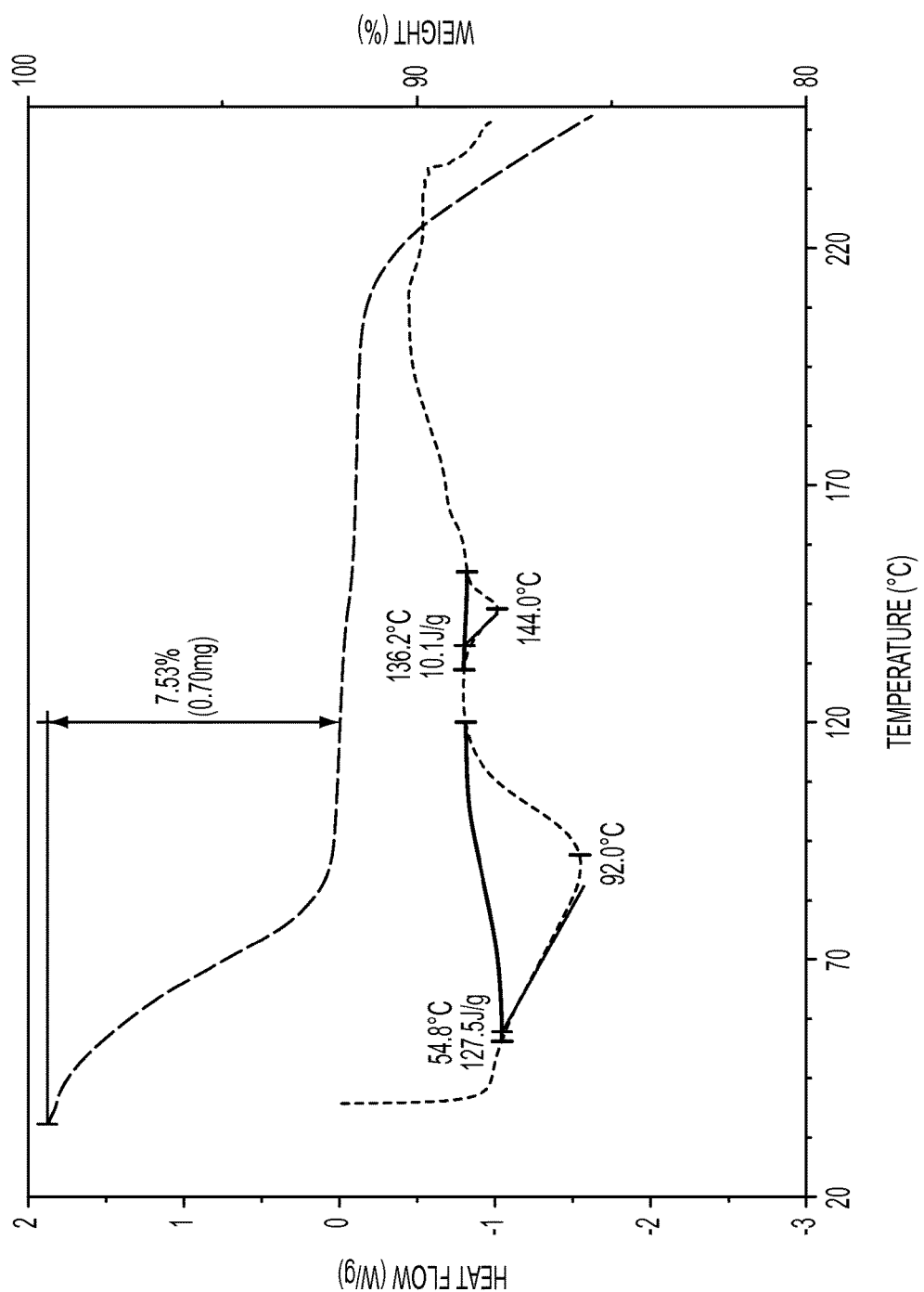
FIG. 73 depicts a DSC thermogram and TGA trace of Form C of compound 6.

FIG. 73 depicts a DSC thermogram and TGA trace of Form C of compound 6.

Example 7

Preparation of Form A of Compound 7

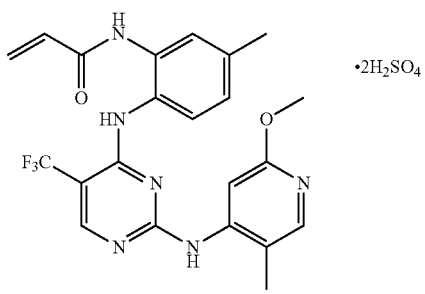

Form A of Compound 7

Form A of compound 7 was prepared as follows.

Procedure: 0.22 g of 98% sulphuric acid was diluted in 10 mL acetonitrile. 0.5 g of compound 1 was charged to the sulphuric acid solution and agitated at 22° C. for 2 hours. The solids were filtered, washed three times, each with 2 mL acetonitrile, and dried under reduced pressure at 40° C. to yield 0.61 g of the bis-sulfate salt.

Characterization of the resulting material demonstrated a crystalline, anhydrous Form A of compound 7.

Table 27, supra, is reproduced below and sets forth the X-ray diffraction peaks observed for Form A of compound 7.

TABLE 27

XRPD Peak Positions for Form A of Compound 7
Position (° 2θ)

| |
|---|
| 7.3 |
| 8.7 |
| 9.6 |
| 11.4 |
| 11.5 |
| 14.1 |
| 17.9 |
| 18.2 |
| 19.0 |
| 19.2 |
| 20.5 |
| 20.7 |
| 21.0 |
| 22.2 |
| 23.5 |
| 24.3 |
| 24.3 |
| 27.5 |
| 28.6 |
| 31.1 |

[1]In this and all subsequent tables, the position 2θ is within ±0.2.

FIG. 74 depicts an XRPD pattern of Form A of compound 7.

Figure 75:
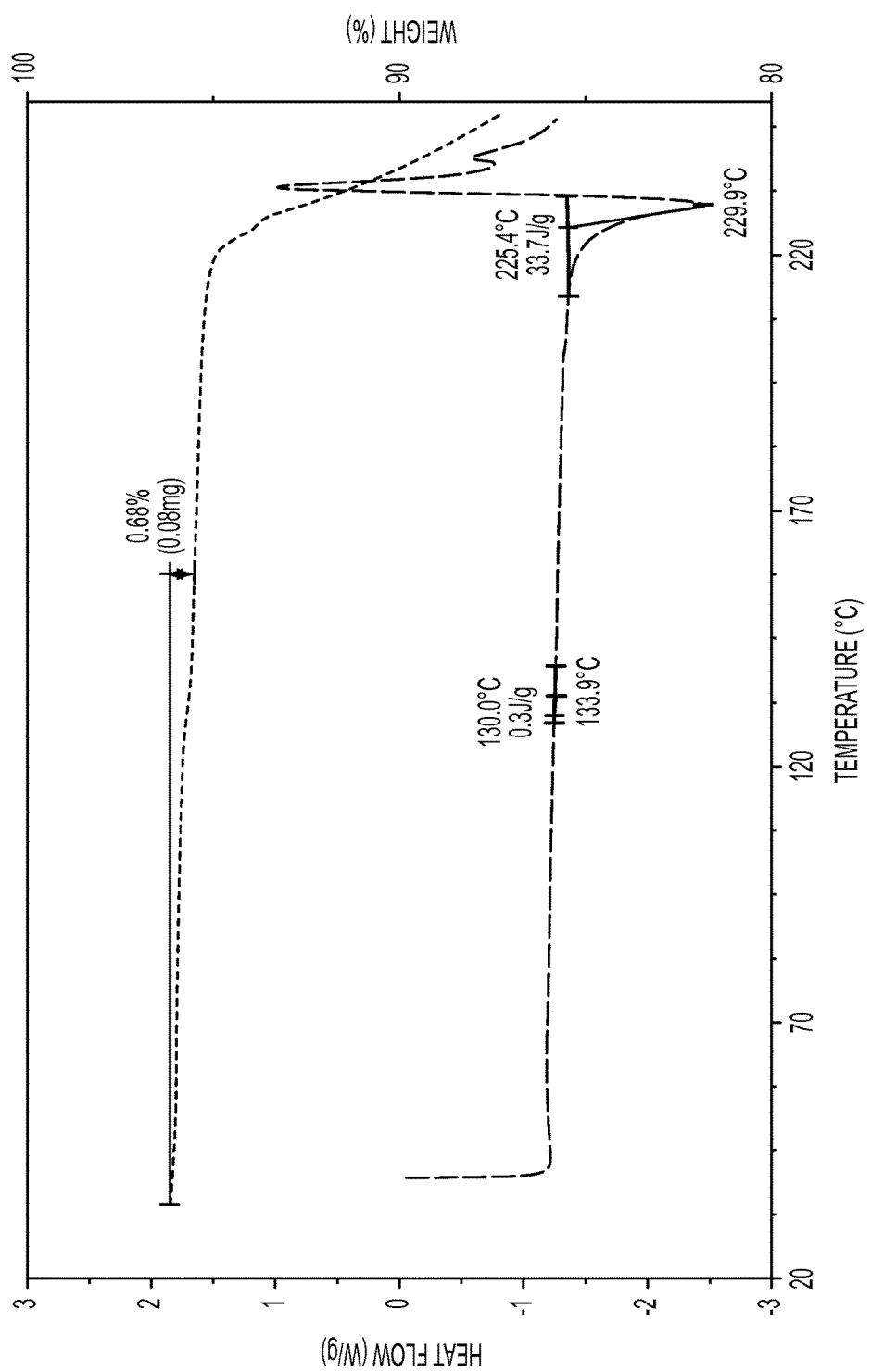
FIG. 75 depicts a DSC thermogram and TGA trace of Form A of compound 7.

FIG. 75 depicts a DSC thermogram and TGA trace of Form A of compound 7.

Figure 76:
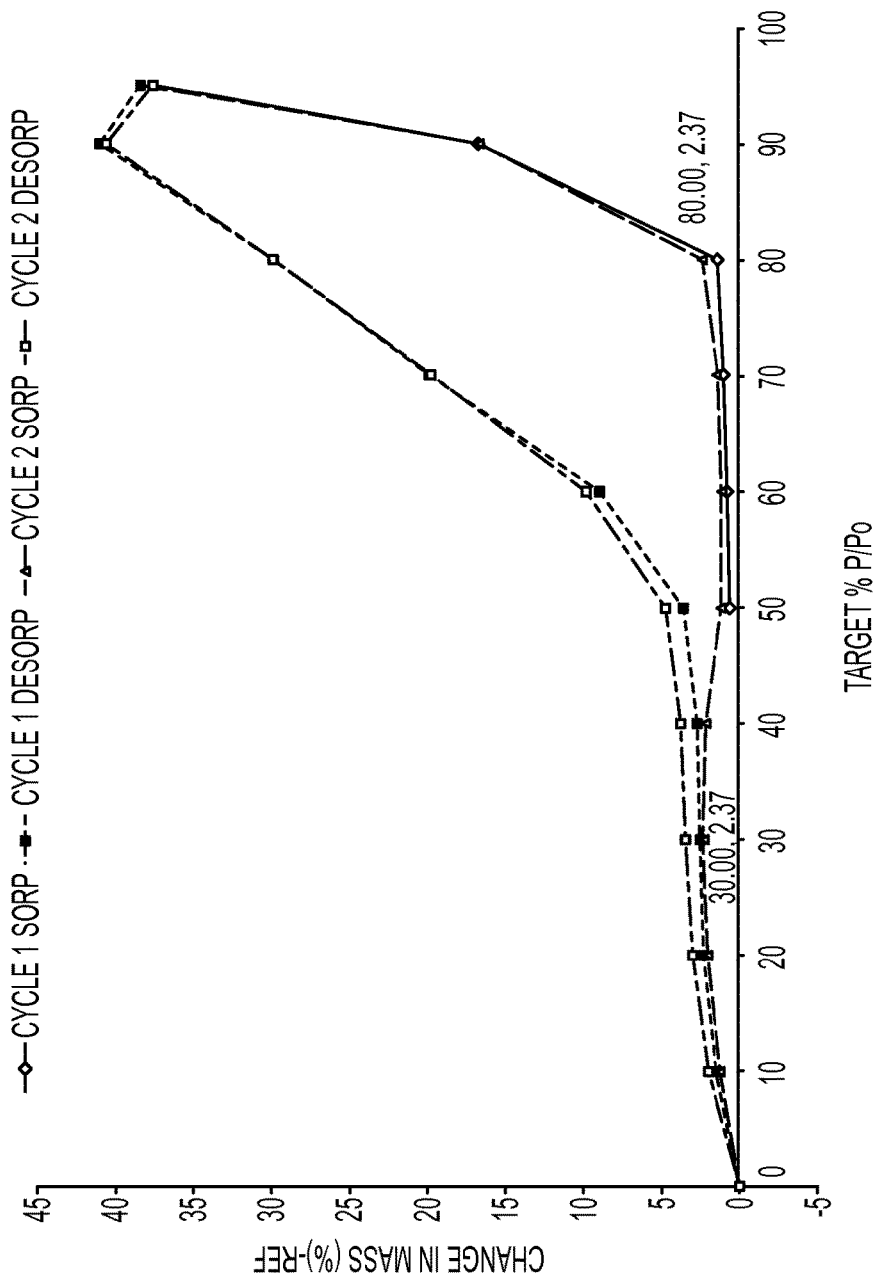
FIG. 76 depicts a DVS plot of Form A of compound 7.

FIG. 76 depicts a DVS plot of Form A of compound 7.

Elemental analysis—Calculated: C, 40.37; H, 3.85; N, 12.84; S, 9.80; Found: C, 40.27; H, 3.92; N, 12.69; S, 9.63.

Example 8

Preparation of Forms A-D of Compound 8

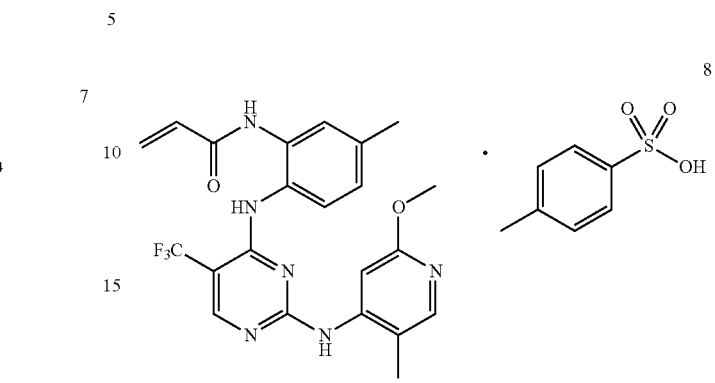

Form A of Compound 8

Form A of compound 8 was prepared as follows.

Procedure: Compound 1 was dissolved in tetrahydrofuran. An equal molar equivalent of 1.3 M p-toluenesulfonic acid monohydrate in methanol was charged. The sample was shaken at ambient temperature at 200 RPM for 1 hour. The solvent was removed under nitrogen purge. The resulting solids were slurried in acetonitrile with a stir bar at ambient temperature overnight, then filtered and dried in a vacuum oven at 30° C. overnight.

Characterization of the resulting material demonstrated a crystalline Form A of compound 8.

Table 28, supra, is reproduced below and sets forth the X-ray diffraction peaks observed for Form A of compound 8.

TABLE 28

XRPD Peak Positions for Form A of Compound 8
Position (° 2θ)

| |
|---|
| 8.6 |
| 9.0 |
| 12.4 |
| 12.8 |
| 13.4 |
| 16.1 |
| 16.4 |
| 16.6 |
| 17.0 |
| 17.9 |
| 19.1 |
| 20.0 |
| 20.5 |
| 22.9 |
| 23.5 |
| 23.7 |
| 23.8 |
| 24.8 |
| 27.8 |
| 30.7 |

[1]In this and all subsequent tables, the position 2θ is within ±0.2.

FIG. 77 depicts an XRPD pattern of Form A of compound 8.

Figure 78:
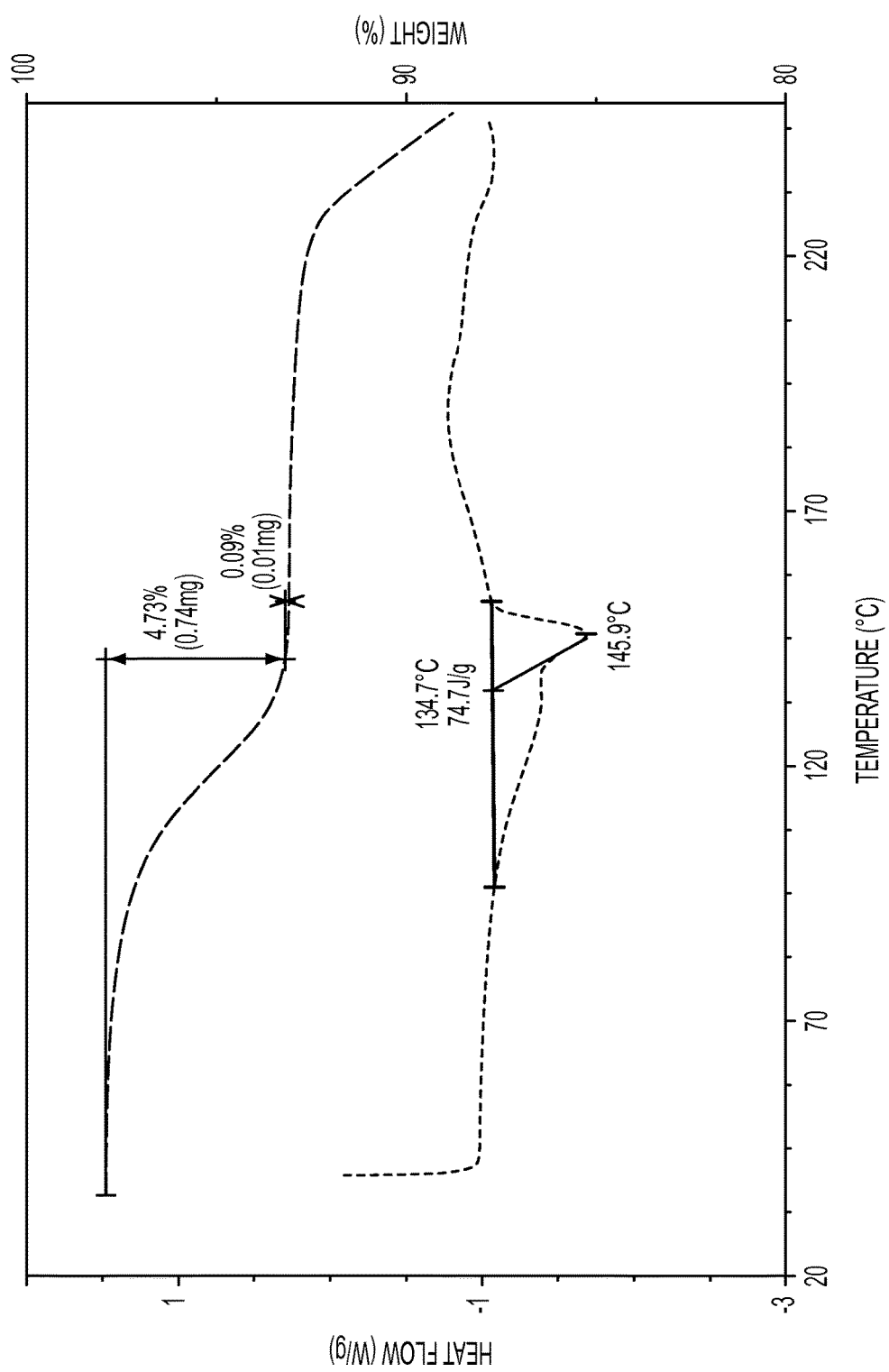
FIG. 78 depicts a DSC thermogram and TGA trace of Form A of compound 8.

FIG. 78 depicts a DSC thermogram and TGA trace of Form A of compound 8.

Form B of Compound 8

Form B of compound 8 was prepared as follows.

Procedure: Compound 1 was dissolved in tetrahydrofuran. An equal molar equivalent of 1.3 M p-toluenesulfonic acid monohydrate in methanol was charged. The sample was shaken at ambient temperature at 200 RPM for 1 hour. The solvent was removed under nitrogen purge. The resulting solids were slurried in acetone with a stir bar at ambient temperature overnight, then filtered and dried in a vacuum oven at 30° C. overnight.

Characterization of the resulting material demonstrated a crystalline Form B of compound 8.

Table 29, supra, is reproduced below and sets forth the X-ray diffraction peaks observed for Form B of compound 8.

TABLE 29

| XRPD Peak Positions for Form B of Compound 8 Position (° 2θ) |
| --- |
| 8.6 |
| 8.9 |
| 12.2 |
| 16.2 |
| 16.5 |
| 16.9 |
| 17.2 |
| 17.9 |
| 19.0 |
| 19.1 |
| 20.1 |
| 23.1 |
| 23.4 |
| 23.6 |
| 24.6 |
| 24.7 |
| 25.1 |
| 26.3 |
| 27.6 |
| 28.2 |

[1]In this and all subsequent tables, the position 2θ is within ±0.2.

FIG. 79 depicts an XRPD pattern of Form B of compound 8.

Figure 80:
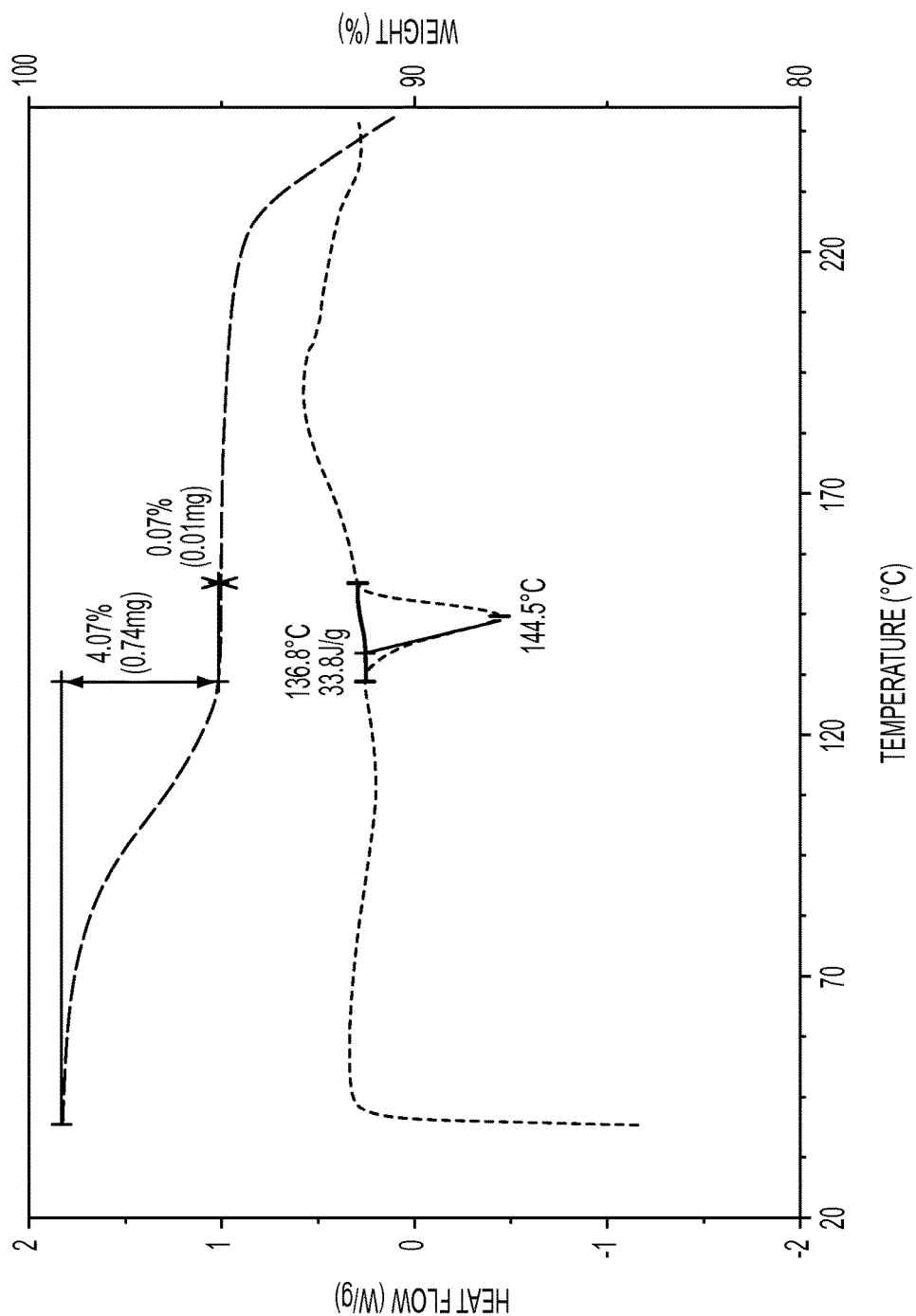
FIG. 80 depicts a DSC thermogram and TGA trace of Form B of compound 8.

FIG. 80 depicts a DSC thermogram and TGA trace of Form B of compound 8.

Form C of Compound 8

Form C of compound 8 was prepared as follows.

Procedure: Compound 1 was dissolved in tetrahydrofuran. An equal molar equivalent of 1.3 M p-toluenesulfonic acid monohydrate in methanol was charged. The sample was shaken at ambient temperature at 200 RPM for 1 hour. The solvent was removed under nitrogen purge. The resulting solids were slurried in methylethyl ketone with a stir bar at ambient temperature overnight, then filtered and dried in a vacuum oven at 30° C. overnight.

Characterization of the resulting material demonstrated a crystalline, anhydrous Form C of compound 8.

Table 30, supra, is reproduced below and sets forth the X-ray diffraction peaks observed for Form C of compound 8.

TABLE 30

| XRPD Peak Positions for Form C of Compound 8 | |
| --- | --- |
| Peak No. | Position (° 2θ) |
| 8.8 | 23.1 |
| 9.5 | 23.8 |
| 12.5 | 24.2 |
| 13.3 | 24.6 |
| 14.2 | 25.2 |
| 16.9 | 26.3 |
| 17.4 | 30.3 |
| 17.8 | 31.1 |

TABLE 30-continued

| XRPD Peak Positions for Form C of Compound 8 | |
| --- | --- |
| Peak No. | Position (° 2θ) |
| 18.9 | 31.8 |
| 20.1 | 38.0 |

[1]In this and all subsequent tables, the position 2θ is within ±0.2.

FIG. 81 depicts an XRPD pattern of Form C of compound 8.

Figure 82:
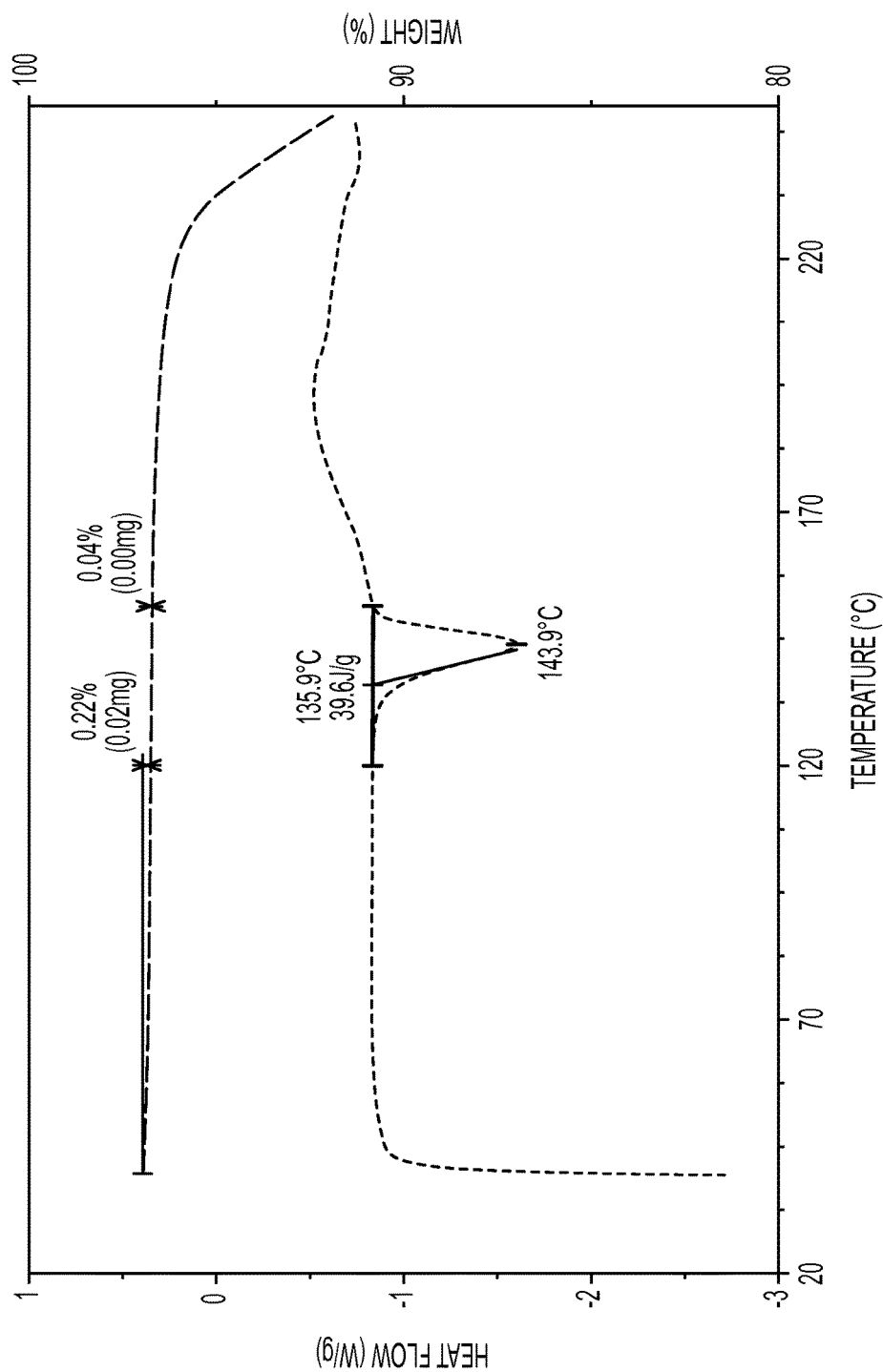
FIG. 82 depicts a DSC thermogram and TGA trace of Form C of compound 8.

FIG. 82 depicts a DSC thermogram and TGA trace of Form C of compound 8.

Figure 83:
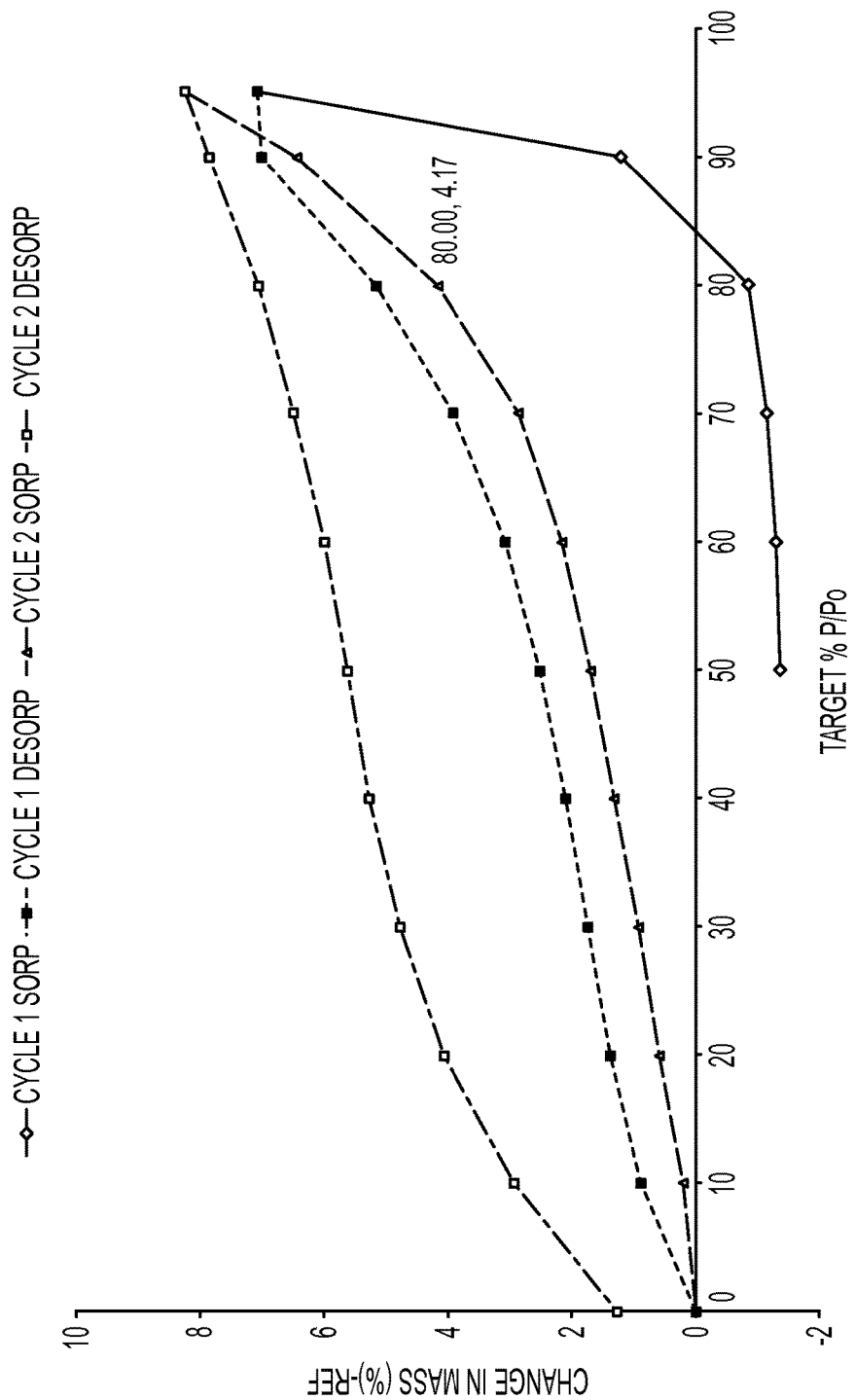
FIG. 83 depicts a DVS plot of Form C of compound 8.

FIG. 83 depicts a DVS plot of Form C of compound 8.

Elemental analysis—Calculated: C, 55.23; H, 4.64; N, 13.33; S, 5.08; Found: C, 54.78; H, 4.58; N, 13.18; S, 5.35.

Form D of Compound 8

Form D of compound 8 was prepared as follows.

Procedure: Compound 1 was dissolved in MeOH/CH$_2$Cl$_2$ (1/1 v/v, pre-mixed). An equal molar equivalent of 0.31 M p-toluenesulfonic acid monohydrate in methanol was charged. The sample was shaken at ambient temperature at 200 RPM for 1 hour. The solvent was removed under nitrogen purge. The resulting solids were slurried in methanol at ambient temperature overnight. No solids were obtained. The solution was dried under nitrogen purge, then was added methyl tert-butyl ether, and the solution was slurried overnight. No solids were obtained. The solution was then dried, hexane was added, and the solution was slurried overnight, then dried in a vacuum oven.

Characterization of the resulting material demonstrated an amorphous Form D of compound 8.

FIG. 84 depicts a DSC thermogram and TGA trace of Form D of compound 8.

Example 9

Preparation of Forms A-B of Compound 9

Form A of Compound 9

Form A of compound 9 was prepared as follows.

Procedure: Compound 1 was dissolved in tetrahydrofuran. An equal molar equivalent of 1.25 M benzenesulfonic acid in methanol was charged. The sample was shaken at ambient temperature at 200 RPM for 1 hour. The solvent was removed under nitrogen purge. The resulting solids were slurried in methyl ethyl ketone (or acetone) with a stir bar at ambient temperature overnight, then filtered and dried in vacuum oven at 30° C. overnight.

Characterization of the resulting material demonstrated a crystalline, anhydrous Form A of compound 9.

Table 31, supra, is reproduced below and sets forth the X-ray diffraction peaks observed for Form A of compound 9.

TABLE 31

XRPD Peak Positions for Form A of Compound 9

| Peak No. | Position (° 2θ) |
|---|---|
| 8.9 | 23.6 |
| 12.5 | 24.0 |
| 13.2 | 25.2 |
| 15.6 | 25.5 |
| 17.6 | 26.1 |
| 18.0 | 27.0 |
| 18.5 | 27.9 |
| 19.1 | 29.6 |
| 20.6 | 30.3 |
| 21.7 | 39.5 |

[1]In this and all subsequent tables, the position 2θ is within ±0.2.

FIG. 85 depicts an XRPD pattern of Form A of compound 9.

Figure 86:
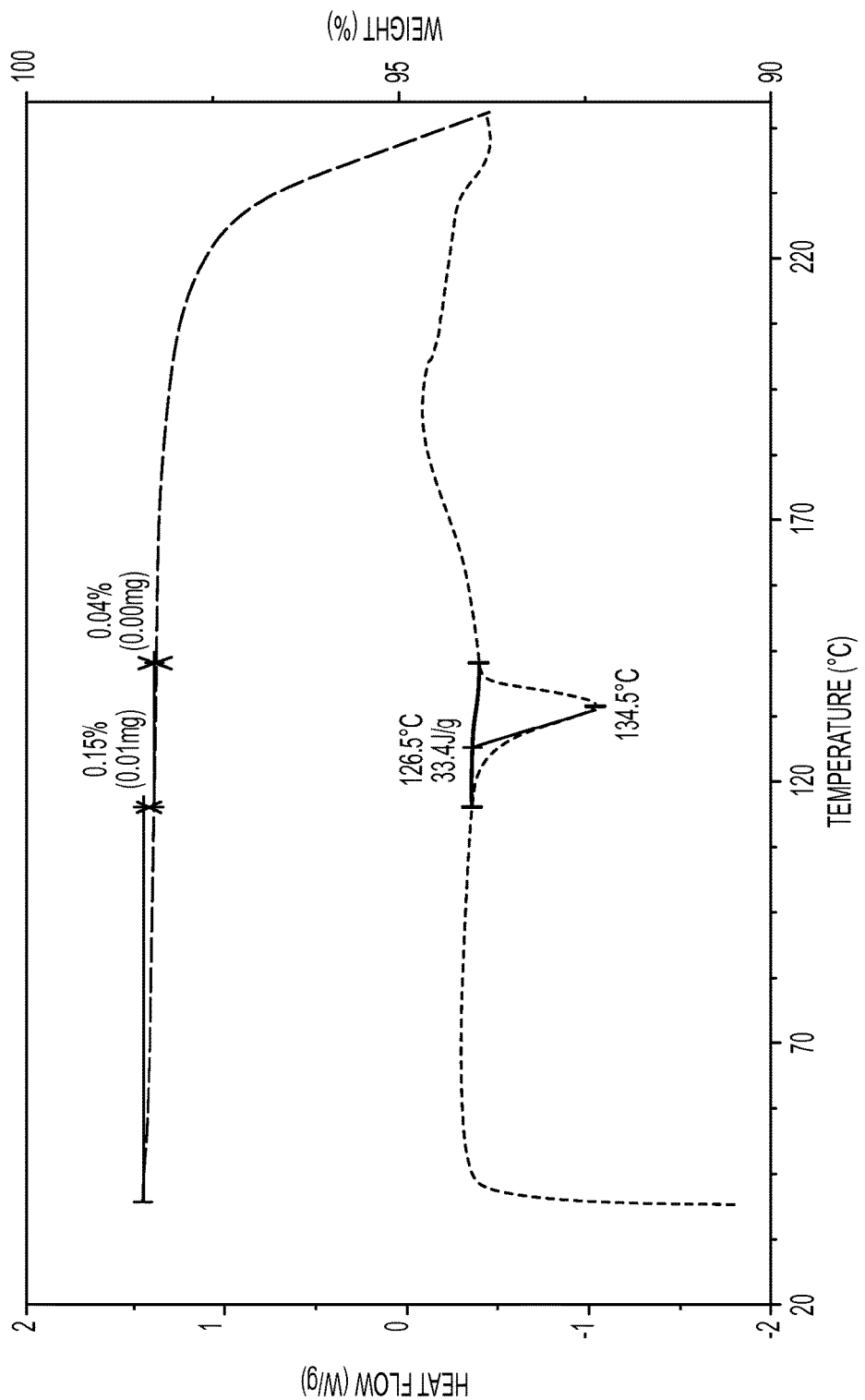
FIG. 86 depicts a DSC thermogram and TGA trace of Form A of compound 9.

FIG. 86 depicts a DSC thermogram and TGA trace of Form A of compound 9.

Figure 87:
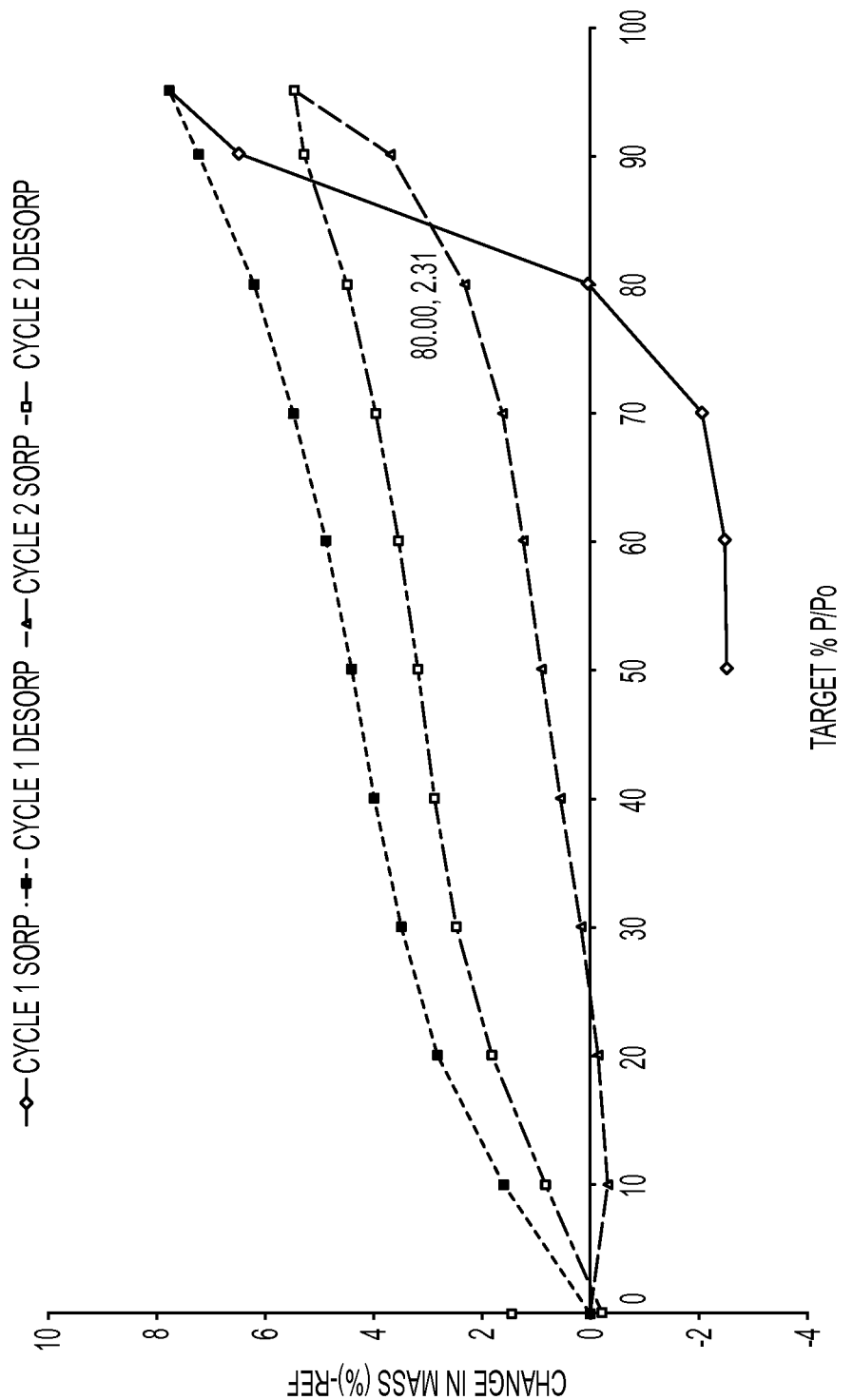
FIG. 87 depicts a DVS plot of Form A of compound 9.

FIG. 87 depicts a DVS plot of Form A of compound 9.

Elemental analysis—Calculated: C, 54.54; H, 4.41; N, 13.63; S, 5.20; Found: C, 54.20; H, 4.38; N, 13.60; S, 5.59.

Form B of Compound 9

Form B of compound 9 was prepared as follows.

Procedure: Compound 1 was dissolved in MeOH/CH$_2$Cl$_2$ (1/1 v/v, pre-mixed). Equal molar equivalent of 0.14 M benzenesulfonic acid in methanol was charged. The sample was shaken at ambient temperature at 200 RPM for 1 hour. The solvent was removed under nitrogen purge. The resulting solids were slurried in methanol at ambient temperature overnight, no solids were obtained. So it was dried under nitrogen purge, then added with methyl tert-butyl ether and slurried overnight, then dried in a vacuum oven.

Characterization of the resulting material demonstrated an amorphous Form B of compound 9.

FIG. 88 depicts a DSC thermogram and TGA trace of Form B of compound 9.

Example 10

Preparation of Forms A-B of Compound 10

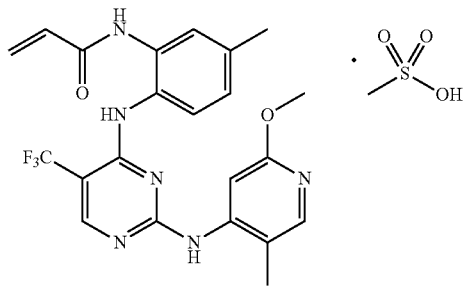

10

Form A of Compound 10

Form A of compound 10 was prepared as follows.

Procedure: Compound 1 was dissolved in MeOH/CH$_2$Cl$_2$ (1/1 v/v, pre-mixed). An equal molar equivalent of 0.31 M methanesulfonic acid in acetonitrile was charged. The sample was shaken at ambient temperature at 200 RPM for 1 hour. The solvent was removed under nitrogen purge. The resulting solids were slurried in methanol at ambient temperature overnight, no solids were obtained. The material was dried under nitrogen purge, followed by the addition of methyl tert-butyl ether, overnight slurry, filtration and drying in a vacuum oven.

Characterization of the resulting material demonstrated an amorphous Form A of compound 10.

FIG. 89 depicts a DSC thermogram and TGA trace of Form A of compound 10.

Form B of Compound 10

Form B of compound 10 was prepared as follows.

Procedure: Compound 1 was dissolved in MeOH/CH$_2$Cl$_2$ (1/1 v/v, pre-mixed). An equal molar equivalent of 0.31 M methanesulfonic acid in acetonitrile was charged. The sample was shaken at ambient temperature at 200 RPM for 1 hour. The solvent was removed under nitrogen purge. Acetonitrile/water (1/1 v/v) was charged and slurried overnight, no solids were obtained. It was dried and slurried in hexane overnight and then dried in vacuum oven.

Characterization of the resulting material demonstrated a partially crystalline Form B of compound 10.

Table 32, supra, is reproduced below and sets forth the X-ray diffraction peaks observed for Form B of compound 10.

TABLE 32

XRPD Peak Positions for Form B of Compound 10
Position (° 2θ)

| 6.1 |
| 7.9 |
| 8.3 |
| 16.3 |
| 22.6 |

[1]In this and all subsequent tables, the position 2θ is within ±0.2.

FIG. 90 depicts an XRPD pattern of Form B of compound 10.

FIG. 91 depicts a DSC thermogram and TGA trace of Form B of compound 10.

Example 11

Preparation of Form A of Compound 11

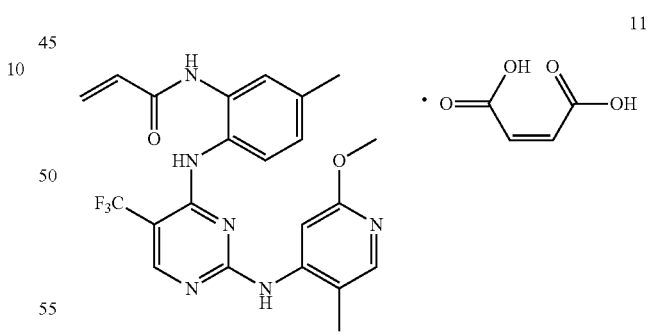

11

Form A of Compound 11

Form A of compound 11 was prepared as follows.

Procedure: Compound 1 was dissolved in MeOH/CH$_2$Cl$_2$ (1/1 v/v, pre-mixed). Equal molar equivalent of 0.25 M maleic acid in methanol was charged. The sample was shaken at ambient temperature at 200 RPM for 1 hour. The solvent was removed under nitrogen purge. The resulting solids were slurried in ethyl acetate at ambient temperature overnight, then filtered and dried in vacuum oven at ambient temperature.

Characterization of the resulting material demonstrated a crystalline, anhydrous Form A of compound 11.

Table 33, supra, is reproduced below and sets forth the X-ray diffraction peaks observed for Form A of compound 11.

TABLE 33

XRPD Peak Positions for Form A of Compound 11
Position (° 2θ)

| 5.2 |
| 8.9 |
| 9.2 |
| 10.4 |
| 12.0 |
| 13.3 |
| 13.4 |
| 15.3 |
| 16.1 |
| 18.7 |
| 20.9 |
| 23.0 |
| 23.2 |
| 23.9 |
| 24.6 |
| 25.6 |
| 26.1 |
| 26.3 |
| 26.7 |
| 27.0 |

[1] In this and all subsequent tables, the position 2θ is within ±0.2.

FIG. 92 depicts an XRPD pattern of Form A of compound 11.

Figure 93:
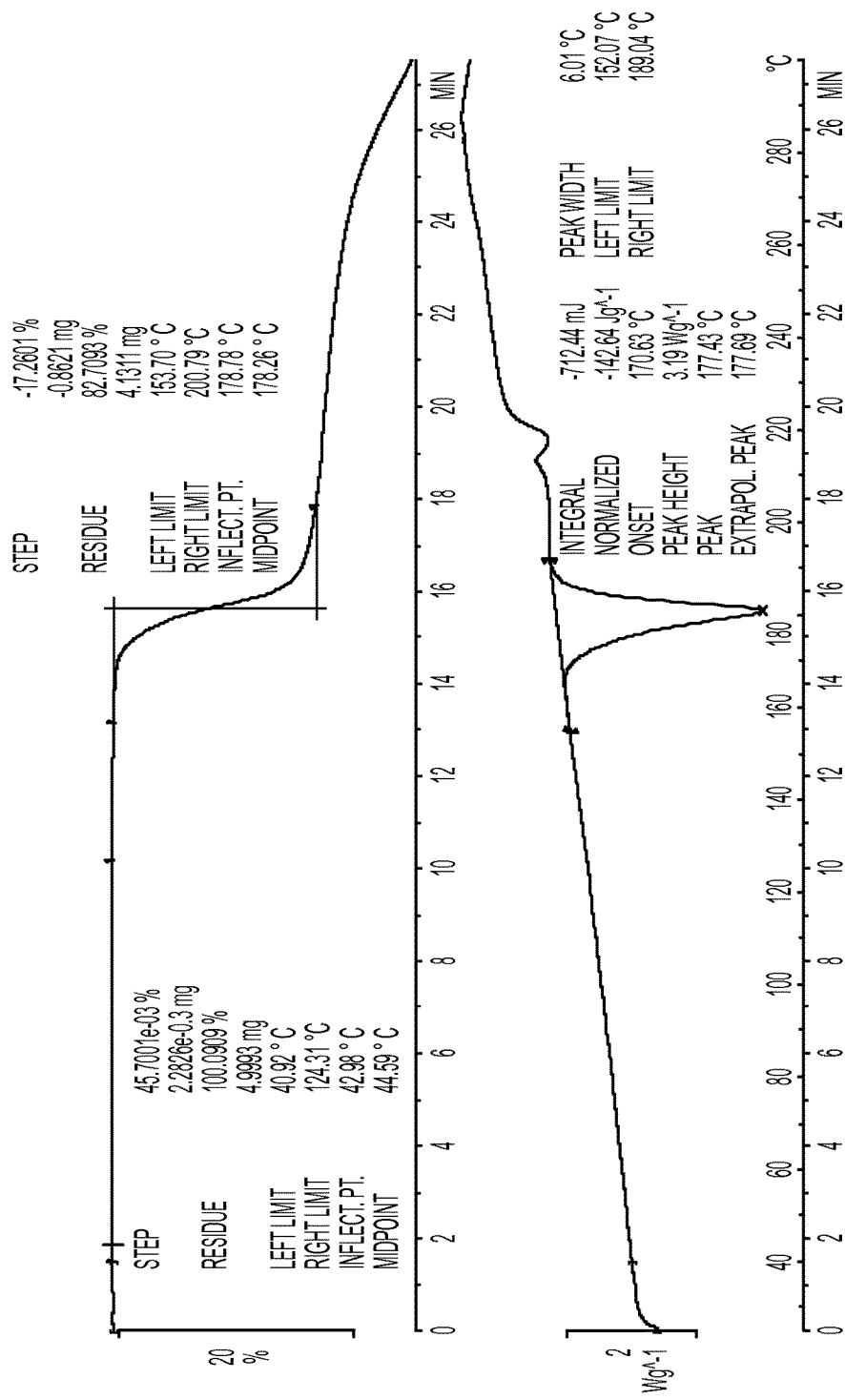
FIG. 93 depicts a DSC thermogram and TGA trace of Form A of compound 11.

FIG. 93 depicts a DSC thermogram and TGA trace of Form A of compound 11.

Elemental analysis—Calculated: C, 54.54; H, 4.41; N, 13.63; S, 5.20; Found: C, 54.20; H, 4.38; N, 13.60; S, 5.59.

Example 12

Preparation of Forms A-C of Compound 12

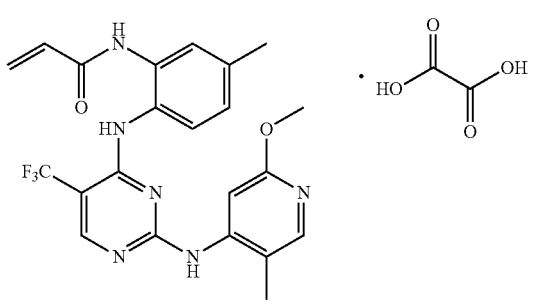

Form A of Compound 12

Form A of compound 12 was prepared as follows.

Procedure: Compound 1 was dissolved in MeOH/CH$_2$Cl$_2$ (1/1 v/v, pre-mixed). Equal molar equivalent of 0.15 M oxalic acid in methanol was charged. The sample was shaken at ambient temperature at 200 RPM for 1 hour. The solvent was removed under nitrogen purge. The resulting solids were slurried in acetonitrile at ambient temperature overnight, then filtered and dried in vacuum oven at ambient temperature.

Characterization of the resulting material demonstrated a crystalline, anhydrous Form A of compound 12.

Table 34, supra, is reproduced below and sets forth the X-ray diffraction peaks observed for Form A of compound 12.

TABLE 34

XRPD Peak Positions for Form A of Compound 12
Position (° 2θ)

| 5.4 |
| 5.8 |
| 6.8 |
| 9.7 |
| 10.3 |
| 12.3 |
| 13.4 |
| 14.4 |
| 16.4 |
| 17.4 |
| 17.7 |
| 20.3 |
| 22.0 |
| 23.4 |
| 23.7 |
| 24.9 |
| 25.2 |
| 26.9 |
| 30.2 |
| 35.4 |

[1] In this and all subsequent tables, the position 2θ is within ±0.2.

FIG. 94 depicts an XRPD pattern of Form A of compound 12.

Figure 95:
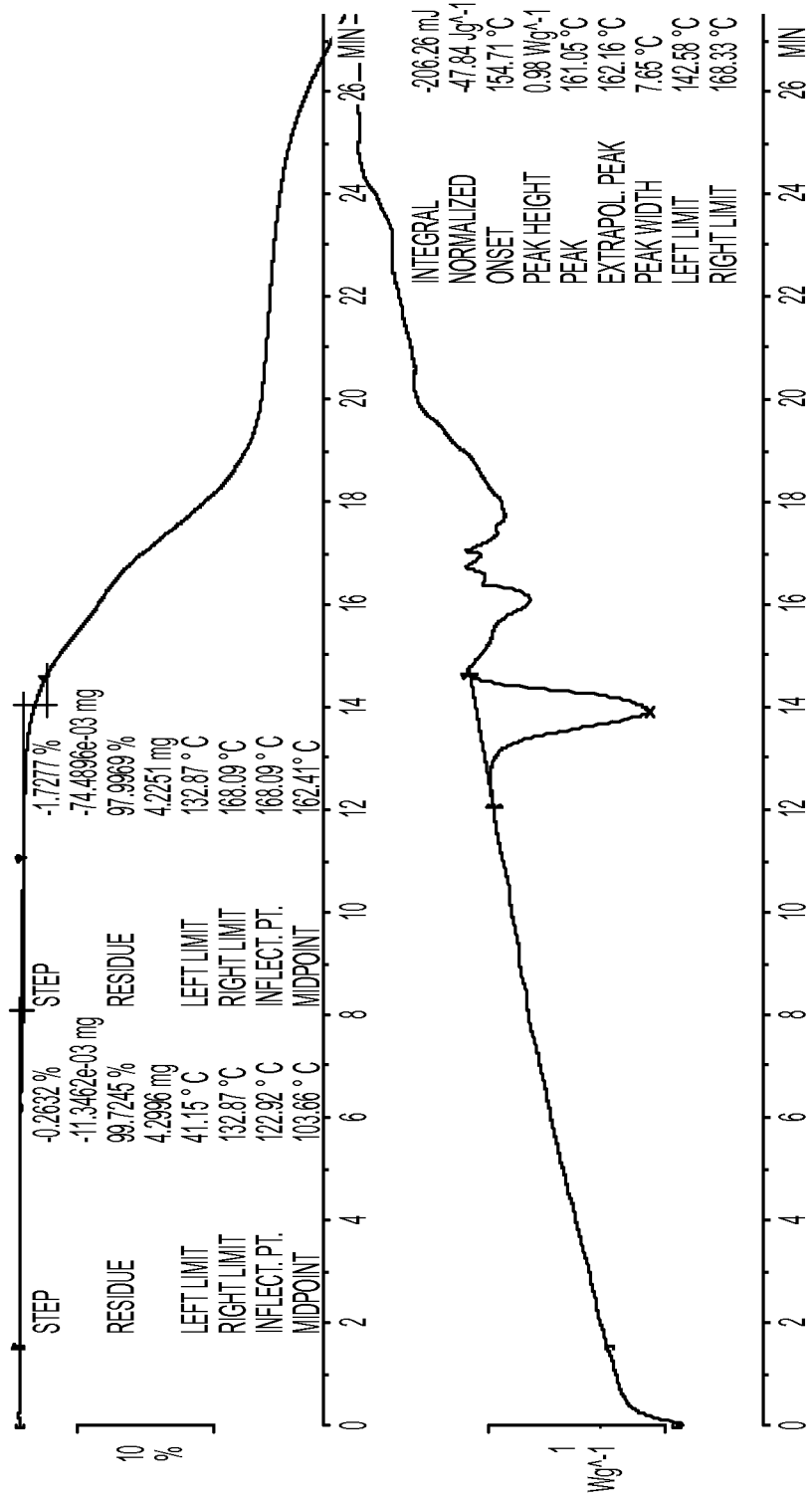
FIG. 95 depicts a DSC thermogram and TGA trace of Form A of compound 12.

FIG. 95 depicts a DSC thermogram and TGA trace of Form A of compound 12.

Form B of Compound 12

Form B of compound 12 was prepared as follows.

Procedure: Compound 1 was dissolved in MeOH/CH$_2$Cl$_2$ (1/1 v/v, pre-mixed). Equal molar equivalent of 0.15 M oxalic acid in MeOH was charged. The sample was shaken at ambient temperature at 200 RPM for 1 hour. The solvent was removed under nitrogen purge. The resulting solids were slurried in acetone at ambient temperature overnight, then filtered and dried in vacuum oven at ambient temperature.

Characterization of the resulting material demonstrated a crystalline Form B of compound 12.

Table 35, supra, is reproduced below and sets forth the X-ray diffraction peaks observed for Form B of compound 12.

TABLE 35

XRPD Peak Positions for Form B of Compound 12
Position (° 2θ)

| 5.0 |
| 5.8 |
| 8.3 |
| 9.1 |
| 9.9 |
| 12.5 |
| 13.4 |
| 14.8 |
| 15.2 |
| 16.7 |
| 17.4 |
| 20.3 |
| 21.7 |
| 24.8 |
| 25.3 |
| 26.3 |
| 26.8 |

TABLE 35-continued

XRPD Peak Positions for Form B of Compound 12
Position (° 2θ)

28.1
29.2
30.6

[1]In this and all subsequent tables, the position 2θ is within ±0.2.

FIG. 96 depicts an XRPD pattern of Form B of compound 12.

Figure 97:
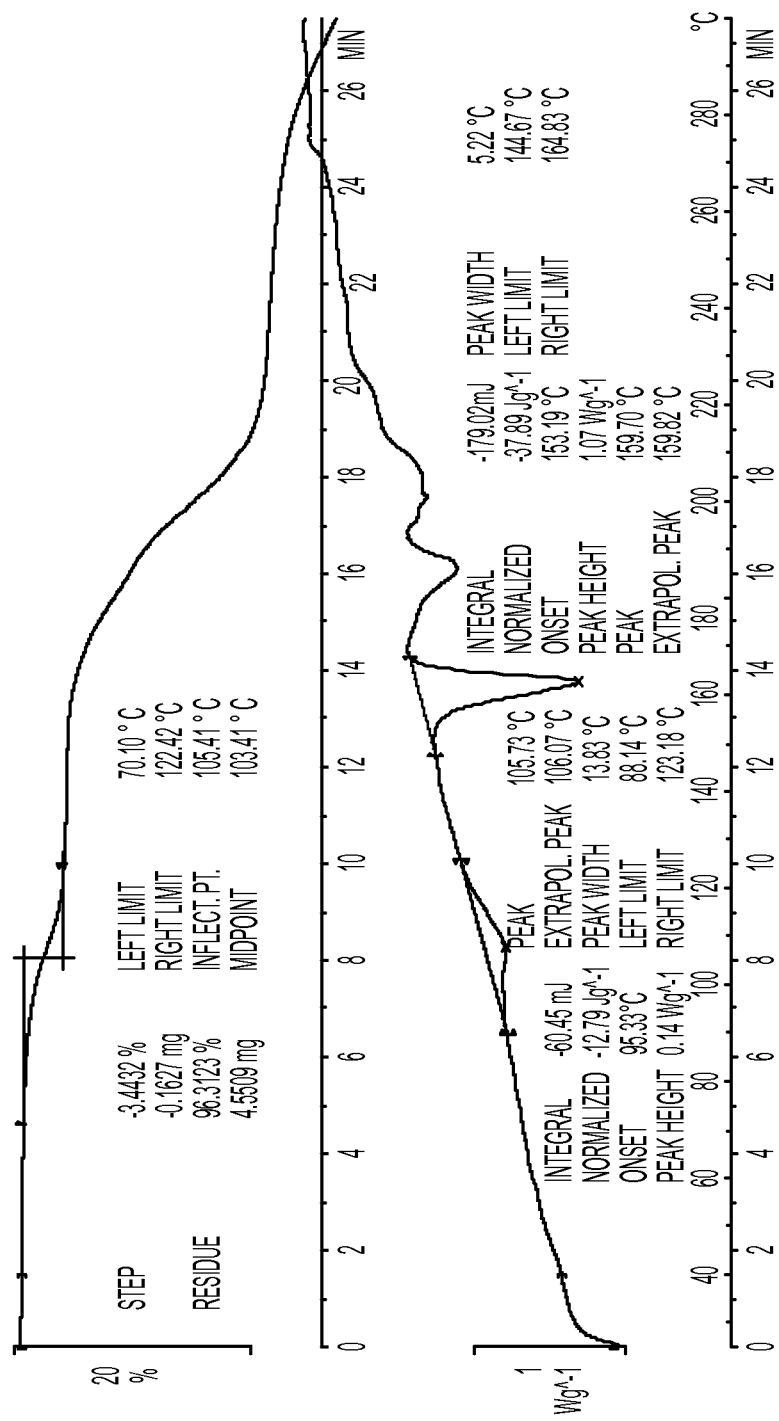
FIG. 97 depicts a DSC thermogram and TGA trace of Form B of compound 12.

FIG. 97 depicts a DSC thermogram and TGA trace of Form B of compound 12.

Form C of Compound 12

Form C of compound 12 was prepared as follows.

Procedure: Compound 1 was dissolved in MeOH/CH$_2$Cl$_2$ (1/1 v/v, pre-mixed). Equal molar equivalent of 0.15 M oxalic acid in methanol was charged. The sample was shaken at ambient temperature at 200 RPM for 1 hour. The solvent was removed under nitrogen purge. The resulting solids were slurried in ethyl acetate at ambient temperature overnight, then filtered and dried in vacuum oven at ambient temperature.

Characterization of the resulting material demonstrated a crystalline, anhydrous Form C of compound 12.

Table 36, supra, is reproduced below and sets forth the X-ray diffraction peaks observed for Form C of compound 12.

TABLE 36

XRPD Peak Positions for Form C of Compound 12
Position (° 2θ)

5.6
5.8
8.4
9.3
10.1
12.4
13.4
14.9
16.2
16.6
17.5
18.5
21.8
22.2
23.4
25.2
25.9
26.3
26.9
36.5

[1]In this and all subsequent tables, the position 2θ is within ±0.2.

FIG. 98 depicts an XRPD pattern of Form C of compound 12.

Figure 99:
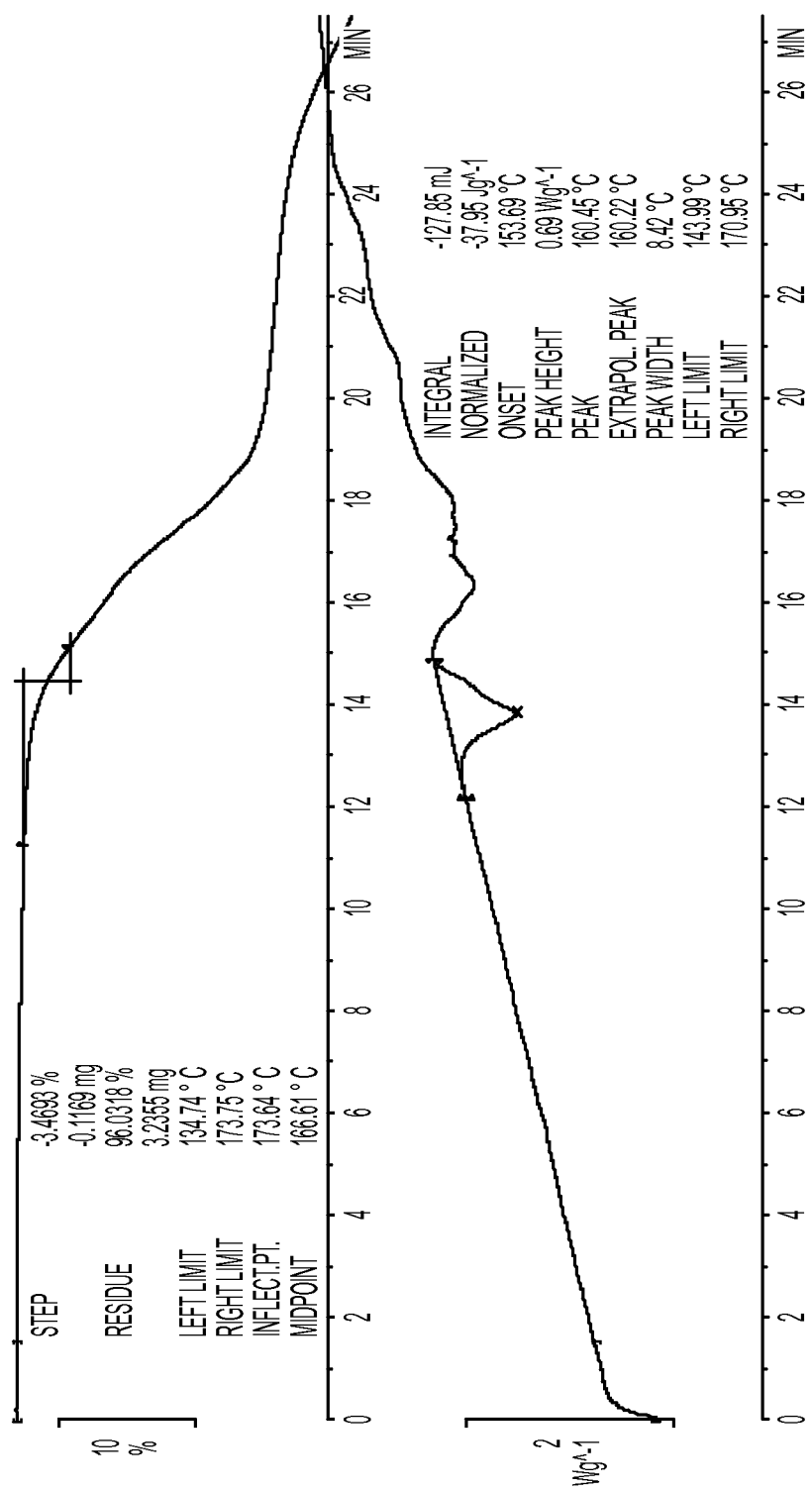
FIG. 99 depicts a DSC thermogram and TGA trace of Form C of compound 12.

FIG. 99 depicts a DSC thermogram and TGA trace of Form C of compound 12.

Example 13

Solubility in Water at Ambient Temperature

Each of compounds 1 through 9 were weighed into separate 8 mL clear glass vials. After addition of 3.2 mL of water, the vials were capped and shaken on an orbital shaker at 300 RPM at ambient temperature for 24 hours. The samples were removed from the shaker and the pH of each was measured using a calibrated pH meter. Next, a portion of the each sample was withdrawn and filtered using a PVDF-membrane syringe filter. The filtrate was analyzed using HPLC/UV with appropriate dilution. The solubility was reported as free base-equivalent value because the free base was used as the standard for HPLC analysis. The rest of the samples were shaken for another 24 hours for 48-hour solubility measurement using the same procedure. After the 48-hour solubility tests were run, the solid residues were recovered through filtration using 0.2 μm Nylon-membrane centrifuge tube filters at 14000 RPM for 5 min and analyzed using XRPD.

For the bis-phosphate complex and bis-sulfate salt, measurements were only performed at the 24-hour time point. The results are shown in Table 37, below.

TABLE 37

Solubility in Water at Ambient Temperature

| Sample | Conc. (μg/mL) at 24 hours | Conc. (μg/mL) at 48 hours | pH at 48 hrs |
| --- | --- | --- | --- |
| Compound 1 (free base) | 0.07 | 0.05 | 6.33 |
| Compound 2 (phosphate salt) | 19.40 | 91.69 | 2.48 |
| Compound 3 (bis-phosphate complex) | 113 | Not Determined | Not Determined |
| Compound 4 (HCl salt) | 162.33 | 134.08 | 2.29 |
| Compound 5 (HBr salt) | 190.63 | 207.42 | 2.27 |
| Compound 6 (sulfate salt) | 560.02 | 409.83 | 1.98 |
| Compound 7 (bis-sulfate salt) | 1170 | Not Determined | Not Determined |
| Compound 8 (tosylate salt) | 218.34 | 184.83 | 2.00 |
| Compound 9 (besylate salt) | 173.63 | 143.49 | 2.10 |

Example 14

A Single Oral Dose Pharmacokinetic (PK) Study in Dogs with Various Salt and Free Base Forms of Compound 1

The pharmacokinetics of compound 1 (free base, administered to dosing group 1), compound 2 (phosphate salt, administered to dosing group 4), compound 4 (hydrochloride salt, administered to dosing group 2), compound 5 (bromide salt, administered to dosing group 5), and compound 6 (sulfate salt, administered to dosing group 3) were evaluated in dogs (2/sex/group) in a parallel design study. In addition, the effect of food on the systemic exposure to compounds 1, 2, 4, 5 and 6 was also evaluated. Compounds 1, 2, 4, 5 and 6 were orally administered at 15 mg/kg to dogs in a fasted state (overnight fast) on day 1 and administered under fed conditions (a meal was provided one hour prior to dosing) on day 9. Doses were administered as a suspension in 5% Captisol/0.2% Tween 80/0.05M Citrate buffer (compound 1) and 5% Captisol/0.2% Tween (compounds 2, 4, 5 and 6). Animals were habituated (days 2 to 8) to consume their entire daily ration (~400 g) in 1 hour. Pharmacokinetic samples were collected on days 1 and 9 at 0, 0.5, 1, 2, 4, 6, 8, 12, and 24 hours after dosing. The summary of pharmacokinetic parameters are shown in Table 38 below.

TABLE 38

Mean (SD) Pharmacokinetic Parameters in Dogs

| Salt Type | Day 1 (Fasted) | | Day 9 (Fed) | |
| --- | --- | --- | --- | --- |
| | $C_{max}$ ng/mL | $AUC_{last}$ (ng · h/mL) | $C_{max}$ ng/mL | $AUC_{last}$ (ng · h/mL) |
| Compound 1, Form C | 98.1 (51.9) | 286 (162) | 293 (112) | 1890 (980) |
| Compound 4, Form A | 323 (135) | 856 (285) | 818 (47) | 3350 (839) |
| Compound 2, Form A | 345 (78) | 1080 (511) | 790 (218) | 3880 (1250) |
| Compound 6, Form A | 364 (204) | 1120 (597) | 740 (433) | 5590 (2480) |
| Compound 5, Form A | 393 (171) | 1680 (1210) | 826 (211) | 5030 (1020) |

Number of animals used were 2/sex/group

Figure 100B:
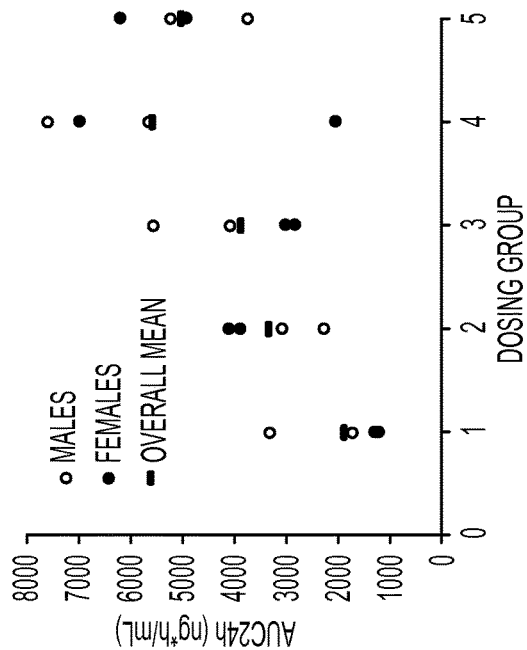
FIG. 100B depicts PK data in dogs under fed conditions.
Figure 100A:
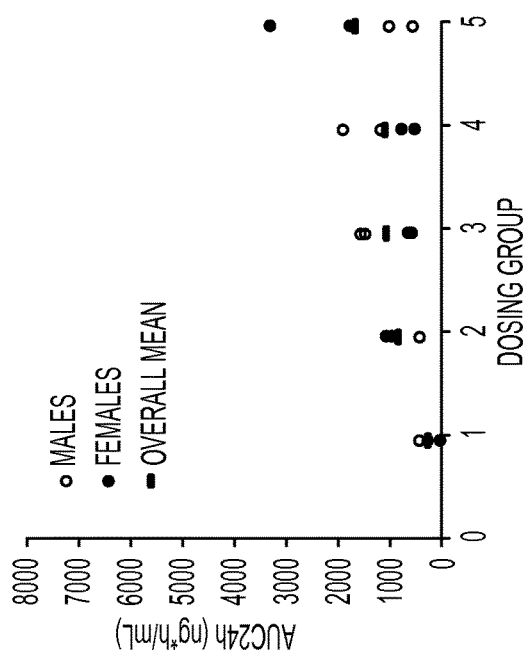
FIG. 100A depicts PK data in dogs under fasted conditions.

Compounds 2, 4, 5 and 6 demonstrated enhanced oral bioavailability in dogs when compared to Compound 1 under both fasted and fed conditions with their mean systemic exposure ($AUC_{last}$) to Compound 1 increasing by approximately either 3- to 6-fold (fasted; see FIG. 100(*a*)) or 2- to 3-fold (fed; see FIG. 100(*b*)).

In dogs, a positive food effect was observed with both free base (Compound 1) and salt forms (Compounds 2, 4, 5 and 6). Systemic exposure increased by approximately 3- to 7-fold under fed conditions as compared to fasted conditions.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. Compound 2:

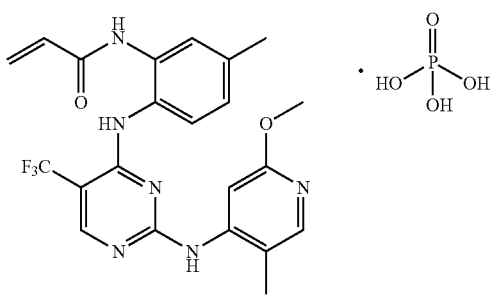

2. The compound according to claim 1, wherein said compound is crystalline.

3. The compound according to claim 1, wherein said compound is a crystalline solid substantially free of amorphous compound 2.

4. The compound according to claim 2, having one or more peaks in its XRPD selected from those at about 6.8, about 10.1, and about 20.8 degrees 2-theta.

5. The compound according to claim 4, having at least two peaks in its XRPD selected from those at about 6.8, about 10.1, and about 20.8 degrees 2-theta.

6. The compound according to claim 5, wherein said compound is of Form A.

7. The compound according to claim 2, having an XRPD substantially similar to that depicted in FIG. 13.

8. The compound according to claim 2, having one or more peaks in its XRPD selected from those at about 3.6, about 7.3, and about 15.0 degrees 2-theta.

9. The compound according to claim 8, having at least two peaks in its XRPD selected from those at about 3.6, about 7.3, and about 15.0 degrees 2-theta.

10. The compound according to claim 9, wherein said compound is of Form B.

11. The compound according to claim 2, having an XRPD substantially similar to that depicted in FIG. 17.

12. The compound according to claim 2, having one or more peaks in its XRPD selected from those at about 8.4, about 9.3, and about 16.5 degrees 2-theta.

13. The compound according to claim 12, having at least two peaks in its XRPD selected from those at about 8.4, about 9.3, and about 16.5 degrees 2-theta.

14. The compound according to claim 13, wherein said compound is of Form C.

15. The compound according to claim 2, having an XRPD substantially similar to that depicted in FIG. 21.

16. The compound according to claim 2, having one or more peaks in its XRPD selected from those at about 9.1, about 10.4, and about 25.1 degrees 2-theta.

17. The compound according to claim 16, having at least two peaks in its XRPD selected from those at about 9.1, about 10.4, and about 25.1 degrees 2-theta.

18. The compound according to claim 17, wherein said compound is of Form D.

19. The compound according to claim 2, having an XRPD substantially similar to that depicted in FIG. 25.

20. A pharmaceutical composition comprising the compound according to claim 1 and a pharmaceutically acceptable carrier or excipient.

21. The pharmaceutical composition according to claim 20, wherein said pharmaceutical composition is substantially free of impurities.

* * * * *